(12) United States Patent
Boyden et al.

(10) Patent No.: US 7,623,625 B2
(45) Date of Patent: Nov. 24, 2009

(54) COMPTON SCATTERED X-RAY VISUALIZATION, IMAGING, OR INFORMATION PROVIDER WITH SCATTERING EVENT LOCATING

(75) Inventors: Edward S. Boyden, Cambridge, MA (US); Roderick A. Hyde, Redmond, WA (US); Muriel Y. Ishikawa, Livermore, CA (US); Edward K. Y. Jung, Bellevue, WA (US); Eric C. Leuthardt, St. Louis, MO (US); Robert W. Lord, Seattle, WA (US); Nathan P. Myhrvold, Medina, WA (US); Dennis J. Rivet, St. Louis, MO (US); Michael A. Smith, Phoenix, AZ (US); Clarence T. Tegreene, Bellevue, WA (US); Thomas A. Weaver, San Mateo, CA (US); Charles Whitmer, North Bend, WA (US); Lowell L. Wood, Jr., Bellevue, WA (US); Victoria Y. H. Wood, Livermore, CA (US)

(73) Assignee: Searete LLC, Bellevue, WA (US)

( * ) Notice: Subject to any disclaimer, the term of this patent is extended or adjusted under 35 U.S.C. 154(b) by 260 days.

(21) Appl. No.: 11/786,741

(22) Filed: Apr. 11, 2007

(65) Prior Publication Data

US 2008/0253520 A1 Oct. 16, 2008

(51) Int. Cl.
*G01N 23/201* (2006.01)

(52) U.S. Cl. .......................... 378/86; 378/87

(58) Field of Classification Search ...................... 378/7, 378/8, 19, 86–90
See application file for complete search history.

(56) References Cited

U.S. PATENT DOCUMENTS

| | | | |
|---|---|---|---|
| 3,243,589 A | 3/1966 | Sinclair | |
| 3,769,507 A | 10/1973 | Kenney et al. | |
| 3,927,318 A | 12/1975 | Macovski | |
| 3,936,638 A | 2/1976 | Gibbons | |
| 4,229,651 A | 10/1980 | Danos | |
| 4,759,348 A | 7/1988 | Cawood | |
| 4,866,749 A | 9/1989 | Uematu | |

(Continued)

OTHER PUBLICATIONS

UK Intellectual Property Office Combined Search and Examination Report; Application No. GB0806599.7; Oct. 29, 2008; p. 1.

(Continued)

*Primary Examiner*—Irakli Kiknadze

(57) ABSTRACT

One aspect relates to determining a location of an at least one scattering event occurring within an at least some matter of at least a portion of an individual, wherein the determining the location of the at least one scattering event is based at least in part on a combination of: a relative position and/or angle at which an at least one applied X-ray being applied to the at least some matter of the at least the portion of the individual, an applied energy level of the at least one applied X-ray being applied to the at least some matter of the at least the portion of the individual, a detected location of an at least one scattered X-ray resulting from scattering of the at least one applied X-ray scattering during the at least one scattering event, and a scattered energy level of the at least one scattered X-ray.

39 Claims, 26 Drawing Sheets

U.S. PATENT DOCUMENTS

| | | | |
|---|---|---|---|
| 5,003,980 | A | 4/1991 | Loo et al. |
| 5,105,452 | A | 4/1992 | McInerney |
| 5,125,017 | A | 6/1992 | Lempriere |
| 5,147,354 | A | 9/1992 | Boutacoff et al. |
| 5,170,422 | A | 12/1992 | Fiebiger |
| 5,430,787 | A | 7/1995 | Norton |
| 5,703,923 | A | 12/1997 | Bardash |
| 5,768,333 | A | 6/1998 | Abdel-Mottaleb |
| 5,989,182 | A | 11/1999 | Hori et al. |
| 6,076,005 | A | 6/2000 | Sontag et al. |
| 6,320,933 | B1 | 11/2001 | Grodzins et al. |
| 6,477,233 | B1 | 11/2002 | Ribbing et al. |
| 6,484,051 | B1 | 11/2002 | Daniel |
| 6,563,906 | B2 | 5/2003 | Hussein et al. |
| 6,661,876 | B2 | 12/2003 | Turner et al. |
| 6,754,304 | B1 | 6/2004 | Kumakhov |
| 6,847,041 | B2 | 1/2005 | Okada et al. |
| 6,895,077 | B2 | 5/2005 | Karellas et al. |
| 6,927,398 | B2 | 8/2005 | Katagiri |
| 6,929,602 | B2 | 8/2005 | Hirakui et al. |
| 7,057,187 | B1 | 6/2006 | Yun et al. |
| 7,081,627 | B2 | 7/2006 | Heismann et al. |
| 7,099,428 | B2 | 8/2006 | Clinthorne et al. |
| 7,149,335 | B2 | 12/2006 | Kaufhold |
| 7,149,567 | B2 | 12/2006 | Demos et al. |
| 7,154,989 | B2 | 12/2006 | Ueno et al. |
| 7,224,772 | B2 | 5/2007 | Jacobs et al. |
| 7,412,022 | B2 | 8/2008 | Jupiter et al. |
| 2002/0004204 | A1 | 1/2002 | O'Keefe |
| 2003/0205675 | A1 | 11/2003 | Nelson et al. |
| 2004/0202279 | A1 | 10/2004 | Besson et al. |
| 2005/0006589 | A1 | 1/2005 | Joung et al. |
| 2005/0017181 | A1 | 1/2005 | Kearfott et al. |
| 2005/0035291 | A1 | 2/2005 | Hill et al. |
| 2006/0192129 | A1 | 8/2006 | Yun et al. |
| 2006/0197025 | A1 | 9/2006 | Burr et al. |
| 2006/0291618 | A1 | 12/2006 | Eberhard et al. |
| 2008/0253525 | A1 | 10/2008 | Boyden et al. |
| 2008/0253526 | A1 | 10/2008 | Boyden et al. |
| 2008/0253527 | A1* | 10/2008 | Boyden et al. ............... 378/87 |
| 2008/0253528 | A1* | 10/2008 | Boyden et al. ............... 378/87 |
| 2008/0253529 | A1 | 10/2008 | Boyden et al. |
| 2008/0253530 | A1 | 10/2008 | Boyden et al. |
| 2008/0253531 | A1 | 10/2008 | Boyden et al. |
| 2008/0253627 | A1* | 10/2008 | Boyden et al. ............. 382/128 |
| 2009/0086894 | A1 | 4/2009 | Boyden et al. |

OTHER PUBLICATIONS

Basgall, Monte; "'Force-Imaging' Ultrasound Attracting More Funding as its Promise Widens"; Office of News & Communications; bearing a date Jun. 29, 2005; pp. 1-3.

Borden, Mark A.; Sarantos, Melissa R.; Stieger, Susanne M.; Simon, Scott I.; Ferrara, Katherine W.; Dayton, Paul A.; "Ultrasound Radiation Force Modulates Ligand Availability on Targeted Contrast Agents"; PubMed Central; bearing a date of Jul. 2006; pp. 1-11; vol. 5, No. 3.

Wagner, Christopher R.; Perrin, Douglas P.; Howe, Robert D.; "Force Feedback in a Three-Dimensional Ultrasound-Guided Surgical Task"; pp. 1-8.

Ackerman, Jeremy; "UNC Ultrasound/Medical Augmented Reality Research"; Ultrasound Visualization Research; bearing a date of Jun. 15, 2000; printed on Oct. 19, 2006; pp. 1-4; located at http://www.cs.unc.edu/Research/us/.

Bushberg, PhD, Jerrold T.; Seibert, PhD, J. Anthony; Leidholdt, Jr., PhD, Edwin, M.; Boone, PhD, John M.; "X-Ray Production, X-Ray Tubes, and Generators"; The Essential Physics of Medical Imaging; bearing a date of 2002; pp. 97-144 (total pages 50); Second Edition; Lippincott Williams & Wilkins.

Campbell, Christopher S.; Zhai, Shumin; May, Kim W.; Maglio, Paul P.; "What You Feel Must Be What You See: Adding Tactile Feedback to the Trackpoint"; Human-Computer Interaction—Proceedings of Interact '99; pp. 383-390; IOS Press; located at http://www.almaden.ibm.com/u/zhai/papers/interact99/interact99.pdf.

Heimer, Malcolm L.; Shiroff, Robert; Jacobs, Alan M.; Kenney, Edward S.; Weidner, Willian A.; "Implementing an automatic control system for dynamic radiography"; Medical & Biological Engineering & Computing; bearing a date of Mar. 1977; pp. 168-178; vol. 15, No. 3; Medical & Biological Engineering & Computing.

Herr, Michael D.; McInerney, Joseph J.; Lamser, Dennis G.; Copenhaver, Gary L.; "A Flying Spot X-Ray System for Compton Backscatter Imaging"; IEEE Transactions on Medical Imaging; bearing a date of Sep. 1994; pp. 461-469; vol. 13, No. 3; IEEE.

Hossack, J. A.; "Extended Focal Depth Imaging for Medical Ultrasound"; IEEE Ultrasonics Symposium; bearing a date of 1996; pp. 1535-1540; IEEE.

Jacobs, Alan M.; Kenney, Edward S.; "Dynamic Radiography, A New Imaging Technique Using Penetrating Radiation"; Proceedings of SPIE; bearing a date of Feb. 1972; pp. 17-22 (total pages 8); vol. 29, SPIE.

Johns, Paul C.; Leclair, Robert J.; Wismayer, Matthew P.; "Medical X-Ray Imaging with Scattered Photons"; SPIE Regional Meeting on Optoelectronics, Photonics, and Imaging; bearing a date of May 2002; pp. 355-357; SPIE TD01.

Kawakita, Kunihiko; Hata, Koichi; Sato, Hideki; Saito, Yahachi; "Development of microfocused x-ray source by using carbon nanotube field emitter"; The Journal of Vacuum Science and Technology B; bearing dates Mar. and Apr. 2006; pp. 950-952; vol. 24, No. 2; American Vacuum Society.

McInerney, J. J.; Nellis, S. H.; Zelis, R.; Jacobs, A. M.; Kenney, E. S.; McMasters, I. B.; Herr, M. D.; Atkinson, D. J.; "Microprocessor controlled multichannel dynamic radiograph"; Medical & Biological Engineering & Computing; bearing a date of Nov. 1982; pp. 661-670; vol. 20; Medical & Biological Engineering & Computing.

Stetten, George; Chib, Vikram; "Magnified Real-Time Tomographic Reflection"; Lecture Notes in Computer Science; bearing a date of 2001; pp. 683-690 (total pages 10); vol. 2208; MICCAI.

Tilley, David G.; Jacobs, Alan M.; Kenney, Edward S.; Weidner, William A.; Miller, Kenneth L.; "Dynamic radiography—a technique employing scattered radiation to monitor surface motion"; Medical & Biological Engineering & Computing; bearing a date of Mar. 1976; pp. 141-150; vol. 14, No. 3; Medical & Biological Engineering & Computing.

Towe, Bruce C.; Jacobs, Alan M.; "X-Ray Backscatter Imaging"; IEEE Transactions on Biomedical Engineering; bearing a date of Sep. 1981; pp. 646-654; vol. BME-28, No. 9; IEEE.

Yelin, D.; Rizvi, I.; White, W. M.; Motz, J. T.; Hasan, T.; Bouma, B. E.; Tearney, G. J.; "Three-dimensional miniature endoscopy, A single optical fibre acts as a flexible probe to transmit a superior image of an internal landscape." Nature; bearing a date of Oct. 19, 2006; p. 765; vol. 443; Nature Publishing Group.

Yue, G. Z.; Qiu, Q.; Gao, Bo; Cheng, Y.; Zhang, J.; Shimoda, H.; Chang, S.; Lu, J. P.; Zhou, O.; "Generation of continuous and pulsed diagnostic imaging x-ray radiation using a carbon-nanotube-based field-emission cathode"; Applied Physics Letters; bearing a date of Jul. 8, 2002; pp. 355-357; vol. 81, No. 2; American Institute of Physics.

Zhang, J.; Yang, G.; Cheng, Y.; Gao, B.; Qui, Q.; Lee, Y. Z.; Lu, J. P.; Zhou, O.; "Stationary scanning x-ray source based on carbon nanotube field emitters"; Applied Physics Letters; bearing a date of 2005; pp. 184104-1-184104-3; vol. 86; American Institute of Physics.

U.S. Appl. No. 12/011,983, Boyden et al.

U.S. Appl. No. 12/011,993, Boyden et al.

Battista et al.; "Compton Scatter Imaging of Transverse Sections: Corrections for Multiple Scatter and Attenuations"; Phys. Med. Biol.; Bearing a date of 1977; pp. 229-244; vol. 22, No. 2.

Harding, G. and Tischler, R.; "Dual-Energy Compton Scatter Tomography"; Phys. Med. Biol.; Bearing a date of 1986; pp. 477-489; vol. 31, No. 5; The Institute of Physics, Great Britain.

* cited by examiner

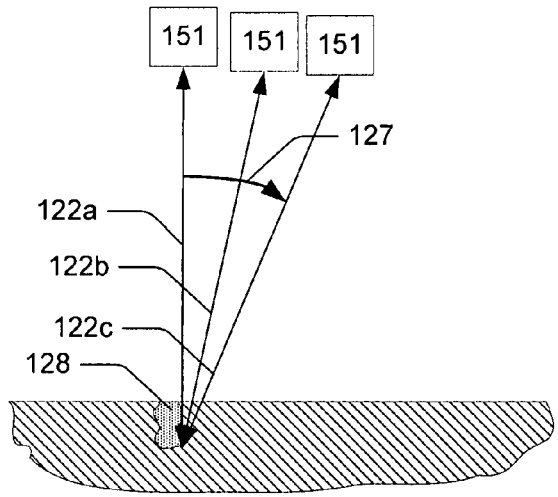

FIG. 12a

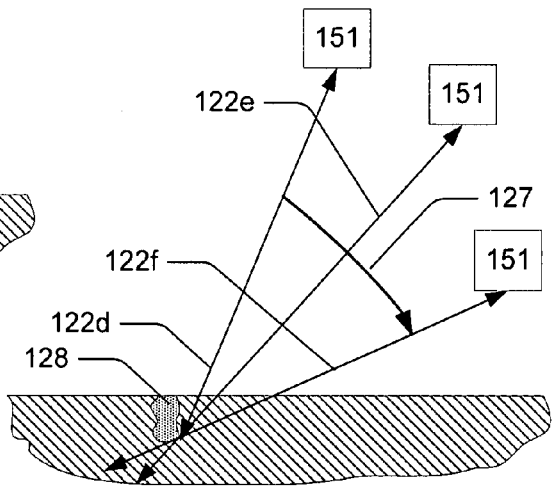

| visualizing, imaging, or deriving at least a first set of visualizations, images, or information 1302 |

↓

| controlling or adjusting the Compton scattered X-ray visualizer, imager, or information provider 100 such as to visualize, image, or provide additional information 1304 |

↓

| operating the Compton scattered X-ray visualizer, imager, or information provider 100 to capture, or otherwise obtain, the additional information 1306 |

↓

| obtaining a more detailed or adjusted visualization, image, or information [by tomographically or volumetrically integrating the provided information] 1308 |

FIG. 13

Good subsequent scan angle to determine depth of irregularities

Good initial scan angle to locate irregularities

4600 → determining a location of an at least one scattering event occurring within an at least some matter of at least a portion of an individual, wherein the determining the location of the the at least one scattering event is based at least in part on a combination of: a relative position and/or angle at which an at least one applied X-ray being applied to the at least some matter of the at least the portion of the individual, an applied energy level of the at least one applied X-ray being applied to the at least some matter of the at least the portion of the individual, a detected location of an at least one scattered X-ray resulting from scattering of the at least one applied X-ray scattering during the at least one scattering event, and a scattered energy level of the at least one scattered X-ray 4602

FIG. 46

4700 → applying at least one applied X-ray substantially toward an at least some matter of an at least a portion of an individual 4702 visualizing, imaging, or providing information of the at least some matter of the at least the portion of the individual at least partially in response to the applying the at least one applied X-ray substantially toward the at least some matter of the at least the portion of the individual, the visualizing, imaging, or providing information of the at least some matter of the at least the portion of the individual at least partially based on a combination of a relative position and an angle of the at least one applied X-ray; an applied energy level of the at least one applied X-ray; a detected location of at least one scattered X-ray which resulted from the at least one applied X-ray scattering during the at least one scattering event within the at least some matter of the at least the portion of the individual; and a scattered energy level of the at least one scattered X-ray 4704

FIG. 47

COMPTON SCATTERED X-RAY VISUALIZATION, IMAGING, OR INFORMATION PROVIDER WITH SCATTERING EVENT LOCATING

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

1. For purposes of the USPTO extra-statutory requirements, the present application constitutes a continuation-in-part of U.S. patent application Ser. No. 11/786,744, entitled "COMPTON SCATTERED X-RAY DEPTH VISUALIZATION, IMAGING, OR INFORMATION PROVIDER", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Apr. 11, 2007, which is currently co-pending, or is an application of which a currently co-pending application is entitled to the benefit of the filing date.

2. For purposes of the USPTO extra-statutory requirements, the present application constitutes a continuation-in-part of U.S. patent application Ser. No. 11/786,739, entitled "COMPTON SCATTERED X-RAY VISUALIZATION, IMAGING, OR INFORMATION PROVIDER USING IMAGE COMBINING", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Apr. 11, 2007, which is currently co-pending, or is an application of which a currently co-pending application is entitled to the benefit of the filing date.

3. For purposes of the USPTO extra-statutory requirements, the present application constitutes a continuation-in-part of U.S. patent application Ser. No. 11/786,776, entitled "SCINTILLATOR ASPECTS OF COMPTON SCATTERED X-RAY VISUALIZATION, IMAGING, OR INFORMATION PROVIDiNG", naming Edward S. Boyden, Glenn B. Foster, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Apr. 11, 2007, which is currently co-pending, or is an application of which a currently co-pending application is entitled to the benefit of the filing date.

4. For purposes of the USPTO extra-statutory requirements, the present application constitutes a continuation-in-part of U.S. patent application Ser. No. 11/786,759, entitled "COMPTON SCATTERED X-RAY VISUALIZATION, IMAGING, OR INFORMATION PROVIDER WITH TIME OF FLIGHT COMPUTATION", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Apr. 11, 2007, which is currently co-pending, or is an application of which a currently co-pending application is entitled to the benefit of the filing date.

5. For purposes of the USPTO extra-statutory requirements, the present application constitutes a continuation-in-part of U.S. patent application Ser. No. 11/786,743, entitled "TOOL ASSOCIATED WITH COMPTON SCATTERED X-RAY VISUALIZATION, IMAGING, OR INFORMATION PROVIDER", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Apr. 11, 2007, which is currently co-pending, or is an application of which a currently co-pending application is entitled to the benefit of the filing date.

6. For purposes of the USPTO extra-statutory requirements, the present application constitutes a continuation-in-part of U.S. patent application Ser. No. 11/786,775, entitled "COMPTON SCATTERED X-RAY VISUALIZATION, IMAGING, OR INFORMATION PROVIDER IN SOFT MATTER SUCH AS TISSUE, ORGANS, OR BLOOD, AND/OR IN HARD MATTER SUCH AS BONES OR TEETH", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Apr. 11, 2007, which is currently co-pending, or is an application of which a currently co-pending application is entitled to the benefit of the filing date.

7. For purposes of the USPTO extra-statutory requirements, the present application constitutes a continuation-in-part of U.S. patent application Ser. No. 11/786,758, entitled "VOLUMETRIC TYPE COMPTON SCATTERED X-RAY VISUALIZATION, IMAGING, OR INFORMATION PROVIDER", naming Edward S. Boyden, Roderick A. Hyde, Muriel Y. Ishikawa, Edward K. Y. Jung, Eric C. Leuthardt, Robert W. Lord, Nathan P. Myhrvold, Dennis J. Rivet, Michael A. Smith, Clarence T. Tegreene, Thomas A. Weaver, Charles Whitmer, Lowell L. Wood, Jr. and Victoria Y. H. Wood, as inventors, filed Apr. 11, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

Certain aspects of this disclosure can relate to, but are not limited to, a variety of embodiment of Compton scattered X-ray visualizer, imager, or information providers, and associated mechanisms and/or techniques.

BRIEF DESCRIPTION OF THE FIGURES

FIGS. 12a and 12b are a diagram illustrating motion of certain embodiments of the Compton scattered X-ray visualizer, imager, or information provider such as may occur during certain types of volumetric visualization, imaging, or information providing;

FIG. 13 shows a flow chart of one embodiment of visualization, imaging, or information providing, such as may occur using certain embodiments of the Compton scattered X-ray visualizer, imager, or information provider as described with respect to FIGS. 12a and 12b;

FIG. 46 is a flow chart of an embodiment of a Compton depth scattering visualizing, imaging, of information providing technique as can be performed by certain embodiments of the Compton scattered X-ray visualizer, imager, or information provider of FIG. 1, and other locations through this disclosure; and FIG. 47 is a flow chart of another embodiment of a Compton depth scattering visualizing, imaging, of information providing technique as can be performed by certain embodiments of the Compton scattered X-ray visualizer, imager, or information provider of FIG. 1, and other locations through this disclosure.

DETAILED DESCRIPTION

Figure 1:
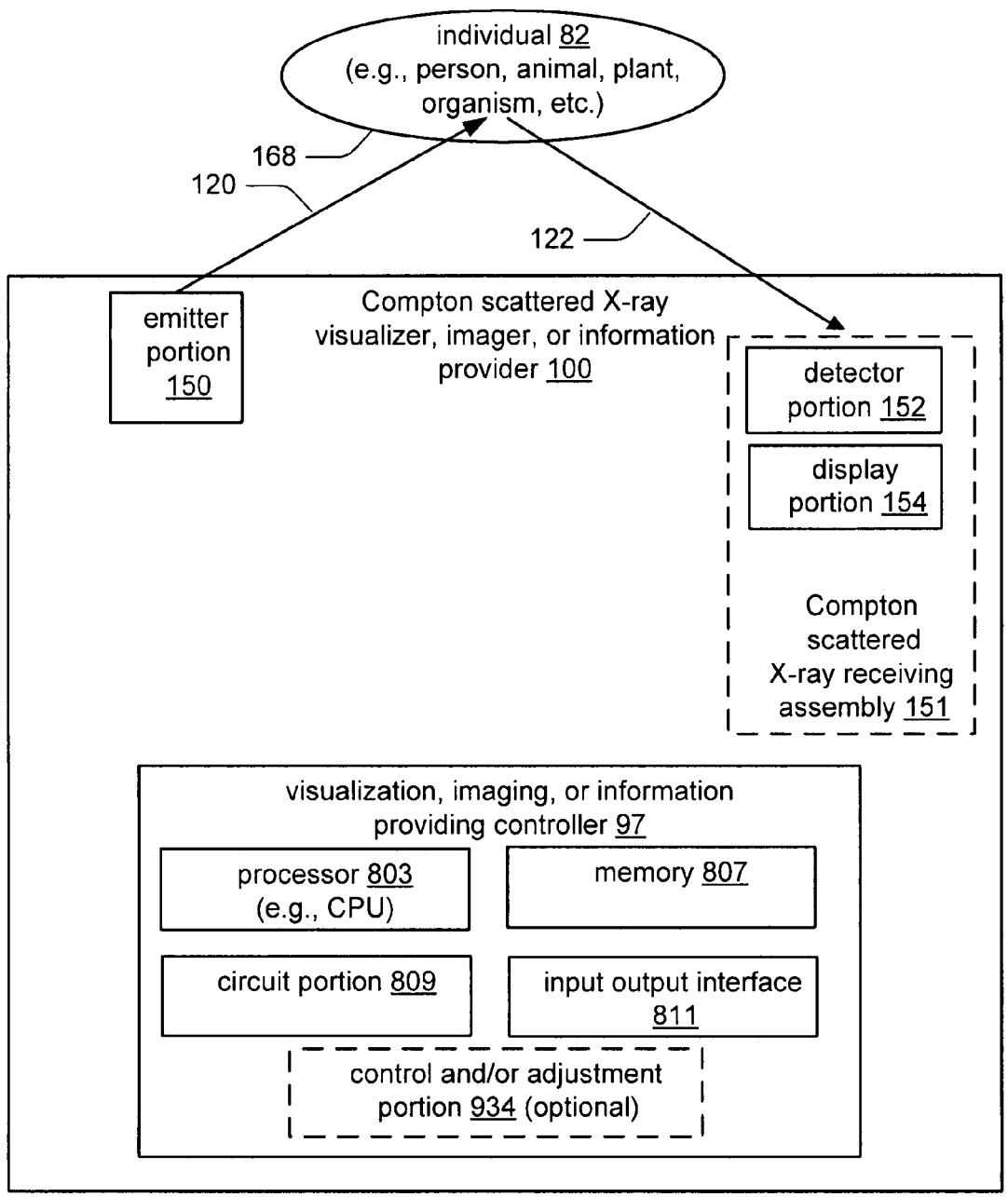
FIG. 1 is a block diagram of one embodiment of a Compton scattered X-ray visualizer, imager, or information provider.

At least certain portions of the text of this disclosure (including claims, detailed description, and/or drawings as set forth herein) can support various different claim groupings and/or various different applications. Although, for sake of convenience and understanding, the detailed description can include section headings that generally track various different concepts associated with claims or general concepts contained therein, and the detailed description is not intended to limit the scope of the invention as set forth by each particular claim. It is to be understood that support for the various applications or portions thereof thereby, can appear throughout the text and/or drawings at one or more locations, irrespective of the section headings.

1. Certain Embodiments of a Compton Scattered X-Ray Visualizer, Imager, or Information Provider; and Associated Visualization, Imaging, or Information Providing Techniques This disclosure describes a number of applications, a variety of embodiments, as well as associated techniques, pertaining to different embodiments of a Compton scattered X-ray visualizer, imager, or information provider 100 as described in block form with respect to FIG. 1. Certain embodiments of the Compton scattered X-ray visualizer, imager, or information provider 100, as described in this disclosure, can visualize, image, and/or provide information pertaining to a variety of matter of at least a portion of an individual. Certain embodiments of the Compton scattered X-ray visualizer, imager, or information provider 100 can be configured to visualize, image, or provide information pertaining to the matter of the at least the portion of the individual within at least one range of visualization, imaging, or information providing depth to at least one prescribed visualization, imaging, or information providing depth 170.

The visualization, imaging, or information providing may result in certain instances in an application of at least one applied X-ray across at least one surface (or some other location such as with embodiments embedded in matter, tissue, etc.). Such scattered X-rays can be scattered at one or more scattering event within an at least one substantially scattered depth range to at least one prescribed substantially scattered depth. Certain embodiments of the Compton scattered X-ray visualizer, imager, or information provider 100 can operate within the at least one range of visualization, imaging, or information providing depth to the at least one prescribed visualization, imaging, or information providing depth 170 within the at least one matter of the at least the portion of the individual. Certain embodiments of the Compton scattered X-ray visualizer, imager, or information provider 100 can visualize, image, and/or provide information within a region or volume extending between at least two prescribed visualization, imaging, or information providing depths 170. Each region or volume can be being spaced a range of depths or distances from a surface 168 (or location of the at least a part of the Compton scattered X-ray visualizer, imager, or information provider 100) of the at least the portion of the individual. The region or volume can be of some selected thickness, which when made thinner may approach a two-dimensional surface.

Certain of the "range of depths to a prescribed depth" as described in this disclosure are characterized either by the at least one range of visualization, imaging, or information providing depth to at least one prescribed visualization, imaging, or information providing depth, or alternately the at least one substantially scattered depth range to at least one prescribed substantially scattered depth. The at least one range of visualization, imaging, or information providing depth to at least one prescribed visualization, imaging, or information providing depth pertains to the region of the matter of the at least the portion of the individual that is undergoing visualization, imaging, or information providing. The at least one substantially scattered depth range to at least one prescribed substantially scattered depth pertains to the region of the matter of the at least portion of the individual to which the applied X-rays are being applied substantially down to the prescribed substantially scattered depth (as well as a potential variety of ranges of substantially scattered depth).

Certain X-ray photons of the applied X-rays can continue deeper into the matter of the at least the portion of the individual then the substantially scattered depth range to the prescribed substantially scattered depth and may thereupon be scattered. The visualized, imaged, or information provided regions within the at least some matter of the at least the portion of the individual can dimensionally vary considerably in different embodiments of the Compton scattered X-ray visualizer, imager, or information provider 100, as well as different individuals, or portions thereof. For instance, such range of depths of the prescribed depths can vary from an infinitesimal dimension, through a few to hundreds of microns, to a considerable amount of the distance through such individuals as humans or animals depending on configuration, type, use, or matter being imaged by the Compton scattered X-ray visualizer, imager, or information provider 100.

The quality, resolution, potential applications, and/or accuracy, of visualization, imaging, or information providing can vary, in different embodiments, varying from probes using one or more emitter portion(s) 150 and/or one or more Compton scattered X-ray receiving assembly 151. The variation of the quality, resolution, potential applications, and/or accuracy, of visualization, imaging, or information providing can continue to visualizers including one or more emitter portion(s) 150 and/or the Compton scattered X-ray receiving assembly 151 can be used to obtain some depth information about at least some matter in the at least the portion of the individual. The variation of the quality, resolution, potential applications, and/or accuracy, of visualization, imaging, or information providing can further continue to sophisticated imaging systems allowing for detailed visualization, imaging, or information providing.

Within this disclosure, including the appended claims, the terms "imaging", "visualization", "probing", and/or "information providing" can, depending context, be considered as being included within the inclusive term "visualization, imaging, or information providing". Within this disclosure, certain embodiments of the Compton scattered X-ray receiving assembly 151 could be at least partially internal to the individual, at least partially external to the individual, configured as a complete unit, and/or configured as a number of combined units at least some of which may interact together.

Certain embodiments of the one or more emitter portion(s) 150 and/or the one or more Compton scattered X-ray receiving assembly 151 can be configured as discrete units, arrays of distinct devices, or alternately as arrays of composite devices made using such processes as semiconductor processing, very large scale integration (VLSI), ultra large scale integration (ULSI), and/or other known semiconductor or other manufacturing processes. The depth visualization, imaging, or information processing associated with the one or more emitter portion(s) 150 and/or one or more Compton scattered X-ray receiving assembly 151 should be selected to be suitable for operation of the particular device(s), as well as the potential user input.

The associated visualizing, imaging, information providing, and/or processing technologies can therefore be designed, used, and/or scaled based, at least in part, on the sophistication and complexity of the Compton scattered X-ray visualizer, imager, or information provider 100 performing the visualization, imaging, or information providing. Compton scattered X-ray visualization, imaging, or information providing can be performed by a variety of either at least partially internal embodiments, and/or at least partially external embodiments. Certain embodiments of the Compton scattered X-ray visualizer, imager, or information provider 100, as described in the disclosure, can be at least partially generalized to, and generally at least partially operate according to, the disclosure as described with respect to the FIG. 1 block diagram.

For a variety of reasons, in general, certain conventional types of visualization, imaging, or information providing can perform certain activities of types of diagnosis better or worse than others. This disclosure describes a number of embodiments of the Compton scattered X-ray visualizer, imager, or information provider 100 that may each be configured for visualization, imaging, or information providing such as to detect particular illnesses, injuries, cancers, tumors, bone conditions, teeth, implants, etc. in either a devoted or multipurpose manner. The FIG. 1 embodiment of the Compton scattered X-ray visualizer, imager, or information provider 100, shown in block diagram format, can be applied to a variety of configurations as well as applications, etc.

Figure 2:
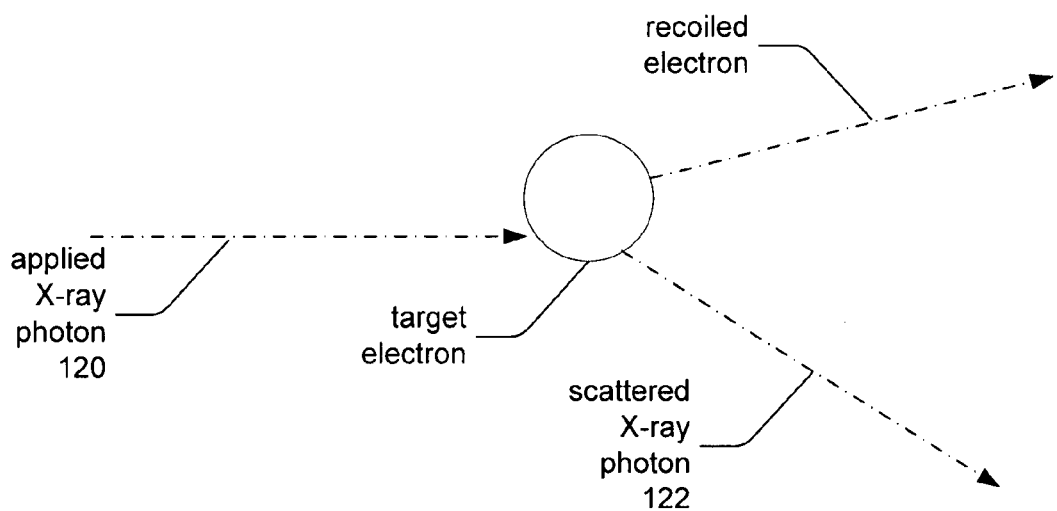
FIG. 2 is a diagram of a scattering event in which an X-ray photon is scattered, such as can be performed by certain embodiments of the Compton scattered X-ray visualizer, imager, or information provider.

FIG. 2 shows, in general, a scattering event associated with an X-ray photon of an applied X-ray 120 contacting a target electron 120 (the target electron may be included in the "matter" of the individual as described in this disclosure) to form the X-ray photon of a scattered X-ray 122. The X-ray photons of the applied X-ray 120 generally lose energy during its transition to the scattered X-ray 122, as a result of the energy transferred/used by scattering within the scattering event.

Certain embodiments of the Compton scattered X-ray visualizer, imager, or information provider 100 can thereby include, but is not limited to, the at least one emitter portion 150 as well as the at least one Compton scattered X-ray receiving assembly 151. Certain embodiments of the Compton scattered X-ray receiving assembly 151 can visualize, image, and/or provide information which can thereupon be analyzed, displayed, computed, and/or processed, etc. Certain embodiments of the at least one Compton scattered X-ray receiving assembly 151 can include, but is not limited to, at least one detector portion 152 and/or the at least one display portion 154. Certain embodiments of the Compton scattered X-ray visualizer, imager, or information provider may allow the visualization, image, or information provided to be captured and/or combined based at least partially on: deconvolution, transform (e.g., integral transform, inverse Fourier transform, inverse FFT, etc.), image subtraction, weighted subtraction, functional subtraction, weighted subtraction, functional subtraction, inverse integral transform, subtractive inverse integral transform, inverse functional transform, and subtractive inverse functional transform, or other such processes or computations. Such visualization, imaging, or information providing may occur either on a one time, multiple times, repetitive, continuous, or other similar basis, perhaps in an as-programmed, user controlled, as-desired, or other suitable manner.

Within this disclosure, deconvolution techniques can be used to limit or reduce the obscuring effect(s) of depth of matter, tissue, X-ray opaque matter, noise, etc. as applied to cloud desired images, etc. As such, deconvolution can be used to clarify the visualization(s), image(s), and/or provided information. Deconvolution techniques and technologies are well established and understood, and have been in use in certain technological areas since prior to World War II. Deconvolution is conventionally used in image processing, signal processing, and other computer-based imaging techniques. Certain embodiments of the Compton scattered X-ray visualizer, imager, or information provider 100 can utilize deconvolution, transforms, and other distortion diminishing techniques. Such distortion diminishing techniques may be used to limit distorting effects resulting at least partially from, for example: X-ray opaque matter, obscuring matter, signal noise, etc. such as to identify or visualize aircraft hidden in clouds, limit signals and/or images in noisy backgrounds, etc. Other such distortion-limiting image processing techniques may be applied, where appropriate, in a manner as would be obvious to one skilled in the art.

The "matter" of the human or animal individuals can, depending upon context include, but is not limited to: tissue, flesh, muscle, optically opaque tissue, organ(s), bone(s), bone part(s), hair, bone fragment(s), implant(s), fat, blood vessel(s), blood capillary(s), skin(s), teeth, epidermis, dermis, brain, tumors, cysts, contrast agents such as iodinated contrast agents, gadolinium, certain fluid(s), blood or blood component(s), CSF, irrigant, IV fluids, water, aqueous solutions, implant materials such as ceramic, steel, titanium, nitinol, etc. Plant and organism embodiments can include such matter (naturally occurring or man-made or applied) that can be imaged, depending on the structure and/or location being imaged as a portion of, and/or associated with, the plant or organism.

Certain embodiments of the Compton scattered X-ray visualizer, imager, or information provider 100 can achieve relatively high resolution of their depth visualizations, images, and/or information provided. As such, certain embodiments of the Compton scattered X-ray visualizer, imager, or information provider 100 can be configured such that the matter of the at least the portion of the individual can be inclusively imaged as at least a portion of the individual 82. Certain embodiments of the Compton scattered X-ray visualizer, imager, or information provider 100 can depth visualization, image, and/or provide information relating to a considerable number of distinct types of matter as compared with, for example, certain conventional X-ray techniques.

Certain embodiments of the Compton scattered X-ray visualizer, imager, or information provider 100 can thereby visualize, image, and/or provide information relating to such matter of the at least the portion of the individual as such tissue as flesh, tissue, muscle, fat, fluid (blood, lymph, spinal fluid, etc.) in a controllable and/or adjustable manner. In this manner, an initial depth visualizing, imaging, or information providing can be performed of a region, and upon locating areas of interest, the Compton scattered X-ray visualization, imaging, or information providing can be filtered, processed, analyzed, compared, transformed, adjusted, magnified, angled, etc. as described in this disclosure to visualize, image, and/or provide information relating to desired regions.

Certain embodiments of the Compton scattered X-ray visualizer, imager, or information provider 100 can be used to visualize, image, and/or provide information relating to the spine of humans or animals, such as may be the case with certain spinal surgeons. Such depth visualizing, imaging, or information providing of spine (as well as associated plates, pins, blood vessels, muscles, etc.) can be performed prior to, during, and/or following surgery; and can provide imaging, visualizing, or provide information of appropriate or desired quality depending on the desired purpose, equipment, condition, or application. Such Compton scattered X-ray visualization, imaging, or information providing following surgery can be provided at one or more suitable angles, such as to illustrate interaction with plates, pins, constructs, etc. relative to the spine, associated nerves, bones, and associated pins, constructs, etc. Those embodiments of the Compton scattered X-ray visualizer, imager, or information provider 100 that are configured to image the matter, spine, bones, tissue, implants, etc. should be configured based on the desired depth imaging, depth visualizing, and/or examination, and may be adjusted and/or controlled, perhaps on a near real time basis.

Figure 38:
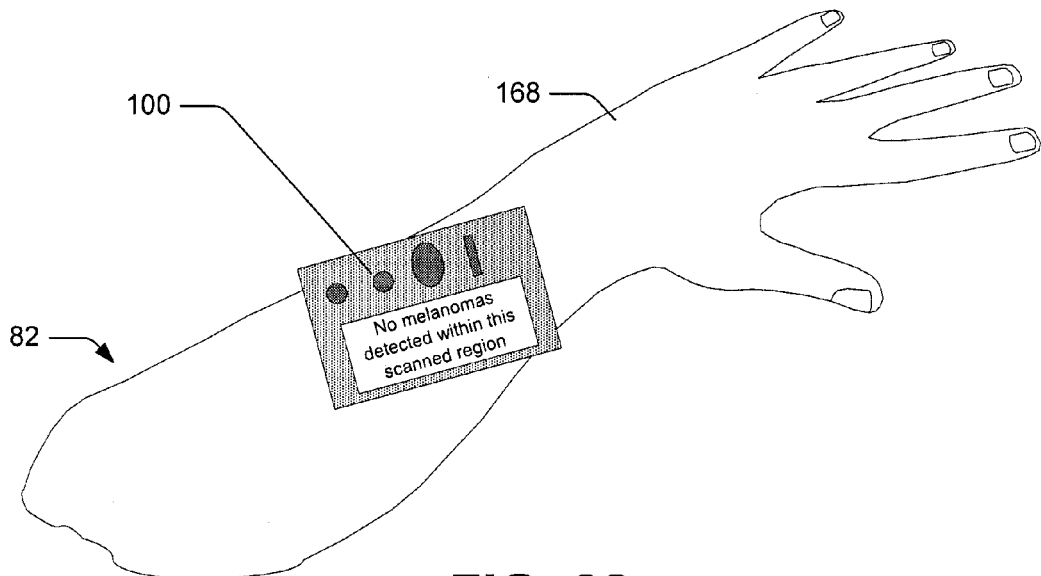
FIG. 38 shows another embodiment of the Compton scattered X-ray receiving assembly that is configured to output information.

Certain embodiments of the Compton scattered X-ray visualizer, imager, or information provider 100 as described with respect to the figures, and at other locations through this disclosure, primarily pertain to displays that can display visualizations and/or images over various embodiments of the Compton scattered X-ray receiving assembly 151. By comparison, certain embodiments of the Compton scattered X-ray visualizer, imager, or information provider 100, as described with respect to FIG. 38 and at other locations through this disclosure, primarily pertain to displays that can display information in such a form as text, data, graphs, or other processed information, or a combination or modification thereof, etc. More particularly, FIG. 38 illustrates an example of text, data, etc. being presented in other non-image or non-visualization form. The various embodiments of the Compton scattered X-ray visualizer, imager, or information provider 100, as described in this disclosure, can also include a graphical user interface, buttons, switches, or other mechanism to allow a user or individual to provide input as to the visualization, imaging, or information providing as desired, suitable, and/or designed. As such, within this disclosure, each of the terms "visualize", "image", or "provide information" is, depending on context, intended to be inclusive of each of these terms.

Certain embodiments of the Compton scattered X-ray visualizer, imager, or information provider 100 can be configured for a variety of particular applications. The user of certain embodiments of the Compton scattered X-ray visualizer, imager, or information provider 100 may select a particular aspect such as quality, refresh rate, real-time aspects, resolution, color, etc. based on the particular task at hand. For example, a doctor examining a patient's external skin may obtain one or more visualizations, images, or provided information, or may treat certain surface aberrations using certain embodiments of the Compton scattered X-ray visualizer, imager, or information provider 100. Also, a surgeon/user who is using certain embodiments of the Compton scattered X-ray visualizer, imager, or information provider 100 that may be attached, integrated, or otherwise secured to a surgical tool which can be used in such procedures as cutting, separating, ablating, deforming, processing, tactile feedback providing, adding material, removing material, or otherwise handling matter such as tissue, bone, fluid, blood, etc.

Certain embodiments of the Compton scattered X-ray visualizer, imager, or information provider 100 may be satisfied with relatively various quality depth visualizations or images that can range from very detailed or excellent images to relatively sketchy images. Detailed images, for example, can provide an excellent representation of the matter of the at least the portion of the individual. Relatively sketchy visualizations can be adequate to indicate a relative position of a desired visualized item such as a blood vessel, bone, portion, nerve, construct, etc. Certain embodiments of the Compton scattered X-ray visualizer, imager, or information provider 100 can be provided at a refresh rate sufficient rate to operate as desired, or operate a tool in combination as desired without contacting blood vessels, nerves, or other matter to be protected within the individual, for example. As such, certain embodiments of the Compton scattered X-ray visualizer, imager, or information provider 100 can be associated with a variety of tools, and can be used to assist in deforming, separating, distorting, guiding, cutting, avoiding, and other such embodiments of the tools.

Certain tools that can be associated with, or operatively coupled to, certain embodiments of the Compton scattered X-ray visualizer, imager, or information provider 100 can provide tactile feedback to a user. Such tactile feedback providing tool can be used particularly in combination with certain embodiments of the Compton scattered X-ray visualizer, imager, or information provider 100, such as to allow the user to "feel" or "touch" the various regions of the individual for treatment or examination purposes (even if only remotely while similarly observing the region). While tactile feedback mechanisms may not be shown in the figures; this is generally understood by those skilled in the robotics, automation, surgical, and other such arts or technical areas. Certain orthopedic surgeons, etc., who are interested in general positions of such particular matter as bones, organs, etc. may be satisfied with depth visualizations and/or images that have limited resolution or image quality. As such, certain embodiments of the tactile feedback provider may be considered as "tools" within certain meanings and/or certain contexts as applied within this disclosure. Additionally, certain users may select to use certain scintillator or fluoroscope embodiments of the Compton scattered X-ray visualizer, imager, or information provider 100.

A user may desire to use certain embodiments of the Compton scattered X-ray visualizer, imager, or information provider 100 to image, visualize, image, and/or provide information at a considerable depth into tissue, and/or obtain depth visualizations or images that may have a high resolution or quality. Certain visualizations or images that can be produced by certain embodiments of the Compton scattered X-ray visualizer, imager, or information provider 100 may be of similar quality of MRI, CAT Scans, PET scans, etc. Certain embodiments of the Compton scattered X-ray visualizer, imager, or information provider 100 can be performed relatively quickly as compared with conventional imaging modalities, such as in certain instances to be applied on a near-real time basis. The user may thereupon select to use certain embodiments of the Compton scattered X-ray visualizer, imager, or information provider 100 that rely upon consider image processing to achieve suitable visualization, imaging, or information providing quality, as described in this disclosure. As such, the user can select one or more suitable embodiments of the Compton scattered X-ray visualizer, imager, or information provider based, at least in part, on the particular task at hand.

Certain embodiments of the Compton scattered X-ray visualizer, imager, or information provider 100 can be applied from a variety of embodiments of mechanisms that can be configured to provide visualization, imaging, or information providing structures, including depending on context, but not limited to: platforms, tables, hand-held, endoscopes, attached to or integrated within a tool, etc. Within this disclosure, the description of the particular visualization, imaging, or information providing structure being used is intended to be illustrative in nature but not limiting in scope. As such, it is intended that a description of an embodiment of the Compton scattered X-ray visualizer, imager, or information provider 100 being applied to a particular visualization, imaging, or information providing structure may be applied to other visualization, imaging, or information providing structures, while remaining within the scope of the present disclosure, depending on context.

Certain embodiments of the Compton scattered X-ray visualizer, imager, or information provider 100 can utilize results from scattering events to determine the amount of energy loss and/or change in direction of the X-ray photons resulting from contact (or close interaction) with electrons, neutrons, protons, or other portions of atoms and/or matter. The energy level variation (almost always a loss as a result of conservation of energy principles) of the X-ray photons of the applied X-ray 120 that, upon the scattering event, becomes the scattered X-ray 122, and the scattered energy level can be used to derive the energy transfer based on Compton equations as described with respect to FIG. 2. The scattering angle of the scattered X-ray resulting from the scattering event, and position of the scattering event, can be derived based upon a combination of: a) the initial energy level and trajectory of the applied X-ray, b) the detected position of the Compton scattered X-ray receiving assembly 151, c) the scattered energy level of the scattered X-ray 122, and d) the energy loss resulting at least partially from the scattering event. The scattering angle and position of the scattering events can to be determined based at least partially on the Compton scattered X-ray equations used herein, as well as geometric equations. By compiling a large number of scattering angles and positions of scattering events by one or more of the Compton scattered X-ray receiving assembly 151, an image can be derived having a continuously improving image quality.

Compton scattered X-ray visualization, imaging, or information providing can be performed using a variety of mechanisms and involving a variety of techniques. Determination of the depth within matter of the at least the at least the portion of the individual that is being visualized, imaged, and/or information provided, can be at least partially derived involving analytical determination, computation as well as numerical calculation such as can be performed by computers and/or controllers; or alternately can involve experimentation or analysis. Certain aspects of visualization, imaging, or information providing can be based on such factors as each particular matter being visualized, imaged, or information provided, the energy level and/or frequency of the X-ray photons of the applied X-ray 120 and/or scattered X-ray 122, and/or other such factors. Certain versions of such visualization, imaging, or information providing that rely on tomography may result from generating a series or number of relatively thin slices, that by being relatively thin can enhance visualizing, imaging, or image providing consistency or homogeneity across each slice.

Consistency of the matter being visualized are imaged across the thickness can thereby improve imaging quality, especially in the direction parallel to a direction at which the visualization, imaging, or image providing be being performed (e.g., through the thickness of the visualizing, imaging, or information providing axis slice). Similarly, imaging quality may diminish in certain embodiments of the Compton scattered X-ray visualizer, imager, or information provider 100 as the matter becomes more heterogeneous across the thickness of the imaging slice. Such visualization, imaging, or information providing may be taken in a straight, curved, complex, or some other desired or suitable or desired shape.

Certain techniques similar to those that provide slices, such as used in conventional tomography imaging techniques, can also be applied to certain embodiments of the Compton scattered X-ray visualizer, imager, or information provider 100.

Certain embodiments of the slices as can be utilized during visualization, imaging, and image providing by the Compton scattered X-ray visualizer, imager, or information provider 100 can be arranged in a straight, curved, complex, or some other desired or suitable or desired shape. Combining a number of the slices, which may be considered as a three dimensional region of visualizing, imaging, or information provider having a limited thickness that can be imaged by the Compton scattered X-ray visualizer, imager, or information provider 100, can produce a thicker image of the particular matter. This disclosure initially describes a variety of techniques for such Compton scattered X-ray visualization, imaging, or information providing.

Certain embodiments of visualization, imaging, or information providing can be used to visualize, image, or provide information within the at least one visualization, imaging, or information providing depth range to the at least one prescribed visualization, imaging, or information providing depth (e.g., from a surface, or alternately spaced from the surface). The actual or maximum at least one visualization, imaging, or information providing depth range to the at least one prescribed visualization, imaging, or information providing depth being visualized, imaged, or information provided may vary between different embodiments of the Compton scattered X-ray visualizer, imager, or information provider 100, and may be based on particulars of the scattered X-ray depth visualizing, imaging, or information providing; the matter undergoing depth visualizing, imaging, or information providing; as well as the processor characteristics and operation of the visualization, imaging, or information providing controller 97. Some of the X-ray photons of the applied X-ray scatter to provide the scattering event wherein the scattered X-ray may scatter at a depth greater than the at least one substantially scattered depth range to the at least one prescribed substantially scattered depth.

Based on the energy level of the X-ray photons of the applied X-rays, the number of applied X-rays with the scattering event occurring at the range of depths greater than the at least one substantially scattered depth range to the at least one prescribed substantially scattered depth can, for certain visualization, imaging, or image providing, can be assumed to be ignored either computationally, be effectively filtered out, limited by weighting techniques, or removed using image processing techniques; or even accepted. Certain visualizations, images, or provided information can be provided even by ignoring a limited percentage of deeper scattered X-rays. Certain embodiments of the Compton scattered X-ray visualizer, imager, or information provider 100 can be configured to limit the effects of the X-ray photons of the Compton scattered X-rays 120 that are returning from the scattering event occurring through greater depths than the at least one substantially scatted depth range to the at least one prescribed substantially scattered depth 170. Additionally, certain of the depth visualizing, imaging, or information providing effects of these X-ray photons of the Compton scattered X-rays 120, that scatter at the range of scattering depths greater than the at least one substantially scattered depth range to the at least one prescribed substantially scattered depth, can be included with at least some of the distorting effects either ignored, filtered, and/or otherwise limited using image processing techniques, deconvolution, and other techniques.

Another embodiment of Compton scattered X-ray visualization, imaging, or information providing can control or adjust the depth visualizing, imaging, or information providing at least partially by increasing, such as by ramping up, the energy of the photons of the applied X-rays. By changing the energy level or frequency of the X-ray photons of the applied X-ray 120, the effective range of visualizing, imaging, or information providing depth to the prescribed visualizing, imaging, or information providing depth into the matter of the at least the portion of the individual can change. As such, the energy level and/or frequency of at least some of the X-ray photons of the applied X-rays that are being used to visualize, image, and/or provide information can be tuned as to effect variation in depth of the Compton scattered X-ray visualization, imaging, or information providing.

Within this disclosure, the term "individual" can, depending on context, pertain to a person, animal, plant, organism, of whom at least a portion thereof is being imaged and/or examined by the Compton scattered X-ray visualizer, imager, or information provider 100. The term "user" can, depending on context, pertain to those persons using and/or operating certain embodiments of the Compton scattered X-ray visualizer, imager, or information provider 100, such as, but not limited to: doctors, physicians, dentists, veterinarians, researchers, assistants, technicians, researchers, persons performing medical forensics and/or autopsies, users, and/or other persons, assistants to, derivatives from, etc. who can view or utilize the visualized, imaged, or information provided portion of the individual using certain embodiments of the Compton scattered X-ray visualizer, imager, or information provider 100.

Within this disclosure, the term "user" can also include, in addition to the human users as described above: computers, automated systems, controllers, robotic devices, other devices etc. that can be used to automate visualization, imaging, providing information, inspection, or analyzing of certain depth image information as output by certain embodiments of the Compton scattered X-ray visualizer, imager, or information provider 100. Consider, for example, that certain depth image information can be more readily utilized or processed by computers based on computer-vision, machine based imaging, machine vision, machine-based devices, etc. to determine certain aspects thereof. For example, certain computer-based embodiments of the Compton scattered X-ray visualizer, imager, or information provider 100 that are being associated with surgical tools might be adapted to quantitatively determine or interpret the relative depth of certain blood vessels, nerves, etc. Such visualization, imaging, or information providing may be effective in the vicinity of non-homogenous matter, for certain embodiments.

Certain computer-based or machine based embodiments of the Compton scattered X-ray visualizer, imager, or information provider may prove quite effective at visualizing, imaging, information providing, or otherwise analyzing through particular X-ray opaque matter (perhaps at least partially relying on deconvolution, transforms, or other such techniques to limit the obscuring effects). Such techniques may accomplish such tasks as determining depths of cancer, tumors, bones, or other matter within the individual, and may thereby limit, reduce, or double-check the human scanning over large regions of the individual has be performed. Certain computer based embodiments, (or even human-vision embodiments) of the Compton scattered X-ray visualizer, imager, or information provider 100 can be configured in home-test form, emergency form, task-specific form, relatively low power form, or even in a form that can be used without the assistance of a skilled user. As such, within this disclosure, in certain instances, particularly with certain simplified or devoted embodiments of the Compton scattered X-ray visualizer, imager, or information provider 100, the term "user" can also include the individual, the individual's family or friend's thereof, and/or care providers for the individual who can assist in operating certain embodiments of the Compton scattered X-ray visualizer, imager, or information provider for the individual. Certain such home-test embodiments of the Compton scattered X-ray visualizer, imager, or information provider might preferably be used for one, or a few, devoted purposes such as, but not limited to: mammograms, cancer or tumor screening, blood flow, tissue aberrations, possible bone break or tissue tear, etc., as described in this disclosure.

Certain computer vision based embodiments of the Compton scattered X-ray visualizer, imager, or information provider 100 can be configured to model certain matter aberrations within the at least the portion of the individual perhaps using, or without, deconvolution, transform, or other such techniques. Certain computer vision based embodiments of the Compton scattered X-ray visualizer, imager, or information provider may prove superior to certain human-vision embodiments in determining extent, dimensions, degrees, etc. of certain aberrations, such as melanomas, tumors, cancers, bone growth, etc., the scattered X-rays by using mapping techniques such as are commonly used in tomography, MRI, and other conventional imaging techniques.

Within this disclosure, Compton scattered X-ray visualization, imaging, or information providing can, depending on context, pertain to depth visualizing, imaging, or information providing of a volume of matter that can have an arbitrary thickness depending on the desired visualization, imaging, or information providing application, but may be considered to be three dimensional. The three dimensional volume (having some thickness) being visualized, imaged, or information provided can be at least partially separated from an internal or external surface such as external skin or membrane, internal lumen, etc. Certain embodiments of the Compton scattered X-ray visualizer, imager, or information provider 100 can be positioned at regions adjacent the surface 168 to provide some location that can be used to relatively position to visualize, image, and/or provide information relating to portions of the individual. The surface 168 of the individual can provide some location at which certain embodiments of the Compton scattered X-ray visualizer, imager, or information provider 100 can be positioned, angled, moved, or otherwise displaced to enhance the visualization, imaging, or information providing. As such, in certain instances, proximate or adjacent the surface can provide a good location from which to visualize, image, or provide information.

As described with respect to FIG. 1, as well as at other locations in this disclosure, certain embodiments of the Compton scattered X-ray visualizer, imager, or information provider 100 can include, but are not limited to, at least one emitter portion 150 and/or at least one Compton scattered X-ray receiving assembly 151. Certain embodiments of the at least one emitter portion 150 can be configured to emit or direct at least some applied X-rays 120 toward the at least the portion of the individual 82. Certain embodiments of the at least one emitter portion 150 can be adjustable and/or controllable such as to be able to respectively control and/or adjust generation and/or direction of the applied X-rays being applied to the at least some matter of the at least the portion of the individual. At least some of the applied X-rays are thereupon scattered within the scattering event to form the scattered X-rays, which can thereupon be received by the at least one Compton scattered X-ray receiving assembly 151. Certain embodiments of the at least one emitter portion 150 can be used to adjust or control the at least one visualizing, imaging, or information providing within the at least one visualization, imaging, or information providing depth range to the at least one prescribed visualization, imaging, or information providing depth of certain embodiments of the Compton scattered X-ray visualizer, imager, or information provider 100. Within this disclosure, the applied X-ray 120 or the scattered X-ray 122 can include (e.g., comprise) a number of X-ray photons whose characteristic energy level and/or frequency can dictate the characteristics of the X-ray beams.

Certain embodiments of the Compton scattered X-ray receiving assembly 151 can be configured to detect at least some Compton scattered X-rays 122 being Compton scattered from the at least the portion of the individual 82. Certain embodiments of the Compton scattered X-ray receiving assembly 151 can operate based, at least in part, by receiving scattered X-rays 122 from a first Compton scattered X-ray visualizer, imager, or information provider 100 scattered of scattering of events from applied X-rays 120 that were generated by a different Compton scattered X-ray visualizer, imager, or information provider 100. Certain embodiments of the Compton scattered X-ray receiving assembly 151 are controllable and/or adjustable such as to be able to respectively control and/or adjust the characteristics of the at least some Compton scattered X-rays 122 that can be detected. Certain embodiments of the at least one Compton scattered X-ray receiving assembly 151 can include, but is not limited to, each, or any combination of the at least one detector portion 152 and/or the at least one display portion 154.

The operation of certain embodiments of emitter portion 150 and/or the Compton scattered X-ray receiving assembly 151 may be at least partially controlled or adjusted utilizing at least partially by the visualization, imaging, or information providing controller 97, as described in this disclosure (although certain embodiments utilize relatively little or no control and/or adjustment). Certain embodiments of the Compton scattered X-ray receiving assembly 151 can visualize, image, and/or provide information relating to the at least the portion of the individual 82 based, at least in part, on detecting the Compton scattered X-rays 122 Compton scattered from the at least the portion of the individual. The structure and operation of certain illustrative, but non-limiting, embodiments of each of the respective at least one emitter portion elements 150, at least one Compton scattered X-ray receiving assembly 151, at least one detector portion elements 152, and/or at least one display portion elements 154 are described in considerable detail in this disclosure, including the specification, claims, and/or figures.

The potential variety of visualization, imaging, or information providing, as described in this disclosure, can indicate the variety of potential embodiments of the Compton scattered X-ray visualizer, imager, or information provider 100 which can vary in complexity from relatively simple probes to relatively complex systems. More complex systems can include arrays of a considerable number of the emitter portion(s) 150 and/or a considerable number of the scattered X-ray receiving assemblies 151. The different embodiments of the Compton scattered X-ray visualizer, imager, or information provider 100 can be arranged in a variety of suitable configurations. Certain embodiments of the scattered X-ray receiving assemblies 151 can be used to determine a location of scattering events based at least partially on the applied X-ray energy level, position, and trajectory of the applied X-ray 120, as well as the scattered X-ray location and energy level of the scattered X-ray 122. Certain embodiments of the Compton scattered X-ray visualizer, imager, or information provider 100 can, depending on context, be fabricated using a range of devices, systems, or fabrication techniques ranging from distinct components to semiconductor processing, and may involve suitable image processing, hardware, and/or software, etc. to perform suitable image deconvolution, transforms, filtering, modulation, etc.

Certain embodiments of the Compton scattered X-ray visualizer, imager, or information provider 100 are configured to operate in association with at least one tool portion relative to, for example, at least some matter of the at least the portion of the individual. The particular component and/or configuration selected may depend, at least in part, on the application of the Compton scattered X-ray visualizer, imager, or information provider 100 and/or the associated tool. For instance, certain embodiments of the Compton scattered X-ray visualizer, imager, or information provider 100 can be associated with a particular tool, including but not limited to: a cutting tool, a scalpel, a gamma knife, a laser cutter, a tactile feedback provider, an ablator, a scope, a Bovie electrocautery device, a material adding tool, a material removing tool, etc. such as to allow a user to search, image, or visualize within a particular region for a specific component, chemical, etc. as a tool-based process is being performed. Such imaging, visualization, or information providing may be used relative to the location of blood vessels, cancer, tumors, organs, etc. Alternately, certain embodiments of the Compton scattered X-ray visualizer, imager, or information provider 100 can be configured to detect, visualize, image, and/or provide information relative to an area of potential interest, such as a field of surgical operation, within the at least the portion of the individual in which at least the at least the portion of the individual.

Figure 3:
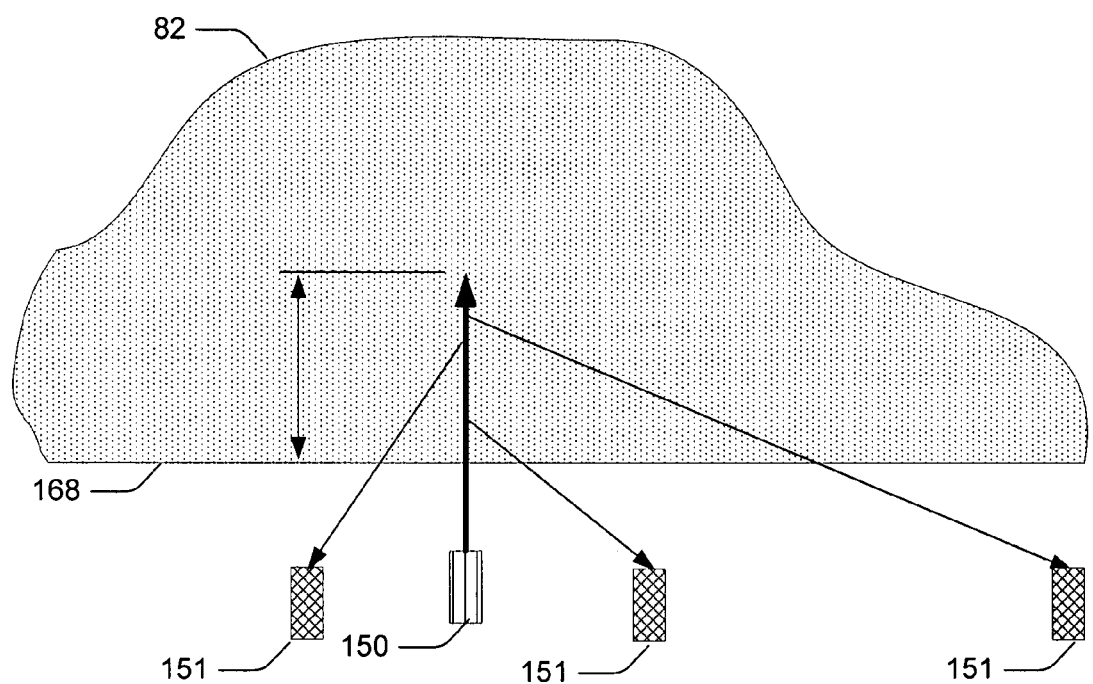
FIG. 3 is a diagram of an embodiment of the Compton scattered X-ray visualizer, imager, or information provider.

FIG. 3 illustrates an embodiment of the Compton scattered X-ray visualizer, imager, or information provider 100 being configured to have one or a few emitter portion(s) 150, as well as one or a few scattered X-ray receiving assemblies 151. Certain embodiments of the Compton scattered X-ray receiving assembly 151 may utilize suitable X-ray detection such as depth subtraction or combination, time of flight, and/or scintillator (and/or fluoroscope) aspects, as described in this disclosure. Certain embodiments of the Compton scattered X-ray visualizer, imager, or information provider 100 can operate, by at least one of the emitter portion(s) 150 emitting the X-ray photons of the applied X-rays 120. Certain embodiments of the Compton scattered X-ray visualizer, imager, or information provider 100 can operate along a specific direction or prescribed depth into the at least some matter of the at least the portion of the individual that can scatter upon the scattering events within the matter of the at least the portion of the individual. Certain scintillator or other embodiments of the Compton scattered X-ray visualizer, imager, or information provider 100 can utilize convolution or deconvolution, one or more transforms and/or inverse transforms, and/or other techniques to increase imaging quality of visualizing, imaging, or information providing, etc. through X-ray opaque or other matter. Certain embodiments of the Compton scattered X-ray visualizer, imager, or information provider 100 can provide an image deconvolution operation that can clarify between scattered X-rays returning to the Compton scattered X-ray receiving assembly 151 from a number of separated, but closely aligned, scattering events.

A number of X-ray photons can be expected to scatter within the at least one substantially scattered depth range to the at least one prescribed substantially scattered depth at least partially from the scattered X-ray. The particulars of the at least one substantially scattered depth range to the at least one prescribed substantially scattered depth will correspond, at least in part, on the energy level of the X-ray photons (which corresponds to the frequency of the X-ray photons of the applied X-rays 120). It might be desirable to simplify at least certain of the embodiments or applications of the Compton scattered X-ray visualizer, imager, or information provider 100. Simplification might be for such purposes as to reduce expenses, simplifying image processing or system computations, focusing on depth visualizing a single or a few aberrations, such as melanomas, tumors, cancers, tissue edges, blood pools, blood vessels, liquids, organ edges, tissue matter change delineations, etc.

Certain of such embodiments of the Compton scattered X-ray visualizer, imager, or information provider 100 can be configured to image a particular material, element, chemical, fluid, fluid flow, solid, or other detectable aspect. For instance, certain of these embodiments of the Compton scattered X-ray visualizer, imager, or information provider 100 can be attached to a probe, tool, cutter, tactile feedback provider, laser device, Bovie electrocautery, separator, visualizer, imager, etc.

Certain tool-based embodiments of the Compton scattered X-ray visualizer, imager, or information provider 100 could be placed on the end of a probe that is inserted into the body. For example, as a probe or other tool passes through tissue (e.g., brain, heart, or other organ or even flesh, muscle, etc.) an alarm that could be audio, video, or other can be set off which notifies the user that the probe is coming into close proximity to a blood vessel or other sensitive location. Another example is this could be part of a drill (e.g., such as could be used to penetrate the pedicle of the spine or by a dentist), such as it could notify the user if the drill tip is coming into too close proximity to adjacent vital structures such as a nerve root, spinal canal, or artery. Still another example is that this is attached to an electrocautery instrument that will terminate current flow when the instrument is passing too close to defined danger zones such as blood vessel, nerve, vital organ structure, etc.

Certain surgeons operating in a manner to avoid blood vessels, nerves, etc. (while often necessary to keep their patient healthy and/or alive) can be slow and/or laborious in certain circumstances, and can considerably extend the duration of operations. The presence of blood vessels, nerves, etc. in locations where surgeons may not clearly see via their tools due to a skewering matter, tissue, bones, etc., can also result in additional risks to the patients (e.g., individuals). Surgeons attempting to operate too quickly can risk the likelihood of injury, or even death, to their patients by contacting, severing, or rupturing their blood vessels, nerves, brain tissue, or other organ and/or matter. Allowing a surgeon to detect blood vessels, nerves, spinal portions, sensitive tissue, etc. can be utilized in an attempt to operate in, or negotiate around, a sensitive matter or region without contacting the sensitive matter or region by, for example, visualizing, imaging, providing information, the sensitive matter or region. Such allowing surgeons to effectively determine relative locations of tools, etc. to sensitive matter or regions could therefore be expected to increase the rate at which surgeons might safely be able to operate while safely negotiating past the sensitive matters or regions within the individual, as well as increasing the rate at which they can safely and accurately operate.

If more than one emitter portion 150 are operating, then there should be some mechanism to limit confusion between the applied X-rays provided by each emitter portion as detected by certain embodiments of the Compton scattered X-ray receiving assembly 151. Such differentiation or combination of scattered X-rays at each Compton scattered X-ray receiving assembly 151 between the applied X-rays 120 being generated by each of the emitter portions 151 can rely on, for example: altering the transmission time, coding of the carrier signal, differentiating signal weightings, shifting frequency of the applied X-rays 120 between the different ones of the applied X-rays, altering the energy levels of the photons altering the pulse durations of the applied X-rays, etc. as described in this disclosure. Otherwise differentiating each of the applied X-rays 120, and/or the directing at least certain ones of the applied X-rays 120 in a different direction along non-interfering directions and sets of potential scattering events, such that the scattered X-rays returning from different scattering events can be distinguished from each other each other. Such techniques similar to deconvolution, inverse transforms, time division multiplexing, frequency division multiplexing, code division multiplexing, etc. (which are known to those skilled in the communications arts) can be utilized to distinguish between, or clarify, different applied X-rays being received by different emitter portion this 150, and thereby limit interference at the at least one Compton scattered X-ray receiving assembly 151 between multiple ones of the scattered X-rays scattered from different scattering events.

Figure 4:
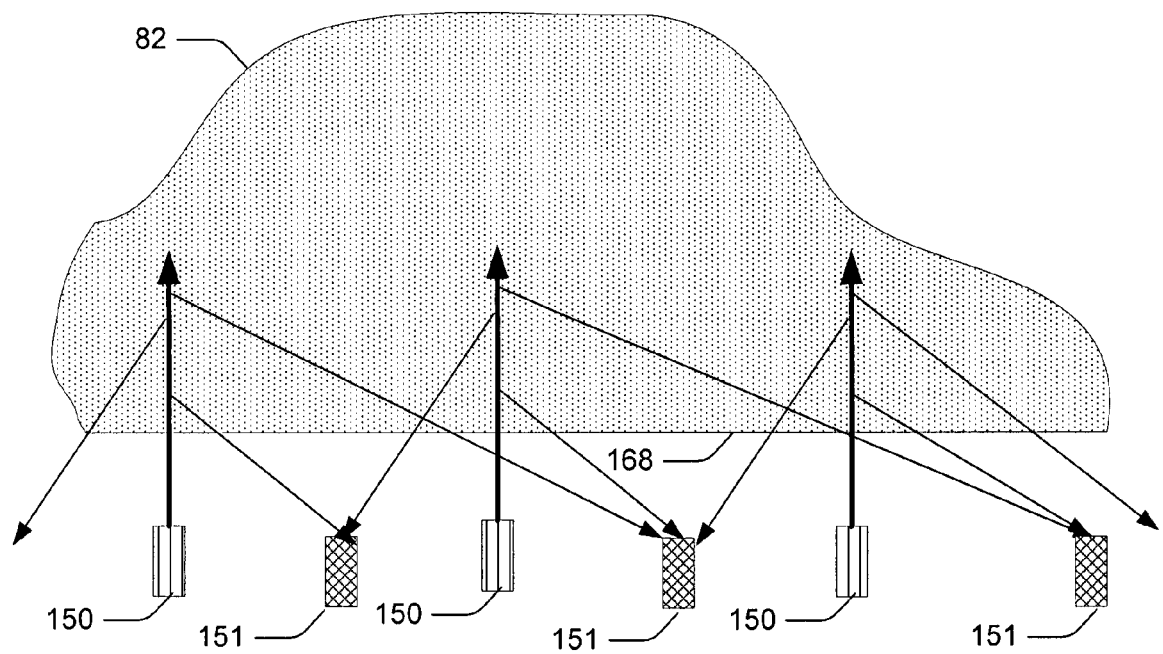
FIG. 4 is a diagram of another embodiment of the Compton scattered X-ray visualizer, imager, or information provider.

FIG. 4 illustrates another embodiment of the Compton scattered X-ray visualizer, imager, or information provider 100 that can be configured with one or more of the emitter portions 150, as well as one or more Compton scattered X-ray receiving assemblies 151 (similar to as described with regards to FIG. 3 to that illustrates only one emitter portion). Multiple ones of the emitter portion 150 may, or may not be, arranged in a desirable associated relative configuration, such as at least one array, conforming to the matter, etc. Certain embodiments of the emitter portions 150 can be configured to emit the applied X-rays 120 (as well as the scattered X-rays 122) in a manner that can be differentiated from other ones (as well as other scattered X-rays 122) based at least partially on deconvolution, transforms, time multiplexing, frequency multiplexing, code division multiplexing, directing of a variety of X-ray beams such as pencil beams, fan beams, etc. to a desired location, and/or other such scattering event differentiating techniques, use of collimators, lenses, filters, etc. For example, certain embodiments of the multiple emitter portions 150 can emit their applied X-ray at different deconvolution or transform characteristics at different times, having different frequencies, with different weightings, or based on different coding algorithms such as is generally understood with a variety of multiplexing techniques. Certain such embodiments of the Compton scattered X-ray visualizer, imager, or information provider 100 may be utilized as a visualizer having limited resolution; and may provide especially useful in conjunction with a tool as to provide visualization, imaging, or information providing for blood vessels, cancer, or other aberrations to visualization, imaging, or information providing as described in this disclosure.

Certain embodiments of the one or more Compton scattered X-ray receiving assemblies 151 can include a streak camera, a pixellated streak camera, an avalanche detector, a CCD device, or other device that can detect the presence, energy level, and/or condition of scattered X-rays, preferably at a suitable rate to provide the desired resolution. Certain embodiments of the streak camera and/or the pixellated streak camera might be configured to act quite quickly, and certain ones can function in the low or fractional picosecond range, such as may be particularly useful for time of flight calculations.

Certain embodiments of Compton scattered X-ray visualizer, imager, or information provider 100 can include one or more collimated (e.g., "pencil", "fan", or other) beam of the applied X-rays 120, as illustrated in FIGS. 3 and 4. Certain embodiments of these beams can scan the at least the portion of the individual in two directions while the one or more scattered X-ray receiving assemblies 151 can measure the Compton scattered X-rays resulting from the interactions of the primary X-rays with the bodily tissues. A variety of depth visualizing and/or imaging information, particular to a given 3-D voxel within the display of the one or more scattered X-ray receiving assemblies 151, can be derived using the two-dimensionally scanned X-ray beams, which can be detected in several ways as described herein.

Certain embodiments of the Compton scattered X-ray visualizer, imager, or information provider 100 can utilize time-resolved detection of the scattered X-rays 122. Here, the time-of-return, Δt, of each scattered X-ray from a scattering event corresponding uniquely to a position, x, along the illuminating collimated X-ray beam, such that:

$$x = A^* \Delta t + B \qquad (1)$$

where A and B are proportionality constants determined by the relative location of the illuminating X-ray beam and the X-ray detector. There can be a sufficient temporal pause (or other time, spatial, or coding technique understood by those skilled in multiplexing) between illumination at specific 2-D ray angles to limit scattered signal confusion between multiple ones of the scattered X-ray is received at each Compton scattered X-ray receiving assembly 151. If determined to be significant, the background from multiple scattered X-rays can be reduced by adding energy discrimination to the detector, since each scattering event results in a reduction in X-ray photon energy levels. For example, energy is lost by the moving X-ray photon particle during collisions with other moving particles forming the matter of the at least the portion of the individual, that can be described based on Newton's equation, Compton's equation, as well as other geometric or other equations, as described in this disclosure or elsewhere but generally known.

By scanning the body repeatedly in one, two, or three orthogonal directions, but at varying energies so that the radiation penetrates progressively more or less deeply so scattering events can occur up to a progressively respectively deeper, or shallower, prescribed depth. Thereupon, a model (which may be three or two dimensional) of the subcutaneous bodily structures can be progressively refined by comparing it to the time-integrated backscattered X-ray return from each illuminating beam angle and then performing a de-convolution similar to those used in tomography imaging. In addition to helping provide depth discrimination, such progressive illumination at different energies can reveal differences in the absorption and/or scattering characteristics of various scattering events occurring in particular matter. The value of the scattering characteristics of a scattering event can be an enhanced or diminished, in certain instances, by adding contrast agent, etc., such as to increase the contrast of the resulting image. In certain instances, the energy level of the applied X-ray can be increased, decreased, ramped, and/or otherwise altered (preferably in a gradual and/or predictable manner as described elsewhere in this disclosure, such that changes in the energy level will have little effect on imaging distortion) such as to allow adjustability or control of the visualizing, imaging, or information providing by certain embodiments of the Compton scattered X-ray visualizer, imager, or information provider 100.

Certain embodiments of the Compton scattered X-ray visualizer, imager, or information provider 100 can be configured to operate in some controlled combination of the techniques as described in this disclosure.

Certain embodiments of the Compton scattered X-ray visualizer, imager, or information provider 100 can therefore be configured to visualize, image, and/or provide information at least partially by employing a nearly monochromatic illuminating X-ray "pencil" beam, flooding beam, fan-beam, scanning beam, or other such emitter portion 150. The location of the scattering events along one or more of the beam of the applied X-ray (in which, in certain instances, multiple ones thereof can be intersected to increase the intensity) can be determined where the X-ray photon of the scattering X-ray scatters based on the unique relation between the change in its wavelength, $\Delta\lambda$, and its scattering angle, $\theta$. For the usual case of the scattering events for each once-scattered X-ray photon, the change in wavelength of the X-ray photon upon scattering is given by the Compton formula:

$$\Delta\lambda = h(1-\cos\theta)/mc \qquad (2)$$

where h is Planck's constant, m, the mass of the electron, and c, the speed of light.

If necessary, time resolution, directional resolution, deconvolution, or other such image combination techniques can be added to at least certain of the approaches, as described in this disclosure, to assist in suppressing background noise or other distorted affects from scattered X-rays emanating from scattering events. Such image combination techniques can include, but are not limited to, image subtraction, image differentiation, image transformation, deconvolution, weighted subtraction, functional subtraction, and group including inverse integral transform, subtractive inverse integral transform, inverse functional transform, and subtractive inverse functional transform, or other image processing techniques.

Figure 5:
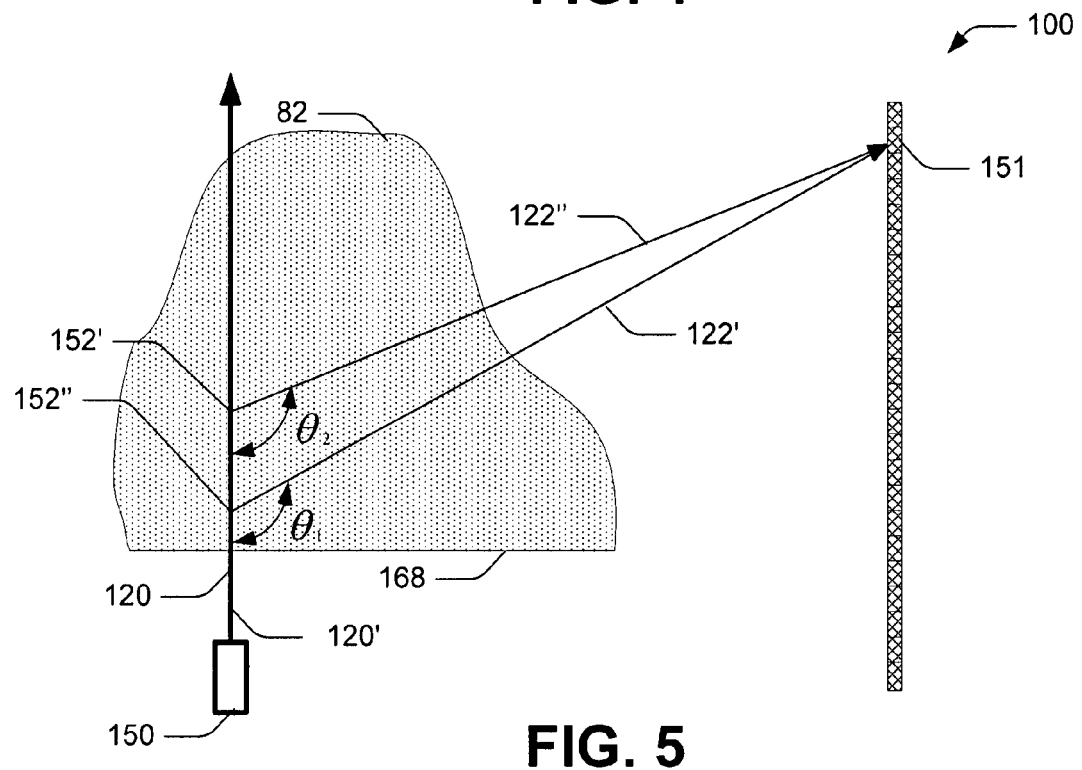
FIG. 5 is a diagram of yet another embodiment of the Compton scattered X-ray visualizer, imager, or information provider.

A number of other embodiments of the Compton scattered X-ray visualizer, imager, or information provider 100 are described, which can be configured to determine the location of scattering at least partially based on some characteristics of the scattered X-rays being received at the Compton scattered X-ray receiving assembly 151. FIG. 5 illustrates an embodiment of the Compton scattered X-ray visualizer, imager, or information provider 100 that are configured with one or more of the emitter portions 150, and/or one or more of the scattered X-ray receiving assemblies 151. Consider that certain embodiments of the Compton scattered X-ray receiving assemblies 151 can be configured with one or more of the emitter portions 150, as well as one or more scattered Compton scattered X-ray receiving assemblies 151. The one or more emitter portion 150, as described with respect to FIG. 5, can be configured as a pencil beam emitter, a fan emitter, or other emitter that can controllably direct the applied X-rays 120 as desired or designed in a particular path or direction and/or we associated X-ray photons having a particular energy level. For example, if there are a number of the one or more emitter portion(s) 150, then each one may be configured or designed to emit the X-rays along a controllable direction, time, angle, depth, etc. such as to not interfere with others.

Certain embodiments of the Compton scattered X-ray visualizer, imager, or information provider 100 can be configured and/or designed such that the applied X-ray 120 of FIG. 5 can be directed along an emitted X-ray path 120', that extends substantially continuously in a prescribed direction. While FIG. 5 illustrates the applied X-ray 120 being substantially perpendicular across the surface into the matter of the at least the portion of the individual, some other angle can be provided with the surface as well, and still comply with Compton equations as described with respect to FIG. 2. At least one Compton scattered X-ray receiving assembly 151 (illustrated in FIG. 5 as an array of receiving assemblies) is situated at an angle relative to the applied X-ray 120, and can thereby be configured to receive a variety of scattered X-rays 122', 122", etc. that have been scattered at a variety of illustrative locations 152', 152", etc. that have been scattered from a scattering event situated along the path of the applied X-ray 120. The location of each scattering events 152', 152" can be situated along the path of the applied X-ray 120, can be determined based, at least in part, on scattering angle, $\theta_1$ and $\theta_2$, etc., the X-ray photons of the scattered X-ray can exhibit at different energy level (corresponding to different X-ray photon frequency). For example, the greater the scattering angle $\theta$ (such as $\theta_1$ and $\theta_2$ in FIG. 5), the greater the associated energy loss. As such, based on the energy level of the X-ray photon within the scattered X-ray 122, the scattering angle $\theta$ (such as $\theta_1$ and $\theta_2$ in FIG. 5), as well as the scattering events location 152', 152", can be derived utilizing equation 2, as described above. Various embodiments of various computations, certain ones as described in this disclosure, can be used to locate the position of the scattering events 152', 152", etc., can be derived based at least in part on deconvolution, transforms, etc. to provide geometric visualization, imaging, or information providing techniques, etc. a number of one, two, or three-dimensional arrays of the Compton scattered X-ray receiving assembly 151 can be arranged to about the applied X-ray 120, in a manner to enhance the determination of the position of the scattering events 152', 152". Such determination can be based at least in part on the location of the multiple received arrays of the Compton scattered X-ray receiving assembly 151.

The FIG. 5 embodiment of the Compton scattered X-ray receiving assembly 151 can be used to derive at least one position of the scattering event 152 in which X-ray photons of the applied X-ray 120 is scattered such as by contact, or traveling close to: atoms, electrons, neutrons, or other such matter. The embodiment of the emitter portion 150 as described with respect to FIG. 6 can be similar, or identical, to those embodiments as described with respect to FIGS. 1 to 9, as well as other locations in this disclosure. Certain embodiments of the Compton scattered X-ray receiving assembly 151, as described with respect to FIG. 6, can include a slit collimator 172 or other such device that can limit the angle at which scattered X-rays can reach the Compton scattered X-ray receiving assembly 151. Certain embodiments of the collimator can also be configured as a lens, filter, correlator, or other device that can be used to limit passage of the scattered X-rays to the Compton scattered X-ray receiving assembly 151 to only within a range of degrees, etc. Certain embodiments of the slit collimator, lens, filter, etc. could be provided between the path of the applied X-ray 120' and the Compton scattered X-ray receiving assembly 151. Those scattered X-rays being applied from the position of the scattering event of the Compton scattered X-ray receiving assembly 151 will only be detected if flowing in a direction substantially aligned with the slits of the slit collimator. The structure and use of slit collimators, lenses, filters, etc. are generally understood by those skilled in the optics, X-ray, electromagnetics, and other similar areas; and will not be further described in this disclosure. Alternate types of collimators, lenses, filters, etc. that can limit the passage of the scattered X-rays to those within an angular range such as to detect scattering events within that angular range may also be utilized.

Figure 6:
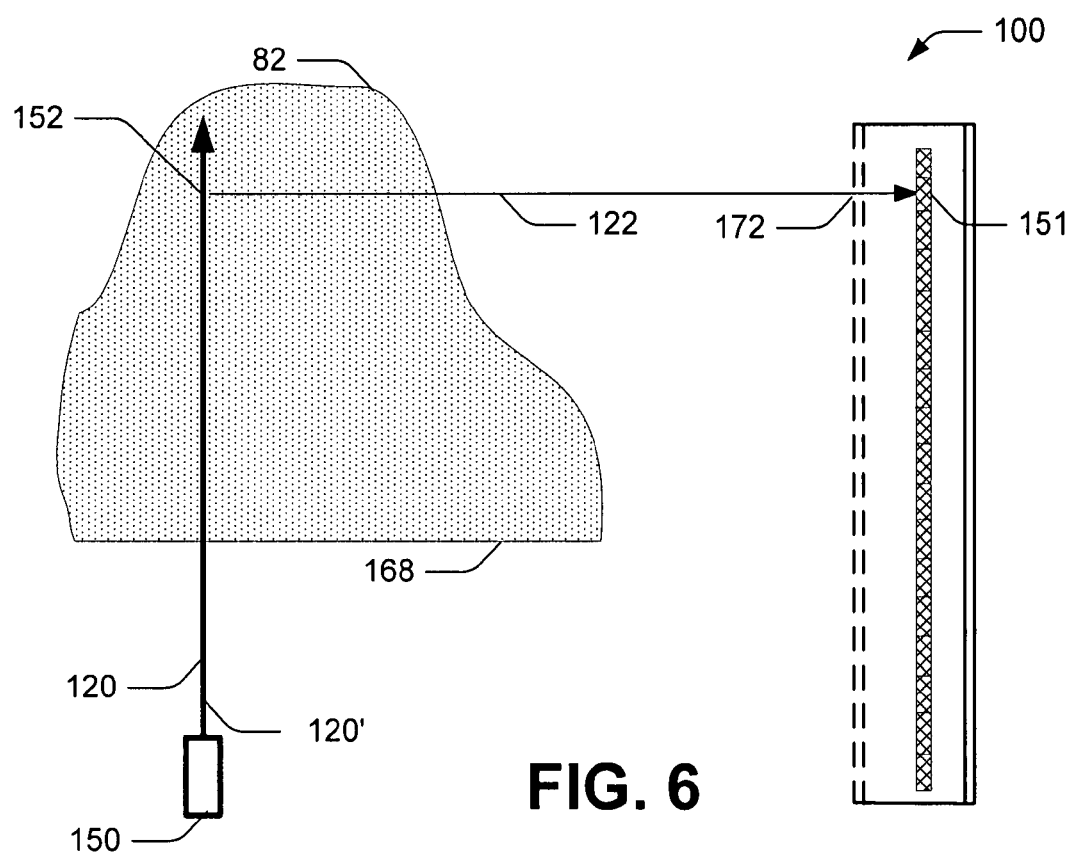
FIG. 6 is a diagram of another embodiment of the Compton scattered X-ray visualizer, imager, or information provider including a collimator.

Only one slit is shown in the slit collimator 172 as illustrated in FIG. 6. One or more of the slits of the slit collimator 172 can be arranged, such as to be aligned with only a particular element of the Compton scattered X-ray receiving assembly 151. While a single slit collimator is described with respect to FIG. 6, it is to be understood that multiple slit collimators can be respectively associated with at least one unit of the Compton scattered X-ray receiving assembly 151. In addition, utilizing one or more of a variety of technologies that are generally understood, the scattered X-rays can be steered, beam formed, or otherwise directed in a manner as desired or appropriate. By using the embodiment of the Compton scattered X-ray receiving assembly 151 as described with respect to FIG. 6, location of one or more scattering events occurring along one more applied X-rays 120 can be determined.

Figure 7:
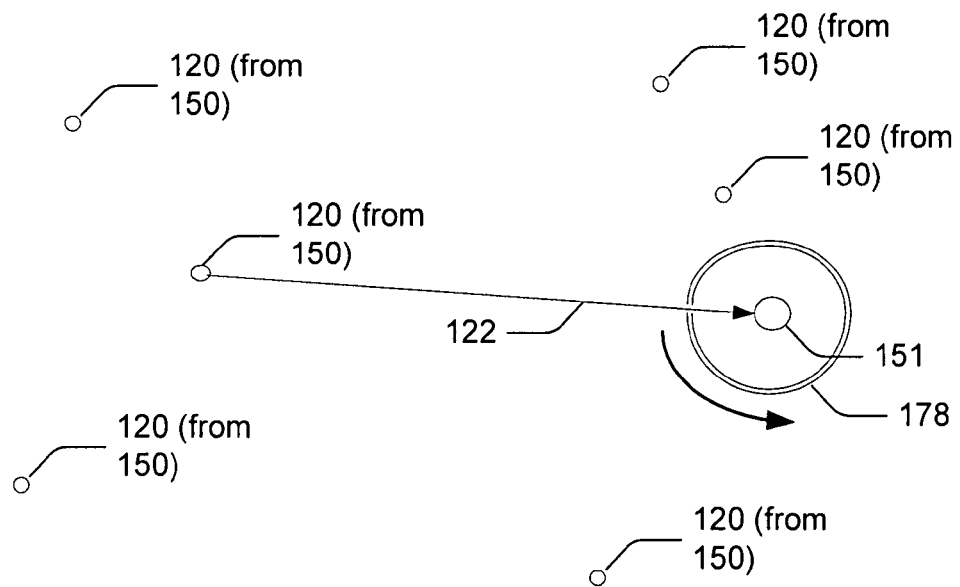
FIG. 7 is a diagram of another embodiment of the Compton scattered X-ray visualizer, imager, or information provider including a scanning shield portion.

Certain embodiments of the Compton scattered X-ray visualizer, imager, or information provider 100, as described with respect to FIG. 7, can be configured such that the Compton scattered X-ray receiving assembly 151 can be steered or directed in a plane perpendicular to that of the which the Compton scattered X-ray receiving assembly can sense the position of the scattering event. For example, the paths of the applied X-rays 120 as shown in FIG. 2 are extending in a direction substantially perpendicular to the paper, while in FIGS. 1, 3-6, etc. the path of the applied X-ray 120 extend substantially within the plane of the paper. Certain ones of the scattering event detection, imaging, visualizing, and/or information providing mechanisms, as described above, may utilize such exemplary mechanisms to determine the position of the scattering event as: subtraction or combination, deconvolution, transforms, time of flight, scattering angle, loss of energy level of the X-ray photons of the scattering X-rays, geometric scattering computation, collimator, other derivatives, etc., and other locations through this disclosure. Each Compton scattered X-ray receiving assembly 151 as described with respect to FIG. 7 includes a scanning shield portion 178, which can be configured to limit light passing to that within certain angular ranges. More specifically, provided that there are an array, or a number of, the applied X-rays 120, then the scanning shield portion 178 can limit passage of only one or a number of applied X-rays 120 at any one time period. Certain embodiments of the scanning shield portion 178 and/or the emitter portion(s) 150 can be dynamic, such as being rotatable; or alternately limit passage of only one or certain applied X-rays 120 continuously if the scanning shield portion 178 and the emitter portion(s) 150 are fixed or static.

As such, certain embodiments of the at least one slit collimator 172, as described with respect to FIG. 6, can be viewed as limiting scattered X-rays 122 scattered from the applied X-ray 120, and passing to the Compton scattered X-ray receiving assembly 151 in a directional substantially parallel to an axial direction of the applied X-ray 120. By comparison, certain embodiments of the scanning shield portion 178, as described with respect to FIG. 7, can be viewed as limiting scattered X-rays 122 which have been scattered from the applied X-ray 120, and passing to the Compton scattered X-ray receiving assembly 151, in a directional substantially perpendicular to an axial direction of the applied X-ray 120. Both the scanning shield portion 178 as described with respect to FIG. 7, and the slit collimator 172 as described with respect to FIG. 6, can be viewed as embodiments of collimators, since they both limit passage of the scattered X-rays from scattering events that are situated within an angular range to the Compton scattered X-ray receiving assembly 151. In addition, the material forming the housing material (as compared to the slits which may be air, or some X-ray transmissive material) of the scanning shield portion 178 and the slit collimator 172 should limit passage of X-rays there through, such as to limit screened X-rays from being applied to the Compton scattered X-ray receiving assembly 151.

Within this disclosure, both the scanning shield portion 178 and the slit collimator 172 are intended to be illustrative in nature, but not limiting in scope. It is envisioned that certain processes as performed by either the scanning shield portion 178 and/or the slit collimator 172 could also be configured as a lens, a filter, a beamformer, or other electromagnetic or X-ray type mechanism, etc. As such, certain embodiments of the scanning shield portion 178 could limit passage of the scattered X-rays being applied to the Compton scattered X-ray receiving assembly 151 to within a range of angles, etc.

It is generally understood that with certain electromagnetic, optical, and/or X-ray technologies, certain operations can be performed utilizing two or more devices and/or their associated technique(s). Such devices, or technique, are often considered as equivalents, each of which is able to perform the desired function, operation, or technique. As such, certain embodiments of the collimator 172, scanning shield portion 178, etc. can be performed either by the device as described herein, or other generally known electromagnetic, optical, or X-ray equivalent devices and/or modifications thereof. Such generally equivalent devices are known by those skilled in the art can be utilized, and are intended to remain within the scope of the present disclosure.

This disclosure thereby illustrates a number of exemplary mechanisms (and associated techniques of certain embodiments of the Compton scattered X-ray receiving assembly 151) which can geometrically, computationally, or otherwise derive position of the scattering events within some matter. Such deriving the positions of the scattering events can be based at least in part on characteristics of at least some scattered X-rays 122 (while assuming a static or predictable applied X-ray).

Figure 10:
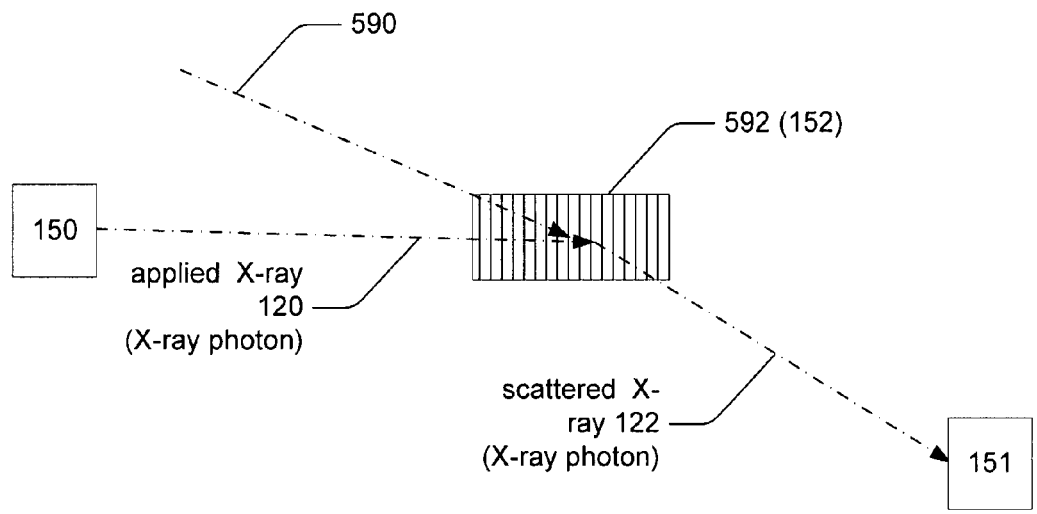
FIG. 10 is a diagram of another embodiment of the Compton scattered X-ray visualizer, imager, or information provider in which an other electromagnetic radiation beam is applied to the applied X-ray.

Considering the embodiment of the Compton scattered X-ray visualizer, imager, or information provider 100 as described with respect to FIG. 10, the at least one emitter portion 150 (as described with respect to FIG. 1) can at least partially utilize the applied X-ray 120 having its energy level that can be used to detect a position of the scattering event. Certain embodiments of the at least one emitter portion 150 can direct the applied X-ray 120 as to contact a contributing X-ray, beam, or other electromagnetic radiation beam 590 (which may include, but is not limited to, another applied X-ray having a prescribed energy level) as described with respect to FIG. 10. Such a contributing X-ray can alter the intensity of the applied X-ray by allowing the applied X-ray 120 to interfere (e.g., constructively or otherwise) with the contributing X-ray, beam, or other electromagnetic radiation beam 590, to at least partially form in identifiable intersection point 592. As evidenced by the enhanced scattered X-ray 122 that can be selectively viewed by certain embodiments of the Compton scattered X-ray receiving assembly 151, the enhanced scattered X-ray will have an improved illumination corresponding to the increased energy level, as compared with the corresponding scattered X-ray resulting either from either applied X-ray 120 alone, or alternately the contributing X-ray, beam, or other electromagnetic radiation beam 590 alone.

Additionally, crossing or merging the applied X-ray 120 as to contact a contributing X-ray, beam, or other electromagnetic radiation beam 590 can enhance the probability of the scattering event 152 occurring within the matter of the at least a portion of the individual within the point of intersection 592. Increasing the probability of the scattering event can thereupon improve the visualizing, imaging, or information providing associated with the location of the scattering event 152. Within this embodiment of the Compton scattered X-ray visualizer, imager, or information provider 100, the point of intersection 592 can thereby correspond to the location of the scattering event 152. The enhanced illumination resulting from the point of intersection 592 can be filtered, amplified, and/or otherwise processed as to further ease in display, visualization, information providing, imaging, etc. A conventional gamma knife (as generally understood in the medical technologies) can represent a cutting or destructing tool by which multiple gamma rays intersect as to provide a region of increased or combined energy, which can thereupon be detected in the form of a stronger applied X-ray 122, as described in this disclosure.

Figure 11:
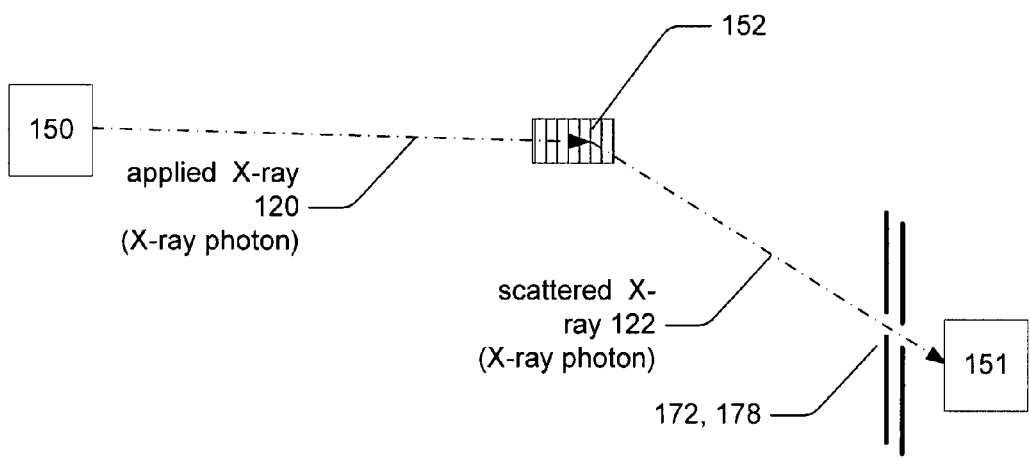
FIG. 11 is a diagram of another embodiment of the Compton scattered X-ray visualizer, imager, or information provider including a collimator or scanning shield portion.

FIG. 11, for example, illustrates an embodiment of the Compton scattered X-ray visualizer, imager, or information provider 100 that can be used for spatially confined imaging in which the output from the scattering event 152. Certain embodiments of the Compton scattered X-ray receiving assembly 151 are X-ray associated with a collimator 172 or 178, as described with respect to FIGS. 6 or 7 in this disclosure. As such, certain embodiments of the Compton scattered X-ray receiving assembly 151 will only be able to detect scattered X-rays scattering from scattering events 152 that are within a spatially confined region. As such, certain embodiments of the emitter portion 150 can be configured as pencil beams, fan beams, flooding beams, or as having other beam configurations. However, each applied X-ray provided by the emitter portion 150 could be directed within the spatially confined imaging region (of the scattering event) such as to illuminate that region sufficiently such that the scattered X-ray can be detected by the associated Compton scattered X-ray receiving assembly 151.

For the combination of any of the one or more emitter portion 150 and any of the Compton scattered X-ray receiving assemblies 151 as described in this disclosure, a variety of scattered X-ray, applied X-ray, matter, and other parameters can be determined that can be stored in a database, etc., and thereupon be used to derive the location of the position of the scattering events 152', and/or 152", etc. along the applied X-ray path 120' as described with respect to FIG. 5 utilizing known geometric, material, X-ray, and other calculations. Since certain scattering of the applied X-ray photons 120 can be intermitted at certain ones of the position of the scattering events 152', 152", etc.; the visualization, imaging, or information providing parameters at the various positions of the scattering events can be intermittently obtained. As the X-ray photons of the applied X-rays scatter at each position of the scattering event based on Compton scattered X-ray, the visualization, imaging, or information providing parameters of each position of the scattering event 152', and/or 152", such as can be used to image there from, and can be determined.

The relative angle and/or position of the applied X-rays 120 can thereby be determined, derived, or computed based at least in part on the angle of the one or more emitter portion from each particular scattering event location 152', 152", etc. The frequency (or the energy level which corresponds to the frequency) of the X-ray photons forming the applied X-rays 120 can be determined based at least in part on the known or determined input frequency to the one or more emitter portion 150 (or the measured output). The angle of the scattered X-ray photons being received by the one or more Compton scattered X-ray receiving assemblies 151 can be determined based at least in part on the original path of the applied X-ray, as well as the scattered frequency of at least some of the X-ray photons of the scattered X-rays.

Certain visualization, imaging, or information providing techniques can rely of generation of image information or visualization information that can represent data or other form of information. Such data, text, information, etc. can be stored or maintained in a database storage, processed using understood image processing techniques, etc., such as described with respect to certain embodiments of the visualization, imaging, or information providing controller 97 as described with respect to FIG. 1.

Certain embodiments of the Compton scattered X-ray visualizer, imager, or information provider 100 can visualize, image, and/or provide information at least partially by making 2-D scans from different "vantage points" outside the body, detecting the time-integrated X-ray return signal from each 2-D X-ray/vantage-point combination, and doing a tomography-like reconstruction of such as depth-related 3-D structure as described with respect to FIGS. 12*a*, 12*b*, and 13.

FIGS. 12*a* and 12*b* illustrate two views of one embodiment of the Compton scattered X-ray visualizer, imager, or information provider 100 which can be configured to just and/or controlled in imaging perspective by which the angle of the scattered X-ray changes from 122*a*, 122*b*, 122*c*, as indicated by an arrow 127, can be used to image the portion of the individual. During the visualization, imaging, and/or information providing, as described with respect to FIG. 12*a*, a variety of image information (similar in certain ways to conventional tumble graphic imaging or volumetric imaging techniques) can be derived. However, there can also be a considerable amount of information that can be determined based upon the scattering of the applied X-rays from a certain direction, or a limited range of directions. For example, a depth of the tissue aberration (or other tomography-type feature) 128 is largely uncertain during the visualization, imaging, or information providing as described with respect to FIG. 12*a* as a result of the relative direction in which the Compton scattered X-ray receiving assembly 151 receives the scattered X-rays.

As the angle of the scattered X-ray continues to increases through an angle, as described with respect to FIG. 12*b* as 122*d*, 122*e*, and 122*f*, the depth determination or extent of the feature 128 (using volumetric, tomographic, or other such techniques) can be improved as the angle of the scattered X-ray continued to increase. As such, the depth can be more readily and accurately be determined as the angle of the scattered X-ray increases from perpendicular. Such dimensions, extends, etc. of the features can be determined to more fully and accurately map the visualization, image, or provided information relative to the matter of the at least a portion of the individual, such as: tissue, tissue aberrations, organs, edge features, bones, constructs, inserts, bony portions, fluid or blood vessels, reservoirs, pooling, etc.

While the imaging perspective described with respect to FIGS. 12*a* and 12*b* can be used to adjust or control the angle of the scattered X-rays relative to matter of the least to portion of the individual, there can be a variety of other imaging perspectives that can be similarly adjusted, controlled, and/or otherwise utilized. For instance, the at least in the portion of the individual could be moved relative to the applied X-ray and/or the scattered X-ray. As the field of view of the visualization, imaging, or information provided is zoomed, focused, filtered, transformed, or otherwise modified to provide other "new" or "modified" (e.g., and/or adjusted or controlled) information, such new or modified information can be added to the enhanced the model, visualization, image, or information; such new or modified information can be compared with the original information to provide a more accurate or detailed model, visualization, image, or information. The techniques used for adjustment and/or control of the visualization, imaging, or information providing, certain ones of which are described relative to FIGS. 42 through 45, can be used to improve a quality of visualization, imaging, or information provided based on a variety of vantage points, and can be utilized for tomography or volumetric-type imaging.

Certain embodiments of the Compton scattered X-ray visualizer, imager, or information provider 100 can thereby be configured to provide tomography visualization, imaging, or information providing. The tomography provided would be expected to be similar to the tomography provided by other imaging mopdalities such as CAT scans, PET scans, and MRI, with the exception that certain embodiments of the Compton scattered X-ray visualizer, imager, or information provider would image matter to the prescribed imaging depth. Other embodiments of the Compton scattered X-ray visualizer, imager, or information provider 100, by comparison, would be expected to image through the matter of the at least some matter of the at least the portion of the individual. Additionally, the embodiments of the Compton scattered X-ray visualizer, imager, or information provider 100 can generally utilize Compton scattering, as compared to transmissive X-rays as with CAT scans, transmissive positrons as with PET scans, and magnetic fields as with MRI. Each imaging modality would therefore be expected to visualize, image, of provide information somewhat differently with potentially somewhat different output (either with or without the use of contrast agents).

FIG. 13 show a flowchart 1300 of one embodiment of the Compton scattered X-ray visualizer, imager, or information provider 100 that can be configured to provide a tomography-type and/or volumetric visualization, image, or information in a manner that includes illustrative, but not limiting, processes 1302, 1304, 1306, and/or 1308. Process 1302 can include, but is not limited to, visualizing, imaging, or deriving at least a first set of visualizations, images, or information. For example, certain visualization, image, or provided information (e.g., relatively crude in certain instances) can be obtained using certain embodiments of the Compton scattered X-ray visualizer, imager, or information provider 100 as described in this disclosure. Process 1304 can include, but is not limited to, controlling or adjusting the Compton scattered X-ray visualizer, imager, or information provider 100 such as to visualize, image, or obtain "additional" information. Process 1306 can include, but is not limited to, operating the Compton scattered X-ray visualizer, imager, or information provider 100 to capture, or otherwise obtain, the new information, such as to allow imaging from a modified vantage point. Process 1308 can include, but is not limited to, obtaining a more detailed or final visualization, image, or information by tomographically or volumetrically integrating the additional information. As such, viewing certain regions from different perspectives, such as to limit unknowns and uncertainties in the visualization, imaging, or provided information as the tomogreaphic-type embodiments of the Compton scattered X-ray visualizer, imager, or information provider 100 change some aspect (e.g., energy level, direction, depth, etc) in a manner as to improve the quality of the visualizing, imaging, or information providing.

Certain scintillation, time of flight, energy loss, and image combination type embodiments of the Compton scattered X-ray visualizer, imager, or information provider 100 can generally provide their final-quality visualization, image, or provided information based on processing of each interaction of the at least one emitter portion 150 and its associated at least onhe Compton scattered X-ray receiving assembly 151. By comparison, certain tomographic or volumetric embodiments of the Compton scattered X-ray visualizer, imager, or information provider 100 have a considerable number of unknowns following each interaction of the at least one emitter portion 150 and its associated at least onhe Compton scattered X-ray receiving assembly 151, wherein such unknowns are generally reduced or limited using tomographic or volumetric techniques, in a similar manner as with conventional tomography, as generally understood in the medical imaging technologies.

Certain tomography or volumetric aspects of certain embodiments (or output) of the Compton scattered X-ray visualizer, imager, or information provider 100 can therefore be quite similar in processing characteristics to those of conventional tomography imagers, such as CAT scans, PET scans, etc. (such that they can result from generating a number of two-dimensional slices). The slices are typically, but not necessarily, planar. The slices can thereupon be combined to allow information of any three-dimensional volumetric image in a similar manner as with conventional CAT scans, MRIs, etc. Depending upon the desired configuration, a variety of shapes, Compton or other configurations of slices can be generated. Within this disclosure, volumetric imaging may, depending upon context, be considered as including tomography. A description of conventional tomography or volumetric imaging devices, etc., such as may be utilized for conventional medical visualizing, imaging, or information providing, are described, for example, in X-ray 13 of "The Essential Physics of Medical Imaging, Second Edition", J. T. Bushburg, et al., Lippincott Williams and Wilkins, 2002 (incorporated by reference herein in its entirety). Such conventional tomography devices are commercially available and is not described in greater detail.

Is the understood that certain embodiments of the Compton scattered X-ray visualizer, imager, or information provider 100 may rely upon the adjustment and/or control to affect imaging of new matter of new directions, locations, positions, energy levels, etc. Such adjustment or control may be useful for tomography-type Compton scattered X-ray visualization, imaging, or information providing.

Certain embodiments of the deconvolution and/or tomography processes necessary to perform such operations can be considered as computationally similar to those used in normal X-ray CT scans, except that scattered instead of transmitted X-rays are detected (instead of the X-rays being transmitted through the individual as is the case with conventional CT scans as compared with X-rays undergoing Compton scattering as described in this disclosure).

Certain embodiments of the Compton scattered X-ray visualizer, imager, or information provider 100 can visualize, image, and/or provide information at least partially by use of an angle-collimated X-ray detector such that the intersection of the illuminating beam and detector sensitivity direction can define a unique 3-D voxel as described with respect to FIG. 5. Such angle-collimated X-ray detectors can be used to derive visualization, imaging, or information providing information in the one or more Compton scattered X-ray receiving assemblies 151. Certain embodiments of the Compton scattered X-ray visualizer, imager, or information provider 100 can visualize, image, and/or provide information at least partially by combinations of the embodiments described elsewhere in this disclosure, that allows visualization, imaging, or information providing at higher resolution and/or higher contrast information from the subcutaneous bodily structures.

Figure 14:
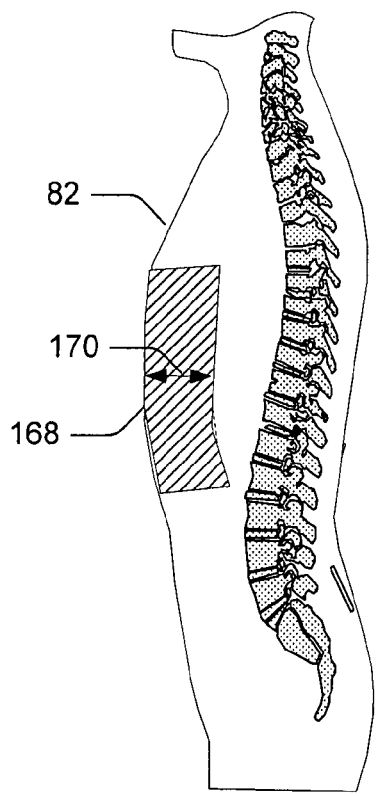
FIG. 14 is a diagram of an embodiment of the Compton scattered X-ray visualizer, imager, or information provider configured to visualize, image, and/or provide information from at least a surface of an individual.

Certain embodiments of the Compton scattered X-ray visualizer, imager, or information provider 100 can control the depth to which it can image based, at least in part, on photons energy level of the applied X-ray as applied to the matter of the at least the portion of the individual. The greater the energy level of the photons of the applied X-rays (and correspondingly the lesser the frequency of the photons of the applied X-ray 120), generally the greater depth a larger percentage of the applied X-ray can travel into the matter of the at least the portion of the individual, scatter, and return to effect Compton scattered X-ray visualization, imaging, or information providing. As such, generally, a larger number of, or percentage of, X-ray photons having greater energy levels (and therefore correspondingly lower frequencies) can generally visualize, image, and/or information provide down to a greater at least one visualization, imaging, or information providing depth range to the at least one prescribed visualization, imaging, or information providing depth than X-ray photons having a generally lower energy level (and correspondingly higher frequencies). This generalization assumes consistency of such factors as angle or position of applied X-rays, materials being imaged, etc. Certain embodiments of the Compton scattered X-ray visualizer, imager, or information provider 100, as described in this disclosure with respect to FIG. 14, can facilitate Compton scattered X-ray visualization, imaging, or information providing of a region of the scattering events extending from at least a surface 168.

These embodiments of the Compton scattered X-ray visualizer, imager, or information provider 100 might be particularly useful for Compton scattered X-ray visualization, imaging, or information providing for the at least the portion of the individual near the surface 168 of the individual (the surface may be underneath and at least partially internal surface or at least partially external surface). For example, certain embodiments of the Compton scattered X-ray visualizer, imager, or information provider 100, that can image from a surface to within the at least one depth range to the at least one prescribed depth, may be suitable for such Compton scattered X-ray visualization, imaging, or information providing even without complex image processing. Such visualization, imaging, or information providing from different depths may not interfere with each other provided a relatively homogeneous material across the visualization, imaging, or information providing depth range. By comparison, certain embodiments of the Compton scattered X-ray visualizer, imager, or information provider 100 can visualize, image, or information provide one and relatively non-homogeneous material across the at least one visualization, imaging, or information providing depth range provided suitable processing capability.

Certain embodiments of the Compton scattered X-ray visualizer, imager, or information provider 100 can visualize, image, or provide information relating to at least partially internal and/or at least partially external matter of the at least the portion of the individual utilizing a variety of Compton scattered X-ray visualization, imaging, or information providing techniques. Such visualization, imaging, or information providing can be configured to provide for, for example: examinations, testing of cancer, sicknesses, injuries, tissue aberrations, etc. (such cancers and/or tumors can include, but are not limited to, breast cancer, lung cancer, prostate cancer, bladder cancer, cervical cancer, etc.); as well as both internal or external visualizing, imaging, or information providing aberrations of certain matter of the at least the portion of the individual (such as tissue, bone, dental, etc. or a combination); Compton scattered X-ray visualization, imaging, or information providing lumen matter and matter examinations; Compton scattered X-ray visualization, imaging, or information providing edges, discontinuities, or matter inconsistencies or aberrations of organs, tissue, or other matter; Compton scattered X-ray visualization, imaging, or information allowing a variety of heart examination and/or treatments, heart valve structure, operation examination and/or treatments, brain examination and/or treatment, lung examination, liver examination, other organ, matter, or tissue examination and/or treatments etc. Within this disclosure, the term "depth" visualizing, imaging, or information providing can include, but is not limited to, depth visualizing, imaging, or information providing at least one volume of matter beneath the surface 168 of the at least the portion of the individual, perhaps including the surface 168 of the at least the portion of the individual.

Certain embodiments of the Compton scattered X-ray visualizer, imager, or information provider 100 can be configured to detect specific elements, or sets, combinations, alloys, and/or mixtures of specific elements, such as may be used to obtain signatures of pathological state or tissue identity. While iron and calcium are mentioned in this disclosure as examples of elements that may be included in matter which can be used to enhance visualizations, imaging, and/or information providing; it may also be desirable or useful to detect other elements or sets of elements. Depending on context, X-ray scattering signatures of tissue (which may be considered to be one embodiment of visualization, imaging, or information providing information), may be very helpful for a variety of diagnosis or examination purposes, for example.

Another example of an element, which could be detected by certain embodiments of the Compton scattered X-ray visualizer, imager, or information provider 100, is zinc. Zinc can be used as a naturally-occurring indicator of certain types of pathological brain tissue. For example, the elevated presence of zinc in the brain can be used to identify epileptic areas in hippocampus. As such, certain embodiments of the Compton scattered X-ray visualizer, imager, or information provider 100 can be configured to detect particular elements, matter, combinations of matter, materials, metal, alloys, fluids, bones, etc., and as such may be particularly useful for visualization, imaging, or information providing for certain applications. Certain embodiments of the Compton scattered X-ray visualizer, imager, or information provider 100 can be controllable and/or adjustable such as to allow setting or adjusting for particular visualization, imaging, or information providing applications.

Certain embodiments of such Compton scattered X-ray visualization, imaging, or information providing from the surface 168 may be performed from within the at least one visualization, imaging, or information providing depth range to the at least one prescribed visualization, imaging, or information providing depth. Certain of the Compton scattered X-rays returning to the Compton scattered X-ray receiving assembly 151, that scatter at scattering events from matter from different ones of the at least one substantial scattering range to the at least one scattering depth, may overlap and potentially interfere with scattered X-rays that have a contributed X-rays from different scattering events. Such clarification between interfering scattered X-rays resulting from different scattering events at different depths, and/or positions, etc., can limit confusion among image information obtained from different scattering events at varying depths.

Assuming a relatively narrow visualization, imaging, or information providing depth range to the at least one prescribed visualization, imaging, or information providing depth based at least partially on scattering from scattering events. The overlap of X-rays Compton scattered from different depths can be considered as originating from a single one of the at least one substantial scattering range to the at least one scattering depth, assuming the material is substantially homogenous across the range of depths. The overlapped X-rays can thereupon be processed or treated as originating from the same location. For example, Compton scattered X-ray visualization, imaging, or information providing of the skin, and/or some other relatively homogeneous matter, of a person may appear consistent, even if the Compton scattered X-rays scattering from within the at least one substantially scattered depth range to the at least one prescribed substantially scattering depth.

Certain embodiments of the Compton scattered X-ray visualizer, imager, or information provider 100 can be configured to visualize, image, or provide information based at least partially on scattered X-rays being scattered the slightly overlapped depths of scattering events, and can thereby reduce quality or uniformity of imaging or visualization. For example, consider the Compton scattered X-rays could be expected to be Compton scattered, down to similar scattering depths, within similar type matter within the person, assuming substantially homogeneous or consistent matter down to the imaging depth. Certain types of Compton scattered X-ray visualization, imaging, or information providing can be performed as scanning, such as to screen for, or detect, aberrations of the matter (e.g., skin) such as cancers, lesions, tumors, moles, cuts, abrasions, etc. Certain embodiments of the Compton scattered X-ray receiving assembly, which can be used to visualize, image, or provide information relating to a considerable variety of matter, such as regents made up of relatively thin matter that are selected to increase the homogeneity of the region. By selecting or using the relatively thin image region, the matter's homogeneity thereby generally increases to thereby provide improved visualization, imaging, or information providing. By using relatively thin image regions, which are therefore more homogeneous, certain embodiments of the Compton scattered X-ray visualizer, imager, or information provider 100 may utilize such devices as scintillators (and/or fluoroscopes, certain of which can include scintillators) which can directly convert scattered X-rays into viewable and/or visible light, as described in this disclosure. Within this disclosure, "viewable" light can, depending on context, be intended to include, but is not limited to, visible light such as is recognized as being viewable by most sighted humans, as well as at least certain infra-red and ultra-violet light.

Within this disclosure, such conversion of X-ray photons by scintillators into viewable and/or visible light that may be viewed (directly or by subsequent processing) by certain users of embodiments of the Compton scattered X-ray visualizer, imager, or information provider 100. By comparison, certain embodiments of the Compton scattered X-ray receiving assembly 151 may include a photodiode or other photodetector operably associated with the output of the scintillator (not shown, and considered as a portion of the scintillator) which can output to certain portions of the Compton scattered X-ray receiving assembly. As such, certain scintillator-based embodiments of the Compton scattered X-ray visualizer, imager, or information provider 100 can provide viewable and/or visible light directly to a user, or alternately output viewable and/or visible light that can be further analyzed, amplified, filtered, or otherwise processed such that could be viewed by the user following the multiple steps such as by a machine, machine-based processor, optical processing device, etc. Certain scintillators, for example, could be operably coupled to photodiodes, whose outputs can be further analyzed.

Certain scintillator embodiments of the Compton scattered X-ray visualizer, imager, or information provider 100 being applied to certain relatively thin organisms, plants, etc. may also visualize, image, or provide information about the thickness of at least some matter of the at least certain portions of the individual using such techniques. Certain such scintillator (and/or fluoroscope) embodiments of the Compton scattered X-ray visualizer, imager, or information provider 100 may be operationally simpler, and therefore involve relatively little processing as compared with other visualization, imaging, or information providing techniques by other (more processor-complex) embodiments of the Compton scattered X-ray visualizer, imager, or information provider 100. The scintillator embodiments of the Compton scattered X-ray visualizer, imager, or information provider 100 can create images based, at least in part, on the scattered X-rays 122 received by the Compton scattered X-ray receiving assembly 151; since the Compton scattered X-rays being produced by the former are being converted directly into viewable or visible light using scintillators (and/or fluoroscope-based technology).

Figure 15:
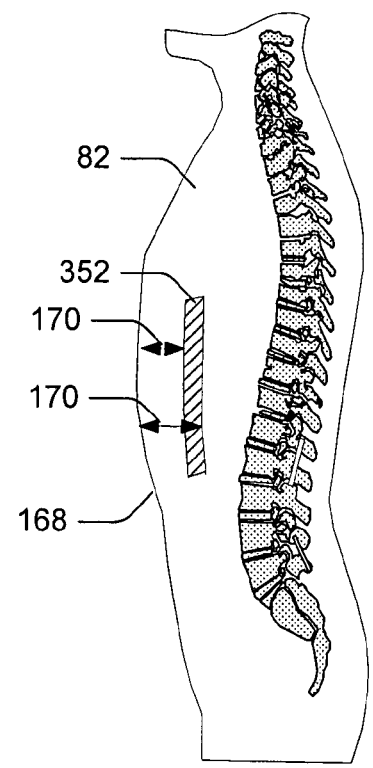
FIG. 15 is a diagram of an embodiment of the Compton scattered X-ray visualizer, imager, or information provider configured to visualize, image, and/or provide information within a volume from a first prescribed depth to a second prescribed depth.
Figure 16:
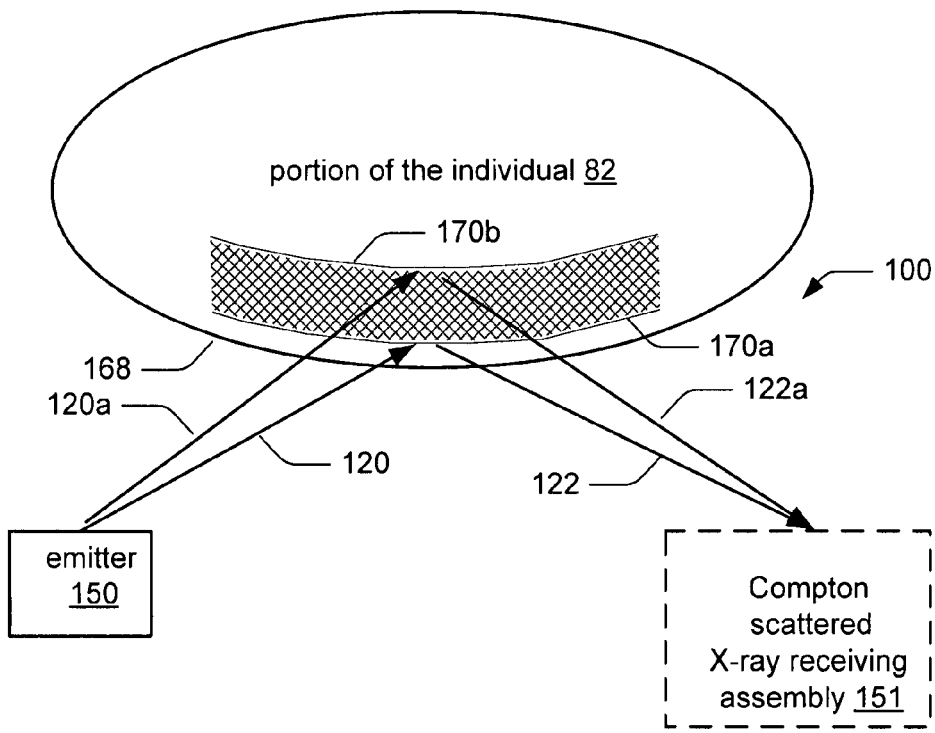
FIG. 16 shows another embodiment of the Compton scattered X-ray visualizer, imager, or information provider.

Certain embodiments of the Compton scattered X-ray visualizer, imager, or information provider 100, as described in this disclosure with respect to FIGS. 15 and 16, can facilitate Compton scattered X-ray visualization, imaging, or information providing between a first one of the at least one visualization, imaging, or information providing depth range to the first one of the at least one prescribed visualization, imaging, or information providing depth from the surface 168. Such visualizing, imaging, or providing information can occur either from an internal or external surface of the portion of the individual (or the first one of the at least one visualization, imaging, or information providing depth range to the first one of the at least one prescribed visualization, imaging, or information providing depth from the surface 168) to a second one of the at least one visualization, imaging, or information providing depth range to a second one of the at least one prescribed visualization, imaging, or information providing depth from the surface.

Certain of such Compton scattered X-ray visualization, imaging, or information providing techniques can be obtained at least partially by combination (e.g., image differentiation, image subtraction, image transformation, deconvolution, weighted subtraction, functional subtraction, and group including inverse integral transform, subtractive inverse integral transform, inverse functional transform, and subtractive inverse functional transform, time of flight calculation, or other such computation or image processing techniques). With such combination of images, etc., multiple depth visualizations or images can be obtained, in the form of depth visualization or image information, from Compton scattered X-ray visualization, imaging, or information providing from the surface 168 down to multiple different depths 169, 170, thereby imaging through a depth 172.

Certain occurrences of the depth visualizations, images, and/or provided information can thereupon be obtained from the shallower depth visualizations, images, and/or provided information value using image combining (such as by using image subtraction, image differentiation, image transformation, deconvolution, weighted subtraction, functional subtraction, and group including inverse integral transform, subtractive inverse integral transform, inverse functional transform, and subtractive inverse functional transform, or other such image processing or computational techniques), from between multiple depth visualizations, images, and/or provided information values. To depth-image a relatively thick portion of the individual (e.g., a slice that is thicker than can be depth imaged by itself with desired resolution, image quality, etc.), a number of relatively thin image slices can be imaged, and the number of images can thereupon be added, summed, or otherwise combined using a variety of appropriate image processing techniques.

As described in this disclosure, the visualization, imaging, or information providing of slices can be performed by successive image combination, by which the information, data, value, etc. of the shallower image can be combined, subtracted, or otherwise transformed out from that of the thicker image for each successive image slice, to obtain image information of the particular image slice.

Such techniques can also be utilized by certain image combining processes (e.g., image subtraction, image differentiation, image transformation, deconvolution, weighted subtraction, functional subtraction, and group including inverse integral transform, subtractive inverse integral transform, inverse functional transform, and subtractive inverse functional transform, time of flight techniques; scintillator [or fluoroscope] techniques, or other Compton-based techniques). The image slices can at least partially involve combining relatively thick portions of the individual, and can thereupon be digitally, analog, or otherwise combined using combining image processing techniques, and can be clarified such as to limit distorting aspects such as opaque X-ray matter, noise, etc, such as involving deconvolution, transforms, etc. Certain of the visualizations, images, and/or information can be maintained to form a model, which can be relied on for visualization, imaging, or information providing purposes. Alternately, a two-dimensional image slice having some thickness and either a substantially planar or curvilinear surface (simple curve, complex curve, or other) can be visualized, imaged, or have information provided within the at least the portion of the individual at a location nearby, or away from, the surface of the at least the portion of the individual. For example, certain examples of visualization, imaging, or providing information can occur with the at least one emitter being positioned adjacent the skin, within lumens, etc.

Alternately, time of the flight computations can be used to derive visualization, imaging, or information providing information, as described in this disclosure. Certain embodiments of the Compton scattered X-ray visualizer, imager, or information provider 100 can visualize or image a volume or portion extending between two of the at least one visualization, imaging, or information providing depth ranges from the surface 168 can utilize time of flight computations (such as described with respect to FIG. 17). Certain time of flight computations can operate at least partially by determining a total distance from the emitter portion 150, to the particular scattering event of the at least the portion of the individual, and thereupon continue to the Compton scattered X-ray receiving assembly 151. Such distance can be determined, for example, by measuring the duration for X-rays to travel that distance. The distance can thereby be determined at least partially based on the combined temporal duration (time) of the travel by the applied X-ray 120 and/or the scattered X-ray 122. Certain embodiments of the Compton scattered X-ray visualizer, imager, or information provider 100 of FIG. 17 can include a time of flight calculator 160 (which can be included in the visualization, imaging, or information providing controller 97 of FIG. 1), which can derive the time of flight duration(s), and thereupon compute the total time of flight distance(s).

Figure 17:
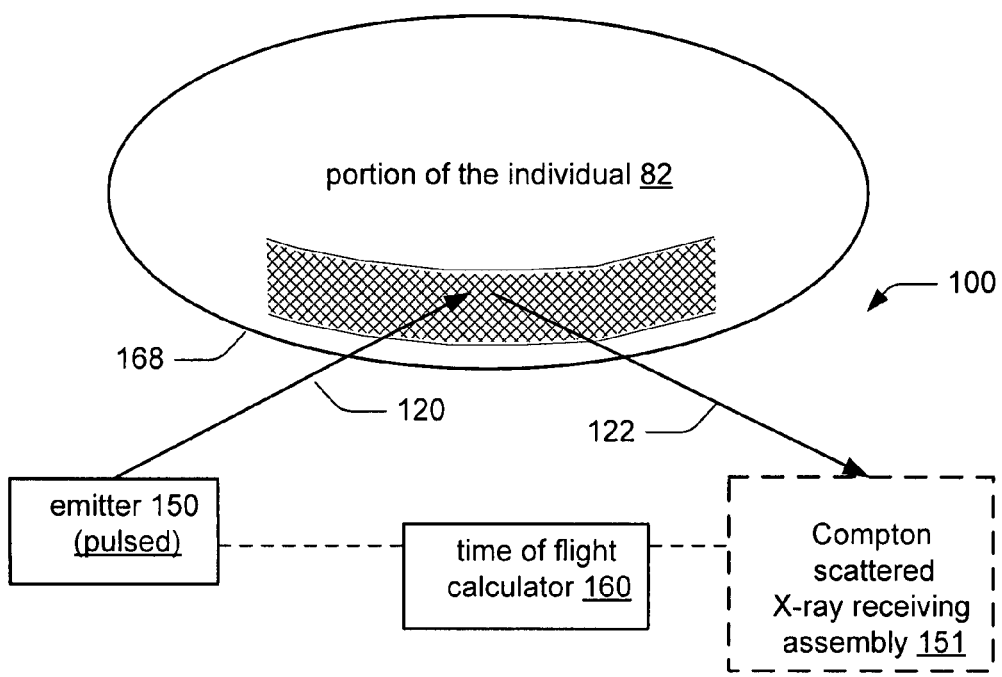
FIG. 17 shows yet another embodiment of the Compton scattered X-ray visualizer, imager, or information provider.

Certain embodiments of time of flight computation such as can utilize the time of flight calculator 160, as described with respect to FIG. 17, can involve generation of relatively brief pulses of the applied X-ray (e.g., X-ray photon radiation), which are directed by the at least one emitter portion 150 towards the imaged region of the at least the portion of the individual. Thereupon, the X-rays forming the pulses or bursts of applied X-rays can be Compton scattered within the matter of the at least the portion of the individual at the scattering event, such as can be detected by the at least one Compton scattered X-ray receiving assembly 151 following scattering of the brief pulse (also considered a form of time modulation). Time of flight calculations can be derived based, at least partially, on the time required for the applied X-rays to travel to and scatter at the scattering event (within the matter of the at least the portion of the individual), and thereupon have the scattered X-rays travel to the at least one Compton scattered X-ray receiving assembly 151. Considering the total distance between the point of Compton scattered X-ray at the scattering event and the Compton scattered X-ray receiving assembly, and thereupon the angle of scattering and scattering event through which the X-rays travel through the at least the portion of the individual. The location of the scattering event within the matter of the at least a portion of the individual can thereupon be determined relying on calculations based on the speed of X-rays, their direction traveled, and thereupon their distance traveled (the speed of X-rays correspond to the speed to light).

The total distance from the emitter portion 150, to the location of the scattering event, and thereupon to the Compton scattered X-ray receiving assembly 151, can thereby be used to derive the at least one visualization, imaging, or information providing depth range to the at least one prescribed visualization, imaging, or information providing depth at least partially using time of flight calculations. With time of flight calculations, precision in the detected timing and measured distance is important in accurately determining the location of scattering within the matter. Therefore, certain embodiments of the detector portions of the Compton scattered X-ray receiving assembly and/or emitter portions, as described with respect to FIG. 17, could have at least low picosecond range detection operational duration to provide suitable accuracy. Such picosecond range detection operational duration to provide suitable accuracy can be performed using, for example, certain streak cameras, pixellated streak cameras, an avalanche detector, CCD, or other detector embodiments of the Compton scattered X-ray receiving assembly 151. Other embodiments of the detector portions could operate with considerably longer signal detection duration rate while perhaps accepting reduced quality or resolution in visualization, imaging, or information providing.

Certain embodiments of the Compton scattered X-ray visualizer, imager, or information provider 100 can utilize a variety of controllers, computers, etc. (considered as a portion of the visualization, imaging, or information providing controller 97) as certain users such as to provide a variety of automation and/or enhanced reliably of operation or analysis. As such, with certain embodiments of the Compton scattered X-ray visualizer, imager, or information provider 100, a variety of human or automated users can visualize, image, and/or provide information relating to the subsurface of the at least the portion of the individual 82 at certain typically controllable depths. The mechanism for Compton-type scattering are generally understood by those skilled with X-ray technology, and will not be described in greater detail except where suited to this particular disclosure.

With individuals such as humans and/or animals, for example, the external surface 168 can include such surfaces as skin, mucous membranes, and other such external surfaces etc. Certain individuals such as plants or organisms (living in the environment such as outside, living in humans, animals, plants, or other organisms, and/or human-designed or human created) can have at least one external surface 168 that may come in contact with the external environment from which much of the potential visualization, imaging, or information providing could be performed. Examples of the external surface may include the outer layer of a leaf, a trunk, a stalk, a fruit, a root portion, a vegetables, etc. It may not be necessary, in those embodiments of the Compton scattered X-ray visualizer, imager, or information provider 100, that are applied within the matter of the individual (such as via incision, or other breach of the surface), to visualize, image, and/or provide information at least partially through the surface.

Certain individuals, such as organisms, plants, or portions thereof, can be visualized, imaged, or have information provided using certain embodiments of the Compton scattered X-ray visualizer, imager, or information provider 100 for such purposes as to determine health, internal structure, insect infestation, contamination, illness, etc. Certain types of individuals such as fruits, roots, or vegetables as produced by plants can be visualized, imaged, or have information provided using certain embodiments of the Compton scattered X-ray visualizer, imager, or information provider 100 as to determine freshness of the item, suitability of the item, insect infestation, disease, contamination, inconsistency from desired state, etc. A forestry store or market (which may commercially sell certain meats, vegetables, fruits, plants, etc., for example) may utilize certain embodiments of the Compton scattered X-ray visualizer, imager, or information provider 100 such as to visualize, image, and/or provide information relating to meats, plants, vegetables, fruits, etc. to determine their health, condition, etc. Such determination of the condition can be applied either prior to purchase, following storage for some duration, or prior to selling, etc. such visualization, imaging, or information providing of plants, organisms, troops, roots, etc. can be based, at least in part, and changing X-ray scattering characteristics as the matter rots, disintegrates, melts, distorts, ages, or otherwise changes.

With such individuals as humans and/or animals, the term "internal" can pertain to those locations accessible through normally open openings (e.g., mouth, ears, nose, various lumens, blood vessels, urethra, anal, etc.) and/or normally closed openings, such as may be accessed via an incision as described in this disclosure. The interior of such individuals as organisms, cells, bacteria, viruses, etc. can be accessed through normally closed openings such as incisions, pipettes, probes, tools, tactile feedback devices, cutters, displays, etc. As such, the term "surface", whether situated at least partially internally and/or at least partially externally relative to the at least the portion of the individual, should relate to, and/or be considered relative to, and based on, the particular aspects, conditions, and/or particulars of the at least the portion of the individual.

Certain embodiments of the Compton scattered X-ray visualizer, imager, or information provider 100 can provide position determination, control, and/or adjustment of certain of the at least one emitter portions 150 and/or the at least one detector portions 152 (and/or the at least one Compton scattered X-ray receiving assembly 151). Such adjustment and/or control of the portions or entirety of the Compton scattered X-ray visualizer, imager, or information provider 100 can be used to control and/or adjust the amount of matter through which the Compton scattered X-ray visualizer, imager, or information provider 100 can visualize, image, and/or provide information, such as when Compton scattered X-ray visualization, imaging, or information providing (to within the at least one visualization, imaging, or information providing depth range to the at least one prescribed visualization, imaging, or information providing depth). Such control and/or adjustment is typically characterized by the energy level and/or frequency of the X-ray photons.

For example, assume that a particular Compton scattered X-ray visualizer, imager, or information provider 100 is configured (e.g., based on X-ray photon energy and/or frequency) to visualize, image, and/or provide information at the at least one controllable and/or adjustable prescribed visualization, imaging, or information providing depth. If the at least one emitter portion 150 can be arranged to direct the applied X-ray 122 substantially perpendicular to the surface 168 of the at least the portion of the individual, the visualization, imaging, or information providing could occur within the at least one prescribed visualization, imaging, or information providing depth of, for example, 5 mm. However, as the angle of the applied X-rays by the emitter portion to the surface 168 of the matter changes from perpendicular to some slant from a surface of the at least the portion of the individual, such as illustrated in FIGS. 16 to 17, the at least one prescribed visualization, imaging, or information providing depth also changes. The at least one prescribed visualization, imaging, or information providing depth corresponds to the maximum depth which the X-rays can pass to, scatter at, and return from during the Compton scattered X-ray visualization, imaging, or information providing. Therefore, as the angle of the X-rays applied by the emitter portion to the surface 168 of the at least some matter of the at least the portion of the individual changes (e.g., from perpendicular to some angle), the effective perpendicular depth visualizing, imaging, or information providing could change, which typically changes as a cosine function of the change of angle.

With almost all types of individuals, most surfaces 168 are not completely planar. Consider that people, animals, organisms, and plants are not typically flat, but instead have some degree of curvature over our surfaces. For the purpose of this disclosure, such visualization, imaging, or information providing concepts can be explained and more easily modeled assuming a planar initial contact surface, which may become closer to true as the depth imaged or visualized region becomes incrementally smaller.

Within this disclosure, "Compton scattered X-ray visualization, imaging, or information providing", as may therefore be performed within some set distance from the surface 168 at which X-ray based electromagnetic radiation from the Compton scattered X-ray visualizer, imager, or information provider 100 is being emitted and Compton scattered, and can thereupon be detected. Certain aspects of such Compton scattered X-ray visualization, imaging, or information providing may rely on the configuration and/or operation respective emitter portions and/or detector portions that can respectively apply X-rays proximate to, and/or receive X-rays from, the surface 168 of the at least the portion of the individual.

The matter of the at least the portion of the individual which can be visualized, imaged, or have information provided using a variety of embodiments and/or configurations of the Compton scattered X-ray visualizer, imager, or information provider 100, can vary. For instance, for Compton scattered X-ray visualization, imaging, or information providing humans or animals, the soft matter that can be visualized, imaged, or have information provided can include but is not limited to: soft tissue, fluid (blood, spinal, lymph, etc.) bone portions interspersed among tissue, tissue forming organs, muscles, fat, flesh, etc. Additionally, relatively hard matter such as: bones, bone portions, joints, spine portions, teeth, etc. can be visualized, imaged, or have information provided using certain configurations or embodiments of the Compton scattered X-ray visualizer, imager, or information provider 100. As such, the interior bones, teeth, etc. can be depth imaged to provide a considerable amount of internal visualization, imaging, or information providing. As such, the particulars of the at least some matter can have some effect on the visualizing, imaging, or information providing.

Certain embodiments of the Compton scattered X-ray visualizer, imager, or information provider can additionally visualize, image, and/or provide information relating to such matter can be associated with, or positioned in or nearby the at least the portion of the individual as plastic, metal, implants, pins, constructs, fillings, orthopedic braces, dental braces, etc. Certain embodiments of the Compton scattered X-ray visualizer, imager, or information provider can be either stand-alone devices, or provide input into the at least the portion of the individual such as a tool, implant, tactile feedback providers, injecting device, probe, cutter, drill, separator, ablator, Bovie electrocautery device, material adder, material remover, etc. Certain portions of the Compton scattered X-ray visualizer, imager, or information provider 100, as described in this disclosure, can pertain to visualizing, imaging, or information providing within the medical areas, orthopedic areas, research areas, dental areas, orthodontia areas, veterinarian areas, livestock areas, wild animal or aquatic animal areas, etc.

Compton scattered X-ray visualization, imaging, or information providing of such individuals as plants or organisms can involve depth visualizing, imaging, or information providing at least some of the various particular components or structure of the plant or organism. Such Compton scattered X-ray visualization, imaging, or information providing of plants, organisms, etc. can be for research, commercial, medical, veterinarian, dental, or other purposes. For instance, certain organisms being visualized, imaged, or have information provided can within a human, animal, or other host, can be distinct, or can be at least partially integrated in human, plant, organism, animal, etc.

There may be particular aspects of particular type of Compton scattered X-ray visualization, imaging, or information providing, as can be performed by particular embodiments of the Compton scattered X-ray visualizer, imager, or information provider 100 as described in this disclosure. For example, certain embodiments of the Compton scattered X-ray visualizer, imager, or information provider 100 might be particularly useful in Compton scattered X-ray visualization, imaging, or information providing a region within the at least the portion of the individual that is physically separated from the location where the applied X-rays 120 initially pass through the surface. As such, certain embodiments of the Compton scattered X-ray visualizer, imager, or information provider 100 may have to image through considerable matter, tissue, etc. that may not be desired to be included in the visualization, imaging, or information providing, such as by using image combining (e.g., image subtraction, time of flight Compton scattered X-ray depth visualization, or other technique such as by using image subtraction, image transformation, deconvolution, image subtraction, weighted subtraction, functional subtraction, and group including inverse integral transform, subtractive inverse integral transform, inverse functional transform, and subtractive inverse functional transform, or other such image processing techniques), and/or other imaging, or information providing, techniques as described in this disclosure; the depth visualizing or imaging effects of such matter that is not desired to be visualized, imaged, or have information provided can be computationally limited. Certain embodiments of the Compton scattered X-ray visualizer, imager, or information provider 100 can be configured or operated to most effectively image the matter of the at least the portion of the individual situated nearby the external or internal surface 168 (e.g., via skin or other internal or external surface, or alternately through an incision, cut, etc.) of the at least the portion of the individual.

Certain embodiments of the Compton scattered X-ray visualizer, imager, or information provider 100 are described in this disclosure as having their energy level and/or frequency of the applied X-rays that can be controlled and/or adjusted. The term controllable can, depending on context, indicate the ability of the user and/or other entity to control the depth, and/or range of depths, at which the Compton scattered X-ray visualizer, imager, or information provider 100, can image through the matter of the at least the portion of the individual. Such control can be based at least in part on controlling the energy level and/or frequency of at least some applied X-rays 120. By comparison, the term adjustable can, depending on context, indicate that some adjustment can be made to the depth at which the Compton scattered X-ray visualizer, imager, or information provider 100 visualizes, images, or provides information into the matter of the at least the portion of the individual. Such adjustment can be based, at least in part, on controlling the energy level and/or frequency of at least some applied X-rays 120. Such control or adjustment of depth, or range of depths, can be made during initial and/or subsequent depth visualizing, imaging, or information providing, and can be empirically determined or not. A variety of embodiments of the Compton scattered X-ray visualizer, imager, or information provider 100 may be controllable and/or adjustable based at least in part on controlling the energy level and/or frequency of at least some applied X-rays 120, as described in this disclosure; while other embodiments may not.

Certain embodiments of the visualization, imaging, or information providing controller 97, of the Compton scattered X-ray visualizer, imager, or information provider 100, as described in this disclosure, can utilize a variety of software, hardware, firmware, depth visualizing or imaging technology, electronic and/or electric circuitry to facilitate the desired Compton scattered X-ray visualization, imaging, or information providing. A variety of the software, hardware, firmware, depth visualizing or imaging technology, electronic and/or electric circuitry is understood in the field of controllers, optical systems, electronics, and/or computers; and might be effectively performed by a variety of types of the visualization, imaging, or information providing controller 97. For instance, certain embodiments of Compton scattered X-ray visualization, imaging, or information providing that can rely at least partially on visualization, imaging, or information providing image subtraction or combination, filtering, and/or processing, etc., as described in this disclosure, such as are particularly likely to involve software, hardware, firmware, and/or electronic to perform suitable image processing such as transforms, etc. As such, certain embodiments of the Compton scattered X-ray visualizer, imager, or information provider 100 can allow transitioning or reconfiguration between different types of Compton scattered X-ray visualization, imaging, or information providing such as by operation selection, reprogramming, modification, replacement, or reconfiguration of the visualization, imaging, or information providing controller 97 (such as may control operation of the emitter portion 150 and/or the Compton scattered X-ray receiving assembly 151 of FIG. 1). The operational or processing requirements of the visualization, imaging, or information providing controller 97 may be quite demanding, for certain applications.

Figure 18:
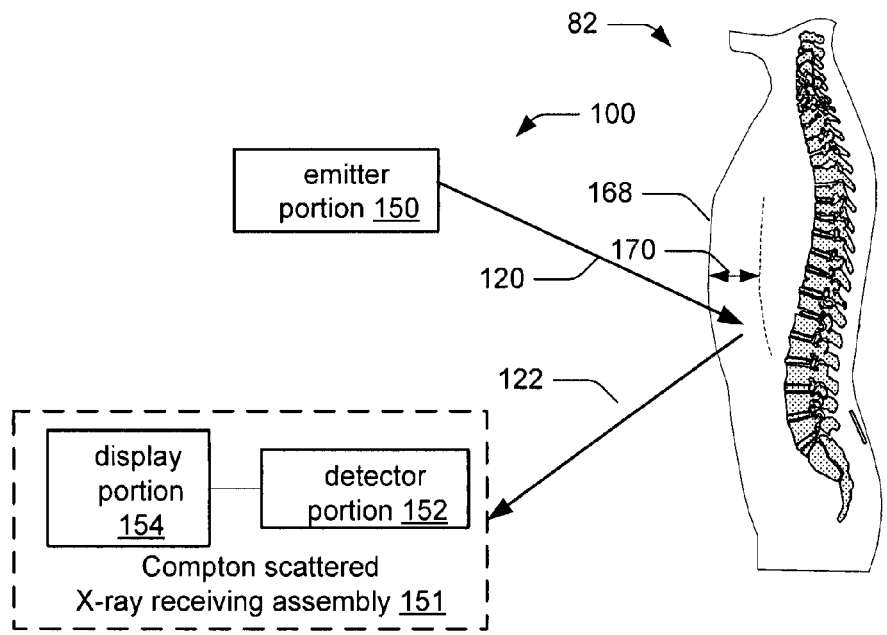
FIG. 18 shows a diagram of an at least the portion of an individual (e.g., human) being visualized, imaged, or image provided by one embodiment of the Compton scattered X-ray visualizer, imager, or information provider.

There are a number of embodiments of the Compton scattered X-ray visualizer, imager, or information provider 100 that can be used to visualize, image, or provide information. FIGS. 18 and 20, for example, illustrate two respective exemplary but not limiting embodiments of the Compton scattered X-ray visualizer, imager, or information provider 100, each embodiment conforms generally to the description on this disclosure relating to the FIG. 1 block diagram. Exemplary, but not limiting, logic pertaining to the respective FIGS. 18 and 20 embodiments of the Compton scattered X-ray visualizer, imager, or information providers 100, and can be applied to certain large flow charts as described respectively relative to FIGS. 19 and 21.

It is envisioned that one or more distinct components, or portions, of certain embodiments of the Compton scattered X-ray visualizer, imager, or information provider 100, can be included in one or more separate or distinct Compton scattered X-ray visualizer, imager, or information providers 100

(such as described with respect to FIG. 1) can be operationally combined or configured as desired. Such components or portions from the one or more separate or distinct Compton scattered X-ray visualizer, imager, or information providers 100 can interoperate, using known networking concepts. Each portion or component of the Compton scattered X-ray visualizer, imager, or information provider can thereby perform one or more distinct functions or operations associated with the Compton scattered X-ray visualizer, imager, or information provider.

As such, at least certain portions or components of different embodiments of one or more of the Compton scattered X-ray visualizer, imager, or information provider 100 can interface and/or interact with each other such as to transfer, transmit, and/or receive images, visualize, image, and/or provide information therebetween. Such transfer, transmission, and/or reception techniques can be provided in a manner utilizing techniques understood by those skilled in computing, hard-wired, wireless, networking, optical, communications, and other similar technologies. Such transmission, transferring, and/or receiving can be performed utilizing wireless, optical, wired based and/or other known technologies.

There can be a variety of, and embodiments of, devices and/or techniques which can be used by the at least one emitter portion 150, that can generate the applied X-rays. For example, certain embodiments of the at least one emitter portion 150 of the Compton scattered X-ray visualizer, imager, or information provider 100 can utilize X-ray devices, tubes, etc. to generate X-rays. A variety of X-ray tubes may be used to generate X-rays for a variety of conventional X-ray devices and/or conventional fluoroscopy devices, such as are generally known and are commercially available. Conventional X-ray devices, tubes, etc., such as may be utilized for conventional medical visualizing, imaging, or information providing, are described, for example, in chapter 5 of "The Essential Physics of Medical Imaging, Second Edition", J. T. Bushburg, et al., Lippincott Williams and Wilkins, 2002 (incorporated by reference herein in its entirety). The X-ray tubes, devices, etc. can, depending on context, be considered as those devices that can be configured to produce X-rays including X-ray photons of a particular energy level or range, frequency or range, power or range, etc. he the For conventional transmissive X-ray imaging, for example, the X-rays can pass through the at least the portion of the individual 82. By comparison, those embodiments of the at least one emitter portion 150 of the Compton scattered X-ray visualizer, imager, or information provider 100 can visualize, image, and/or provide information utilizing such Compton scattered X-ray mechanisms as Compton backscatting, Compton forward scattering, etc. of the applied X-ray in a manner that can rely on X-rays that have characteristics (frequency, energy level, power, etc. of the X-ray photons).

Certain external embodiments of the Compton scattered X-ray visualizer, imager, or information provider 100 may be configured such that the particular frequency or X-ray photon energy, or such other operational characteristic(s) of at least some of the X-ray photons included within the applied X-ray, can pertain to the depth of the Compton scattered X-ray visualization, imaging, or information providing. As such, the frequency or energy level of a number of X-ray photons included in the applied X-ray, if controlled or adjusted, can have the effect of controlling or adjusting the depth(s) of Compton scattered X-ray visualization, imaging, or information providing into the matter of the at least the portion of the individual 82. Certain embodiments of the Compton scattered X-ray visualizer, imager, or information provider 100 can visualize, image, and/or provide information down to within the at least one visualization, imaging, or information providing depth range to the at least one prescribed visualization, imaging, or information providing depth, which range of depths can be at least partially adjusted and/or controlled. Such determination can be either at least partially empirically, empirically, such as by calculation, derivation, or determination. Certain embodiments of the Compton scattered X-ray visualizer, imager, or information provider 100 can obtain the X-ray Compton scattered X-ray information in the form of information, data, depth visualizations, images, and/or provided information, etc.

The at least one substantially scattered depth range to the at least one prescribed substantially scattered depth distance from the surface 168 of the individual, such that the electromagnetic radiation of the applied X-ray passes into the at least the portion of the individual, scatters, and may therefore cause a reduction in the energy level of the X-ray upon scattering. The latter distance can thereby be controlled to effectively control the Compton scattered X-ray visualization, imaging, or information providing characteristics as per the former. Certain of the at least one visualization, imaging, or information providing depth range to the at least one prescribed visualization, imaging, or information providing depth, which can vary along with varied surface configurations, roughness, material non-uniformities, etc.

By controlling the characteristics of the X-rays photons (e.g., frequency and/or energy level of the X-ray photons of the X-rays, intensity of the X-rays, angle of the X-rays, etc.), the perpendicular distance from the surface 168 of the at least the portion of the individual that the applied X-ray passes can be controlled and/or adjusted. Such control and/or adjusting of the energy level, frequency, direction, intensity, position, and/or other aspect or parameter of the applied X-rays can considerably limit the amount and type of matter of the at least the portion of the individual through which the X-rays may be applied. For instance, certain embodiments of the Compton scattered X-ray visualizer, imager, or information provider can be configured to emit the X-ray based electromagnetic radiation (of the applied X-ray or the scattered X-ray) at one or more selected organ(s) and/or matter, while limiting the application of the X-ray electromagnetic radiation to other organs, matter, etc. Certain embodiments of the Compton scattered X-ray visualizer, imager, or information provider 100 can control the angle at which it applies its X-ray photons to the surface 168 of the at least the portion of the individual.

Due to the uncertain health effects of application of X-rays on humans, other individuals, and/or users, it may be desirable, in many instances, to limit the amount of X-ray electromagnetic radiation applied to the at least the portion of the individual, and/or any nearby users, when using the Compton scattered X-ray visualizer, imager, or information provider 100. Additionally, it would be expected to ease acceptance of certain embodiments of the Compton scattered X-ray visualizer, imager, or information provider 100 by the appropriate regulatory agencies, in the amount of X-rays being applied to individuals and/or users (particularly human) could be limited considerably. As such, by the certain embodiments of the Compton scattered X-ray visualizer, imager, or information provider 100 be configured to image a relatively small portion of the individual using depth-imaging techniques (e.g., imaging scan in a small portion underneath, primarily imaging matter through a depth, primarily certain organs, etc.), it can inherently limit the amount and extent of X-rays pass.

For example, certain regions or locations of particular individuals (e.g., the embryo in pregnant women, certain organs, certain tissue, radiation-weakened individuals, elderly or informed, certain animals or organisms, etc.) might be particularly susceptible to the application of X-ray electromagnetic radiation, and as such are especially critical to shield from the application of X-rays. As such, it might be particularly desirable to configure at least certain embodiments of the Compton scattered X-ray visualizer, imager, or information provider 100 to allow control of the particular range of depth to the prescribed depth of the applied X-rays 120 (as well as their released amount) within the at least the portion of the individual. By limiting the amount and energy level of the X-ray photons of the applied X-rays being applied to the at least some matter of the at least the portion of the individual by such techniques as bandwidth limiting, X-ray energy reduction, filtering, shielding, etc., the application of the X-ray to the user and/or individual can be limited.

Allowing relatively precise directional control of applied X-rays 120 using correlators, lenses, etc. such as emitted by the at least one emitter portion 150, as compared with certain conventional X-ray imagers (conventional transmissive or fluorescent X-rays) can considerably reduce the X-ray dosage to the at least the portion of the individual. Also, X-ray dosages to nearby users can be limited. Such use of relatively low-energy applied X-rays, precise application of applied X-rays to limited region of the individual, and associated reduced dosage of nearby areas, users, and/or individuals by certain embodiments of the Compton scattered X-ray visualizer, imager, or information provider 100 could improve the public's and professional perception and acceptance thereof.

With certain embodiments of the Compton scattered X-ray visualizer, imager, or information provider 100, the user such as a doctor, researcher, veterinarian, surgeon, etc. (each of whom may be involved in examination, surgery, and/or research, etc.) can appropriately subsurface visualize, image, and/or provide information relating to the at least the portion of the individual 82. Depending on context, certain types of Compton scattered X-ray visualization, imaging, or information providing can be applied from nearby or proximate the surface 168 down to within the at least one visualization, imaging, or information providing depth range to the at least one prescribed visualization, imaging, or information providing depth. Certain embodiments of the Compton scattered X-ray visualizer, imager, or information provider 100 can vary from the micron range up to and including substantially through a major portion of the individual 82.

The resolution of certain embodiments of the Compton scattered X-ray visualizer, imager, or information provider 100 might be effective for certain diagnosis, examination, surgical, research, and other purposes; and certain embodiments Compton scattered X-ray visualizer, imager, or information provider could provide desired or appropriate resolutions through the visualized, imaged, or information provided portion of the individual 82.

It may be desired for certain visualization, imaging, or information providing applications to adjust and/or control the visualization, imaging, or information providing by certain embodiments of the Compton scattered X-ray visualizer, imager, or information provider 100. Within this disclosure, the term "control", as it relates to Compton scattered X-ray visualization, imaging, or information providing, can mean, but is not limited to, controlling the energy level, frequency, angle, additional matter imaged through, and/or other characteristics of the applied X-ray 120 by certain embodiments of the Compton scattered X-ray visualizer, imager, or information provider 100. Within this disclosure, the term "adjust" can mean, but is not limited to, depending on context, adjusting the at least one range of visualization, imaging, or information providing depth to the at least one prescribed visualization, imaging, or information providing depth. Such control or adjustment can occur by altering or adjusting certain characteristics of the applied X-rays such as energy level, frequency, depth, angle from perpendicular to the surface 168, etc.

Such control and/or adjustment of certain embodiments of the Compton scattered X-ray visualizer, imager, or information provider 100 can make the Compton scattered X-ray visualizer, imager, or information provider more applicable to a variety of applications. For example, certain controllable embodiments of the Compton scattered X-ray visualizer, imager, or information provider 100 can visualize, image, and/or provide information a variety of matter within the at least the portion of the individual at a variety of depths, or range of depths. Certain embodiments of the Compton scattered X-ray visualizer, imager, or information provider 100 can adjust the depth of Compton scattered X-ray visualization, imaging, or information providing and/or their resolution based on controlling the X-ray characteristics of the applied X-ray. Certain embodiments of the Compton scattered X-ray visualizer, imager, or information provider 100 can therefore be configured to be adjustably tunable, such that the user can adjust the energy of the X-ray photons. By adjusting the energy of the X-ray photons of the applied X-rays, for example, the at least one substantially scattered depth range to the at least one prescribed substantially scattered depth of Compton scattered X-ray visualization, imaging, or information providing into the matter of the at least the portion of the individual can be adjusted.

Certain embodiments of the Compton scattered X-ray visualizer, imager, or information provider 100 can utilize steered, focused, directed, filtered, scanned, and/or processed X-rays. Certain embodiments of the Compton scattered X-ray visualizer, imager, or information provider 100 can visualize, image, and/or provide information along a variety of one, two, or three dimensional patterns, in certain instances such as by scanning to create a two or three dimensional visualize, image, and/or provide information within the at least the portion of the individual 82. Certain embodiments of the Compton scattered X-ray visualizer, imager, or information provider 100 can be configured to be low or non-contact, as well as low or non-invasive, such as by utilizing an embodiment of the emitter portion 150 having no or limited contact with the surface 168.

Certain embodiments of the Compton scattered X-ray visualizer, imager, or information provider may allow the operation and/or structure of the detector portion and the display portion to be at least partially combined. Certain embodiments of the Compton scattered X-ray visualizer, imager, or information provider 100 can allow the user, or a controller, to alter the Compton scattered X-ray visualization, imaging, or information providing of subsequent or sequential depth visualizations, images, and/or provided information based at least in part on results from prior captured images. Such sequential Compton scattered X-ray visualization, imaging, or information may allow such exemplary users as doctors, surgeons, veterinarians, researchers, etc. to determine the region within the at least the portion of the individual that is being visualized, imaged, or have information provided. It may be desirable to provide for such changes in visualization, imaging, or information providing using a variety of image processing techniques to effect such changes as magnification; zooming; changing a relative angle, depth, or position of the visualization, image, or provided information, and/or changing a variety of other visualizing, imaging, or information providing parameter such as may be desired or useful by the user or individual.

A variety of configurations and/or operational combinations of the at least one emitter portion(s) 150, the at least one Compton scattered X-ray receiving assembly 151, the at least one detector portion, and/or the at least one display portion(s) 154 may be associated with the Compton scattered X-ray visualizer, imager, or information provider 100. As described in this disclosure, certain embodiments of the at least one emitter portion 150 can be directed such as to apply X-ray based electromagnetic radiation at a precisely controllable region of the at least the portion of the individual 82; such as may thereupon be detected by certain embodiments of the at least one detector portion 152. Such application and/or detection of the electromagnetic radiation can be done once, multiple continuous times without feedback by a user and/or controller, multiple sequential times with feedback by a user and/or controller, or other ways or combinations thereof. The application or detection of X-rays may rely on transmission of a variety of beams such as pulse, continuous, pencil beam, fan, flooding, or other types of the applied X-rays.

Certain embodiment(s) component(s), and/or portion(s) of the Compton scattered X-ray visualizer, imager, or information provider 100 can be configured as an at least partially external device, such as to depth-examine the at least some matter of the at least the portion of the individual either directly through the matter itself, or alternately below an either external or internal surface 168 of the at least the portion of the individual. For certain external embodiments of the Compton scattered X-ray visualizer, imager, or information provider 100, the "subsurface" Compton scattered X-ray visualization, imaging, or information providing can, depending upon context, relate to Compton scattered X-ray visualization, imaging, or information providing beneath the skin or other external surface. Certain embodiment(s) component(s), and/or portion(s) of the Compton scattered X-ray visualizer, imager, or information provider can be configured as an at least partially internal device, such as to examine an internal portion of the individual 82 through an incision, or alternately through a normally open opening in the at least the portion of the individual.

For certain internal embodiments of the Compton scattered X-ray visualizer, imager, or information provider 100, a "subsurface" undergoing visualization, imaging, or information providing can, depending upon context, relate to being applied through a normally open portions of the individual, such as beneath the surface 168, within a region at least partially forming the lumen, within a cavity, or within another body opening. For internal embodiments of the Compton scattered X-ray visualizer, imager, or information provider 100 that can be applied through normally closed portions of the individual (e.g., an incision, a wound, etc.), the term "subsurface" can, depending upon context, including the Compton scattered X-ray visualizer, imager, or information provider 100 being applied through the normally-closed opening, incision, etc. Various embodiments of the Compton scattered X-ray visualizer, imager, or information provider 100 can visualize, image, or provide information through a variety of such matter as tissue, bone portions, fluid, blood, etc. through the range of depths to the prescribed penetration depth 170, as described with respect to FIG. 18.

Figure 19:
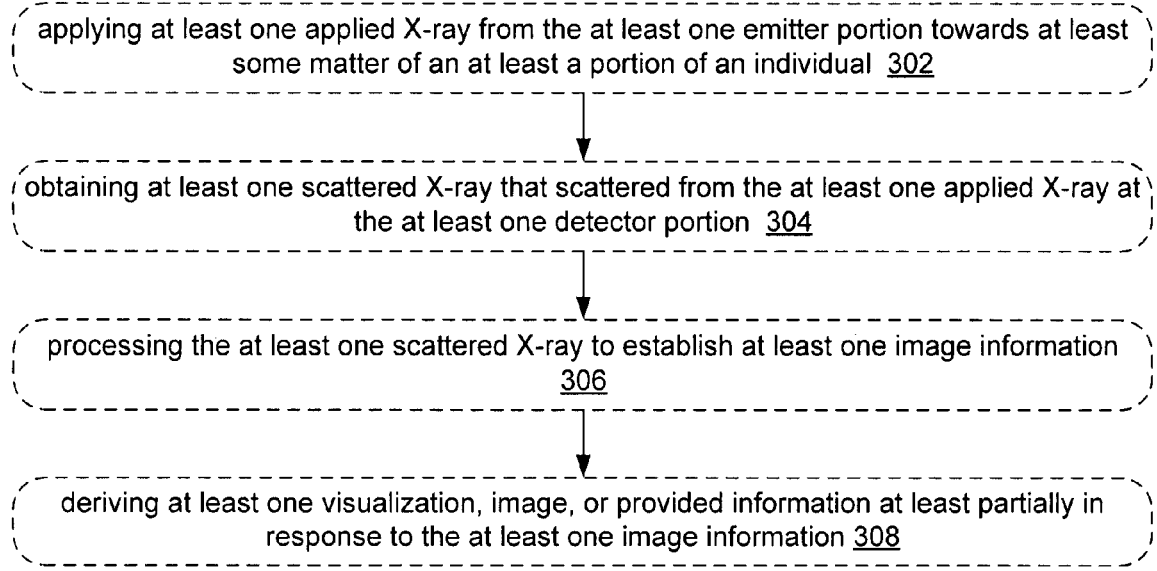
FIG. 19 shows a block diagram of a Compton scattered X-ray visualization, imaging, or information providing process using the Compton scattered X-ray visualizer, imager, or information provider such as described with respect to FIG. 18.
Figure 20:
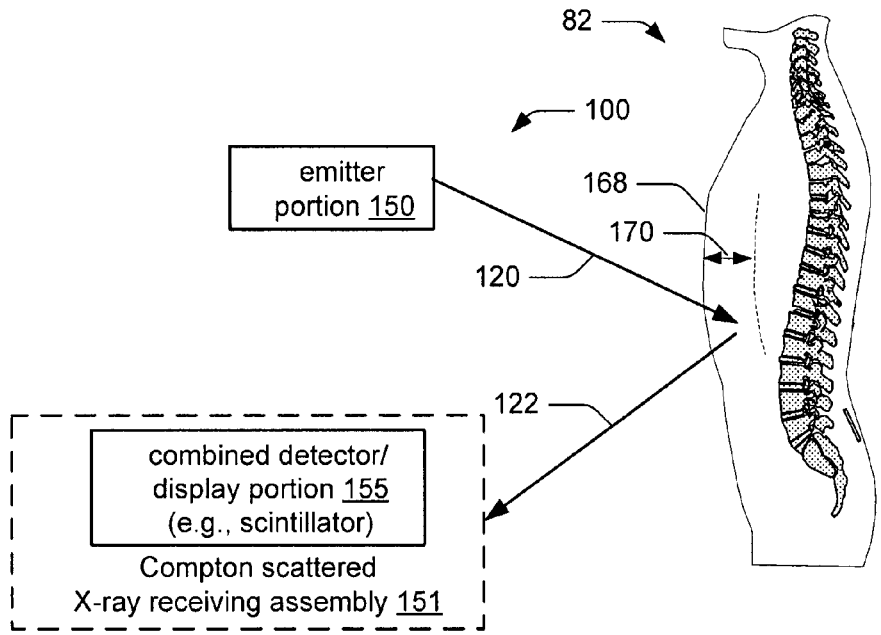
FIG. 20 is a diagram of the at least the portion of the individual being visualized, imaged, or image provided by another embodiment of the Compton scattered X-ray visualizer, imager, or information provider.

FIG. 19 shows one embodiment of a flowchart of a Compton scattered X-ray visualization, imaging, or information providing technique 300 that can be performed by the embodiment of the Compton scattered X-ray visualizer, imager, or information provider 100 as described in this disclosure of the Compton scattered X-ray receiving assembly 151. Certain embodiments of the Compton scattered X-ray receiving assembly 151 can include operationally distinct ones of the at least one detector portion 152 from the at least one display portion 154. Certain embodiments of the subsurface Compton scattered X-ray visualization, imaging, or information providing technique 300 can include one or more operations 302, 304, 306, and/or 308 to be applied within the at least one visualization, imaging, or information providing depth range to the at least one prescribed visualization, imaging, or information providing depth into the at least some matter.

Certain embodiments of operation 302 can include, but is not limited to, applying at least one applied X-ray from an at least one emitter portion 150 towards an at least some matter of an at least a portion of an individual. For example, certain embodiments of the at least one emitter portion(s) 150 can apply X-rays toward the desired matter (e.g., tissue, fluid, bone, teeth, joint, fat, muscle, etc.) of the at least the portion of the individual in a manner that the X-rays can be Compton scattered within the at least some matter. Such application of applied X-rays can thereupon be used by certain embodiments of the Compton scattered X-ray visualizer, imager, or information provider 100 to allow depth visualizing, imaging, or information providing. A considerable percentage of the applied X-rays that are scattered and returned to be detected by the Compton scattered X-ray receiving assembly 151 could be scattered between within the at least one substantially scattered depth range to the at least one prescribed substantially scattered depth. The value of the at least one substantially scattered depth range to the at least one prescribed substantially scattered depth can be based at least partially on the energy level of the X-ray photons of the applied X-ray 120. The energy level of the X-ray photons of the applied X-ray 120 is considered to be directly related to frequency.

Certain embodiments of the operation 304 can include, but is not limited to, obtaining at least one (e.g., Compton) scattered X-ray that scattered from the at least one applied X-ray at the at least one detector portion 152. In effect, certain of the Compton scattered X-rays 122 can be received at the detector portion 152, at least partially based on the scattering of the applied X-rays 120 at the scattering event (e.g., within the at least some matter of the at least the portion of the individual). Certain of the applied X-rays can be applied by the at least one emitter portion 150 during operation 302.

Certain embodiments of the operation 306 (which is optional) can include, but is not limited to, processing the at least one Compton scattered X-ray received during operation 304, to visualize, image, and/or provide information about the at least the portion of the individual. For example, certain embodiments of the visualization, imaging, or information providing controller 97 can derive visualizations, images, and/or provide information such as can be displayed.

Certain embodiments of the operation 308 can include, but is not limited to, deriving the at least one visualization, image, and/or provided information as can be at least partially processed and/or captured during operation 306. For example, certain embodiments of the display portion 154 and/or the Compton scattered X-ray receiving assembly 151 (which may be a scintillator and/or fluoroscope embodiment) can display a visualization, image, and/or provide information of at least a portion of the matter of the at least the portion of the individual.

Figure 21:
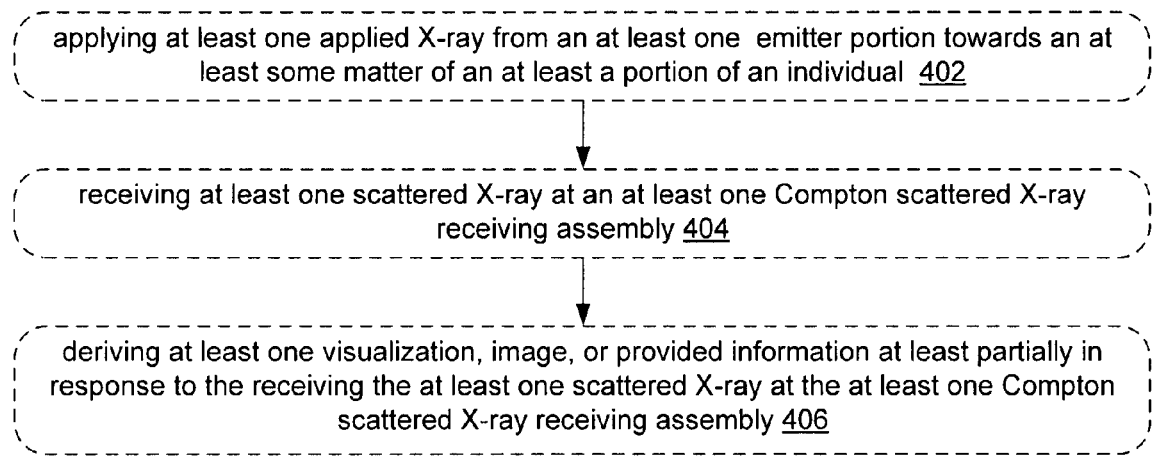
FIG. 21 shows a block diagram of another Compton scattered X-ray visualization, imaging, or information providing process using the Compton scattered X-ray visualizer, imager, or information provider such as described with respect to FIG. 20.

Certain embodiments of the Compton scattered X-ray visualizer, imager, or information provider may be configured to, at least partially, convert scattered X-rays directly into viewable or visible light, without the processing the scattered X-ray such as may be provided with certain scintillator embodiments of the Compton scattered X-ray visualizer, imager, or information provider 100. FIG. 21 shows one embodiment of a flowchart of a Compton scattered X-ray visualization, imaging, or information providing technique 400 that can be performed by the embodiment of the Compton scattered X-ray visualizer, imager, or information provider 100 without processing. Certain embodiments of the subsurface Compton scattered X-ray visualization, imaging, or information providing technique 400 can include one or more of operations 402, 404, and/or 406 as described in this disclosure to visualize, image, and/or provide information using a scintillator (and/or fluoroscope) embodiment of the Compton scattered X-ray receiving assembly 151. Certain scintillator (and/or fluoroscope) embodiments of the Compton scattered X-ray receiving assembly 151 can visualize, image, or provide information within the at least one visualization, imaging, or information providing depth range to the at least one prescribed visualization, imaging, or information providing depth into the matter of the at least the portion of the individual.

Certain embodiments of the operation 402 can include, but is not limited to, applying at least one applied X-ray from the at least one emitter portion towards the at least some matter of the at least the portion of the individual. For example, certain embodiments of the at least one emitter portion(s) 150 can apply X-rays toward the desired matter (e.g., tissue, fluid, bone, teeth, joint, fat, muscle, etc.) of the at least the portion of the individual in a manner that the X-rays can be Compton scattered within the matter.

Certain embodiments of the operation 404 can include, but is not limited to, receiving at least some (e.g., Compton) X-ray at the at least one Compton scattered X-ray receiving assembly 151 as described in this disclosure, in response to the applied X-rays 120 applied by the at least one emitter portion 150. A considerable percentage of the applied X-rays that are scattered and returned to be detected by the Compton scattered X-ray receiving assembly 151 will be scattered through the at least one substantially scattered depth range to the at least one prescribed substantially scattered depth. Such scattering can be based at least partially on the energy level (or frequency, which is related thereto) of the X-ray photons of the applied X-ray 120, as described in this disclosure.

Certain embodiments of the operation 406 can include, but is not limited to, deriving at least one visualization, image, or provided information at least partially in response to the receiving the at least one scattered X-ray at the at least one Compton scattered X-ray receiving assembly 151. For example, certain scintillator (and/or fluoroscope) embodiments of the display portion 154 and/or the Compton scattered X-ray receiving assembly 151 can display a depth visualization or image of at least a portion of the matter of the individual.

Certain embodiments of the Compton scattered X-ray visualizer, imager, or information provider 100 thereby can provide a mechanism to visualize, image, and/or provide information down to, or at, one or more depths (in many instances controllably) into at least partially X-ray matter such as to capture depth visualizations, images, and/or provided information. Within this disclosure, much of the matter being depth-imaged by certain embodiments of the Compton scattered X-ray visualizer, imager, or information provider 100 can be expected to be interspersed, mixed, compounded, or at least partially combined with other matter such as bones, metal, etc. within the individual such as typically exists in at least certain portions of the individual 82. Certain embodiments of the X-ray Compton scattered X-ray, such as can be performed by certain embodiments of the Compton scattered X-ray visualizer, imager, or information provider 100, can thereby be used to visualize, image, and/or provide information matter that can be at least partially combined with relatively electromagnetic radiation-Compton scattered X-ray matter.

Certain embodiments of the Compton scattered X-ray visualizer, imager, or information provider 100 can be configured to be used to visualize, image, and/or provide information at least portions of certain matter that is relatively "hard", considering the applied X-rays 120, such as bones, bone fragments or portions, spinal portions, cranial portions, metal, implants, etc. Such re-configurations as altering the frequencies of the applied X-rays 120 may be used to configure the Compton scattered X-ray visualizer, imager, or information provider 100 to visualize, image, and/or provide information matter(s) having varied characteristics. By depth visualizing, imaging, or information providing of hard matter such as bones, spinal portions, certain implants, etc., it can become possible to examine a two-dimensional, or three-dimensional portion of the bone, etc. with considerable resolutional accuracy. Such depth visualizing, imaging, or information providing of hard matter can be controlled and/or adjusted as described in this disclosure. Such Compton scattered X-ray visualization, imaging, or information providing of hard matter can be performed prior to surgery or examination, during surgery or examination, following surgery or examination. Certain embodiments of the Compton scattered X-ray visualizer, imager, or information provider 100 can visualize, image, and/or provide information hard matter in combination with other matter. For example, a bone can be imaged in combination with associated joints, muscles, tendons, surgical pins, plates, etc. Additionally, a brain portion can be visualized, imaged, or have information provided relative to associated cranial portions (e.g., skull), etc. Providing such adjustability or control of Compton scattered X-ray visualization, imaging, or information providing can allow doctors, surgeons, dentists, etc. to obtain accuracy of Compton scattered X-ray visualization, imaging, or information providing of a variety of matter within the at least the portion of the individual.

Certain embodiments of the Compton scattered X-ray visualizer, imager, or information provider 100 can be configured to visualize, image, or provide information relating to a combination of at least some soft matter such as tissue, blood cells, bodily fluids, etc. as combined with certain embodiments of the at least some hard matter such as bones, teeth, etc. Such visualization, imaging, or providing information of a combination of at least some hard matter with at least some soft matter may be particularly useful when considering junction matter regions, such as the intersection of gums with teeth; the intersection of bones with tendons, ligaments, muscles, tissue, etc.

A variety of embodiments of the Compton scattered X-ray visualizer, imager, or information provider 100 can be configured to image edges, sides, inconsistencies, or non-uniformities of matter, tissue, organs, etc. It may therefore be possible to locate particular organs, matter, tissue, etc. based on such inconsistencies, or non-uniformities of the organs, matter, tissue, etc. For example, as applied X-rays 120 are applied to visualize, image, and/or provide information a region of the at least the portion of the individual where an organ is situated, the edge portion of the organ may scatter the applied X-rays in a direction that differs from the remainder of the organ. Such Compton scattered X-ray along the edge may lead into a detectable difference of the depth Compton scattered X-ray image at the edge of the X-ray Compton scattered X-ray organ. Such differences of characteristics of Compton scattered X-ray based at least in part on angle, position, or other aspect of the matter can be used by certain embodiments of the Compton scattered X-ray visualizer, imager, or information provider 100, as described in this disclosure.

Figure 8:
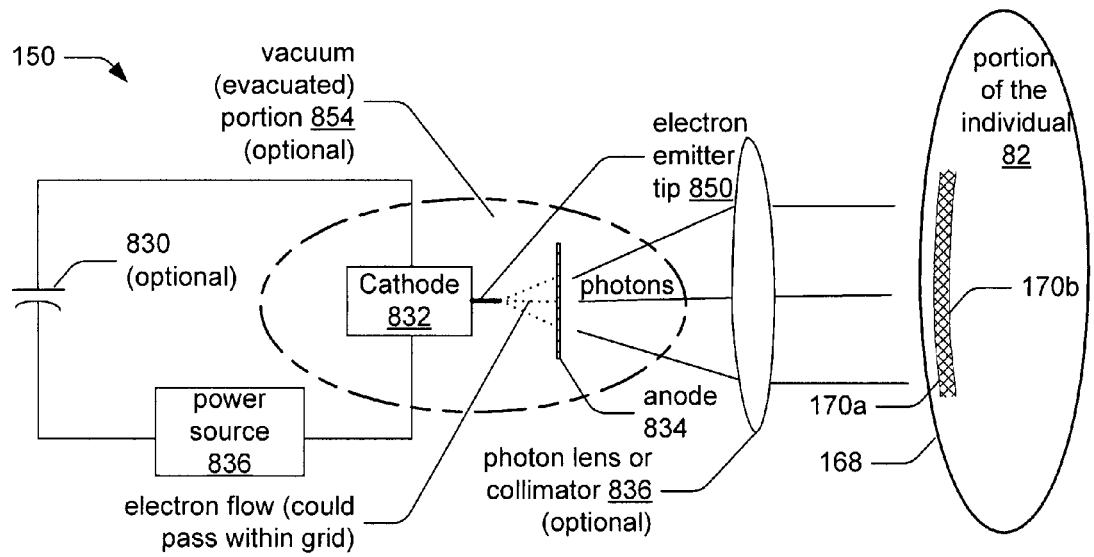
FIG. 8 shows a diagram of one embodiment of an at least one emitter portion that can be included in certain embodiments of the Compton scattered X-ray visualizer, imager, or information provider.
Figure 9:
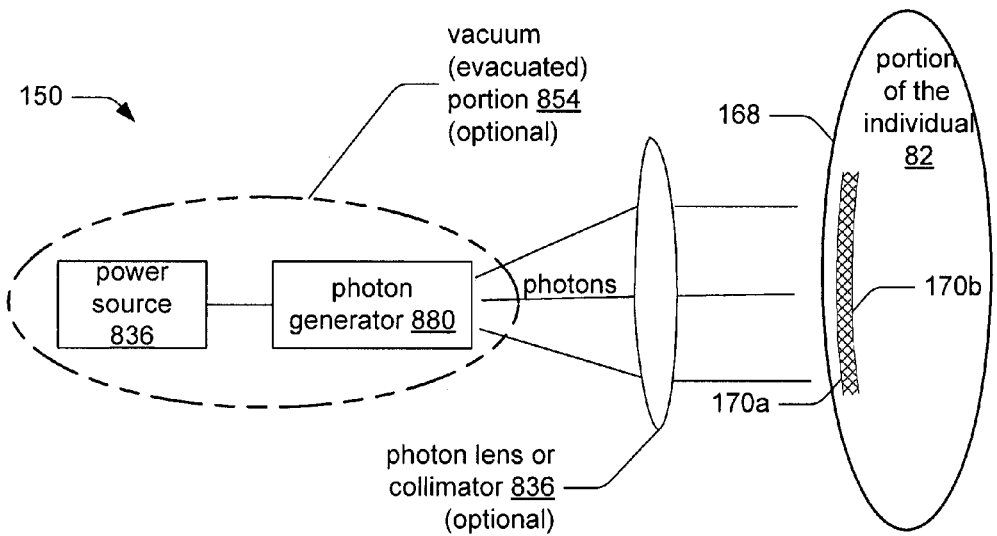
FIG. 9 shows a diagram of another embodiment of the emitter portion that can be included in certain embodiments of the Compton scattered X-ray visualizer, imager, or information provider.

FIG. 8 shows one embodiment of the emitter portion 150 that can be included in certain embodiments of the Compton scattered X-ray visualizer, imager, or information provider 100, as described in this disclosure, while FIG. 9 shows another embodiment. Certain embodiments of the at least one emitter portion 150 can emit the applied X-rays toward the at least the portion of the individual 82 over an angle such as with a pencil beam, fan beam, area beam, or other beam; while other embodiments can emit the applied X-rays in a narrow beam such as a pencil beam. Certain embodiments of the emitter portion 150 can emit collimated X-rays, while others can emit incoherent X-rays. Certain embodiments of the at least one emitter portion 150 can include such adjustable optical elements as Bragg optics elements to adjust the pattern/direction of the applied X-ray emission, while others may not be adjustable or controllable. The configuration, design, and usage of certain embodiments of the emitter portion 150 can depend, at least in part, on the particular characteristics of the Compton scattered X-ray visualization, imaging, or information providing (as well as the characteristics of the at least the portion of the individual being visualized, imaged, or have information provided).

In general, certain embodiments of the emitter portion 150 are therefore configured to direct at least one X-ray towards the at least the portion of the individual. Certain embodiments of the at least one emitter portion 150, can include, but are not limited to, a power source 836, a cathode 832, a field emission tip 850, and/or an anode 834. Other illustrative potential structures of the at least one emitter portion 150 are described in this disclosure, while still others are generally understood by those skilled with X-ray tubes and generating devices. Certain embodiments of the power source 836 and the cathode 832 can be arranged in an electron circuit such as to provide an electric (e.g., electron) flow from the cathode 832, such as can be at least partially discharged via the electron emitter tip 850 and the anode 834. Certain embodiments of the electron emitter tip 850 can be in electrical communication with the cathode, such as to be configured as to be capable of discharging the electron flow that can be at least partially directed at the anode 834.

Certain embodiments of the electron emitter tip 850 may be configured as an electron discharge region that can generate and/or direct the electron flow in a pattern, frequency, energy level, configuration, or other parameter as described with respect to FIG. 8. Certain embodiments of the electron emitter tip 850 are configured to establish the electron flow, and as such may include such elements as a triode, antenna, nanostructure, or other such component. Certain embodiments of the electron emitter tip 850 can also be configured to include one or more (carbon) nanotubes, which may be effectively configured as electromagnetic radiation antennas. Certain embodiments of the electron emitter tip 850 can thereby utilize one or more discrete elements, while other embodiments can utilize a number or array of carbon nanotubes, etc.

Certain embodiments of the electron emitter tip 850 can be fixed, while other embodiments can be adjusted or displaced such as to change such as to alter the pattern of electron emission, such as by moving the electron source. One example of a movable or adjustable electron emitter tip 850 can include, for example, utilizing adjustment or displacement of a flexible carbon nanotube electrically coupled to the cathode.

Certain embodiments of the anode 834 can be configured and/or biased during operation as to attract electrons from the combination of the cathode 832 and/or the electron emitter tip 850. Upon contact of the electron flow into certain embodiments of the anode 834, certain embodiments of the anode can thereupon generate X-ray photons of the desired frequency and/or energy level. In certain embodiments of the emitter portion 150, the electron flow emanating from the electron emitter tip 850 can remain substantially static, and as such may not be directable or scannable. With other embodiments of the emitter portion 150, the electron emitter tip 850 of the cathode 832 can steer, scan, or otherwise displace the electron flow to the desired location relative to the anode 834. Certain embodiments of the Compton scattered X-ray visualizer, imager, or information provider 100 can be configured to include a stepper motor, or other motor or displacement mechanism (not shown) to control or adjust the positions of the emitter portion 150 and/or the detector portion 152. The respective emitter portion 150 and/or detector portion 152 may be configured to operationally pan and tilt during operation such as to provide a desired degree of adjustability. Certain embodiments of the electron emitter tip 850 can be configured as an X-ray source (e.g., in certain instances the size may be in the small mm range such that it may, in certain instances, fit within certain blood vessels or lumens such as to allow depth visualizing, imaging, or information providing from these locations). In other embodiments, the size of the electron emitter tip 850 may be considerably larger such as to interface with an external or larger portion of the individual 82.

Certain embodiments of the electron emitter tip 850 beam can be configured to be displaceable or moveable such as to allow control and/or adjustment of the Compton scattered X-ray visualizer, imager, or information provider 100, such as by scanning, shifting, axially moving, beam focusing control, rotating, panning, or otherwise moving to alter the path of the electron flow. For example: one or more Micro Electro-Mechanical System (MEMS) devices, a rotating crystal, an electromechanical or X-ray scanning mechanism, or other suitable means may be included in the certain embodiments of the electron emitter tip 850 such as to provide control and/or adjustment of the electron emitter tip. Certain embodiments of the emitter portion 150 can be configured to produce X-rays that are at least partially incident on a lens (not shown), but which may include a crystal which is configured as a lens) that can be displaceable to move and/or scan the X-ray beam. Alternately, certain embodiments of the emitter portion 150 can be configured as an array type device, with different ones are different groups of the elements being a controlled either manually or at least partially by the depth visualization, imaging, or information providing controller 97. Such scanning of the X-ray beam can follow a raster-type scan, use a fan type beam, pencil type beam, or other scan, perhaps similar to those utilize to in certain other conventional tomography scanners, or may follow some other pattern. In certain instances, the scanning of the at least one emitter portion 150 may be coordinated with the scanning of the at least one detector portion 152, or alternately a scanning detector portion may be associated with an emitter portion that generates X-rays which effectively "flood" the at least the portion of the individual 82 being visualized, imaged, or have information provided. The selection of the particular scanning or flooding configuration may affect X-ray dosage of the user and/or nearby individuals, as described in this disclosure.

Various embodiments of the power source 836, as described with respect to FIG. 8, may be configured as desired, as long as it provides adequate power to the cathode to establish the electron flow from the particular embodiment of the electron emitter tip 850, depending on the configuration of electron emitter tip as well as the anode. Certain embodiments of the emitter portion 150 can thereby be configured to direct electrons, as provided by the power source 836, the cathode 832, and/or the electron emitter tip 858. The electrons may therefore be directed from the electron emitter tip 850 to the anode 834 as described with respect to FIG. 8. Altering or controlling the electron flow may have a corresponding effect on the generation of photons by the anode 834. Certain embodiments of the emitter portion 150 may alternately be powered optically, such as to include the photon generator 880 as applied to the power source 836, as described with respect to FIG. 9.

Certain embodiments of the photon generator 880 can alternately utilize, for example, an optically fed photoelectric stack, an optical fed battery, a solar panel, or a variety of other device that can generate X-ray photons. Certain embodiments of the at least one emitter portion 150 utilizing the photon generator 880 as described with respect to FIG. 9, can be adjustable, controlled, fixed, dispersed, and/or focused, etc. as to control and/or adjust generation of X-ray photons as described with respect to the FIG. 8 embodiment of the emitter portion.

With certain embodiments of the emitter portion 150, as described with respect to FIG. 8, an electron grid (not shown) may be positioned, adjusted, and/or controlled from a location such as operationally proximate to the electron flow. For example, the electron grid may be situated adjacent a path at least partially situated between the electron emitter tip 850 and the anode 834. Certain embodiments of the electron grid may be configured, upon activation, to steer, scan, or otherwise control the flow or velocity of electrons passing from the electron emitter tip 850 to the anode 834. Such steering, scanning, accelerating, decelerating, or otherwise controlling the flow or velocity of electrons can in addition control or alter the characteristics or position(s) at which the photons generated contact the particular anode 834.

Certain basic embodiments of the anode 834 can be configured in a variety of forms. For example, the anode can include a thin metal foil, or other configuration, that can be positioned in suitable proximity to the electron emitter tip 850. Certain embodiments of the anode 834 can be provided to be controllable and/or adjustable such as to include at least one anode wheel, cassette, cartridge, etc. (not shown) that can emit X-ray photons whose characteristics can be adjusted and/or controlled, such as by displacement, rotation, etc., such as to provide varied anode metals or other materials anodes (or having different shapes, dimensions, or other configurations) in communication with the electron flow.

By using an anode wheel, cartridge, canister, or other such mechanism that can alter the material and/or configuration of the anode, the characteristics of the X-ray photons (such as energy level and/or frequency) being generated by the at least one emitter portion can be controlled or altered. Such controlling and/or altering of the X-rays being emitted can control and/or alter the at least one substantially scattered depth range to the at least one prescribed substantially scattered depth, and thereby the at least one visualization, imaging, or information providing depth range to the at least one prescribed visualization, imaging, or information providing depth, being performed by certain embodiments of the Compton scattered X-ray visualizer, imager, or information provider 100 as described in this disclosure. Certain other uses of anode wheels is known in certain conventional X-ray tubes, which can function largely to maintain all portions of the anode within acceptable temperature ranges by altering the portion of the anode wheel which the electron flow contacts, and is therefore being instantaneously heated by the electron flow. The anode wheels could also include a motive mechanism (not shown) to allow suitable rotation and/or displacement of the anode wheel (either rotationally and/or axially) such as may utilize a stepper motor, a pneumatic drive, an electric motor, etc. Certain embodiments of the anode wheel could also include a variety of control mechanisms (not shown) to control such rotation and/or displacement. A variety of such control, rotation, and/or displacement mechanisms are generally understood by those skilled in the anode wheel art.

Certain embodiments of the anode 834 can thereby be configured to generate the X-ray photons at controllable and/or adjustable energy levels, frequencies, or other characteristic based at least in part on the characteristic of the electron flow being applied to the anode 834, and additionally on the material of the anode 834. As such, it may be possible to generate X-rays having particular characteristics by selecting particular materials (e.g., different metals) or configurations of the anode that can be either shifted in position relative to (e.g., in front of) the electron flow. Additionally, moving or angling the anode relative to the electrons (or vice versa) may result in different characteristics of the applied X-ray. Certain embodiments of the Compton scattered X-ray visualizer, imager, or information provider 100 can thereby be adjusted or controlled by shifting or steering the electron flow relative to the anode 834 such that the portion of the anode which the electron flow contacts may be made of multiple varied materials and/or configurations. Certain embodiments of the anode 834 can be configured in the shape of a wheel (e.g., to form an anode wheel) that when rotated can result in positioning of the desired metal in contact with the electron flow such as to provide control and/or adjustment of the applied X-rays.

There can be a variety of additional components that can be applied to certain embodiments of the emitter portion 150 within certain embodiments of the Compton scattered X-ray visualizer, imager, or information provider 100 as described with respect to FIGS. 8 and/or 9. Certain embodiments of the at least one emitter portion 150 can further include a collimator or X-ray lens 842 that can focus, angle, or direct the photons emitted from the emitter portion as desired. Certain embodiments of the X-ray lens or collimator 842 can be controllable such as to provide control of such Compton scattered X-ray visualization, imaging, or information providing processes as emitter portion directability, signal or image filtering, image zooming, starting, stopping, or pausing Compton scattered X-ray visualization, imaging, or information providing, signal or image processing, etc.

Certain embodiments of the Compton scattered X-ray visualizer, imager, or information provider 100 can utilize an optional vacuum (at least partially evacuated) portion 854, as described with respect to FIGS. 8 and/or 9, which can be utilized to limit contact of the electrons of the electron flow traveling from the cathode 832 to the anode 834 with extraneous gas, air, suspended solids, liquid, and/or other minute particles suspended in the air. As such, certain embodiments of the optional vacuum (at least partially evacuated) portion 854 can limit interaction of the photons with additional particles. Additionally, certain embodiments of the vacuum portion 854 may thereby be configured to at least partially limit combustion of certain of the electronic components contained therein as a result of the heat being generated upon the exposure to air. Certain embodiments of the vacuum (at least partially evacuated) portion 854 can thereby be configured as a vacuum tube, such as may be configured as an interlumenal X-ray source and is generally understood by those skilled in the X-ray tube technologies.

Certain embodiments of a capacitor 830 can optionally be arranged in an electronic circuit including the power source 836 and the cathode 832 as described with respect to FIG. 8. Certain embodiments of the cathode 832 can be configured with the capacitor 830 to store particular levels of electric voltage such as can be applied to the cathode 832, and subsequently released as desired as the electron flow via the electron emitter tip 850.

While this disclosure describes certain embodiments of the at least one emitter portion 150, it is to be understood that any mechanism that can transmit X-rays whose frequency, energy level, or other characteristic can be controlled or adjusted may be used in certain embodiments of the Compton scattered X-ray visualizer, imager, or information provider 100. The embodiments of the at least one emitter portion 150 as described in this disclosure with respect to FIGS. 1, 8, 9, as well as other locations in this disclosure, is intended to be illustrative in nature, but not limiting in scope. As mentioned in this disclosure, for example, certain embodiments of the emitter portion 150 could be at least partially replaced by an optical-generating portion as described with respect to FIG. 9. It is envisioned that the at least one emitter portion 150 can thereby be configured slightly differently in operation and/or configurations, such as to generate photons in a different manner, but are still intended to be within the scope of the present disclosure as being within the claimed limitations. For example, the vacuum (evacuated) portion 854, such as a vacuum tube, may include one or more discrete emitter tip elements or one or more (carbon) nanotubes be configured as the electron emitter tip 850 as described with respect to FIG. 9.

Certain embodiments of the emitter portion 150 of the Compton scattered X-ray visualizer, imager, or information provider 100, as described with respect to FIGS. 8 and 9, may therefore be adjustable and/or controllable such as by being configured for repositioning, angling, filtering, or some other suitable technique. For instance, certain embodiments of the Compton scattered X-ray visualizer, imager, or information provider 100 can include a stepper motor such as may be configured such that it can pan and tilt, thereby providing some control and/or adjustment to emitted photons that can be emitted by the at least one emitter portion 150. Such stepper motors may thereupon be considered to represent one illustrative embodiment of an adjustment or control portion that can also be accomplished by use of a photon lens or collimator 842.

Figure 22:
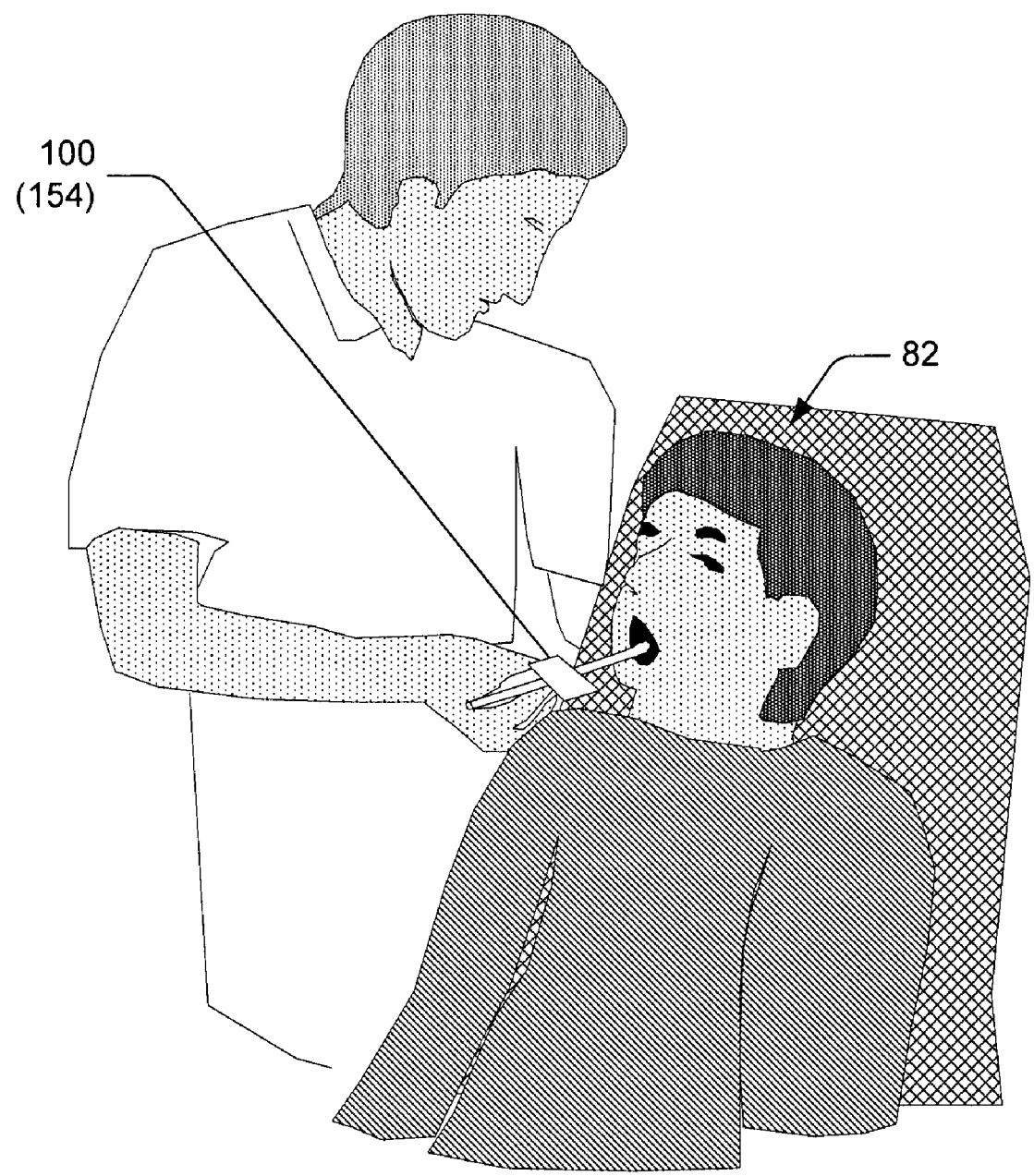
FIG. 22 is a diagram of an embodiment of the Compton scattered X-ray visualizer, imager, or information provider as used by a dentist.

Certain embodiments or configurations of the Compton scattered X-ray visualizer, imager, or information provider 100, as described with respect to FIG. 1, can visualize, image, and/or provide information teeth, dental plates or surfaces 168, etc. such as may be used by dentists, oral hygienists, etc. as described with respect to FIG. 22. Certain embodiments of the Compton scattered X-ray visualizer, imager, or information provider 100 can allow Compton scattered X-ray visualization, imaging, or information providing of at least one tooth at one or more angles, positions, magnifications, etc. as desired. The particular display portion 151 that may be selected may be based upon user preference, ease of use, design choice, etc. The embodiment of the Compton scattered X-ray visualizer, imager, or information provider 100, as illustrated in FIG. 22, could be attached to a probe, for example. Similar user configurations of certain embodiments of the Compton scattered X-ray visualizer, imager, or information provider 100 can be applied to tools being used by doctors, surgeons, veterinarians, as well as other users as described in this disclosure. As the visualization, imaging, or information providing can be performed by certain embodiments of the Compton scattered X-ray visualizer, imager, or information provider 100 from a number of different angles, positions, etc., it may be desired to display at least the display portion reflect the change in angle, position, etc.

As the user/dentist, as illustrated in FIG. 22, moves or repositions the probe, it might be preferred to have the Compton scattered X-ray visualizer, imager, or information provider 100 to adequately reflect the angle or position of the visualization, imaging, or information providing. With sufficient changes of the angle, material of the anode, and/or position of the visualization, imaging, or information providing, certain embodiments of the Compton scattered X-ray visualizer, imager, or information provider 100 can derive and/or display a three-dimensional model of the one or more teeth. Certain embodiments of the Compton scattered X-ray visualizer, imager, or information provider 100 can therefore provide information or images such as to determine where and/or how to treat the at least the portion of the individual (patient). Certain dental embodiments of the Compton scattered X-ray visualizer, imager, or information provider 100 can be applied to a dental drill, and thereupon be displayed at a location and magnification such as can be made viewable and/or visible to the user. Certain embodiments of the Compton scattered X-ray visualizer, imager, or information provider 100 that are operatively associated with certain tools, tactile providers, etc. need not be directly connected (or may be removably connected, to the tool, tactile provider, etc.

Certain of the images can also be provided to the patient as well using the same or other Compton scattered X-ray visualizer, imager, or information provider 100. Certain embodiments of the Compton scattered X-ray visualizer, imager, or information provider 100, when attached to a tool performing a desired operation, can act as a double check to ensure the tooth being imaged by the user is indeed the one that should be dealt with. For example, a dentist can check that the correct tooth is being drilled. A doctor can ensure the correct arm, leg, or other body part is being treated, etc. There can be a large variety of tools that may be used by such users as surgeons, assistants, veterinarians, dentists, etc. as generally understood to be used in each particular area. It is envisioned that certain embodiments of the Compton scattered X-ray visualizer, imager, or information provider 100 may be applied to a variety of tools and/or tactile feedback devices that could benefit by use with visualization, imaging, or information providing, as described in this disclosure.

The location of the drill or other tool including certain embodiments of the Compton scattered X-ray visualizer, imager, or information provider 100 as taken relative to the decayed or damaged portions of the teeth can be detected on a substantially real-time, intermittent, or as desired basis. Certain embodiments of the Compton scattered X-ray visualizer, imager, or information provider 100 can be configured to provide tactile feedback, which in the case of a dentists are dental assistant would be useful in determining the security of a tooth, the degree of tooth decay within a particular tooth, the security of braces, caps, filling, dental plates, or other device within the individual. By using certain dental depth visualizing, imaging, or information providing embodiments of the Compton scattered X-ray visualizer, imager, or information provider 100, it may not be necessary for dental patients to use conventional X-ray plates (positioned between the teeth of the person that has to be bitten down by the person) during dental X-rays thereby making dental visits more pleasant.

Such dental depth visualizing, imaging, or information providing can be performed substantially parallel to the drilling or other. As such, the user such as the dentist or dental hygienist can be provided an improved indication of where they are drilling or treating relative to damaged or decayed teeth. Certain embodiments the Compton scattered X-ray visualizer, imager, or information provider 100 can be configured as clinic, emergency, or home-test kits, by which people could check the state of certain illness shows, sicknesses, injuries, painful or uncertain orthodontia, gum, dental, skin, or other conditions, etc. The user can thereby be provided with considerable detail as to the condition of, or decay within the teeth from particularly desired angles.

Additionally, certain embodiments of the Compton scattered X-ray visualizer, imager, or information provider 100 can allow depth visualizing, imaging, or information providing of the gums, portion of teeth hidden by the gum, and other matter and portions within or close to the mouth that may be useful for dental use. Certain embodiments of the Compton scattered X-ray visualizer, imager, or information provider 100 can visualize, image, and/or provide information the relating to teeth, gums, tongue, blood vessels or pools, or other general aspects, etc. Certain dental embodiments of the Compton scattered X-ray visualizer, imager, or information provider 100 can operate through the cheeks, and as such the Compton scattered X-ray visualizer, imager, or information provider 100 can be situated either at partially external to, or at least partially internal of the at least the portion of the individuals mouth.

Certain embodiments of the Compton scattered X-ray visualizer, imager, or information provider 100 can provide "freezing" the state of certain depth visualizations, images, and/or provided information as desired by the user or operator, or alternately as controlled by the Compton visualization, imaging, and/or information providing controller. Such freezing of the depth visualizations, images, and/or provided information can include maintaining an image of the at least the portion of the individual displayed on the display portion 154 and/or the Compton scattered X-ray receiving assembly 151. Since generating new images may require an application of applied X-rays 120 to the at least the portion of the individual, it may be desired to limit such application of the applied X-rays. As such, certain users can judiciously control the application of X-rays to the at least the portion of the individual, the user, and/or others in the vicinity during the Compton scattered X-ray visualization, imaging, or information providing by certain embodiments of the Compton scattered X-ray visualizer, imager, or information provider.

Certain dental or orthodontia embodiments of the Compton scattered X-ray visualizer, imager, or information provider 100 of FIG. 22 can also be used to visualize, image, or provide information relating to teeth of human individuals wearing braces. It is presently difficult, if not impossible, to accurately X-ray image teeth covered by brace bands, wires, etc. due to the distortions caused by the wires, bands, etc. Certain embodiments of the Compton scattered X-ray visualizer, imager, or information provider 100 can provide such accuracy and limited spatial scope of visualization, imaging, or information providing, as to allow Compton scattered X-ray visualization, imaging, or information providing from a single uncovered face of a tooth (e.g., biting surface). As such, certain teeth covered by braces, bands, etc can be visualized, imaged, or have information provided thereto, potentially from a variety of controllable and/or adjustable angles, positions, etc., during orthodontia treatment. Teeth, dental surfaces, fillings, etc. can be visualized, imaged, or have information provided from a variety of angles, positions, etc. such as to provide an improved indication of their configuration, solidity, health, etc. The amount of, and reliability of, dental treatment that can be performed based at least in part on X-rays can thereby be increased during orthodontia treatment.

While this disclosure have described certain embodiments of the Compton scattered X-ray visualizer, imager, or information provider 100 as being substantially externally-applied devices, it should also be understood that certain embodiments of the Compton scattered X-ray visualizer, imager, or information provider can be an at least partially internal device. Such at least partially internal devices can be applied to within the at least the portion of the individual using a scope, a needle, through an incision, via a normally open opening, and/or via a normally closed opening. Certain embodiments of the Compton scattered X-ray visualizer, imager, or information provider 100 can therefore be integrated at least partially a scope devices such as an endoscope embodiments of the Compton scattered X-ray visualizer, imager, or information provider 100, as described with respect to FIG. 23. Such scope-based embodiments could be applied via normally open openings, incisions, punctures, etc. to the interior of the at least the portion of the individual.

Figure 23:
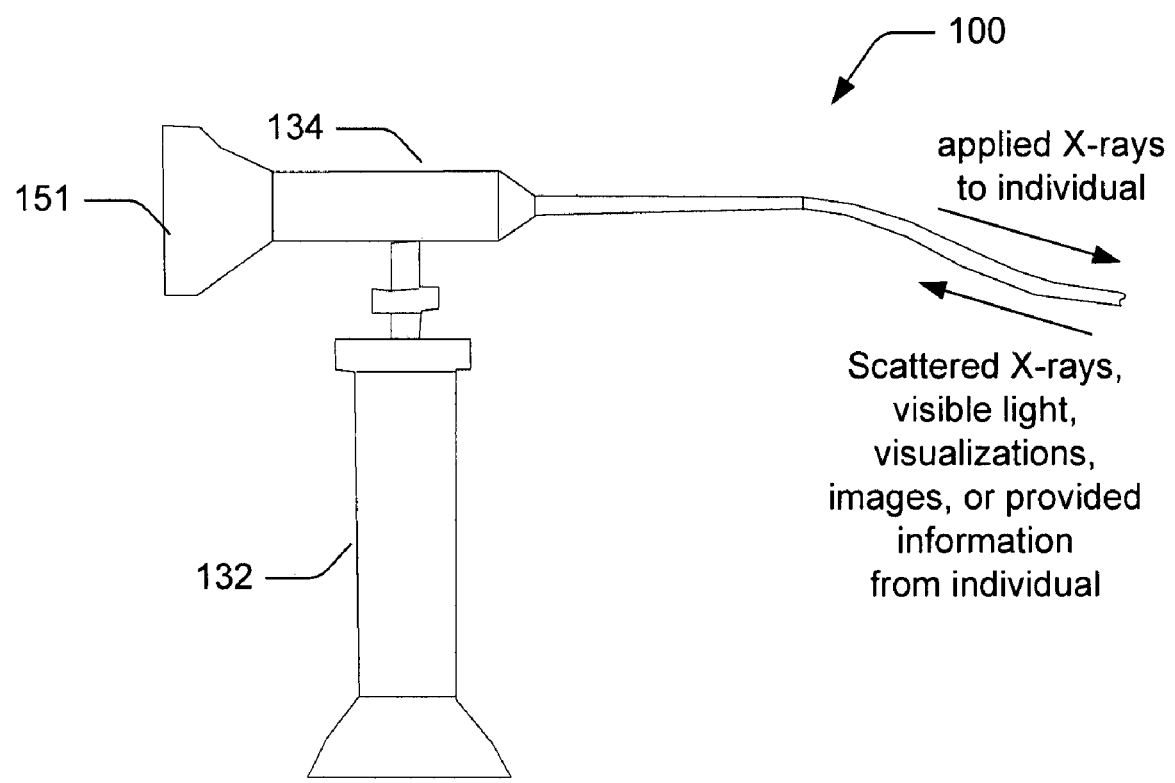
FIG. 23 is a diagram of an internal embodiment (e.g., endoscope-based) of the Compton scattered X-ray visualizer, imager, or information provider.

Certain endoscope embodiment of the Compton scattered X-ray visualizer, imager, or information provider 100, as illustrated in FIG. 23, can include a scope portion 134 or an illumination portion 136, whose operation and structure is generally understood to those skilled in the scope arts. The illumination portion 134 could be used to provide the applied X-rays as described elsewhere to the individual, which thereupon can be scattered. Certain endoscope embodiments of the Compton scattered X-ray visualizer, imager, or information provider 100 can thereupon be configured to receive the scattered X-rays, viewable and/or visible light, visualization, image, or provided information from the individual.

The scope embodiments of the Compton scattered X-ray visualizer, imager, or information provider 100 can include a variety of the Compton scattered X-ray receiving assembly 151. Certain embodiments of the Compton scattered X-ray receiving assembly 151 can include a scintillator (and/or fluoroscope), perhaps with a photomultiplier as described in this disclosure to amplify a relatively weak viewable and/or visible-light output. Certain embodiments of the Compton scattered X-ray receiving assembly 151 can include a fluoroscope as generally known in the art which may operate in certain ways similar to the scintillator (and/or fluoroscope). Certain embodiments of the Compton scattered X-ray receiving assembly 151 can include a detector portion in combination with a display portion as described with respect to FIG. 1 in this disclosure. Certain embodiments of the Compton scattered X-ray visualizer, imager, or information provider 100 can be at least partially adapted with, or at least partially configured to act as, a variety of tools. Such tools can include, but are not limited to: a Bovie electrocautery device as generally understood in the art, an ablator, a cutter, a gamma knife, a scalpel, a saw, a tactile feedback provider, a contact-type probe, a dental drill, etc.

Certain embodiments of the Compton scattered X-ray visualizer, imager, or information provider 100 may be configured as being attached a scope, tube, catheter, or other instrument or tool that can be configured to be inserted into the at least the portion of the individual. For example, certain endoscope embodiments of the Compton scattered X-ray visualizer, imager, or information provider can be configured as described with respect to FIG. 23. Certain configurations of the Compton scattered X-ray visualizer, imager, or information provider 100 may be provided with the emitter portion being situated relative to an endoscope via a surgical implant, and thereby may be similar to other embodiments of the Compton scattered X-ray visualizer, imager, or information provider in certain ways, but with the emitter portion placed inside the individual.

Certain scope-based embodiments of the emitter portion 150, as described with respect to FIG. 23, may be largely applied to an internal portion of the individual such as to include an interluminal X-ray source; while other embodiments of the emitter portion may be applied to an external portion of the individual. Certain embodiments of the emitter portion 150 may be powered by a variety of power sources (traditional or non-conventional) including, but not limited to, solar cells that may include traditional or untraditional power sources. For example, the emitter portion may be fed by one or more optical fibers, for example to power the at least one emitter portion 150, the at least one detector portion 152, and/or the at least one display portion 154. Certain optically fed embodiments of the emitter portion 150 may also include automated shutdown or other safety aspects relating to emission of X-ray based electromagnetic radiation. Certain embodiments of the emitter portion 150 may be implanted within the at least the portion of the individual such as to allow visualization, imaging, or information providing (using certain embodiments of the Compton scattered X-ray receiving assembly 151) on a more continuous basis. Such implants of at least portions of the Compton scattered X-ray visualizer, imager, or information provider 100 can be particularly useful for difficult to access portions of the body, such as the heart, brain, or certain other organs or regions of the body, etc.

Certain embodiments of the Compton scattered X-ray visualizer, imager, or information provider 100 can be configured to control X-ray generation and/or direction at least partially by accelerating or directing electrons for X-ray production. Such accelerating or directing the electrons can effectively reduce X-ray path length, and hence limit multiple Compton scattered X-ray events. Certain embodiments of the at least one emitter portion 150, and/or at least one detector portion 152 can be configured such as by being placed by a scope or other such device in a normally open opening, normally closed opening, or other lumen, such as colon, esophagus, mouth, throat, stomach, blood vessels, lungs, gut, etc.

Certain embodiments of the Compton scattered X-ray visualizer, imager, or information provider 100 can also be applied to cranial, brain, or spinal depth visualizing, imaging, or information providing. It may be difficult to visualize, image, and/or provide information within the skull using certain conventional imaging modalities, as a result of deflections of certain electromagnetic radiation within the interior (e.g., substantially concave) surface 168 of the skull and the associated distortions. Certain embodiments of the Compton scattered X-ray visualizer, imager, or information provider 100 can be configured to access the brain via such openings in the skull as the ear sockets, mouth opening, and/or sinuses. Such Compton scattered X-ray visualization, imaging, or information providing of the brain through such key-hole opening should experience relatively limited visualization, imaging, or information providing distortion, as compared with Compton scattered X-ray visualization, imaging, or information providing at least partially through the skull, boney matter, or other such X-ray distorting or shielding regions.

Certain embodiments of the Compton scattered X-ray visualizer, imager, or information provider 100 can be configured to be applied to relatively small regions of the body, and thereby apply relatively small overall dosages of X-rays. Certain embodiments of the Compton scattered X-ray visualization, imaging, or information providing can be controllably or adjustably applied in small regions, from different angles, etc., than certain conventional full-scale X-ray or certain conventional tomography imagers.

For instance, certain X-ray tomography-type Compton scattered X-ray visualization, imaging, or information providing imagers can capture a visualization, image, or provide information by scanning a series of scans relatively shallow into the at least some matter of the at least one portion of the individual from a variety of angles and/or positions. Such scanning can be performed using a variety of respective applied X-rays and/or scattered X-rays that can be respectively applied/received using respective arrays of emitter portion(s) 150 or Compton scattered X-ray receiving assemblies 151; or alternately one or more of the respective emitter portions and/or the Compton scattered X-ray receiving assemblies 151 that can be moved, scanned, angled, or otherwise repositioned. For instance, the certain array embodiments of the emitter portion 150 or Compton scattered X-ray receiving assemblies 151 can be configured to roughly conform to the general shape of the portion of the individual being imaged, or alternately in some other configuration. As the distinct emitter portion element(s) 150 are actuated to provide the applied X-rays 120, then the corresponding embodiment of the Compton scattered X-ray receiving assembly 151 can collect the data corresponding to the visualization, image, or provided information for each emitter portion element(s) including some unknowns relating to particular visualization, imaging, or information providing limitations. As a number of the distinct emitter portion element(s) 150 that direct the applied X-rays 120 under different directions, positions, energy levels, or other conditions decreases, the number of unknowns relating to particular visualization, imaging, or information providing limitations for at least some matter of the at least the portion of the individual correspondingly decreases, and a more complete and accurate visualization, image, or provided information can be obtained using tomographic techniques.

A similar tomographic technique or embodiment of the of the Compton scattered X-ray visualizer, imager, or information provider 100 can be applied to directing one or more emitter portion(s) 150 or Compton scattered X-ray receiving assemblies 151 at different positions, angles, energy levels, etc. Such techniques can involve physically repositioning and/or angling of the emitter portion 150 and/or the Compton scattered X-ray receiving assembly 151 itself/themselves such as to follow a scan, circular motion around the at least the portion of the individual, or other type of translation, angling, repositioning, changing of energy levels, etc. Alternately, a redirecting device of the applied X-ray or Compton scattered X-ray can be used, such as a filter, lens, modulator, shield, collimator, endoscope or other bendable, movable, or twistable scope or other emitter portion could be used in different embodiments, as described in this disclosure.

Certain embodiments of the Compton scattered X-ray visualizer, imager, or information provider 100 can, by using low energy applied X-rays 120, provide a relatively low-power version of the applied X-ray beam 120 which can be highly suited for intracranial visualization, imaging, or information providing and examination. The power of the applied X-ray beam may generally be configured or set at a level to be insufficient to penetrate, in large numbers, to another region that may not be depth visualized, imaged, or information provided. Such would be the case of brain depth visualizing, imaging, or information providing to limit transmission of excessive doses of X-rays to the cranium, brain, brainstem, embryo, or other such the region, etc.

Certain embodiments of the Compton scattered X-ray visualizer, imager, or information provider 100 can therefore be configured to visualize, image, and/or provide information in the brain, or other intracranial tissue. Certain embodiments of the Compton scattered X-ray visualizer, imager, or information provider 100 could operate with relatively high resolution, or alternately with lower resolution as desired or designed compared to other imaging modalities, and may thereby be similar in certain aspects to that of conventional MRI. Certain embodiments of the at least one emitter portion 150 can thereby be configured to use mono-energetic, collimated, or other sources. When using at least partially internal (e.g., in-body) embodiments of the at least one emitter portion 150, it may be possible to increase X-ray capture fraction by having multiple in-body detector portions 152, not just a single detector portion associated with the emitter portion. With the different embodiments of the Compton scattered X-ray visualizer, imager, or information provider 100, it is likely to be desired to limit dosages of X-rays as applied to the at least the portion of the individual 82 and/or the user (e.g., physician, dentist, veterinarian, assistant, researcher, etc.).

A variety of embodiments of the at least one detector portion 152 can be associated with the Compton scattered X-ray visualizer, imager, or information provider 100 as described at various locations in this disclosure. Certain embodiments of the at least one detector portion 152 may be considered as functionally associated with the at least one display portion 154, since the at least one display portion may be configured to display a version (which may be resized, filtered, scanned, computed, and/or otherwise modified) of what was detected by the at least one detector portion.

Certain embodiments of the at least one detector portion 152 and/or the Compton scattered X-ray receiving assembly 151, as included in certain embodiments of the Compton scattered X-ray visualizer, imager, or information provider 100, can be configured of various sizes, shapes, configurations, and may include a single detector portion or an array of detector portion elements. For example, those embodiments of the Compton scattered X-ray receiving assembly 151 utilizing a distinct detector portion 152 and 154 as described with respect to FIG. 18 differ from those scintillator (and/or fluoroscope) embodiments of the Compton scattered X-ray receiving assembly utilizing a combined detector and display portion as described with respect to FIG. 20. The dimensions of each detector portion element and/or the Compton scattered X-ray receiving assembly 151 can be selected based on such criteria as the desired application, usage, and/or the desired or designed Compton scattered X-ray visualization, imaging, or information providing resolution.

A variety of depth visualizations, images, and/or provided information including, but not limited to, tomography depth visualizations, images, and/or provided information can be constructed by scanning the X-ray beam received at the at least one detector portion 152 over a volume of interest of the at least the portion of the individual 82. As such, the at least one detector portion 152 may be considered as detecting the Compton scattered rays, with time-of-flight, spectral, and/or spatial resolution of the Compton scattered X-rays or other electromagnetic radiation. Specific X-ray energies can be used by the at least one detector portion to detect spectral features (e.g. absorption edges or fluorescence spectra) of specific X-rays received (e.g., Compton scattered) from particular ones of the at least the portion of the individual 82. The targeted portion of the individual can be at least partially endogenous, such as being produced from within the at least the portion of the individual (such as iron in blood, or calcium in tumors). Alternately, the targeted portion can be at least partially exogenous such as being produced outside of the at least the portion of the individual (e.g. high-Z contrast agents that migrate, bind, or are otherwise introduced into regions of interest). The emitted flux, energy level, or frequency of each X-ray photon can be tuned as to detect particular structures, organs, materials, etc. at certain depths and/or regions, as being detected by the at least one detector portion 152.

Certain embodiments of the Compton scattered X-ray visualizer, imager, or information provider can thereby capture a series of depth visualizations, images, and/or provided information, in which the at least one emitter portion and/or the at least one detector portion can operate sequentially utilizing feedback by the user and/or visualization, imaging, or information providing controller 97. Such control and subsequent feedback can be used as to alter and/or control the relative position, angle, magnification, or other aspect of the subsequent depth visualizations, images, and/or provided information. The initial depth visualizations, images, and/or provided information that have been captured can thereupon be displayed to the user at least partially using the at least one display portion 154 and/or the Compton scattered X-ray receiving assembly 151. The location, magnification, angle, and/or other characteristics of the subsequent depth visualizations, images, and/or provided information can be determined, at least in part, from the results of the prior depth visualizations, images, and/or provided information based at least partially on user input.

By allowing capturing of sequentially adjustable depth visualizations, images, and/or provided information, the users and/or individuals can observe the at least the portion of the individual 82 as they may desire. As such, the depth visualizing, imaging, or information providing being performed by the Compton scattered X-ray visualizer, imager, or information provider 100 can be adjusted and/or controlled. Consider that with certain embodiments of the Compton scattered X-ray visualizer, imager, or information provider 100, a user such as a physician, dentist, technician, assistant, etc. can obtain some preliminary depth visualizations, images, and/or provided information from certain embodiments of the Compton scattered X-ray visualizer, imager, or information provider to locate a desired examining feature. Thereupon, the depth visualizing, imaging, or information providing can be adjusted in subsequent images such as more closely or more accurately scan or examine at a desired location, angle, etc., such as to scan or examine for a cancerous growth.

Alternately, the user can use some embodiments of the Compton scattered X-ray visualizer, imager, or information provider to locate a desired organ or the at least the portion of the individual 82. Thereupon, the Compton scattered X-ray visualization, imaging, or information providing as performed by certain embodiments of the Compton scattered X-ray visualizer, imager, or information provider 100 can be modified, altered, repositioned, magnified, etc. such as to more closely or more accurately examine some aspect of the desired examining feature at a variety of angles, positions, magnifications, etc. Each one of the respective at least one emitter portion 150, at least one detector portion 152, at least one display portion 154, and/or the at least one combined detector/display portion 155 (e.g., scintillator and/or fluoroscope), can be respectively fabricated and/or respectively formed.

Certain embodiments of the Compton scattered X-ray visualizer, imager, or information provider 100, as described at a variety of locations through this disclosure, may alternately be scintillator-based and/or fluoroscope-based. Certain embodiments of the Compton scattered X-ray visualizer, imager, or information provider 100 may allow feedback techniques to allow users and/or visualization, imaging, or information providing controller 97. Such feedback techniques may alter and/or control Compton scattered X-ray visualization, imaging, or information providing of subsequent depth visualizations, images, and/or provided information based at least in part on results or user input based on prior captured visualization, imaging, or information providing. Certain embodiments of the at least one Compton scattered X-ray receiving assembly 151, including the at least one display portion 154 as combined with the at least one detector portion 152, can therefore be configured as a scintillator and/or fluoroscope, as described with respect to FIG. 20. With scintillator or fluoroscope embodiments of the Compton scattered X-ray receiving assembly, X-ray photons can be converted to viewable and/or visible photons as described with respect to this disclosure.

Certain embodiments of the scintillators or fluoroscopes can be configured including a substance that can absorb such electromagnetic radiation as X-rays, and thereupon can fluoresce, or otherwise provide such as by Compton scattered X-ray or other imaging mechanism, viewable and/or visible light (viewable and/or visible photons) at a characteristic X-ray frequency or energy level depending upon the received X-ray radiation. The fluorescing of the viewable and/or visible light may, as generally understood by those skilled in the art, be viewed as releasing the previously absorbed energy into or from the X-ray photons.

Certain embodiments of the at least one Compton scattered X-ray receiving assembly 151 of the Compton scattered X-ray visualizer, imager, or information provider 100 can therefore be configured to include scintillators and/or fluoroscopes can convert the scattered X-rays directly to viewable and/or visible light, without associated detectors and displays associated with certain embodiments of the Compton scattered X-ray receiving assembly 151. Certain configurations of conventional scintillators or fluoroscopes can be configured as optical detectors, displays, Compton scattered X-ray visualization, imaging, or information providing, etc. such as described with respect to U.S. Pat. No. 7,057,187 to Yun et al., entitled Scintillator Optical System and Method of Manufacture (incorporated herein by reference in its entirety). Certain embodiments of scintillator can be used for medical depth visualizing, imaging, or information providing as described with respect to U.S. Pat. No. 6,895,077 to Karellas et al., entitled System and Method for X-Ray Fluoroscopic Imaging (incorporated herein by reference in its entirety). Certain conventional CAT scanners utilize scintillator technology.

It is likely that the scintillator (and/or fluoroscope) embodiments of the Compton scattered X-ray visualizer, imager, or information provider 100 might be useful in screening the at least the portion of the individual, perhaps at shallow depths and/or for homogeneous matter (using Compton or fluoroscopy techniques), for skin aberrations, such as cancers, tumors, lesions, etc. As such, the user might scan the users for such aberrations that might occur near the surface 168, and the image processing associated with depth visualizing, imaging, or information providing such aberration with particular concern about processing Compton scattered X-rays Compton scattered X-ray at different depth being limited.

Certain scintillator (and/or fluoroscope) embodiments of the Compton scattered X-ray visualizer, imager, or information provider 100 may be characterized in this disclosure by the characteristics of their viewable and/or visible photonic output. The characteristics of their viewable and/or visible photonic output can include, but are not limited to, e.g., strength, energy level, and/or frequency of emitted viewable and/or visible photons as a function of absorbed X-ray electromagnetic radiation, fluorescence decay times, and/or optical transparency at wavelengths of their emitted viewable and/or visible electromagnetic radiation and/or other such factors. Scintillators (and/or fluoroscopes) may thereby be considered as operating by translating X-ray electromagnetic radiation into viewable and/or visible light electromagnetic radiation. As such, at least certain X-rays detected by the at least one detector portion 152 may be viewed by the user (or individual) without the necessity of at least one distinct display portion(s) 154.

The lower the decay time of certain embodiments of the scintillator and/or fluoroscopes (i.e., the shorter the duration of its flashes of fluorescence), the less so-called "dead time" or delay the detector portion will have and the more ionizing events per unit of time it will be able to detect. The excited atoms can thereupon lose some of this excess energy resulting from the dead time by emitting some viewable and/or visible photons. The amount of viewable and/or visible light produced by the scintillator and/or fluoroscope (and thereby the intensity of viewable and/or visible light output by the display portion) can, in certain embodiments, be amplified by a "photomultiplier" that is operationally included in the scintillator and/or fluoroscope. Certain embodiments of the scintillator and/or fluoroscope of the Compton scattered X-ray visualizer, imager, or information provider 100, as described in this disclosure with respect to FIG. 20, can include the Compton scattered X-ray receiving assembly 151 including a combined detector portion 152 and/or display portion 154. Such combined embodiments of the Compton scattered X-ray receiving assembly 151 can visualize, image, and/or provide information based at least in part on the received photons Compton scattered off the at least the portion of the individual.

The scintillator-based and/or fluoroscope-based embodiments of the Compton scattered X-ray visualizer, imager, or information provider 100 can be useful to provide real-time or near real time Compton scattered X-ray visualization, imaging, or information providing of the at least the portion of the individual. Additionally, certain scintillator-based and/or fluoroscope-based embodiments of the Compton scattered X-ray visualizer, imager, or information provider 100 can be configured to be adjusted to alter subsequent Compton scattered X-ray visualization, imaging, or information providing based on user or controller feedback, or other such aspects. For example, a region that is being visualized, imaged, or have information provided can be modified, angled, magnified, filtered, etc. such as to provide closer examination or Compton scattered X-ray visualization, imaging, or information providing. Certain "scintillator" and/or fluoroscope embodiments of Compton scattered X-ray visualizer, imager, or information provider 100 can be computationally intensive, while other embodiments can view the image directly. By angling the emission of the applied X-ray by the emitter portion 150, the reception of the scattered X-ray by the Compton scattered X-ray receiving assembly 151 and/or the Compton scattered X-ray receiving assembly 151, certain ambiguity as to the shape or configurations or aberrations, junctions, dissimilarities, etc. of the matter can be determined. Such angling, etc. can be provided either visually by the user, or by using image process techniques by the visualization, imaging, or information providing controller 97.

Certain scintillator and/or fluoroscope embodiments of the Compton scattered X-ray visualizer, imager, or information provider 100 can thereby be fabricated from, and therefore include, certain materials which can "convert" an X-ray photon to a viewable and/or visible photon. Certain embodiments of scintillators and/or fluoroscopes can amplify a relatively weak photonic X-ray signal such as by utilizing a photomultiplier (typically for each scintillator and/or fluoroscope element). One advantage of amplifying a relatively weak photonic signal is that an adequate depth visualization, image, or provided information can be obtained while subjecting the patient to a much lower dose of X-rays. Certain embodiments of Charge Coupled Devices (CCDs) may be associated with certain embodiments of the at least one detector portion 152 and/or the Compton scattered X-ray receiving assembly 151. Such embodiments of the Compton scattered X-ray receiving assembly 151 may be referred to in this disclosure as "scintillators" "fluoroscopes", "film screens", or "scintillation counters". Certain embodiments of scintillators and/or fluoroscopes may thereby be considered as direct semiconductor detector portions since they may not be largely computational-based to derive depth visualizations, images, and/or provided information. Certain embodiments of scintillators and/or fluoroscopes can be generated using signal amplification or computer amplification techniques.

Certain exemplary embodiments of scintillators and/or fluoroscopes may be configured as semiconductor detector portions 152, which may be based on converting X-ray photons to electron-hole pairs in the semiconductor, and the electron-hole pairs are thereupon obtained to detect the X-rays. It may be is possible to directly determine the X-ray energy spectrum using so-called called energy dispersive X-ray spectroscopy; and such techniques may additionally be used in small X-ray fluorescence spectrometers. These detector portions are sometimes called "solid detectors". Medical visualization, imaging, or information providing applications of scintillators and/or fluoroscopes in can rely on the concept that certain semiconductor diodes will thereby produce a small amount of current when placed in an X-ray beam.

Certain types of silicon drift detectors (SDDs), such as may be produced by semiconductor fabrication, can provide a relatively high resolving X-ray radiation detection measurement, and thereby be useful for certain embodiments of the Compton scattered X-ray receiving assembly 151. Certain scintillators and/or fluoroscopes, when combined with semiconductor detectors, can provide indirect detection of X-ray radiation. With the advent of large semiconductor array detectors it has become possible to design detector systems using a scintillator and/or fluoroscope screen to convert from X-rays to viewable and/or visible light which is then converted to electrical signals in an array detector, such as may be used to provide visibility to the human eye. Such signal processing and image processing techniques as filtering, amplifying, resizing, etc. can be applied to scintillator-based and/or fluoroscope-based embodiments of the Compton scattered X-ray visualizer, imager, or information provider 100, such as to improve Compton scattered X-ray visualization, imaging, or information providing.

Certain embodiments of the at least one emitter portion 150 can be dispersive such as to apply X-ray based electromagnetic radiation at the at least the portion of the individual 82; such as may thereupon be detected by certain embodiments of the at least one detector portion 152. As such, certain portions of the Compton scattered X-ray visualizer, imager, or information provider 100 can be associated with or include the emitter portion 150; while certain embodiments of the Compton scattered X-ray visualizer, imager, or information provider 100 can be associated with or include the at least one detector portion 152.

Certain embodiments of the Compton scattered X-ray visualizer, imager, or information provider 100 can therefore visualize, image, and/or provide information relating to the at least the portion of the individual that is physically separated from the surface 168 of the at least the portion of the individual. Such visualization, imaging, or information providing can rely on image combination (e.g., image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques). The quality of such Compton scattered X-ray visualization, imaging, or information providing can improve if the matter being imaged becomes more consistent across the thickness of the imaged portion 352 (e.g., horizontally across the thickness 352 as shown in FIG. 15). As such, as the thickness 352 of the at least one prescribed visualization, imaging, or information providing depth becomes thinner, and its consistency across the thickness becomes more uniform, its depth visualizing, imaging, or information providing consistency generally increases and the associated quality and/or reliability of the visualizing, imaging, or information providing quality generally increases.

Selection of a desirable or suitable thickness to image particular matter (e.g. tissue, bones, teeth, etc.) within a particular type of individual may depend, at least in part, on empirical results. For example, scanning skin, muscle, or other tissue across, may be performed in relatively thick slices as compared with depth visualizing, imaging, or information providing bone parts, nodules, or other matter that has a considerable amount of void space or is inconsistent across its imaged thickness. Suitable data, information, visualizations, images, etc. pertaining at least partially to visualization, imaging, or information providing of certain types of matter can be stored in the Compton visualization, imaging, and/or information providing controller 97 (e.g. in a memory, database, or other suitable location), as described with respect to FIG. 1. Or alternately, the visualization, imaging, or provided information can be provided as a written reference to the users and/or operators of the Compton scattered X-ray visualizer, imager, or information provider 100, such as could be accessed and/or set by the user and/or operator.

Figure 24:
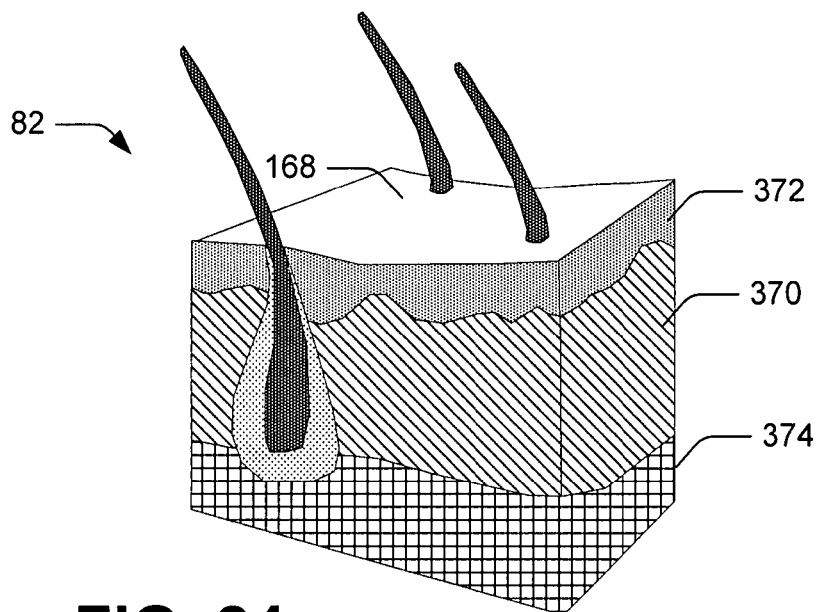
FIG. 24 is a partial cross-section of certain skin and subsurface layers of an individual (e.g., human) that can be visualized, imaged, or have information provided.
Figure 25:
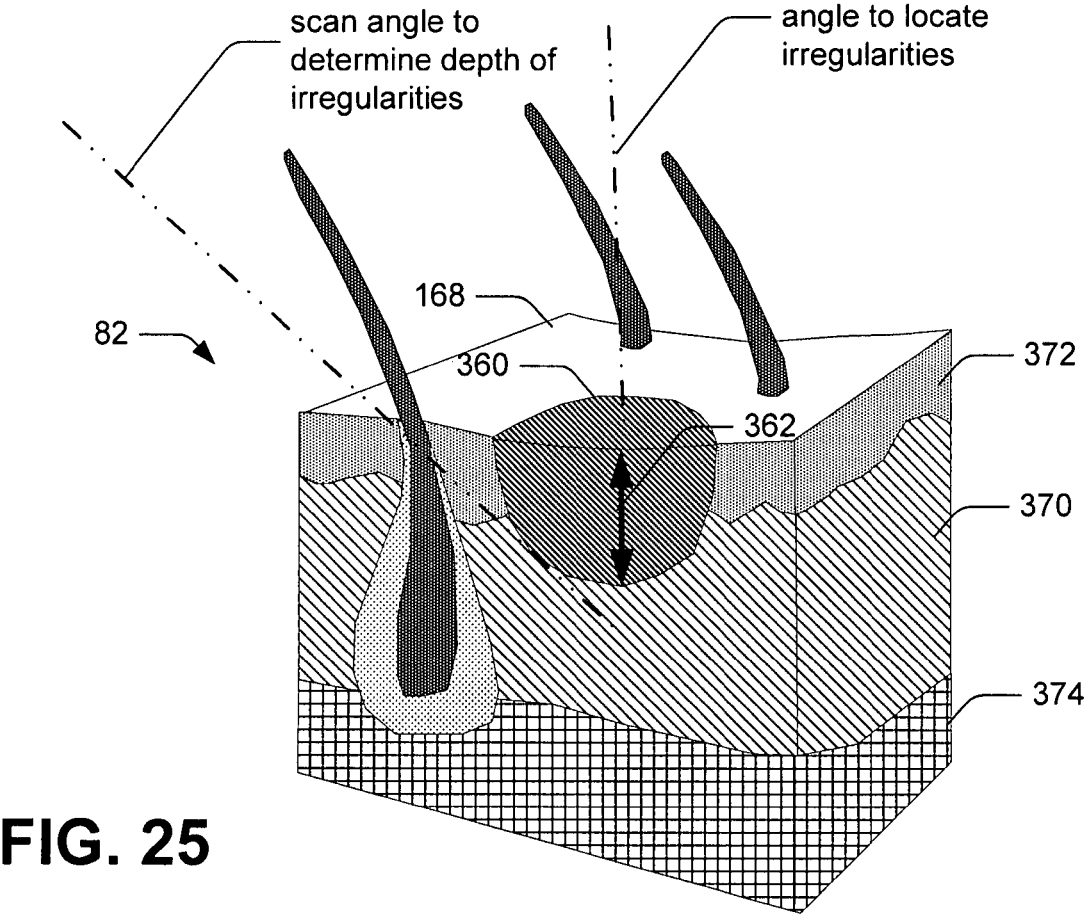
FIG. 25 is a partial cross-section of certain skin and subsurface layers of the individual including a skin aberration (e.g., a melanoma)

There may be a variety of surgical applications of certain embodiments of the Compton scattered X-ray visualizer, imager, or information provider 100 that are now described with respect to FIGS. 24 and 25. The particular suitable applications for certain embodiments of the Compton scattered X-ray visualizer, imager, or information provider 100 may be dependent upon the frequency, energy, or other characteristics of the applied X-ray photons, as well as the energy level and frequency of the applied X-ray photons can be used for the X-ray Compton scattered X-ray visualization, imaging, or information providing. Certain embodiments of the Compton scattered X-ray visualizer, imager, or information provider 100, for example, can be particularly suited or configured for treatment and/or examination near the surface 168 such as skin of the at least the portion of the individual 82, with normal skin being illustrated in FIG. 24. By comparison, certain embodiments of the Compton scattered X-ray visualizer, imager, or information provider 100 can be particularly suited or configured for treatment and/or examination of at least a portion of the individual; even if the portion of the matter being visualized, imaged, or information provided is spaced a considerable depth distance from a surface into matter of the individual 82 (as illustrated in FIGS. 18 and 20). This may be the case for treating person wishing to examine or locate a particular individual's organ(s), bone(s), and/or other regions that may be situated subsurface utilizing the at least one visualization, imaging, or information providing depth range to the at least one prescribed visualization, imaging, or information providing depth from the surface 168.

For example, certain Compton scattered X-ray visualizer, imager, or information provider 100 can be utilized to visualize, image, or provide information relating to some matter aberrations, such as to a tumor, tissue contour, etc. (such as may be useful to resect the visualized, imaged, or information provided aberration). Certain embodiments of the Compton scattered X-ray visualizer, imager, or information provider 100 can be configured to control or adjust the at least one visualization, imaging, or information providing depth range to the at least one prescribed visualization, imaging, or information providing depth during resection of a tumor or aberrative matter. This may be accomplished by varying the energy level, frequency, or other characteristics of the applied X-ray photons (which may require reconfiguring of the at least one emitter portion 150). Such resection can be accomplished in certain instances by allowing the surgeon to visualize, image, and/or provide information relating to tissue margins of the tumor using certain embodiments of the Compton scattered X-ray visualizer, imager, or information provider 100 based on its differential density. The differential density may, in certain instances, be either endogenous to the tissue, or enhanced by a contrast agent which may not otherwise be viewable and/or visible using normal human visual observation.

This use of certain Compton scattered X-ray visualizer, imager, or information providers 100 therefore could allow the surgeon to resect a lesion, tumor, etc. while limiting harm and manipulation (or even removal) to adjacent healthy matter or tissue. This can be useful in depth visualizing, imaging, or information providing organs such as the brain that are particularly sensitive to harm, manipulation, or removal of mater. Additionally, certain embodiments of the Compton scattered X-ray visualizer, imager, or information provider 100 might be configured to allow the user (e.g., surgeon or assistant) to view the aberration of the matter at a number of different angles. By allowing the viewing at different angles, etc., it may be easier for the user to appreciate the shape of the aberration, as well as its proximity to adjacent structures such as nerves, blood vessels, or other sensitive or other areas during particular operations or procedures. By limiting such manipulation, contact, or removal or sensitive matter during particular operations and/or procedures, certain embodiments of the Compton scattered X-ray visualizer, imager, or information provider 100 might likely be configured or designed to perform more radical surgeries or procedures (that might hurt the patient using other imaging techniques) than presently allowable.

Certain embodiments of the Compton scattered X-ray visualizer, imager, or information provider 100 can be configured to visualize, image, and/or provide information relating to the depth of certain layers of the at least the portion of the individual near the surface 168 (e.g., skin) as described with respect to FIG. 24. This may used to examine or visualize, image, and/or provide information relating to the depth of aberrative matter such as tumors in skin as described with respect to FIG. 25. With certain conventional imaging techniques, boundaries and/or depth from the surface 168 may not be clear between different types of matter (such as aberrative matter or tissue and normal matter or tissue, different types of cells, etc.). With X-ray based technologies, such as certain embodiments of the Compton scattered X-ray visualizer, imager, or information provider 100, certain types of aberrative matter such as certain cancers, tumors, etc. can be detected as a result of the associated calcification of the matter of the cancers, tumors, etc.

For example, it is likely that the calcified aberrative matter or tissue of such aberrative matter as breast cancer nodules in skin will absorb a considerable amount of the X-ray based electromagnetic radiation being applied as compared to the non-cancerous matter. As such, certain embodiments of the Compton scattered X-ray visualizer, imager, or information provider 100 can be configured to indicate outlines, depths, regions, volumes, or other such aberrative matter based on aberrative X-ray and/or photonic characteristics of the aberrative matter as compared to the normal matter (e.g., tissue). Additionally, aberrative matter also may have different contrast enhancing properties from normal matter. An example being a brain tumor can reduce the effectiveness of the blood brain barrier, and thereby absorb certain contrast agents to have visualization, imaging, or information provided characteristics unlike adjacent brain tissue.

Certain users using certain embodiments of the Compton scattered X-ray visualizer, imager, or information provider 100 can be used to more easily detect or visualize, image, and/or provide information relating to certain aberrative matter, etc. Such ease of detection can allow for more easily location of a position, extent, depth, and/or other aspects of the aberrative matter such as can enhance simplification or effectiveness of examination, removal, and/or treatment thereof. Removal of certain aberrative matter can be performed using certain matter removal techniques that may or may not be performed by certain embodiments of the Compton scattered X-ray visualizer, imager, or information provider, or associated equipment, including but not limited to: surgical cutting techniques, abrasive techniques, ablative techniques (such as laser ablation), etc.

Consider that certain surgeons, doctors, veterinarians, dentist, etc. may wish to completely locate and remove all (or at least as much as practicable), or only portion of a particular amount of such aberrations as aberrative or undesired matter interspersed in normal matter or tissue (such as a tumor interspersed in tissue, a cavity interspersed in a tooth, etc.). For example, it may be desired to remove a melanoma (i.e., skin cancer) completely as described with respect to FIG. 25 (or other skin aberration), while leaving behind as much matter or tissue as practicable.

As such, it may be necessary to visualize, image, and/or provide information relating to the aberrative matter (e.g., associated with the melanoma, tumor, etc.) one or more subsequent times such as to determine its precise extent. An initial visualization, imaging, or information providing scan may be useful in locating regions where certain matter aberrations such as melanomas may exist, and subsequent visualization, imaging, and/or information providing scans may be applied to each potential located aberration as to be useful in determining the depth or extent of each aberration. In addition, certain tomography type or volumetric type embodiments of the Compton scattered X-ray visualizer, imager, or information provider 100 can be used to map or determine, as accurately as practical or desirable, such aberrations, etc. Certain skin aberrations may include aberrative cells, colonies of cells, growths, or other dissimilar matter as compared to neighboring normal matter, and the aberrative (e.g., cancerous) matter can be based at least partially on the depth to which it has developed. Certain embodiments of the Compton scattered X-ray visualizer, imager, or information provider 100 can be configured to determine a depth of dissimilar matter feature within the at least one normal matter.

Additionally, a brain tumor might be suitable for being visualized, imaged, or information provided by certain embodiments of the Compton scattered X-ray visualizer, imager, or information provider 100, including those embodiments of surgical tools including the Compton scattered X-ray depth visualizer, imager, tactile feedback provider, or information provider 100 that can resect the tumor. As such, the tumor can be resected, with limited adjacent brain tissue that is not infiltrated with tumor effected by the resection. A low grade glioma is one example of a tumors which the Compton scattered X-ray visualizer, imager, or information provider 100 may assist in visually differentiating.

If the feature of an aberration or dissimilar mater, such as a tumor, cancerous matter, tooth decay, etc. is not removed completely, the aberration may continue to grow. Such aberrations as cancer or tumors may even grow uncontrollably, and even metastasize. The surgeon may not be able to determine the depth from a visual inspection or even one-time imaging techniques that use certain conventional imagers. An aberrative growth could be quickly examined, and the depth of the aberrative growth could be reliably determined by a skilled user utilizing certain embodiments of the Compton scattered X-ray visualizer, imager, or information provider 100. A dissimilar matter representing an aberration such as a melanoma, if not treated and/or removed in time, may thereby grow to an extent to be dangerous or even fatal.

The depth of certain matter aberrations such as melanomas may correspond to their seriousness. For example, if a melanoma has reached below a particular depth 362 as described with respect to FIG. 25, then the probability that it has metastasized may increase considerably. As such, there are a variety of medical situations that vital information as to the seriousness of a patient's condition could be obtained relatively and accurately using certain embodiments of the Compton scattered X-ray visualizer, imager, or information provider 100. By utilizing a series of successive images, such aberrations or abnoramlities as melanomas could be examined from a variety of angles, magnifications, and/or positions such as to make certain of their extent. It is likely that at least certain melanomas, breast cancers, other tumors or cancers, etc. can be imaged relative to adjacent matter either based on different densities of the dissimilar matter or alternately using certain contrast agent and/or fluoroscopy techniques.

As such, FIG. 24 shows an example of a partial cross-sectional view of normal matter such as skin; while matter such as skin including a dissimilar matter a melanoma is shown in FIG. 25. Normal skin, for example, is typically made up of layers, including the epidermis 370 and the dermis 372. As illustrated in FIG. 25, a skin aberration or tumor such as a melanoma 360 can develop within the skin, and can be measured by a number of quantitative systems, two of which are referred to as "Breslow Depth" and "Clark's Levels". Breslow Depth quantifies the top-to-bottom measurement of the melanoma in millimeters, similar to as shown by the arrow 362 in FIG. 25. By comparison, Clark's Levels describe how far the melanoma has extended into the particular layers of the skin. Certain embodiments of the Compton scattered X-ray visualizer, imager, or information provider 100, as described in this disclosure, can therefore be used to determine the characteristics of a melanoma using the Breslow Depth and/ or the Clark's Level. Certain embodiments of the Compton scattered X-ray visualizer, imager, or information provider 100 as can be applied to aberrative matter, such as tumors such as melanomas, are intended to be illustrative in nature but not limiting in scope. Determination of a suitable matter thickness or slice thickness for Compton scattered X-ray visualization, imaging, or information providing may pertain to the likely presence or absence of matter aberrations or other matter abnormalities or matter inconsistencies.

As such, by viewing a matter aberration such as a tumor or cancer at a number of angles, positions, magnifications, etc. using certain embodiments of the Compton scattered X-ray visualizer, imager, or information provider 100 as described with respect to FIG. 25, it is likely that the true extent, depth, and condition of their growth can be determined. Such re-examination or subsequent Compton scattered X-ray visualization, imaging, or information providing of the at least the portion of the individual 82 can be performed at a desired angle, position, etc. Such re-examination can be based or selected, at least in part, on input from the user, the individual, or a controller or computerized portion such as to closely examine those regions of interest under a suitable magnification, angle, position, etc.

Certain embodiments of the Compton scattered X-ray visualizer, imager, or information provider 100 can rely on advantages of X-ray technology. X-ray technology provides advantages of being well developed, researched, understood, trusted, etc. X-ray technology can be less expensive than certain other visualization, imaging, or information providing technologies. While certain aspects of X-ray Compton scattered X-ray technology may be less developed than conventional X-ray (e.g., transmissive) technologies, both types of X-ray technologies can be utilized in a variety of medical or non-medical applications including, but not limited to, medical, examination, surgery, geological, security, structural, and other technologies.

By allowing subsequent controllable Compton scattered X-ray visualization, imaging, or information providing as is the case with certain embodiments of the Compton scattered X-ray visualizer, imager, or information provider 100 as described in this disclosure, the users such as physicians, surgeons, dentists, etc. can interactively examine the at least the portion of the individual 82, in a manner as desired. For example, after a desired at least the portion of the individual 82 is located by an initial visualization, imaging, and/or information providing scan, subsequent Compton scattered X-ray visualization, imaging, or information providing scan(s) can further or more closely examine the located portion. With certain embodiments of the Compton scattered X-ray visualizer, imager, or information provider, the at least the portion of the individual with at least part of their body part being examined can interactively visualize, image, and/or provide information relating to their condition using subsequent Compton scattered X-ray visualization, imaging, or information providing if the output/display is provided to the at least the portion of the individual 82. Such subsequent Compton scattered X-ray visualization, imaging, or information providing can be performed on a variety of matter in the at least the portion of the individual.

As with a variety of radiographic visualization, imaging, or information providing techniques, and particularly those utilizing X-rays, it is important to consider the dosage effects of certain electromagnetic radiation provided by the Compton scattered X-ray visualizer, imager, or information provider 100 to the at least the portion of the individual and/or the user. Certain embodiments of the Compton scattered X-ray visualizer, imager, or information provider 100 can visualize, image, and/or provide information relating to a series of depth visualizations, images, and/or provided information sequentially, on a real time basis, at a variety of resolutions, or over a large or small portion of the individual. By judicious Compton scattered X-ray visualization, imaging, or information providing using certain embodiments of the Compton scattered X-ray visualizer, imager, or information provider 100, the radiation doses as applied to the at least the portion of the individual and/or the user can be limited considerably, particularly as compared with many conventional X-ray imaging modalities.

Certain embodiments of the Compton scattered X-ray visualizer, imager, or information provider 100 are configured to image by allowing X-rays to pass into, scatter from, and return from a localized organ, matter, etc. Conventional transmissive X-ray devices, by comparison, typically pass through the entire thickness of the at least the portion of the individual being imaged. For example, certain embodiments of the Compton scattered X-ray visualizer, imager, or information provider 100 can be configured by Compton scattered X-ray visualization, imaging, or information providing a first general area, and thereupon depending upon the initial visualization, image, or provided information. A relatively minor number of visualizations, images, and/or provided information (perhaps localized to small regions) can be examined to consider in considerable degree, for example, one or more regions of interest that have been located by the initial depth interest. Such subsequent depth visualizations, images, and/or provided information may be configured to limit exposure of the at least the portion of the individual or the user to the doses of the original depth visualizations, images, and/or provided information.

By allowing subsequent Compton scattered X-ray visualization, imaging, or information providing with certain embodiments of the Compton scattered X-ray visualizer, imager, or information provider 100, the condition of the at least the portion of the individual may be clearly imaged and/or examined to determine the condition of the at least the portion of the individual. In certain instances, perhaps less drastic treatment (e.g. radiation therapy, chemotherapy) and/or less imaging, visualizing, and/or tests may need to be applied to the at least the portion of the individual based on the more complete or accurate visualization, imaging, or provided information results. Such results may be obtained by (or the relatively precise locating, visualizing, and/or imaging of) certain embodiments of the Compton scattered X-ray visualizer, imager, or information provider 100. In certain instances, perhaps the growths, once clearly examined, can be more accurately treated such as by direct treatment of the relevant location, ablation, etc.

A variety of X-ray based electromagnetic radiation (applied, returning/reflected, etc.) can be utilized for Compton scattered X-ray visualization, imaging, or information providing purposes when visualization, imaging, or information providing the at least the portion of the individual. Certain embodiments of the Compton scattered X-ray visualizer, imager, or information provider 100, as described with respect to this disclosure, the emitter portion 150 can apply an applied X-ray 120 to the at least the portion of the individual. FIG. 18 shows one representative embodiment of the Compton scattered X-ray visualizer, imager, or information provider applying the X-ray (photonic-based electromagnetic radiation) down to the at least one substantially scattered depth range to the at least one prescribed substantially scattered depth within the at least the portion of the individual 82 (e.g., human, shown in cross section).

Certain embodiments of the at least one emitter portion 150 can thereby be positioned relative to the at least the portion of the individual 82, either at least partially internally or at last partially externally to the individual. Certain embodiments of the at least one emitter portion can be configurable to emit the applied X-ray 120 for a controllable depth into the matter of the at least the portion of the individual 82. The subsequent Compton scattered X-ray (scattered from the applied X-ray) can be detected by the at least one detector portion 152 and/or the at least one display portion. The visualization, imaging, and/or provided information relating to information can thereby be derived at least partially in response to Compton scattered X-ray of the X-ray based electromagnetic radiation.

The emitter portion 150 of certain embodiments of the Compton scattered X-ray visualizer, imager, or information provider 100 can be configured to generate at least some of the applied X-ray 120, that can be applied and/or directed to the at least the portion of the individual 82. Some of the applied X-ray 120 can be applied by the at least one emitter portion 150 such as to at least partially penetrate into the at least the portion of the individual. During such instances as when penetrating into matter of the at least the portion of the individual 82, the X-ray based electromagnetic radiation of the applied X-ray can be at least partially deflected, at least partially Compton scattered, and/or at least partially passed through the at least the portion of the individual 82. Compton scattered X-ray (backscatter, forward scatter, or other) of at least some of the applied X-rays can provide at least some of the Compton scattered X-ray 122 which can be detected by certain embodiments of the at least one detector portion 152, and/or the at least one Compton scattered X-ray receiving assembly 151.

Certain examples of the other matter that can effect the Compton scattered X-ray can include, for example: tissue, bones, portions of bones, metal, etc. Certain embodiments of the Compton scattered X-ray visualizer, imager, or information provider 100 may be configured for Compton scattered X-ray visualization, imaging, or information providing matter not normally associated with X-ray Compton scattered X-ray visualization, imaging, or information providing. Such would be the case with locating interfaces between two different types of matter including, but not limited to: "normal" or "regular" opaque matter (such as tissue), as compared with other aberration matter.

Certain embodiments of the Compton scattered X-ray visualizer, imager, or information provider 100 can be configured to combine visualization, imaging, or information providing at least partially by combining information obtained from the Compton scattered X-ray visualizer, imager, or information provider 100 with image information from another source (e.g., MRI, conventional X-rays, other Compton scattering-based systems or portions thereof, other embodiments of the Compton scattered x-ray visualizer, imager, or information provider 100, etc.). Such combinations may take the form or function, for example, of depth, position, varying depth visualizing, imaging, or information providing modalities, etc.; and may include previously gathered depth visualizing information.

Certain of such combined embodiments of Compton scattered X-ray visualizer, imager, or information provider 100 can be useful for instance where the imaging capabilities of the Compton scattered X-ray visualizer, imager, or information provider 100 may be more limited such as to produce a real-time visualization, imaging, or information providing, and thereupon integrating more detail imaging from other imaging modalities. Although certain aspects of the visualization, images, or provided information of particular matter such as tissue, organs, bones, or other portions of the individuals may not precisely match between certain embodiments of the Compton scattered X-ray visualizer, imager, or information provider 100 and the other conventional visualization, imaging, or information providing modalities, it is likely that each modality could be expected to be particularly useful for particular applications, illnesses, injuries, etc.

Certain embodiments of the Compton scattered X-ray visualizer, imager, or information provider 100 may also be configured as to be able to visualize, image, or provide information at a suitable rate considering the matter being imaged and/or the ability of the user to be able to view the distortions. There might be a variety of distortions of the matter which may be particularly useful to visualize, image, or provide information. For example, certain surgeons might be particularly interested in considering the rate at which the heart beating causes deformation of the heart muscle, or alters blood flow through portions of the heart such as the aorta, valves, etc. By comparison, other surgeons may be interested in considering somewhat slower motion of their patients, such as how changes in the body position (e.g., leg or arm position) may be reflected in variation in the associated skeletal bones between successive depth visualization, imaging, or providing information. Certain dentists or orthodontists might be interested in how movement of the jaw can be reflected by changes in the bite of the teeth of their patients.

As described with respect to FIG. 18, certain embodiments of the emitter portion 150 can apply at least one applied X-ray 120 at a desired, or controllable, angle. The depth visualizing, imaging, or information providing angle of the applied X-ray radiation may range from almost parallel, but still incident, to a surface 168 of the at least the portion of the individual 82, to substantially perpendicular to the surface 168 of the at least the portion of the individual 82, and any angle there between). The characteristics of the applied X-ray may include, but are not limited to, a suitable and/or desired position, power, frequency, energy level, duration, as well as a variety of other such characteristics.

Certain embodiments of the Compton scattered X-ray visualizer, imager, or information provider 100 can be configured to include at least one detector portion 152 and/or display portion 154 that can be operable to be at least partially inserted into the at least the portion of the individual. Such configurations can be used to receive at least one Compton scattered X-ray that has been Compton scattered in an at least one opaque matter of the at least the portion of the individual. Certain embodiments of the detector portion can be configured to be adjustable, alignable, scannable, or otherwise modifiable; and may include such scopes as endoscopes that may alternately be inserted through insertion or normally open opening of the individual as is generally understood by the use of an endoscope.

Certain embodiments of the Compton scattered X-ray receiving assembly 151 might preferably be configured as combined detector portion/display portions as described in this disclosure, such that the visualizer, imager, and/or information provider might suitably change as the user moves their vantage point, etc. relative to the at least the portion of the individual. It may be desired to reduce or limit the involved computation associated with depth visualizing, imaging, or information providing. By comparison, those embodiments of the Compton scattered X-ray visualizer, imager, or information provider 100 involved in depth visualizing, imaging, or information providing relatively deep into the at least the portion of the individual may include the distinct detector portions and display portions. Additionally, certain embodiments of the Compton scattered X-ray visualizer, imager, or information provider 100 can be applied in the at least one visualization, imaging, or information providing depth range to the at least one prescribed visualization, imaging, or information providing depth relatively near the surface 168. Recall that such image combining may utilize image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques. Such distinct detector portions and display portions may be configured to computationally differentiate images, visualizations, information, etc. using certain image information. Additionally, such computationally complex visualization, imaging, or information providing displays as time of flight embodiments of the Compton scattered X-ray visualizer, imager, or information provider 100 (or high resolution display portions) may benefit from the distinct detector portions and display portions, which may also simplify the associated image processing. These design choices are intended to be illustrative in nature, but not limiting in scope.

Certain embodiments of the detector portion 152 may be situated within the at least the portion of the individual 82, adjacent to the at least the portion of the individual 82, or external to the at least the portion of the individual 82. Either one detector portion 152, or a plurality of detector portions, may be provided either within the at least the portion of the individual 82, adjacent to the at least the portion of the individual 82, and/or external to the at least the portion of the individual 82.

Within this disclosure, certain embodiments of the at least one display portion 154 can be configured to display the X-ray based electromagnetic radiation such as it has at least been partially received from the at least the portion of the individual 82 by the at least one detector portion. As such, certain embodiments of the at least one display portion 154 can be configured to display X-ray illumination that can be Compton scattered at least partially from the at least the portion of the individual 82. Such Compton scattered X-ray illumination can be based on the Compton scattered X-ray based electromagnetic radiation that can be detected by the at least one detector portion 152.

Certain embodiments of the Compton scattered X-ray receiving assembly 151 can include a variety of the at least one display portion 154. Certain embodiments of the display portion 154 can take a variety of forms that can include, but are not limited to: a cathode ray tube (CRT) display portion, a liquid crystal display portion (LCD) display portion, a personal display or information provider portion (configured to display to one person), a glasses-based display portion, a group display or information provider portion (that can display depth visualizations, images, and/or provided information to more than one person), a plasma display portion, a medical display portion, a computer display portion, a personal display assistant (PDA) display portion, or such other displays that can at least partially provide a display of at least the portion of the individual based at least in part on the Compton scattered X-rays 122.

The selection as to whether the Compton scattered X-ray receiving assembly 151 includes distinct detector portions and display portions, or combined detector portion/display portions can be based at least partially based on functionality and/or desired computation. For example, certain Compton scattered X-ray visualization, imaging, or information providing applications involving depth imaging, visualizing, or providing information from the surface 168 to the at least one visualization, imaging, or information providing depth range to the at least one prescribed visualization, imaging, or information providing depth.

Figure 26:
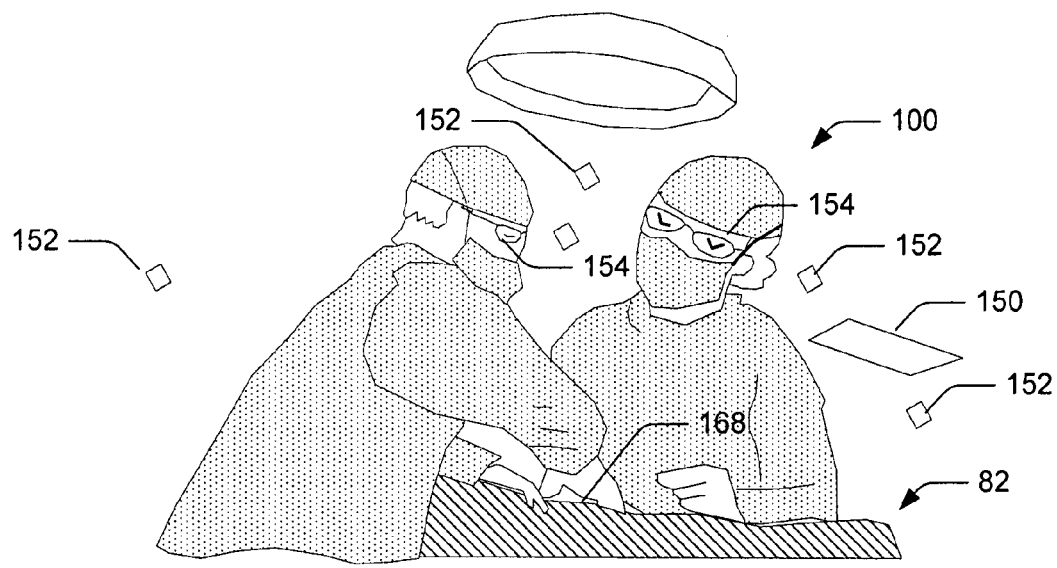
FIG. 26 shows another embodiment of the Compton scattered X-ray visualizer, imager, or information provider including an embodiment of an at least one display portion configured as a personal display or information provider portion.

Certain embodiments of the Compton scattered X-ray receiving assembly 151 may be configured as surgeon's glasses, or other configuration, as illustrated in FIG. 26. Certain embodiments of the Compton scattered X-ray visualizer, imager, or information provider 100 can be configured as personal devices, which can thereby be used primarily by one person. By comparison, certain embodiments of the Compton scattered X-ray visualizer, imager, or information provider 100 can be used as group devices such as can be used by two or more persons or users. Particularly, FIG. 26 shows one embodiment of the Compton scattered X-ray visualizer, imager, or information provider 100 including an embodiment of the at least one display portion 154 configured as a personal display (in this instance, surgeon glasses, dentist glasses, veterinarian glasses, etc.), as described in this disclosure. Certain embodiments of the Compton scattered X-ray visualizer, imager, or information provider 100 can thereby be configured as augmented vision glasses. For instance, certain embodiments of the Compton scattered X-ray visualizer, imager, or information provider 100 can utilize glasses, such as can be worn by surgeons in which at least a portion of the glasses can be configured as a display, such display portion could be viewed by the user. Certain embodiments of the visualizing, imaging, or information provided as provided by certain embodiments of the Compton scattered X-ray visualizer, imager, or information provider 100 can be optically aligned to the user. Certain embodiments of the Compton scattered X-ray visualizer, imager, or information provider 100 can therefore be configured as an X-ray backscatter device is used to deliver a real-time 2D or 3D depth visualization, image, or information to the surgeon. The depth visualizations or images can be presented to the surgeon by means of an external monitor, head-mounted display, or stereoscopic projection. The surgeon can select the depth (from millimeters to substantially through the visualized, imaged, or have information provided portion of the individual 82) at which the visualization, image, or provided information is taken, captured, etc.; the selected depth can be targeted by tuning the intensity, energy level, or frequency of the X-ray photons in the X-ray beam.

There may be a variety of configurations and/or utilizations of certain embodiments of the Compton scattered X-ray visualizer, imager, or information provider 100. For example, certain personalized embodiments of the Compton scattered X-ray visualizer, imager, or information provider 100 can present depth visualization, image, or information to at least one person particularly associated with the Compton scattered X-ray visualizer, imager, or information provider, similar to as described with respect to FIG. 26. Certain personalized embodiments of the Compton scattered X-ray visualizer, imager, or information provider 100 can be configured to be worn as personal devices, such that each of the at least the portion of the individual 82 can obtain the depth visualization, image, or information of the at least the portion of the individual 82 in a manner similar to glasses. For instance, in the embodiment of the Compton scattered X-ray visualizer, imager, or information provider 100 as described with respect to FIG. 26, the emitter portion 150 can be situated proximate the glasses-based embodiment of the Compton scattered X-ray visualizer, imager, or information provider 100 (e.g., on the frame); adhered to the user at a remote location from the glasses (e.g., on cloth, clothes, fabric, metal, or other material); or alternatively situated at a remote location from the user.

Certain embodiments of the detector portion 152 of the Compton scattered X-ray visualizer, imager, or information provider 100, as described with respect to FIG. 26, can thereby be described as surgeons' glasses. The term "surgeon's glasses" is intended to be illustrative and not limiting since these devices can be worn by the user and illustrate visualizations and/or images, as well as provide information, to the user or other person. Certain surgical glass embodiments of the Compton scattered X-ray visualizer, imager, or information provider 100 may or may not contain optical glasses at all. Certain surgical glasses are understood to perhaps include an additional display portion (which may function as typical optical glasses) such as can be viewed by a surgeon, or alternatively may be provided as only a frame without the optical glasses. Certain embodiments of the surgical glasses, can include, for example, at least one liquid crystal display (LCD), at least one light emitting diode (LED) or an embodiment of the Compton scattered X-ray receiving assembly 151 that can be secured by a variety of mechanisms to nearby are to the user, such as can be viewed by the user. With surgeon's glasses, a variety of display portions can be provided to surgeons, etc. through a portion of glasses, while other portions of the glasses allow the surgeon to see during the operation.

Figure 27:
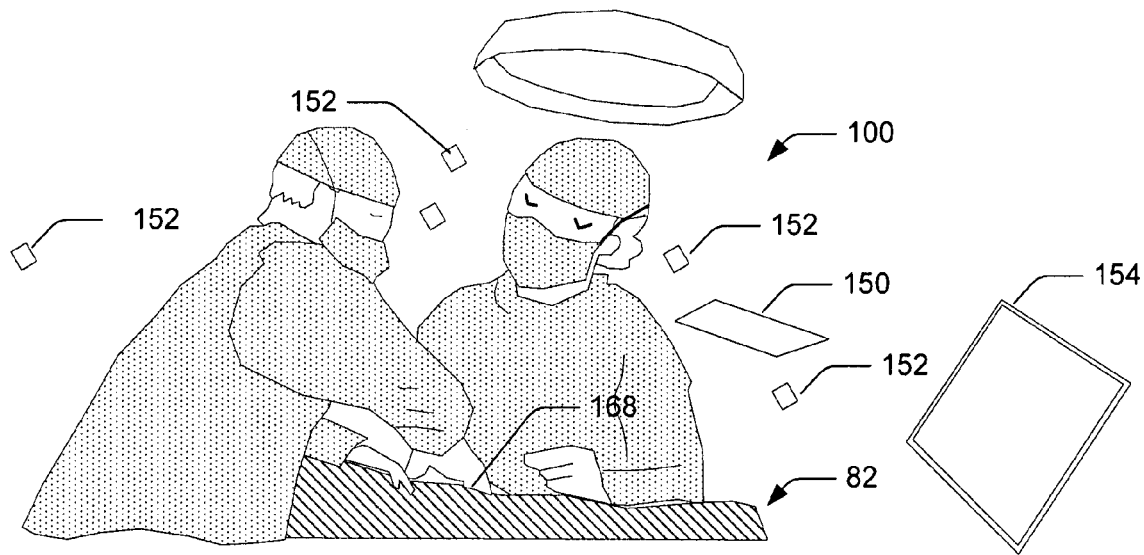
FIG. 27 shows one embodiment of the Compton scattered X-ray visualizer, imager, or information provider including an embodiment of the at least one display portion configured as a group display or information provider portion.

By comparison, a number of embodiments of the Compton scattered X-ray visualizer, imager, or information provider 100 could include at least one display portion 154 can be configured as a group display or information provider portion. For example, FIG. 27 illustrates an instance in which a number of users could view selected portion(s) of the individual through a group display 154, as described in this disclosure such could be viewed by a number of users. For instance, the Compton scattered X-ray visualizer, imager, or information provider 100 can include an LCD display portion, a CRT display portion, a television display portion, a medical display portion, or other applicable embodiments of the Compton scattered X-ray visualizer, imager, or information provider.

Certain of the applied X-ray 120, that are generated and/or applied to the at least the portion of the individual 82 by certain embodiments of the emitter portion 150, may thereupon after at least partially passing into the at least the portion of the individual 82 be subsequently Compton scattered and/or deflected. Such Compton scattering and/or deflection can thereupon be detected by the at least one detector portion 152, as described with respect to FIG. 1. Certain embodiments of the Compton scattered X-ray visualizer, imager, or information provider 100, can include a considerable number of detector portions 152 positioned, for example, around an operation or examination room in which the individual 82 is situated. The particular arrangement of a number of the emitter portions 150 is largely considered to be a design choice.

Certain embodiments of the Compton scattered X-ray visualizer, imager, or information provider 100 can be configured to be adjustable, tunable, and/or controllable. Such adjustability, tunability, and/or controllability can be used to adjust the energy level or frequency of the X-ray photons of the applied X-rays; and thereby affect the depth of Compton scattered X-ray visualization, imaging, or information providing, into the at least some matter of the at least the portion of the individual. Certain external embodiments of the Compton scattered X-ray visualizer, imager, or information provider 100 may be configured to be non-contact, with an emitter portion 150 probe and/or detector portion 152 probe that does not contact the surface 168 of the matter of the at least the portion of the individual. Other embodiments adjustable, tunable, and/or controllable do permit contact of the emitter portion 150 probe and/or detector portion 152 probe with the matter of the at least the portion of the individual. Certain embodiments of the Compton scattered X-ray visualizer, imager, or information provider 100 can provide a number of modalities of depth visualizing, imaging, or information providing (traditional X-ray images, Compton scattered X-ray visualization, imaging, or information providing, etc.) including, but not limited to, density and elemental depth visualizing, imaging, or information providing mode. Certain embodiments of the Compton scattered X-ray visualizer, imager, or information provider 100 can be configured to provide considerable contrast, and thereby may be less dependent on such variables as user skill in depth visualizing, imaging, or information providing, etc.

Different versions of the Compton scattered X-ray visualizer, imager, or information provider 100 can be configured to combine image information with that being performed by different imagers that can produce images in one or a variety of different formats and configurations. Certain embodiments of the Compton scattered X-ray visualizer, imager, or information provider 100 can be applied externally or internally, such as described relative to certain locations in this disclosure. Certain external configurations of the Compton scattered X-ray visualizer, imager, or information provider 100 can utilize either full-body tomography imaging enclosures or partial body tomography imaging enclosures, similar to as generally used during MRIs, CAT scans, PET scans, etc. By comparison, certain embodiments of the at least one emitter portion(s) 151 for certain embodiments of the Compton scattered X-ray visualizer, imager, or information provider 100 can be positioned around the room where the individual is situated. Such configurations can be configured to improve the application of the applied X-rays 120 towards the at least the portion of the individual being imaged. Certain embodiments of the Compton scattered X-ray visualizer, imager, or information provider could used to obtain a CAT-grade or PET-grade tomography scan, based at least in part on the configuration and structure of the at least one emitter portions 150 and/or the at least one Compton scattered X-ray receiving assembly 151.

Figure 28:
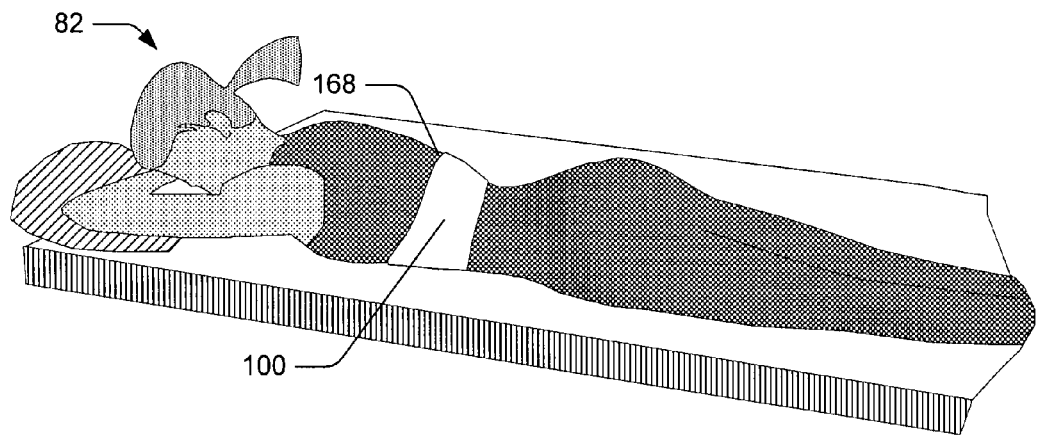
FIG. 28 shows a flexible embodiment of the Compton scattered X-ray visualizer, imager, or information provider.

Certain embodiments of the Compton scattered X-ray visualizer, imager, or information provider 100 may be configured to provide depth visualizing, imaging, or information providing flexibility, as well as to conform to the at least the portion of the individual being imaged as described with respect to FIG. 28. Certain embodiments of the Compton scattered X-ray visualizer, imager, or information provider 100 can be attached to a flexible securing member (perhaps even being attached to the individual using belts, Velcro, straps, or some other known fastener), such as can be used to limit relative displacements between the visualizing components and the at least the portion of the individual. For example, certain embodiments of the Compton scattered X-ray visualizer, imager, or information provider 100 can be configured as a fabric or jointed sleeve that can be at least partially tied to, worn by, or attached to surround the at least part of the patient, as described with respect to FIG. 28. Certain embodiments of the Compton scattered X-ray visualizer, imager, or information provider can be embedded in, or attached to, clothing, fabric, or other material that can be made distinctly for each individual, or can be used by a number of individuals. Such flexible attachment members may be especially desirable for monitoring or examining, or otherwise visualizing, imaging, or providing information relating to particular portion or organ of the individual, such as the heart, brain, or other organs, tissue, or other matter.

For example, at least portions of the Compton scattered X-ray visualizer, imager, or information provider 100 may be applied to securing elements which can be maintained or secured with respect to the at least the portion of the individual. Certain embodiments of the Compton scattered X-ray visualizer, imager, or information provider 100 can be flexibly applied to a more extensive portion of the individual such as the torso; or a smaller portion of the individual such as an arm, leg, finger, etc. Certain embodiments of the Compton scattered X-ray visualizer, imager, or information provider 100 can at least partially include a sleeve or other flexible portion that at least partially be affixed to and/or surrounds the individual. For example, certain embodiments of the Compton scattered X-ray visualizer, imager, or information provider 100 can be configured to limit relative motion between at least one portion of the at least one Compton scattered X-ray receiving assembly 151 relative to the at least the portion of the individual. By limiting the relative motion between the at least one emitter portion 150 and/or the at least Compton scattered X-ray receiving assembly 151 with respect to the at least the portion of the individual, a number of aspects of depth visualizing, imaging, or information providing can be improved, such as clarity and perhaps improved resolution.

Certain embodiments of the Compton scattered X-ray visualizer, imager, or information provider 100 can be configured to act as a shield to limit transmission of X-rays outside of the at least the portion of the individual. Certain embodiments of the Compton scattered X-ray visualizer, imager, or information provider 100 (particularly those flexible configurations as described with respect to FIG. 28) can be configured to include X-ray shielding material to shield users and/or individuals from the X-rays. Consider that the Compton scattered X-ray visualizer, imager, or information provider 100 as described in this disclosure could include an X-ray shielding material such as could limit excessive stray X-rays from passing away towards the user such as a doctor, veterinarian, etc. Such users may be exposed to a higher total dosage of X-rays after depth visualizing, imaging, or information providing a number of individual patients, etc., as compared with the individuals who are seldom imaged. Certain embodiments of the Compton scattered X-ray visualizer, imager, or information provider 100 may also shield at least some of the X-rays from passing to the at least the portion of the individual. In certain instances, such shielding may be removable, replaceable, and/or shiftable such as to shield at least certain portions of the individual at one or more locations depending on which emitter portions 150 and/or detector portions 152 are being utilized.

Figure 29:
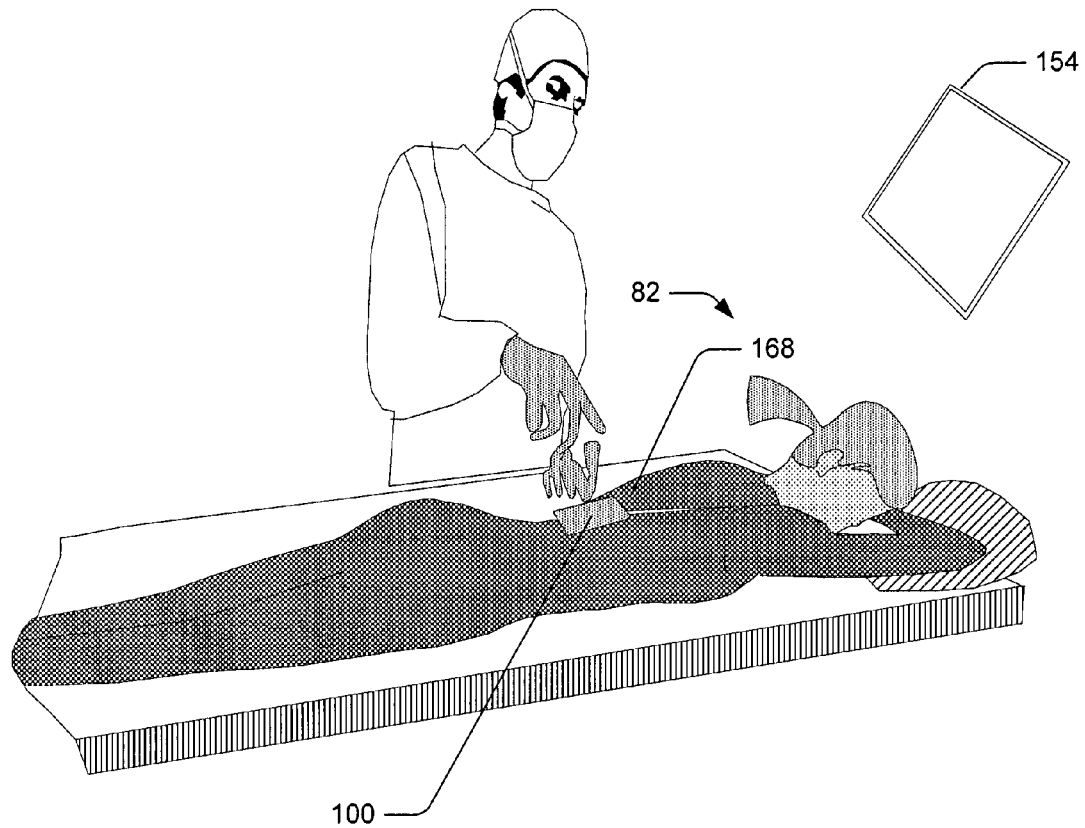
FIG. 29 shows an embodiment of the Compton scattered X-ray visualizer, imager, or information provider that can be positioned by the user.

Certain embodiments of the at least one emitter portion 150 and/or the at least one detector portion 152 can thereby be configured as a hand-held and positional device as described with respect to FIG. 29 such as can be positioned and/or used by the user, the individual, or another person. Is envisioned that at least portions of certain embodiments of the Compton scattered X-ray visualizer, imager, or information provider 100 can be configured similar to a computer mouse (e.g., in dimension and/or position), such as to allow a user to position the device from a useful (and/or non-obstructive) user-selectable vantage point relative to the individual. Certain hand-held devices can transmit data to other detector or display devices, such as can be displayed over displays, glasses, plasma, or a variety of at least portions of certain embodiments of the Compton scattered X-ray receiving assembly 151.

Certain portable or repositionable embodiments of at least portions of the Compton scattered X-ray visualizer, imager, or information provider 100 can utilize wireless and/or wired-based communications relative to other controller and/or computer portions associated therewith to effect data transfer, image transfer, etc. Alternately, certain embodiments of the constant scattered X-ray visualized, imaged, or information provided 100 can include the display and/or simulator as to provide for visualization, imaging, and/or provide information directly there from. Certain user-selectable positionable Compton scattered X-ray visualizer, imager, or information provider 100 could be securable in position by some securement or locking structure relative to the matter of the at least the portion of the individual. Such securement or fastener techniques can be used to limit excessive motion of the Compton scattered X-ray visualizer, imager, or information provider 100 relative to the at least the portion of the individual and/or improve depth visualizing, imaging, or information providing capability or quality of the Compton scattered X-ray visualizer, imager, or information provider. As such, the emitter portion could be positioned and located as desired. Certain embodiments of the emitter portion 150 could include a mount that might hold the emitter portion 150 in position, such as might limit the displacements of the emitter portion to improve the Compton scattered X-ray visualization, imaging, or information providing capabilities of the Compton scattered X-ray visualizer, imager, or information provider 100. By providing a hand-held and/or positionable device, certain users can obtain a desired depth visualization or image at a desired location without while the remainder of the user remains in a desired viewing or other position and/or location.

With certain hand-held positionable embodiment of the Compton scattered X-ray visualizer, imager, or information provider 100, relatively quick feedback rates may be particularly desirable for Compton scattered X-ray visualization, imaging, or information providing. Certain hand-held, positionable, or movable devices may also be useful in providing Compton scattered X-ray visualization, imaging, or information providing at a variety of locations and/or angles of the individual such as may be controlled or adjusted by the user, the individual, a machine (e.g., robot), or an other person.

The emitter portion 150 and/or detector portion 152 can thereby be configured as a remote device, or even a movable device such as can be a hand-held device (perhaps similar in size or shape as a computer mouse, or a digital camera as described with respect to FIG. 29). Such movable, frame secured, securable, or other embodiments of the Compton scattered X-ray visualizer, imager, or information provider 100 can thereby provide applied X-rays and/or receive scattered X-rays from desired or controllable positionable locations. For instance, a doctor could position certain embodiments of the emitter portion adjacent the at least the portion of the individual 82, such that particular subsurface regions of the at least the portion of the individual can be illuminated by or receive the X-ray based electromagnetic radiation adjacent the at least the portion of the individual 82. Such controllability or positionability of visualizing, imaging, or information providing can be performed in a similar manner as a user of a flashlight might apply the flashlight to certain locations to optionally illuminate particular regions at which the flashlight is directed. Similarly, a physician might position the at least one detector portion 152 in close proximity to the portion(s) of the individual being visualized, imaged, or information provided. By comparison, certain embodiments of the emitter portion can be configured as applying a relatively disperse X-ray source that can generally apply X-rays to against large regions (or at least regions of interest) of the at least the portion of the individual 82. Different embodiments of the Compton scattered X-ray visualizer, imager, or information provider 100 (i.e., surgeon positioning and/or region of room filling embodiments of the at least one emitter portion 150, etc.) can be used separately or in combination, and are intended to be illustrative in nature but not limiting in scope.

Figure 30:
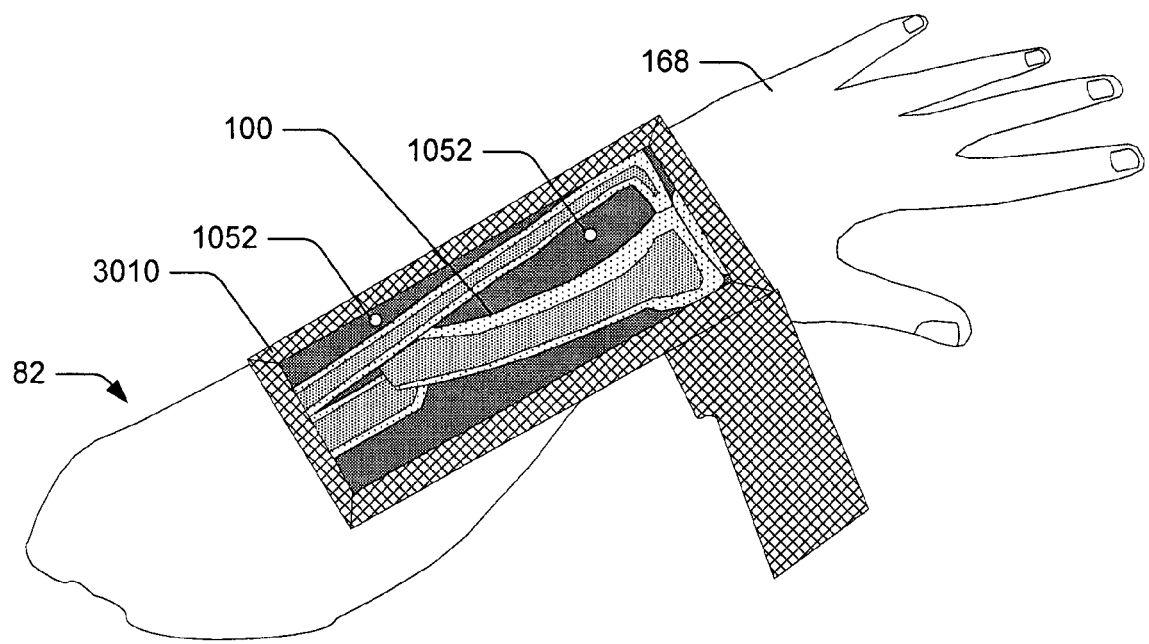
FIG. 30 shows another embodiment of the Compton scattered X-ray visualizer, imager, or information provider.

Certain embodiments of the Compton scattered X-ray receiving assembly 151 and/or the display can be positioned in close proximity to the at least the portion of the individual, as described with respect to FIG. 30. For example, the at least one Compton scattered X-ray receiving assembly 151 that is Compton scattered X-ray visualization, imaging, or information providing a bone in a forearm may be positioned adjacent the forearm, perhaps even in a position that may be viewable by the user and/or the user. Certain embodiments of the Compton scattered X-ray visualizer, imager, or information provider 100 can utilize at least one fiducial 1052 to assist in locating the visualized, imaged, or information provided portion. The embodiments of the Compton scattered X-ray receiving assembly 151 as described with respect to FIG. 31 can be configured for depth visualizing, imaging, or information providing relatively deep portions of the individual, such as skeletal systems, organs, certain internal blood vessels, etc. It is likely that such embodiments of the Compton scattered X-ray visualizer, imager, or information provider 100 that act deep into the matter of the individual can also apply the applied X-rays including at least some X-ray photons having sufficient energy level that can pass deep into the individual. Such deep visualizing, imaging, or information providing would likely utilize the image processing techniques as described with respect to FIGS. 18 and 19, for example.

Figure 31:
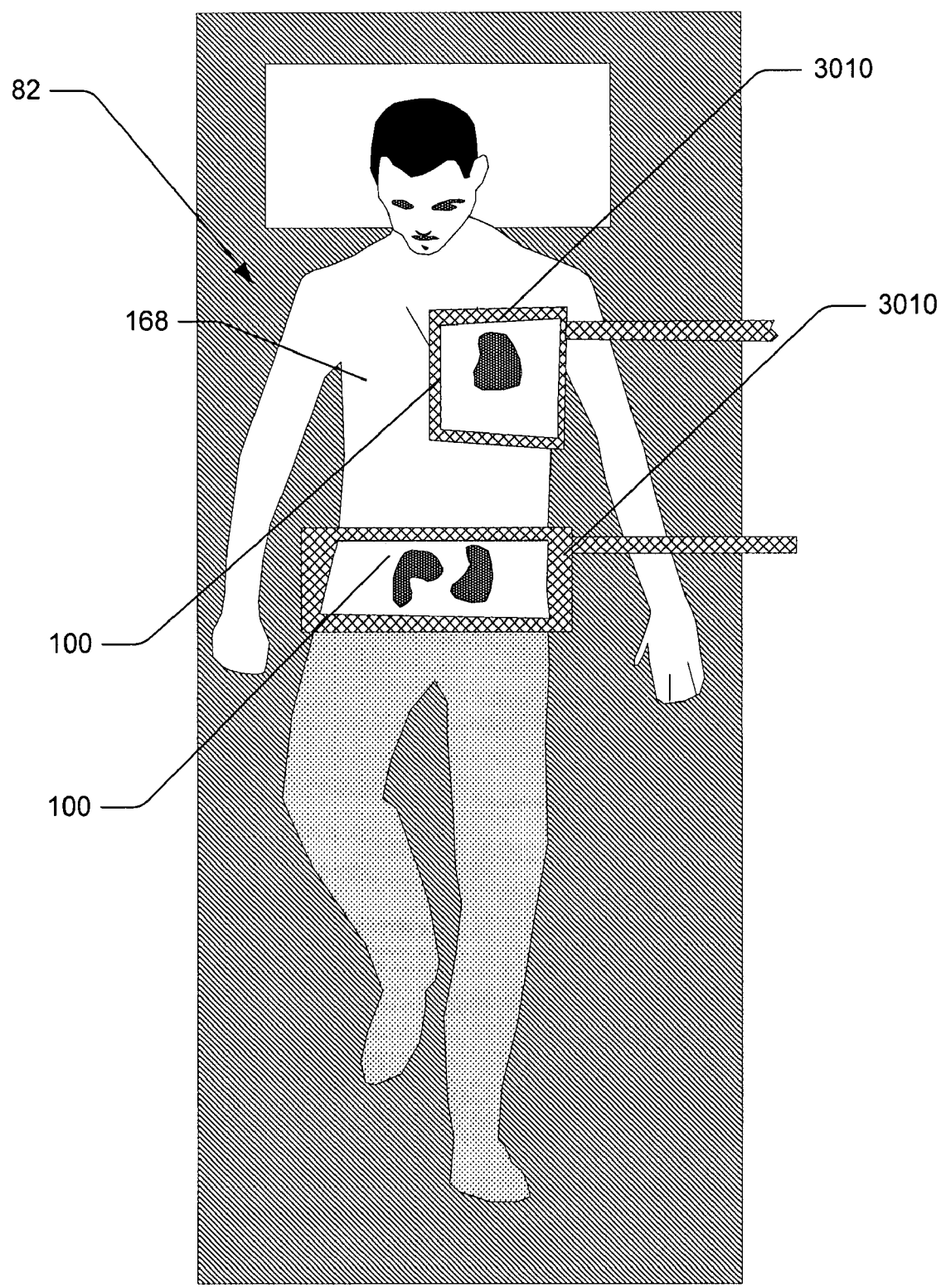
FIG. 31 shows yet another embodiment of the Compton scattered X-ray visualizer, imager, or information provider.

Certain embodiments of the Compton scattered X-ray visualizer, imager, or information provider 100, as described with respect to FIGS. 30 and 31, can include a framework 3010 and be configured such as to contain at least the Compton scattered X-ray receiving assembly 151 (not shown in these figures). Certain embodiments of the framework can be used to be positioned by the user, or secured by a securing device (rigid frame, arm, flexible belt, strap, or other).

Certain embodiments of the entire Compton scattered X-ray visualizer, imager, or information provider 100 as described with respect to FIG. 1 can therefore be configured as a single unitary member utilizing similar technology as is known in graphical user interface (GUI), display, and controller technology such as to integrate all the portions of devices into combined units. By comparison, certain embodiments of the Compton scattered X-ray visualizer, imager, or information provider 100 can be configured as distinct units, only certain ones of which may include their distinct framework 3010 if desired, or practicable. There are a variety of potential advantages to frameworks which include, but are not limited to, allowing a user to hold or providing a securement point (certain ones of which can be adjusted and controlled) to at least certain portions of the Compton scattered X-ray visualizer, imager, or information provider 100.

Certain conventional transmissive X-rays can image three-dimensional matter across the extent of the portion of the person to a two-dimensional image. Certain embodiments of the Compton scattered X-ray visualizer, imager, or information provider 100, by imaging a two-dimensional slice of the individual (e.g., imaging through the bone), might be particularly useful in visualizing, imaging, or providing information pertaining to the individual for orthopedics, knees, bones, joints, organs, and other structural aspects of the individual.

Certain embodiments of the Compton scattered x-ray visualizer, imager, or information provider 100 can be configured to operate based at least in part on tomography. Tomography can be based, at least partially, on obtaining at least one material characterizing distribution function. Within this disclosure, the material characterizing distribution function can be considered as a measurement of electron density, which more or less corresponds to the density of the matter. As such, a variety of visualizations, images, or provided information of at least some matter of at least the portion of the individual based at least upon the material characterizing distribution function. Conventional tomography, such as CAT scan, PET scan, etc. may rely upon obtaining at least some type of distribution function. Those electrons of the outer shells of the matter, thereby are loosely held to the molecule, in such a manner to quantifiably correspond largely to the material characterizing distribution function. By comparison, those electrons of the inner shell of the matter thereby are more securely held to the molecule, and therefore correspond to a lesser degree to the material characterizing distribution function.

Certain embodiments of the Compton scattered X-ray receiving assembly 151 can receive a number of Compton scattered X-ray in such a manner that there exists a number of uncertainties as to certain characteristics (e.g., in density, mass, structure, component, etc.) of the matter. For example, a particular Compton scattered x-ray receiving assembly 151 that receives scattered X-rays from a specific angle and/or position may receive a large number of scattered x-rays that correspond to that angle and/or position, corresponding to the material characterizing distribution function. They may be, for example, no way to differentiate between scattered X-rays from a number of different depths that correspond to a given angle and/or position within the at least some matter of the at least some portion of the individual, upon consideration of the material characterizing distribution function. Conventional tomography can similarly utilizes a material characterizing distribution function.

Certain embodiments of the Compton scattered X-ray visualizer, imager, or information provider 100 can capture a visualization, image, or provided information based on a number of material characterizing distribution function that are obtained from a number of positions, angles, etc. For example, certain embodiments of the Compton scattered X-ray visualizer, imager, or information provider 100 can utilize the material characterizing distribution function obtained when applying an applied X-ray substantially through a considerable portion of the individual that are forward scattered, similar to as described relative to FIG. 5, for example, and other locations through this disclosure. Certain embodiments of the Compton scattered X-ray visualizer, imager, or information provider 100 can utilize the material characterizing distribution function obtained when applying an applied X-ray substantially through a considerable portion of the individual that can thereupon be back scattered, forward scattered, or otherwise Compton scattered similar to as described relative to FIG. 4, for example, and other locations through this disclosure.

Certain embodiments of the Compton scattered X-ray visualizer, imager, or information provider 100 can differentiate between scattered X-rays from different scattering locations and/or angles, based at least partially on tomographic/volumatric considerations. Certain embodiments of the Compton scattered X-ray visualizer, imager, or information provider 100 can differentiate between scattered X-rays from different energy levels, based at least partially on tomographic considerations.

The embodiments of the Compton scattered X-ray visualizer, imager, or information provider 100 that are secured to the at least the portion of the individual, using a sleeve or other such mechanism, will likely be preferred by individuals undergoing imaging as compared with certain MRI images, CAT scans, tomography imagers, and/or other conventional imagers in which the patient is expected to remain substantially motionless. In addition, certain conventional tomography imaging techniques require positioning of the individual in a claustiphobic tube during the relatively extended duration.

Certain types of tomography imagers (both conventional and included as certain embodiments of Compton scattered X-ray visualizer, imager, or information provider 100), may tend to be quite computer-software and processor intensive. Much of the work by the computer software, hardware, or firmware is associated with repositioning, focusing, zooming, angling, refreshing, and other controlling and adjusting aspects of the displayed visualization, image, or provided information. Certain of the depth visualizing, imaging, or information providing components of certain embodiments of the Compton scattered X-ray visualizer, imager, or information provider 100 can be indexed relative to the portion of the individual. Such indexing can be performed such that if a region of interest (e.g., a cancer node) is located, the location can be determined relative to the Compton scattered X-ray visualizer, imager, or information provider 100, such as by longitude or latitude markings on the sleeve in certain embodiments of the Compton scattered X-ray visualizer, imager, or information provider 100. Certain instances of such visualization, imaging, or information providing can be provided on a real time (or near real time) basis.

A considerable portion of this disclosure describes applying Compton scattered X-ray visualizer, imager, or information providers to image to locate, analyze, and/or treat a variety of aberrations such as cancers. It is also envisioned that a number of embodiments of the Compton scattered X-ray visualizer, imager, or information provider 100 can be applied to a variety of surgical, medical examination, medical diagnosis, medical forensics, autopsies and other such applications. Certain embodiments of the Compton scattered X-ray visualizer, imager, or information provider 100 may visualize, image, and/or provide information relating to blood that can be configured to provide high contrast with this technique since it has iron and backscatters considerably.

As such, certain embodiments of the Compton scattered X-ray visualizer, imager, or information provider may be particularly appropriate for brain Compton scattered X-ray visualization, imaging, or information providing and/or surgery, heart Compton scattered X-ray visualization, imaging, or information providing and/or surgery, lung Compton scattered X-ray visualization, imaging, or information providing and/or surgery, etc. Certain embodiments of the Compton scattered X-ray visualizer, imager, or information provider 100 may be configured to examine aberrations of such dissimilar matter such as calcium concentration of portions of matter for Compton scattered X-ray visualization, imaging, or information providing or examination for breast tumors, iodine for thyroid Compton scattered X-ray visualization, imaging, or information providing or examination. Additionally, certain contrast agents may be used to enhance the contrast for Compton scattered X-ray visualization, imaging, or information providing, for example iodine in blood vessels.

Certain embodiments of the Compton scattered X-ray visualizer, imager, or information provider 100 can include a relatively weak powered X-ray based emitter portion 150, such that much of the X-rays generated therefrom may not be transmitted through the at least the portion of the individual. Such relatively weak powered X-ray emitter portions 150 may be desirable since they limit the dosage being applied to the at least the portion of the individual, as well as others near the individual such as the user.

There are a number of Compton scattered X-ray visualization, imaging, or information providing techniques that can be utilized by certain embodiments of the Compton scattered X-ray visualizer, imager, or information provider 100, each of which should consider limiting the overall dosage of X-rays being applied to the at least the portion of the individual and/or other persons. Certain embodiments of the Compton scattered X-ray visualizer, imager, or information provider 100 can be configured to operate on a temporal/positional reflective basis. This may, depending on context, be considered as Compton scattered X-ray visualization, imaging, or information providing at a rate sufficient to indicate accurately the current position of the portion of the individual 82 undergoing Compton scattered X-ray visualization, imaging, or information providing (considering the intended purpose of the at least one visualization, image, or provided information).

Real time depth imaging, visualizing, or information providing, and near real time depth imaging, visualizing, or information providing may be considered as one embodiment of temporal/positional reflective depth visualizing, imaging, or information providing. As such, temporal/positional visualization, imaging, or information providing by certain embodiments of the Compton scattered X-ray visualizer, imager, or information provider 100 can involve updating of Compton scattered X-ray visualization, imaging, or information providing within such a duration as to accurately reflect a state of the at least the portion of the individual 82. By using certain types of temporal/positional reflective visualization, imaging, or information providing using certain embodiments of the Compton scattered X-ray visualizer, imager, or information provider, certain users may be able to locate a region, organ, etc. within the at least the portion of the individual either manually or using a tool. Examples of such tools as described in this disclosure can include, but a re not limited to, an endoscope attachment, a tactile feedback provider, an attachment to a framework, etc.

As such, certain embodiments of the X-ray Compton scattered X-ray information can be utilized or operated by the user and/or the individual on a substantially temporal/positional reflective basis. At the time of operation, Compton scattered X-ray visualization, imaging, or information providing and/or visualize, image, and/or provide information updating can be performed at a substantially temporal/positional reflective basis. Alternatively, certain Compton scattered X-ray visualization, imaging, or information providing and/or visualize, image, and/or provide information updating could be performed sequentially a number of times, or only one or more times using certain embodiments of the Compton scattered X-ray visualizer, imager, or information provider 100.

A number of illustrative but not limiting applications of temporal depth visualizing, imaging, or information providing by certain embodiments of the subcutaneous Compton scattered X-ray visualizer, imager, or information provider 100 are now described. One application of temporal depth visualizing, imaging, or information providing by certain embodiments of the Compton scattered X-ray visualizer, imager, or information provider 100 could include functional brain depth visualizing, imaging, or information providing or functional tomography, in which certain regions of brain activation may be reflected with increases in blood flow. This type of depth visualizing, imaging, or information providing could be used during brain surgeries to detect an area associated with a given cognitive action or sensory stimulation by monitoring or detecting alterations in blood flow. Another application of temporal depth visualizing, imaging, or information providing by certain embodiments of the Compton scattered X-ray visualizer, imager, or information provider 100 would include vascular surgery. Whether the vascular surgery be for clipping an aneurysm or creating a vascular graft, one could use the subcutaneous Compton scattered X-ray visualizer, imager, or information provider 100 to detect alterations in blood flow in the brain, heart, liver, or other organ, tissue, or region of the individual.

Yet another depth visualizing, imaging, or information providing application of certain embodiments of the subcutaneous Compton scattered X-ray visualizer, imager, or information provider 100 could include implantation of orthopedic instrumentation. A user such as a surgeon could image, examine, and/or utilized the implant during installation to ensure that it is being installed properly. As such, the user could insure the implant is not being positioned are located in properly or in the wrong place during attachment or securement. Dentists could similarly image, examine, and/or utilize images relating to their dental work. An example of such installation-based Compton scattered X-ray visualization, imaging, or information providing might include installing a pedicle screw to be used in a spinal construct and/or plate. Certain embodiments of the subcutaneous Compton scattered X-ray visualizer, imager, or information provider 100 may be used to ensure the screw has not breached and gone into the spinal canal, or alternately exited to hit a blood vessel, a nerve root, or another sensitive region. Certain embodiments of the subcutaneous Compton scattered X-ray visualizer, imager, or information provider 100 could thereby help watch the implant placement progression.

Certain embodiments of the Compton scattered X-ray visualizer, imager, or information provider 100 can be applied to different individuals such as a variety of humans of different conditions, sexes, ages (e.g., a human adult, child, or embryo), etc. Additionally, certain embodiments of the Compton scattered X-ray visualizer, imager, or information provider 100 can be applied to at least one other non-human individuals 82 including, but not limited to: at least one animal (domestic, wildlife, livestock as described with respect to FIGS. 32 and 33), at least one organism (natural or synthetic, such as can be visualized, imaged, or have information provided for medical, scientific, clinical or other purposes), at least one plant, etc. By Compton scattered X-ray visualization, imaging, or information providing animals such as pets, wild animals, or livestock, for example, certain embodiments of the Compton scattered X-ray visualizer, imager, or information provider 100 can obtain useful information thereabout, without the necessity of the user having to come into close contact, or only limited contact, with the animal. Such users who often have to come in contact with animals might include, but are not limited to: veterinarian, wildlife managers, zookeepers, other people associated with wild or domestic animals, etc. Such close contact is also possible during use by certain Compton scattered X-ray visualization, imaging, or information providing embodiments. In addition, such Compton scattered X-ray visualization, imaging, or information providing can be done relatively routinely, or in a non-evident manner, such as to make scanning the animals, or a relatively large number of animals, relatively easy without them necessarily being aware of the depth visualizing, imaging, or information providing. Such depth visualizing, imaging, or information providing of certain animals may preferably be performed in a manner that reduces the animal's awareness that anything unusual is occurring, such as may easily be accomplished using certain embodiments of the Compton scattered X-ray visualizer, imager, or information provider 100, The above-mentioned components or embodiments of the Compton scattered X-ray visualizer, imager, or information provider 100, as described with respect to FIG. 1 as well as in other locations in this disclosure, could be distributed or operated outside, in a forest, etc. Such configurations could allow Compton scattered X-ray visualization, imaging, or information providing of wild animals (perhaps controlled and/or adjusted by remote control), livestock, fish, etc. Such embodiments of the Compton scattered X-ray visualizer, imager, or information provider 100 could be useful in detecting illnesses, injuries, etc. in wildlife, whales, dolphins, etc.

Figure 32:
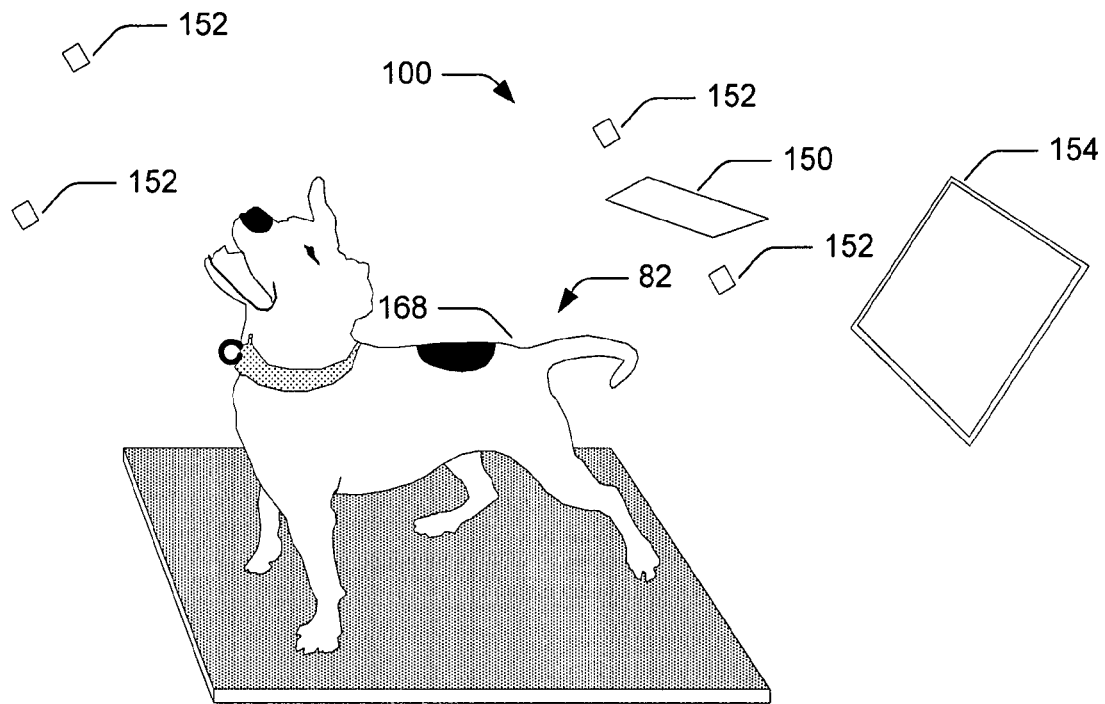
FIG. 32 shows one animal-based embodiment of the Compton scattered X-ray visualizer, imager, or information provider.
Figure 33:
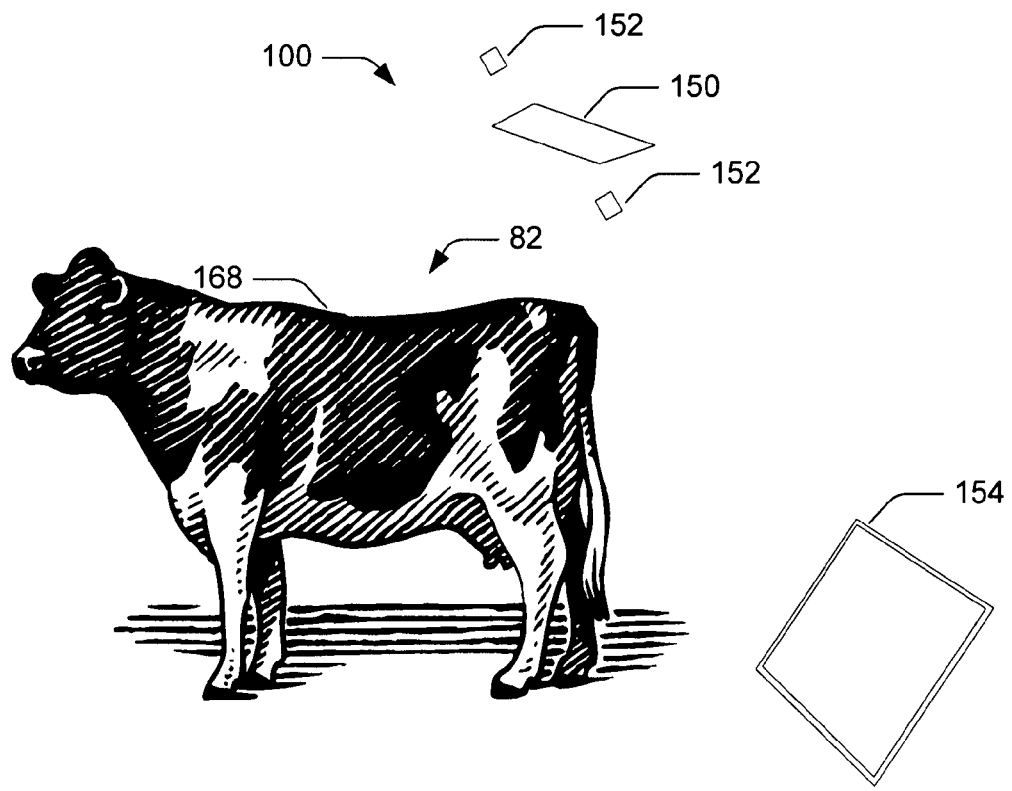
FIG. 33 shows another animal-based embodiment of the Compton scattered X-ray visualizer, imager, or information provider.

Certain embodiments of the Compton scattered X-ray visualizer, imager, or information provider 100 can be applied to animals such pets, livestock, wild animals, aquatic animals and fish, etc. as described with respect to FIGS. 32 and 33, for example. Since animals do not understand conventional imaging or other medical processes, they may be difficult to handle or become agitated or confused under certain conventional imaging circumstances. As such, it may be very difficult to image portions of animals to determine their condition using certain conventional imagers. Certain embodiments of the Compton scattered X-ray visualizer, imager, or information provider 100 could be applied in such manner such as the animal may not even be aware of the ongoing Compton scattered X-ray visualization, imaging, or information providing. Veterinarians could utilize certain embodiments of the Compton scattered X-ray visualizer, imager, or information provider 100 to obtain considerable Compton scattered X-ray visualization, imaging, or information providing information previously unobtainable while keeping a safe distance from uncooperative, uncertain, or dangerous animals.

Certain embodiments of the Compton scattered X-ray visualizer, imager, or information provider 100 could be applied to livestock, such as may be situated in a corral or even a field as described with respect to FIG. 33. Such livestock embodiments of the Compton scattered X-ray visualizer, imager, or information provider may be able to scan them for certain illnesses, conditions, sicknesses, etc. (e.g., mad cow disease). Certain users of the Compton scattered X-ray visualizer, imager, or information provider 100 could be characterized by relative speed, limited expense, reliability, and effectiveness.

As such, certain embodiments of the Compton scattered X-ray visualizer, imager, or information provider 100 can visualize, image, and/or provide information of a wide variety of individuals from the surface 168 of the at least the portion of the individual down to the within the at least one visualization, imaging, or information providing depth range to the at least one prescribed visualization, imaging, or information providing depth. As described herein, the surface could be internal and/or external to the individual. The particular Compton scattered X-ray visualization, imaging, or information providing modality being utilized should be configured based on the matter, region, structure, and other characteristics, of the at least the portion of the individual as well as the condition of the at least the portion of the individual, etc.

Compton scattered X-ray visualization, imaging, or information providing of distinct matter relatively can be based at least partially on different X-ray based characteristics of the distinct matter, the junction location of the different matters, etc. One X-ray characteristic can be based, at least partially, on X-ray absorbance differences between different types of matter. Bones, bone fragments, etc. when being exposed to transmissive X-rays are generally understood to absorb more X-ray based electromagnetic radiation (e.g., X-ray photons) than softer human matter (such as skin, tissue, muscle, blood, bodily fluid, etc.), for example. Even with X-ray Compton scattered X-ray, such as utilized by certain embodiments of the Compton scattered X-ray visualizer, imager, or information provider 100, the bone or bone fragments would be expected to be more dense, and would be expected to absorb more X-rays of certain frequencies/energy levels than other matter such as tissue. As such, certain matter will scatter a greater percentage of the applied or applied X-rays than bone or bone fragments, which will absorb a greater percentage of X-rays.

Similarly, each type of matter such as tissue, muscle, bones, fat, etc. should have distinct X-ray characteristics that can be imaged directly using Compton scattered X-ray techniques, and/or by using certain particular contrast agents or fluoroscopy using certain embodiments of the Compton scattered X-ray visualizer, imager, or information provider. Another X-ray characteristic can be based, at least partially, on Compton scattered X-ray or reflectance differences between different types of matter. Yet another X-ray characteristic can be based, at least partially, on a ratio of photons transmission compared to photons return between different types of matter.

Certain embodiments of the Compton scattered X-ray visualizer, imager, or information provider 100 can utilize a single applied X-ray beam 120 during Compton scattered X-ray visualization, imaging, or information providing such as can be provided by at least one emitter portion 150, as described in this disclosure. By comparison, certain embodiments of the Compton scattered X-ray visualizer, imager, or information provider can utilize multiple applied X-ray beams 120 which may at least partially intersect with each other during Compton scattered X-ray visualization, imaging, or information providing such as can be provided by the at least one emitter portion 150, as described in this disclosure. With certain embodiments of the Compton scattered X-ray visualizer, imager, or information provider 100, the intersection of the multiple applied X-rays 120 can be applied at a location that may be desired to be visualized, imaged, or information provided, such as at a particular depth, etc.

With certain embodiments of the Compton scattered X-ray visualizer, imager, or information provider 100, the intersection location of the multiple applied X-rays can be controllably moved to a desired location such as may be controlled by the user of certain embodiments of the subsurface Compton scattered X-ray visualization, imaging, or information providing controller 97 as described in this disclosure with respect to FIG. 1. Alternately, such movement of the intersection can effect a scan, similar to a raster scan such as is generally known by those skilled with displays. Certain embodiments of the Compton scattered X-ray visualizer, imager, or information provider 100 can thereby be configured to provide a variety of different depth visualizations, images, and/or provided information depending on the Compton scattered X-ray visualization, imaging, or information providing techniques. For instance, by Compton scattered X-ray visualization, imaging, or information providing, certain individuals could be visualized, imaged, or have information provided in a manner appearing similar to (but perhaps having different resolution or characteristics from) imaging by conventional X-ray, fluoroscopy, MRI, CAT scans, or other Compton scattered X-ray visualization, imaging, or information providing modalities.

One aspect of certain embodiments of the Compton scattered X-ray visualizer, imager, or information provider 100 is that relatively small depth visualizations, images, and/or provided information can be captured, displayed, analyzed, and if desired recaptured without waiting for durations associated with processing, or developing, the images are visualizations for a larger region. In certain circumstances, the visualizing, imaging, and/or providing information can be performed without having to wait for processing or developing, and the necessity of having to move or reposition the patient. During certain conventional imaging techniques, the at least the portion of the individual must remain virtually motionless during the conventional imaging process to maintain the image quality. Additionally, certain conventional image techniques take a considerable duration to capture, develop, process, display, etc. By comparison, certain embodiments of the Compton scattered X-ray visualizer, imager, or information provider can capture and/or display certain localized or shallow depth visualizations, images, and/or provided information relatively quickly. As such, the user such as the physician, veterinarian, dentist, or other user can quickly examine the visualize, image, and/or provide information and/or obtain additional subsequent depth visualizations, images, and/or provided information that show desired features, positions, etc.

Certain embodiments of the Compton scattered X-ray visualizer, imager, or information provider 100 may not require maintaining the at least the portion of the individual nearly motionless in an encircling enclosure or tunnel, such as with CT scans, PET scans, or MRI. Certain embodiments of the Compton scattered X-ray visualizer, imager, or information provider 100 might involve a change in Compton scattered X-ray visualization, imaging, or information providing techniques by the users, surgeons, etc., but would likely not diminish Compton scattered X-ray visualization, imaging, or information providing capabilities or resolution as compared with other conventional imaging techniques.

Certain embodiments of the Compton scattered X-ray visualizer, imager, or information provider 100 can be configured such that the at least one matter associated with the at least the portion of the individual 82. For example, the matter of the portion of the human can include at least some, or combination of: flesh, muscle, fat, tissue, bone, teeth, blood, fluids, or other such matter. As such, certain embodiments of the Compton scattered X-ray visualizer, imager, or information provider 100 can visualize, image, and/or provide information relating to not only matter in general, but also different types of matter and junctions between different types of matter. Such Compton scattered X-ray visualization, imaging, or information providing matter can be performed at the range of resolutions as described in this disclosure, and may at least partially rely on additional agents, components, etc. such as may enhance Compton scattered X-ray visualization, imaging, or information providing.

Certain embodiments of the Compton scattered X-ray visualizer, imager, or information provider 100 can allow physicians a number of opportunities to detect certain types of distinct matter, such as tumors or cancer that may be situated in a region of generally normal matter. Certain Compton scattered X-ray visualization, imaging, or information providing modalities may be more successful to detect certain types of cancers as compared with certain visualizers, imagers, or have information providers. It may therefore be useful to provide a Compton scattered X-ray visualization, imaging, or information providing modality that can detect at least one or a considerable number and types of cancers, tumors, and/or other matter aberrations as described in this disclosure. For instance, certain Compton scattered X-ray visualization, imaging, or information providing modalities may not detect certain cancers or other matter aberrations, while other Compton scattered X-ray visualization, imaging, or information providing modalities (perhaps including certain embodiments of the Compton scattered X-ray visualizer, imager, or information provider 100) may detect the cancers or other matter aberrations.

Certain embodiments of the Compton scattered X-ray visualizer, imager, or information provider 100 can be configured or designed to detect at least one of a variety of cancers or tumors such as, but not limited to: breast cancer, skin cancer, colon cancer, bladder cancer, prostate cancer, etc. Such cancer cells or tumors may be situated in the matter at a location that certain conventional imagers may not be able to image, or may be expensive to image well. Certain cancers, such as certain breast cancer and certain melanomas, may be characterized by calcium nodules, which may be difficult be detect using a variety of conventional imaging techniques and/or devices.

Certain embodiments of the Compton scattered X-ray visualizer, imager, or information provider 100 can be well suited to visualize, image, and/or provide information relating to a variety of cancer and/or tumors. Certain tumors or cancers may exhibit angiogenesis that allow depth visualizing, imaging, or information providing by certain Compton scattered X-ray visualizer, imager, or information providers 100. The blood vessel of the patient individual nearby the cancer or tumor may be grown to allow for an increase in blood flow to the tumor or cancer as the tumor or cancer tends to expand and grow outward. Cancer cells or tumor cells may lose their ability to divide in a controlled fashion that can result in the angiogenesis. Tumors can induce blood vessel growth (angiogenesis) by secreting various growth factors, e.g. Vascular Endothelial Growth Factor (VEGF). Such growth factors can induce capillary growth into the tumor, which some researchers suspect supply required nutrients, thereby allowing for tumor expansion. Other clinicians believe that angiogenesis really serves as a waste pathway, taking away the biological end products put out by rapidly dividing cancer cells. In either case, angiogenesis is a necessary and required step for cancer cells to transition and grow from a small harmless cluster of cells to the size of a large tumor. Angiogenesis is also required for the spread of a tumor, or metastasis. The depth of the visualization, imaging, or information providing can be controlled or adjusted as to localize the area being examined.

Certain types of cancer can proliferate to different regions, areas, organs, etc. based on metastasis. Metastasis can occur, for example, when single cancer cells break away from an established solid tumor, enter the blood vessel, and be carried to a distant site, where they can implant and begin the growth of a secondary tumor. Evidence now suggests that the blood vessel in a given solid tumor may in fact be mosaic vessels, comprised of endothelial cells and tumor cells. This mosaicity can allow for substantial shedding of tumor cells into the vasculature. The subsequent growth of such metastases will also require a supply of nutrients and oxygen or a waste disposal pathway as provided by subsequent angiogenesis. A tumor thereby typically consists of a population of rapidly dividing and growing cancer cells. Mutations may rapidly accrue within the population of many cancer cells. These mutations of the cancer cells often allow at least some of the cancer cells to develop drug resistance.

Tumors including certain cancer cells cannot grow beyond a certain size, while permitting the internal cancer cells deep within the tumor to survive (typically as a result of a lack of oxygen and other essential nutrients that can be provided to the interior cancer cells). Certain tumors or cancers may thereby exhibit necrosis, in which, as the size of the tumor or cancer increases, the original cancer cells that are situated deep within the tumor, and thereby distant from the outer boundary of the tumor or cancer may starve and die as a result of lack of nutrients such as may be provided by the healthy cells. Such starvation or dying may occur since the cell is no longer in contact with healthy cells or supplies of nutrients or oxygen. As such, certain necrotic cancer cells may tend to exhibit different photonic and X-ray characteristics than the living cancer cells, as well as the healthy cells. Certain embodiments of the Compton scattered X-ray visualizer, imager, or information provider 100 can therefore be utilized to detect such necrotic cancer cells. Such depth visualizing, imaging, or information providing of tumors and/or cancer provides only one illustrative embodiment of a use of certain embodiments of the Compton scattered X-ray visualizer, imager, or information provider 100.

In addition, certain embodiments of the Compton scattered X-ray visualizer, imager, or information provider 100 can visualize, image, and/or provide information on a temporal/positional reflective basis, and may be performed without positioning the individual in the claustrophobic enclosures, or applying the high-scale electromagnetic radiation associated with, for example, conventional MRI, conventional PET scans, and certain other conventional images.

Certain embodiments of the Compton scattered X-ray visualizer, imager, or information provider 100 can provide different depth visualizing, imaging, or information providing modalities and/or techniques than that of conventional X-ray imaging. For example, conventional X-ray imaging can visualize, image, and/or provide information relating to differences based at least in part on density or atomic number of the matter of the portion of the visualized, imaged, or information provided object, such as differences on density between bone and skin for a person. By comparison, certain embodiments of the Compton scattered X-ray visualizer, imager, or information provider 100 can visualize, image, and/or provide information based at least partially on density of matter such as tissue, as well as providing an additional Compton scattered X-ray visualization, imaging, or information providing modality. Certain embodiments of the Compton scattered X-ray visualizer, imager, or information provider 100 can be expected to visualize, image, and/or provide information to a resolution down to approximately 100 microns, or even less as technology improves.

Certain embodiments of the Compton scattered X-ray visualizer, imager, or information provider 100 can be configured to utilize contrast agents such as, for example, iodine. Certain embodiments of the Compton scattered X-ray visualizer, imager, or information provider 100 can be configured to apply a contrast agent at least partially within the confined depth region. Also, certain embodiments of fluorophores (that when accepted by matter may allow the matter to fluoresce under the application of certain X-rays), as well as other electromagnetic responsive material, can be utilized in a similar manner as contrast agent to matter to enhance the Compton scattered X-ray visualization, imaging, or information providing.

Certain embodiments of the Compton scattered X-ray visualizer, imager, or information provider can be configured to visualize, image, and/or provide information relating to certain fluids and/or fluid locations such as blood (e.g., an element of hemoglobin). Certain blood locations, such as arteries, veins, blood pooling regions, body parts, organs, capillaries, regions, etc., can provide good X-ray contrast based at least partially on iron or other materials in the blood. Therefore, the iron in the blood can cause deflection, absorption, reflection, or Compton scattered X-ray of the X-rays passing there through by some detectable amount. Using conventional techniques, many surgeons, etc. have considerable uncertainty as to the precise location of many blood vessels that they must operate around without contacting or damaging. Such effort by the surgeons, etc. in avoiding the blood vessels is not only dangerous, but also expensive, laborious, and tedious. Certain embodiments of the Compton scattered X-ray visualizer, imager, or information provider 100 can detect blood vessels, as well as other bodily fluid conduits, etc. such as to in many instances allow the surgeons, etc. to operate more safely, quickly, effectively, and efficiently.

Certain embodiments of the Compton scattered X-ray visualizer, imager, or information provider 100 can thereby be configured to observe calcium concentration, such as may exist in certain cancers or tumors. Certain embodiments of the Compton scattered X-ray visualizer, imager, or information provider 100 can be configured to visualize, image, and/or provide information relating to iodine such as may be present and varying concentrations in portions of the brain, such as may be provided by the thyroid. Certain embodiments may be used in combination with a Compton scattered X-ray visualization, imaging, or information providing agent that can be added to the at least the portion of the individual, either intravascular or otherwise.

Certain organs and matter such as tissue that have considerable blood flow either flowing through or contained therein can be visualized, imaged, or have information provided based, at least in part, on the blood situated within the organ or matter. Examples of such organs or matter that can be visualized, imaged, or have information provided as a result of blood can include, but are not limited to: the brain (accounting for approximately 20 percent of the blood flow in the human body at any given time), the heart, the liver, the lung, the appendix, the intestine, as well as certain muscles. The heart therefore is an example of an organ that can be visualized, imaged, or have information provided particularly well based on blood situated relative to the heart. The heart acts to circulate blood throughout the body, and such blood flow through the aorta, the ventricles, and other chambers and regions of the heart can be visualized, imaged, or have information provided (in certain instances in a substantially real-time basis). In addition, the heart additionally includes arteries, veins, and capillaries which can be distinctly visualized, imaged, or have information provided.

There are variety of heart aspects and/or conditions that can be image using certain embodiments of the Compton scattered X-ray visualizer, imager, or information provider 100. For example, the myocardium could be imaged, as can the heart valves, the coronary arteries, the blood vessels, as well as other matter and/or fluid of or within the heart. Certain blood flows through the valves, the aorta, etc. can be imaged, such as to indicate regurgitation and (that workflow) of blood through a valve; as well as valve stenosis (when blood flows through leaky valves). Certain embodiments of the Compton scattered X-ray visualizer, imager, or information provider 100 can visualize, image, and/or provide information relating to portions of the myocardium, such as to screen persons for increased risk of myocardial infractions (heart attacks). Certain embodiments of the Compton scattered X-ray visualizer, imager, or information provider 100 can utilize external and/or Bluetooth image and, such as by utilizing scopes, etc. They can be positioned as desired relative to the heart. Certain embodiments of the Compton scattered X-ray visualizer, imager, or information provider can thereby be extended via scopes or other techniques following blood vessels, lumens, etc. to desired location within the heart. Certain embodiments of the subsurface Compton scattered X-ray visualizer, imager, or information provider 100 can be utilize string open-heart or closed surgery or procedures.

Certain embodiments of the Compton scattered X-ray visualizer, imager, or information provider 100 can image at least portions of other organs, such as long as, liver, brain, etc. The lung and liver include internal nodules whose condition can be detected using certain embodiments of the Compton scattered X-ray visualizer, imager, or information provider. As such, certain organs and matter can be visualized, imaged, or have image provided by certain embodiments of the Compton scattered X-ray visualizer, imager, or information provider 100 based, at least in part, on density or atomic number of the matter. For example, bones, spine portions, cartilage, tendons, ligaments, etc. can be visualized, imaged, or have information provided based on the varying density of the particular organ or matter. Certain embodiments of the Compton scattered X-ray visualizer, imager, or information provider 100 can be utilized by orthopedic surgeons, for example, to determine how bones, bone fragments, boney portions, etc. are situated relative to each other. For example, during a spinal construct or bone fracture surgery, the surgeon could determine whether the bone portions are properly aligned or situated as desired; such as to be able to apply a construct, apply a pin, set, etc. Following surgery, the individual (e.g., patient) could be examined using certain embodiments of the Compton scattered X-ray visualizer, imager, or information provider 100 to determine a variety of orthopedic considerations. For example, are the bones are in the desired location such as aligned, are any pins, fasteners, etc. that have been applied within the individual properly situated or affixed relative to the portions of the individual, etc. Such post-operative examination can be performed with the bone portion(s) exposed, closed up and within the at least the portion of the individual, as well as also contained within a cast or other body part stabilizer. After surgery, certain embodiments of the Compton scattered X-ray visualizer, imager, or information provider 100 could be used to ensure that there has been no retained surgical instruments, sponges, tools, needles, tactile feedback providers, etc. within the at least the portion of the individual.

A variety of organs and/or matter can be visualized, imaged, or have information provided based at least partially on density image combination (e.g., image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques) across the organ. Certain organs can be formed non-uniformly, such as alveoli being formed within lungs, blood vessels, non-uniform heart matter or tissue, etc. Certain organs and matter can include gases, liquids, and/or solids in portions of the organ or matter, such as to make the matter of the organ or tissue non-uniform.

As such, whether the Compton scattered X-ray visualization, imaging, or information providing of the organ or matter is based at least partially on the blood or blood component situated therein, the density image combination (e.g., image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques) across the organ or matter, or the liquid, solid, or gasses contained in at least portions of the organ or matter. It should be understood that certain embodiments of the Compton scattered X-ray visualizer, imager, or information provider 100 can be configured to visualize, image, and/or provide information with considerable definition and at relatively low resolution, while others can be configured with relatively low definition at relatively high resolution. Such definitions, resolutions, and/or other depth visualizing, imaging, or information providing characteristic can be controlled and/or adjusted with certain embodiments of the Compton scattered X-ray visualizer, imager, or information provider 100.

The operation and structure of the certain embodiments of the Compton scattered X-ray visualizer, imager, or information provider 100 can, depending on context, have a considerable number of similarities independent of the type of individual 82. Certain embodiments of the Compton scattered X-ray visualizer, imager, or information provider 100 can be operated and/or scaled differently, however, depending upon the condition and/or portion of the individual being visualized, imaged, or having information provided, desired resolution of Compton scattered X-ray visualization, imaging, or information providing, rate of successive Compton scattered X-ray visualization, imaging, or information providing, temporal duration of Compton scattered X-ray visualization, imaging, or information providing, cooperation or consciousness of the individual, and other such factors.

Certain embodiments of the Compton scattered X-ray visualizer, imager, or information provider 100 can thereby utilize a variety of X-ray Compton scattered X-ray visualization, imaging, or information providing techniques similar to those that can at least partially include, but are not limited to: conventional X-ray imaging (e.g., transmission and/or fluoroscopy), X-ray Computed Tomography (CT or CAT) scans, Positron Emission Tomography (PET) scans, X-ray imaging at least partially using Compton scattered X-ray, X-ray backscattering imaging, X-ray forward-scattering imaging, and/or other combinations, modifications, and/or developments of X-ray imaging, and/or X-ray based imaging modalities. Compton scattered X-ray visualization, imaging, or information providing technologies could be configured to represent among the more affordable and technically accepted visualization, imaging, or information providing technologies available in medicine. The more affordable a particular visualizing, imaging, or information providing modality is, the more likely it is to be routinely used, and thereupon ultimately developed and accepted.

Certain embodiments of the Compton scattered X-ray visualizer, imager, or information provider 100 therefore can rely on a variety of X-ray technologies. X-ray technologies, in general, can be characterized as particle bombardment, in which the particle includes emitted photons following interaction of the target atom situated at the anode with electrons directed at (or near) the target atom. Certain embodiments of the Compton scattered X-ray visualizer, imager, or information provider 100 therefore can rely on emission and detection of X-rays, which can take the form of directed or bombarded particles such as photons (and/or Compton scattered photons there from).

As such, X-ray visualization, imaging, or information providing technology can be associated and/or operatively combined with certain other imaging modalities such as particle bombardment imaging mechanisms (i.e., the particles including photons), as well as other conventional imaging methodologies as described in this disclosure. Such combination of the Compton scattered X-ray visualizer, imager, or information provider 100 with other imaging modalities are intended to be considered as another embodiment of Compton scattered X-ray visualizer, imager, or information provider, for the purpose of this disclosure, depending on context. As such, the X-rays can be characterized as including photons, which represent a form of electromagnetic radiation, which may be characterized by Maxwell's Equations.

There can be a variety of X-ray visualization, imaging, or information providing modalities can be utilized to provide some level of X-ray Compton backscattered X-ray or forward scattered X-ray visualization, imaging, or information providing (which together can be considered for purpose of this disclosure, depending on context, to be referred to as X-ray Compton scattered X-ray visualization, imaging, or information providing). Certain conventional transmission X-ray imaging modality can rely largely on those X-rays that can be applied to the soft matter or tissue of the at least the portion of the individual 82, to be transmitted there through (while being absorbed, diffracted, reflected, etc. off bones or other matter). The electromagnetic radiation of the transmitted X-rays can thereupon be received at a distant location of the at least the portion of the individual 82, after it has passed through the at least the portion of the individual 82. Such techniques can be used to form the X-ray on the opposite side of the at least the portion of the individual 82. Visualization, imaging, or information providing, as performed by certain embodiments of the Compton scattered X-ray visualizer, imager, or information provider 100, can refer to those modalities that relies primarily on the X-ray based electromagnetic radiation that is at least partially reflected, or redirected, as it passes through the soft matter or tissue (or other opaque matter) of the at least the portion of the individual 82.

The term "Compton scattered X-ray visualization, imaging, or information providing", as described in this disclosure, can be performed by one or more of certain embodiments of the Compton scattered X-ray visualizer, imager, or information provider 100. Depending on context, certain type of Compton scattered X-ray visualization, imaging, or information providing can include, but is not limited to, visualization, imaging, or information providing, photography, displaying, visualization, imaging, or information generation, computer generation, partial visualization, imaging, or information integration, visualization, imaging, or information capturing, visualization, imaging, or information synthesizing, and other techniques that can at least partially capture depth visualizations, images, and/or provided information which rely, at least in part, on depth visualizations, images, and/or provided information or information obtained from the Compton scattered X-ray visualizer, imager, or information provider 100.

A sufficient amount of the applied X-ray 120 can penetrate into the at least portion of the individual 82 for a penetration depth 170 to accomplish the desired Compton scattered X-ray visualization, imaging, or information providing. By limiting the amount of X-rays, the dosage can be limited as well. A certain amount of the applied X-ray beams 120 will likely be Compton scattered or otherwise deflected throughout the penetration region from the surface 168 (e.g., skin) subsurface down to, and including, the penetration depth 170.

Certain embodiments of the emitter portion 150 can be associated with a variety of embodiments of X-ray based electromagnetic radiation that can operate at a variety of frequencies and/or energy levels, which may therefore visualize, image, and/or provide information down to or at a variety of depths into the at least the portion of the individual 82 within a first of view of the Compton scattered X-ray visualizer, imager, or information provider 100. Certain embodiments of the emitter portion 150 may be situated within the at least the portion of the individual 82, adjacent to the at least the portion of the individual 82, or external to the at least the portion of the individual 82. Either one, or a plurality of, emitter portion(s) 150 may be provided either within the at least the portion of the individual 82, adjacent to the at least the portion of the individual 82, and/or external to the at least the portion of the individual 82.

Certain embodiments of the detector portion 152 can be configured, by comparison, to receive X-ray electromagnetic radiation in the form of scattered X-rays that can be scattered from the applied X-rays provided by the emitter portion of the Compton scattered X-ray visualizer, imager, or information provider 100, or another device configured to emit applied X-ray. Within this disclosure, certain embodiments of the at least one detector portion 152 can be adjustable such as to receive certain embodiments of the X-ray based electromagnetic radiation such as can be applied to the at least the portion of the individual from the at least one emitter portion 150 (and Compton scattered at least partially within the at least the portion of the individual). Such adjustment of the at least one detector portion 152 can be based on such parameters as direction, signal strength, frequency, energy level, or other such characteristics of the X-ray photons.

Certain embodiments of the at least one emitter portion 150, that is not associated with any particular Compton scattered X-ray visualizer, imager, or information provider 100, may be utilized that can be detected by one or more distinct detector portions 152 and/or one or more distinct Compton scattered X-ray receiving assembly 151. For example, certain embodiments of the at least one emitter portion 150 may be configured as a "flooding" embodiment that can provide X-rays within a relatively larger area of the individual, and perhaps a surrounding area. For instance, a remote or local source of the applied X-ray beams 120 can include the emitter portion 150, and the applied X-ray beams 120 can be at least partially directed at the at least the portion of the individual 82 from a distant emitter portion, or other device, such as could be detected by the detector portion 152. Certain embodiments of operating rooms, examination rooms, medical offices, research facilities, etc. may be provided with a dispersive embodiment of the at least one emitter portion 150, such that each user (doctor, medical assistant, technician, dentist, etc.) operationally nearby may utilize their distinct or combined personal or group detector portion 152, and/or personal or group display or information provider portion 154.

Certain embodiments of the at least one detector portion 152 can be hand-held, and may thereupon be positioned by the user of the Compton scattered X-ray visualizer, imager, or information provider 100. For instance, if a doctor or dentist would like to examine the subsurface of certain at least the portion of the individual, then certain embodiments of the embodiments of the at least one detector portion 152 could be positioned as proximate the at least the portion of the individual as desired to provide the desired depth visualizing, imaging, or information providing quality and images. Such positionable embodiments of the emitter portion 150, the detector portion 152, the Compton scattered X-ray receiving assembly 151, or other components of the Compton scattered X-ray visualizer, imager, or information provider 100 can be useful to image relatively small portions of the individual in a manner to substantially limit application of X-rays to those regions. For example, in a surgical operating room, medical examination room, veterinarian, etc., certain positionable embodiments of the Compton scattered X-ray visualizer, imager, or information provider 100 can be situated closely adjacent the at least the portion of the individual.

The level of applied X-rays can be thereupon be relatively small as compared with flooding-type emitter portions. The user (and/or the visualization, imaging, or information providing controller 97) can thereupon control or adjust the depth visualizing, imaging, or information providing. By allowing precise control of the limited at least some matter in the at least a portion of the individual that is being imaged by capturing one or more sequential, adjustable, controllable, or continuous visualizations, images, or provided information, less X-ray electromagnetic radiation may be applied to the individual, the user, and/or others in the vicinity. Certain embodiments of the detector portion could be mechanically mounted, or motion-stabilized (such as is understood in computer graphic systems), such as to limit relative motion of the visualize, image, and/or provide information on the display portion.

Certain embodiments of the at least one display portion 154, as described in this disclosure, can display at least one visualize, image, and/or provide information based at least partially on the Compton scattered X-ray based electromagnetic radiation that has been received by the at least one detector portion 152. Certain embodiments of the at least one display portion 154 can be adjusted such that the user can observe what they desire, adjust the visualization, image, or provided information, and/or otherwise control a variety of operations of the Compton scattered X-ray visualizer, imager, or information providers 100.

Certain embodiments of the at least one display portion 154 can display at least portion of the visualize, image, and/or provide information relating to the portion of the individual 82 to the individual, such as a patient either alone or in combination with a physician, etc. The fact that certain embodiments of the Compton scattered X-ray visualizer, imager, or information providers 100 can operate on a substantially real-time basis can make the individual more aware of their condition based on an accurate Compton scattered X-ray visualization, imaging, or information providing of at least a portion of their body. Consider certain individuals who may have an injury, illness, sickness, medical condition, etc. who can have an visualize, image, and/or provide information relating to an appropriate location likely be provided with a near-temporal/positional reflective visualize, image, and/or provide information relating to an appropriate location. As such, they can have more knowledge of their treatment or condition, understand their treatment, and/or perhaps even participate in their treatment. Certain embodiments of the Compton scattered X-ray visualizer, imager, or information provider 100 can be configured to control a treating mechanism that can be used to treat the at least the portion of the individual 82 at least partially in response to the X-ray Compton scattered X-ray information.

In certain injuries or conditions such as ligament tears, joint or bone injuries/fractures, organ conditions, etc., certain embodiments of the Compton scattered X-ray visualizer, imager, or information providers 100 could visualize, image, and/or provide information in a substantially continuous manner as the at least the portion of the individual undergoes motion of an affected joint or location. For example, an orthopedic surgeon could consider or examine a knee joint or bone of a patient during flexure, relaxation, or other motion of that body part. In certain instances, dye, contrast agents, or other Compton scattered X-ray visualization, imaging, or information providing-enhancing materials could be applied to at least the portion of the individual such as to improve the Compton scattered X-ray visualization, imaging, or information providing of certain embodiments of the Compton scattered X-ray visualizer, imager, or information provider 100.

Certain embodiments of the Compton scattered X-ray visualizer, imager, or information providers 100 can interface and/or interact with each other to provide Compton scattered X-ray visualization, imaging, or information providing operation(s) between a number of the at least portions of the Compton scattered X-ray visualizer, imager, or information providers. For example, certain embodiments of the Compton scattered X-ray visualizer, imager, or information provider 100 (or portions thereof) can include the one or more emitter portion 150. Certain embodiments of the Compton scattered X-ray visualizer, imager, or information provider 100 can include the one or more detector portion 152, or alternately one or more Compton scattered X-ray receiving assembly 151. Still yet other embodiments of the Compton scattered X-ray visualizer, imager, or information provider 100 can include one or more display portions 154. Various of the emitter portions 150, detector portions 152, and/or display portions 154 can be combined as desired, and utilized in an appropriate configuration for the desired Compton scattered X-ray visualization, imaging, or information providing application, only certain illustrative embodiments of which are described in this disclosure.

Within this disclosure, certain embodiments of the at least one emitter portion 150 can be configured to apply X-ray based electromagnetic radiation at least partially toward the at least the portion of the individual 82. The frequency, energy level, or other operational characteristics and/or structural characteristics of the X-ray based electromagnetic radiation may differ considerably (and be less objectionable or dangerous) than as applied to patients by conventional X-ray (fluoroscopy) techniques. This is largely a result of lower X-ray dosages being applied to the individual since the X-rays can rebound or scatter from the at least the portion of the individual 82 after it has passed through only a relatively short distance within the at least the portion of the individual. As such, electromagnetic shielding that is applied to patients undergoing fluoroscopy can be limited, or at least considerably reduced, by using certain embodiments of the Compton scattered X-ray visualizer, imager, or information provider 100. Certain airport screening systems, for example, use X-ray scatter visualization, imaging, or information providing from security screening without undue concern of excessive radiation being applied to the travelers of users of the X-ray scanning systems.

Applied X-rays of limited strength could be useful in depth visualizing, imaging, or information providing sensitive at least portions of individuals such as embryos, fetuses, etc. within pregnant women. Certain embodiments of the Compton scattered X-ray visualizer, imager, or information provider 100 could image in a manner such that the X-rays stop just short of sensitive matter or tissue, organ, or other matter (e.g., the uterus, heart, brain, etc.) and thereby limit exposure of ionizing radiation to the embryos, fetuses, etc. for example. In actuality, almost any matter within the individual can be considered as sensitive to some degree, particularly relative to desirability of limiting exposure of X-rays there to. As such, certain embodiments of the Compton scattered X-ray visualizer, imager, or information provider 100 are particularly suited to correcting or applying applied X-rays and/or scattered X-ray to controllably limited regions within the individual. Additionally, there may be a considerable number and variety of organs, portions, or segments of the body that would do better with limited applied X-rays. As such, certain embodiments of the Compton scattered X-ray visualizer, imager, or information provider 100 can limit transmission of X-rays during depth imaging to certain of such matter, organs, portions, or segments of the body. Certain embodiments of the Compton scattered X-ray visualizer, imager, or information provider 100 can thereby be configured to visualize, image, and/or provide information relating to areas as desired within the particular individual, and limit exposure of X-ray radiation to other (perhaps sensitive) regions.

Within this disclosure, the Compton scattered X-ray detected by certain embodiments of the detector portion 152 can be back Compton scattered, forward Compton scattered, deflected, or other distortions of the path of the X-ray based electromagnetic radiation that fall within the scope of the present disclosure, while remaining within the intended scope of Compton scattered X-ray. Certain embodiments of the detector portion 152 can be associated with a variety of embodiments of X-ray based electromagnetic radiation, which can operate at a variety of frequencies and/or energy levels, and may therefore visualize, image, and/or provide information down to or at a variety of depths into the at least the portion of the individual 82.

Certain embodiments of the Compton scattered X-ray visualizer, imager, or information provider 100, as described in this disclosure, can be configured with one or more of the emitter portion 150, the at least one Compton scattered X-ray receiving assembly 151, the detector portion 152, and/or the display portion 154, or any combination thereof. With those embodiments of the Compton scattered X-ray visualizer, imager, or information provider 100 having no emitter portion 150, the X-ray based electromagnetic radiation can be at least partially provided by another device. For instance, a number of the display portion(s) 154 (or alternately at least one display portion that can be viewed by numerous persons), can be utilized by or controlled by a number of persons such as surgeons, technicians, assistants, etc. that can be applied by a single strategically located emitter portion 150. The emitter portion 150 may, or may not, be included as a portion of at least one of the Compton scattered X-ray visualizer, imager, or information provider(s) 100.

Certain embodiments of the Compton scattered X-ray visualizer, imager, or information provider 100 can be controlled, such as to allow its operator to select different penetration depths 170 (or range of penetration depths) to which the Compton scattered X-ray visualizer, imager, or information provider can visualize, image, or provide information. Within certain embodiments of the Compton scattered X-ray visualizer, imager, or information provider 100, the penetration depth 170 for visualizing, imaging, and/or information providing may vary as a function of the energy applied to or contained within the applied X-ray, and/or the frequency, energy level, or other characteristics of the X-ray photons of the applied X-ray 120. The matter (e.g., skin, tissue, bone, etc) to which the applied X-ray 120 is being applied will also affect the visualizing, imaging, or information providing characteristics. As certain characteristics of the applied X-ray are increased, it may likely effect the maximum penetration depth 170 (see FIGS. 18 and/or 20) to which the applied X-ray Compton scattered X-ray radiation will likely travel to prior to Compton scattered X-ray, or thereby visualize, image, and/or provide information down to. While a limited number of X-rays might travel within the at least the portion of the individual to a depth greater than the penetration depth 170, certain embodiments of the Compton scattered X-ray visualizer, imager, or information provider 100 can be configured to limit the effects of those few X-rays relative to the visualization, imaging, or information providing.

Certain embodiments of the Compton scattered X-ray visualizer, imager, or information provider 100 can provide for image combination (e.g., image subtraction, time of flight, image transformation, deconvolution, weighted subtraction, functional subtraction, and group including inverse integral transform, subtractive inverse integral transform, inverse functional transform, and subtractive inverse functional transform, or other such image processing techniques) as described with respect to FIG. 16. Within this disclosure, such image combining techniques as relating to Compton scattered X-ray visualization, imaging, or information providing techniques can, depending on context, refer to Compton scattered X-ray visualization, imaging, or information providing between two of the at least one prescribed visualization, imaging, or information providing depths 170*a* and 170*b*. Each prescribed visualization, imaging, or information providing depth 170*a* and 170*b* can be situated at least some distance from the skin or surface 168 of the individual (such as illustrated in FIGS. 16 and/or 17). Certain embodiments of the Compton scattered X-ray visualizer, imager, or information provider 100 can obtain multiple sampled visualize, image, and/or provide information relating to data pertaining to X-ray Compton scattered X-ray Compton scattered X-ray visualization, imaging, or information providing at different depths either sequentially or in parallel. As such, the multiple sampled visualize, image, and/or provide information relating to data can be considered as Compton scattered X-ray visualization, imaging, or information providing a similar sample space down to different penetration depths 170*a* and 170*b*.

Certain ones of the multiple sampled visualize, image, and/or provide information relating to data can thereupon be compared at least partially by image combination (e.g., image subtraction, time of flight, image transformation, deconvolution, weighted subtraction, functional subtraction, and group including inverse integral transform, subtractive inverse integral transform, inverse functional transform, and subtractive inverse functional transform, or other such image processing techniques). As such, those details, images, information, visualizations, etc. that are situated in the shallower penetration depth 170*a*, and not in the deeper penetration depth 170*b*, as described with respect to FIG. 16, can be digitally subtracted out, transformed out, or otherwise computed out. By digitally differentiating the matter, tissue, objects, etc. being visualized, imaged, or have information provided at the shallower penetration depth 170*a* from the deeper penetration depth 170*b*, the depth visualizations, images, and/or provided information or other information relating to matter between the shallower and deeper penetration depths can be obtained.

Certain embodiments of the Compton scattered X-ray visualizer, imager, or information provider 100 can be configured to obtain a X-ray Compton scattered X-ray information at least partially using X-ray Compton scattered X-ray to derive visualize, image, and/or provide information through at least one matter (e.g., tissue or other matter) of the at least the portion of the individual 82. Such visualizing, imaging, or providing information can be provided at least at both a first depth region and at a second depth region, both associated with the at least a common portion of the individual 82. The depth difference between the first depth regions that extends to a first penetration depth 170*a* and the second depth region that extends to a second penetration depth 170*b* can be used for subtraction or combination Compton scattered X-ray visualization, imaging, or information providing techniques, as described in this disclosure.

Certain embodiments of the Compton scattered X-ray visualizer, imager, or information provider 100 that utilize subtraction or combination Compton scattered X-ray visualization, imaging, or information providing techniques can therefore act to visualize, image, and/or provide information at different penetration depths 170*a* and 170*b*. As such, adjustment of the subtraction or combination Compton scattered X-ray visualization, imaging, or information providing technique can be performed at least partially by, for example, controlling and/or adjusting the frequency of energy level of the X-ray photons at two levels to provide two X-rays. Each of the controlling and/or adjusting the frequency of energy level of the X-ray photons can be detected distinctly to the at least one prescribed visualization, imaging, or information providing depths 170*a* and 170*b*. Thereupon, the difference of the shallower level image undergoes image combination (e.g., image subtraction, time of flight, image transformation, deconvolution, image subtraction, weighted subtraction, functional subtraction, and group including inverse integral transform, subtractive inverse integral transform, inverse functional transform, and subtractive inverse functional transform, or other such image processing techniques) from that of the deeper image. The image subtraction or combination depth visualizing, imaging, or information providing techniques can thereby be used to provide information about matter within range of volumes between two penetration depths 170a and 170b in FIGS. 16 and 17 from the surface 168, etc.

Certain embodiments of the Compton scattered X-ray visualizer, imager, or information provider 100 can be configured to visualize, image, and/or provide information at a first controllable one of the at least one visualization, imaging, or information providing depth range to the at least one first prescribed visualization, imaging, or information providing depth to obtain the first Compton scattered X-ray image information. Certain of these embodiments of the Compton scattered X-ray visualizer, imager, or information provider 100 can visualize, image, and/or provide information at a second controllable one of the at least one visualization, imaging, or information providing depth range to the at least one second prescribed visualization, imaging, or information providing depth to obtain the second Compton scattered X-ray information. Certain embodiments of the Compton scattered X-ray visualizer, imager, or information provider 100 can be configured to computationally differentiating the data associated with the first X-ray Compton scattered X-ray information and the second X-ray Compton scattered X-ray information.

Certain embodiments of the Compton scattered X-ray visualizer, imager, or information provider 100 can also utilize a time of flight measurement to visualize, image, and/or provide information at the at least one visualization, imaging, or information providing depth range to the at least one prescribed visualization, imaging, or information providing depth, as described with respect to FIG. 17. Such time of flight measurement can utilize precise pulse signals which can be characterized as at least one input pulse signal and at least one return pulse signal (allowing fractional-second temporal Compton scattered X-ray visualization, imaging, or information providing resolution so as to achieve suitable Compton scattered X-ray visualization, imaging, or information providing resolution). The briefer the duration of the emitted pulse signal and the detected pulse signal, the lesser the achievable resolution (lesser resolution leading to improved Compton scattered X-ray visualization, imaging, or information providing characteristics). Using time of flight techniques, the emitted pulse signals can be applied by certain embodiments of the Compton scattered X-ray visualizer, imager, or information provider 100 to the surface 168 of the at least the portion of the individual 82. Providing the time of flight of the return signal can be measured with sufficient accurately (e.g., resolution in picoseconds for certain embodiments, such as those that utilize streak cameras, pixellated streak cameras, avalanche detectors, CCDs, etc.) then the time of the detected pulse signal can be gated to provide sufficient accuracy, and the time of flight can be determined, from which the distance or depth can be determined.

By using the time of flight embodiments of the Compton scattered X-ray visualizer, imager, or information provider 100, the emitter portion 150 can transmit the at least one input pulse and the detector portion 152 can detect the return time of the at least one return pulse signal. As described with respect to FIG. 17, a time of flight calculation 160 can be determined based on the amount of time required for the at least one input pulse signal to be applied to the at least the portion of the individual; which can thereupon each be Compton scattered into one or more return pulse signal. The Compton scattered return pulse signal(s) will be modified based at least in part on the characteristics of the matter of the individual through which the pulse signals pass (e.g., pulse applied X-ray and/or pulse scattered X-ray).

One use of combination of Compton scattered X-ray visualization, imaging, or information providing (including subtracting, and other such processes) may involve Compton scattered X-ray visualization, imaging, or information providing matter, an organ, etc. that is located within a region that is situated a considerable depth from the surface 168. During depth visualizing, imaging, or information providing of such a deep organ, matter, etc., additional matter, organs, etc. that are positioned between the depth visualizing, imaging, or information providing component(s) of the Compton scattered X-ray visualizer, imager, or information provider 100 and the imaged region may not be necessarily be displayed. Therefore, additional matter, organs, tissue, etc. may not be visualized, imaged, or have information provided using image combination (e.g., image subtraction, time of flight, image transformation, deconvolution, weighted subtraction, functional subtraction, and group including inverse integral transform, subtractive inverse integral transform, inverse functional transform, and subtractive inverse functional transform, or other such image processing techniques).

As such, certain organs, matter, etc. that are situated deep within the at least the portion of the individual may be imaged without depth visualizing, imaging, or information providing interference from shallower matter using subtraction or combination of Compton scattered X-ray visualization, imaging, or information providing techniques, such as with image combination (e.g., image subtraction, time of flight, image transformation, deconvolution, weighted subtraction, functional subtraction, and group including inverse integral transform, subtractive inverse integral transform, inverse functional transform, and subtractive inverse functional transform, or other such image processing techniques). Alternately, certain matter, tissue, organs, etc. can be imaged by positioning the at least one emitter portion 150, the at least one detector portion 152, and/or the at least one Compton scattered X-ray receiving assembly internally at a suitable position relative to the imaged organs, matter, etc. One skilled with the various embodiments, configurations, and uses of the Compton scattered X-ray visualizer, imager, or information provider 100 could determine which depth visualizing, imaging, or information providing technique would provide the better quality depth visualizations, images, and/or provided information or images, less invasively, thereby lowering the X-ray dosages to the user and/or individual.

Certain embodiments of the Compton scattered X-ray visualizer, imager, or information provider 100 can at least partially rely on Compton scattered X-ray visualization, imaging, or information providing matter within the at least the portion of the individual 82, such as muscle, skin, blood vessels, fluids (e.g., blood, lymph), etc. Within this disclosure, the soft Compton scattered X-ray visualization, imaging, or information providing may be compared to hard imaging such as occurs in conventional backscatter imaging that may occur when the imaging modality encounters a hard or reflective surface such as bones, metals, etc. By providing Compton scattered X-ray-based Compton scattered X-ray visualization, imaging, or information providing of soft matter, certain embodiments of the Compton scattered X-ray visualizer, imager, or information provider 100 can allow detection of variations of certain characteristics of the soft matter, such as may be the case of calcification of the skin such as occurs relative to a matter aberration. Such matter aberrations as certain breast cancers can be identified due to the calcification of the tumor or cancer. By allowing Compton scattered X-ray-based Compton scattered X-ray visualization, imaging, or information providing of at least some soft matter, certain embodiments of the Compton scattered X-ray visualizer, imager, or information provider 100 can provide for locating. Such locating or positioning based at least partially on matter aberration can be applied to such varied applications as positioning organs, circulatory portions (e.g., veins, arteries, etc), blood flows, nerves, bones, etc. relative to the at least some matter of the at least the portion of the individual 82.

Certain embodiments of the Compton scattered X-ray visualizer, imager, or information provider 100 can be configured to limit certain contact or damage of arteries, veins, capillaries, or other blood (or other fluid) vessels, etc. Consider the difficulty during surgery, etc., of avoiding such contact that may be at some uncertain location within the individual. Considering the number of blood or other fluid vessels within the body, as well as the likelihood of damage using scopes, tools within incisions, cutting tools, tactile feedback providers, other tools, etc., the scope of the difficulty during surgery, etc. becomes evident. In certain instances, a surgeon may even be unaware if they have damaged a hidden blood vessel or other fluid capillary. Certain embodiments of the Compton scattered X-ray visualizer, imager, or information provider 100 can be positioned to visualize, image, and/or provide information the region in which the physician or veterinarian is working. Alternately, certain embodiments of the Compton scattered X-ray visualizer, imager, or information provider 100 can be connected to, or otherwise associated with, tools being applied to the at least the portion of the individual. Certain embodiments of the Compton scattered X-ray visualizer, imager, or information provider 100 can also allow surgeons, and/or their tools, to avoid or limit contact with particular nerves, organs, matter, etc. Such depth visualizing, imaging, or information providing which allows users such as surgeons, dentists, veterinarians are likely to come in proximity with blood vessels, fluid vessels, nerves, organs, matter, etc. to limit contact their with. Such imaging or visualization to limit contact with certain portions of the body can be performed on a substantially real-time basis, or another basis as desired, and would be expected to considerably reduce the duration of operations, procedures, etc, by such users as doctors, dentists, veterinarians, etc.

Certain embodiments of the Compton scattered X-ray visualizer, imager, or information provider 100 can also be configured to locate, analyze, and/or treat blood pooling or other fluid pooling. With certain injuries from bombs, explosives, injuries, vehicular and other crashes, certain illnesses, etc., it can be difficult with conventional imagers to locate blood pooling within portions of humans, animals, etc. Certain embodiments of the Compton scattered X-ray visualizer, imager, or information provider 100 could determine, for example, a trajectory of a bullet, explosive, bomb, etc. such as could be located by determining the location (such as in a trail or pool) of blood through organs, matter, etc. Other naturally occurring blood or fluid pools could be located, examined, and/or treated.

Another example of a bodily fluid which might be located using certain embodiments of the Compton scattered X-ray visualizer, imager, or information provider 100 is lymph fluid. Following certain cancers, for example, certain lymph nodes may have to be removed. Lymph nodes function to largely remove lymph fluid from the body. With lymph nodes removed, there can be a considerable collection of the lymph fluid in the body, which can add to weight gain to the individual and/or eventually become infected. Other types of bodily fluids may be visualized, imaged, or have information provided.

Certain embodiments of the at least one detector portion 152, as described at various locations through this disclosure, can be controlled and/or adjusted to receive photons at least partially emitted from the at least one emitter portion 150. Such control and/or adjustment can be performed in a manner that can be used to provide Compton scattered X-ray visualization, imaging, or information providing using certain embodiments of the at least one display portion 154.

Certain embodiments of the depth visualization, imaging, or information providing controller 97 can thereby include, but is not limited to, at least one control and/or adjustment portion 934. Certain embodiments of the detector portion 152 of the Compton scattered X-ray receiving assembly 151 can be configured to measure the amount of X-ray based electromagnetic radiation (e.g., scattered X-rays in the form of photons) that is received by the at least one detector portion 152. Certain embodiments of the control and/or adjustment portion 934 can be configured to control and/or adjust the position, angle, or other operating parameter of at least a portion of the at least one Compton scattered X-ray receiving assembly 151. Certain embodiments of the control and/or adjustment portion 934 can be used to enhance, modify, filter, or otherwise effect reception of the X-ray based electromagnetic radiation (e.g., in the form of photons), such as may be emitted from the at least one emitter portion 150. Certain detector portions 152 of certain embodiments of the Compton scattered X-ray receiving assembly 151 can be omni-directional, multi-directional, or at least have a suitable directional range as to suitable detect the X-ray based electromagnetic radiation being emitted towards the at least the portion of the individual. Certain embodiments of the control and/or adjustment portion 934 can be configured to the relative angle(s), frequencies, and/or positions of the at least one emitter portion 150, and/or the at least the portion of the individual 82. Certain embodiments of the control and/or adjustment portion 934 can be configured to ensure suitable transmission or reception of X-ray based electromagnetic radiation to allow proper depth visualizing, imaging, or information providing.

Certain embodiments of the at least one Compton scattered X-ray receiving assembly 151 can also include a detector portion transfer portion, not shown, in which the detected photons, Compton scattered X-ray visualization, imaging, or information providing information, data, etc. relating to the X-rays that can be at least partially Compton scattered at/within the at least the portion of the individual. Certain data, information, images, visualizations, etc. as obtained at least partially be the Compton scattered X-ray receiving assembly 151 can be displayed by the at least one display portion 154, perhaps in a form of the at least one visualization, image, or provided information.

Certain embodiments of the Compton scattered X-ray visualizer, imager, or information provider 100 can be configured to visualize, image, and/or provide information at a substantially real-time basis, while other embodiments can be configured to visualize, image, and/or provide information at a slower repetitive rate. Certain embodiments of the Compton scattered X-ray visualizer, imager, or information provider 100 can even be configured to visualize, image, and/or provide information relating to one or more non-repetitive depth visualizations, images, and/or provided information. Such selection of Compton scattered X-ray visualization, imaging, or information providing on substantially temporal/positional reflective can allow such users as a surgeon, doctor, veterinarian, dentist, etc. to obtain conditional information, location information, etc. at desired subsurface locations of the at least the portion of the individual 82 as quickly as desired. Within this disclosure, the term "subsurface", can, depending on context, refer to depth visualizing, imaging, or information providing matter underneath, or across, the surface 168 of the at least the portion of the individual 82 (possibly depth visualizing, imaging, or information providing the surface of the individual). Certain of the surfaces 168 can include skin, internal surfaces, etc. that can be in communication with outside via an opening such as one which a scope that could be applied, such as mucous membranes, at least partially endothelium, internal membranes or skin(s) at least partially defining or surrounding a lumen, via blood vessels, etc. Certain embodiments of at least portion of the Compton scattered X-ray visualizer, imager, or information provider 100 (such as the emitter portion 150 or the Compton scattered X-ray receiving assembly 151) could be applied to within the at least the portion of the individual 82 using such technologies as a scope, a needle, an injected or implanted device.

Certain embodiments of the Compton scattered X-ray visualizer, imager, or information provider 100 could be configured to, for example, image a moving organ as described with respect to FIG. 31. Such visualization, imaging, or providing information relative to moving organs can be applied to, for example, at least a portion of the heart, kidney, brain, stomach, intestine, or other organ that can be defined based on visualization, imaging, or information providing, or variations such as by edges of the particular organs being visualized, imaged, or information provided.

Consider that a moving two dimensional or three dimensional image of a portion of the heart could be provided using certain embodiments of the Compton scattered X-ray visualizer, imager, or information provider 100. Such depth visualizing, imaging, or information providing could be useful for diagnosis purposes, during surgery, during screening of susceptible individuals, etc. Depth visualizing, imaging, or information providing could be performed on a heart valve, as well as the associated depth visualizing, imaging, or information providing through that heart valve. Heart-based depth visualizing, imaging, or information providing could be provided by positioning the at least one emitter portion 150 and the at least one detector portion 152 in suitable proximity to (or within) the heart utilizing suitable scopes, implants, etc. along with wireless and/or wired-based technology. The configuration, position, motion, reflex of the heart, aorta, arteries, valves, etc. can be used with suitable resolution and refresh rates using certain Compton scattered X-ray visualizer, imager, or information provider 100 configurations.

Certain embodiment the Compton scattered X-ray visualizer, imager, or information provider 100 could be applied to image matter or tissue contained within such internal lumens to the human body (and/or image from the internal lumens). Such internal lumens can include, but are not limited to, those at least partially defining: the respiratory tract, the cardiovascular system (e.g., heart, blood vessels), at least a portion of a CSF-space of the nervous system (e.g., the spinal canal, the ventricles of the brain, the sub-arachnoids space, etc.), at least a portion of the urinary tract (for example a urethra), at least a portion of the lymphatic system, at least a portion of the abdominal cavity, at least a portion of the thoracic cavity, at least a portion of the gastrointestinal tract, at least a portion of a reproductive tract (either the female reproductive tract—e.g., a lumen of a fallopian tube), or the male reproductive tract (including various lumens including but not limited to the epidermis, vas deferens or ductile deferens, efferent duct, ampoule, seminal duct, ejaculatory duct, or urethra), the biliary tract, a nostril or nasal cavity, the oral cavity, the digestive tract, the tear ducts, a glandular system, and/or the reproductive tract. Other body lumens may be found in the auditory or visual system, or in interconnections thereof, e.g., the Eustachian tubes. As such, three can be a considerable variety of applications for certain embodiments of the Compton scattered X-ray visualizer, imager, or information provider 100.

Certain embodiments of the Compton scattered X-ray visualizer, imager, or information provider 100 can be configured to visualize, image, and/or provide information at a single resolution device, such as may be appropriate for a particular Compton scattered X-ray visualization, imaging, or information providing application, a particular resolution, or a particular use. Certain embodiments of the Compton scattered X-ray visualizer, imager, or information provider 100 can be configured to visualize, image, and/or provide information at a variety of resolutions or applications, such as can be controlled by certain embodiments of the visualization, imaging, or information providing controller 97 as described in this disclosure with respect to FIG. 1. Such variation of the Compton scattered X-ray visualization, imaging, or information providing resolution may vary depending on use. For instance, in those instances where the embodiments of the Compton scattered X-ray visualizer, imager, or information provider 100 is being used to determine a location or position of an organ, bone, etc., relatively high resolution (e.g., low quality) Compton scattered X-ray visualization, imaging, or information providing can be utilized. By comparison, in those instances where the embodiments of the Compton scattered X-ray visualizer, imager, or information provider 100 are being used to detect tumors or the like, a relatively improved resolution (high quality) visualize, image, and/or provide information may be obtained and utilized.

Certain embodiments of the X-ray Compton scattered X-ray visualization, imaging, or information providing can thereby utilize one or more emitter portions 150 that can apply X-ray radiation which can be Compton scattered and/or reflected off at least the portion of the individual 82. As such, certain conventional X-ray Compton scattered X-ray visualization, imaging, or information providing may be referred to as "soft X-ray visualization, imaging, or information providing" since it is reflective (relying at least partially on reflection/refraction of X-ray based electromagnetic radiation—photons), instead of being at least partially transmissive as with certain embodiments of the Compton scattered X-ray visualizer, imager, or information provider 100. Certain transmissive types of conventional X-ray visualization, imaging, or information providing can also utilize fluoroscopy. In addition, X-ray Compton scattered X-ray visualization, imaging, or information providing may often utilize less powerful X-ray signals then conventional X-ray imaging since the photons of the former do not have to pass through the at least the portion of the individual 82.

Certain embodiments of the Compton scattered X-ray visualizer, imager, or information provider 100 therefore provide a mechanism to examine or view an aberration in the surface 168 that can be provided in temporal/positional reflective, real time or near real time, or in a controllable repeatable or non-repeatable fashion. Certain embodiments of the Compton scattered X-ray visualization, imaging, or information providing time (duration) can be controlled or adjusted based, at least in part, on such factors as: input from the user, Compton scattered X-ray visualization, imaging, or information providing detail. Other operational characteristics of certain embodiments of the Compton scattered X-ray visualizer, imager, or information provider 100 can be adjusted and/or controlled by certain embodiments of the visualization, imaging, or information providing controller 97, as described in this disclosure.

It is to be understood that the included description(s) of the at least one emitter portion 150, the at least one detector portion 152, and/or the at least one display portion 154, as described in this disclosure, are intended to be illustrative in nature but not limiting in scope. Modifications and/or alterations of the devices 150, 151, 152, and/or 154 from those described in this disclosure are within the intended scope of the present disclosure, depending they still are within the scope of the claims.

As such, certain embodiments of the Compton scattered X-ray visualizer, imager, or information provider 100 may be configured such that the physician, dentist, etc. using them can observe a subsurface visualization, image, and/or provide information of the region of the at least the portion of the individual 82. Certain particulars of the Compton scattered X-ray visualization, imaging, or information providing and/or the region can vary depending on the embodiment of the Compton scattered X-ray visualizer, imager, or information provider 100. For example, certain Compton scattered X-ray visualization, imaging, or information providing can correspond to where they are looking, wherein they desire to look, or alternatively where they direct the Compton scattered X-ray visualizer, imager, or information provider 100 to visualize, image, or provide information. Certain embodiments of the Compton scattered X-ray visualizer, imager, or information provider 100 can present visualizations, images, and/or provide information to a group of persons particularly associated with the Compton scattered X-ray visualizer, imager, or information provider.

With conventional X-rays that are transmitted through the at least the portion of the individual 82, including fluoroscopy as well as conventional transmissive X-rays techniques, X-rays may be configured to be applied such that the electromagnetic radiation is applied with sufficient energy level and/or frequency of the X-ray photons to be applied through the portion of the at least some matter. The X-ray photons resulting from Compton scattered X-ray is traditionally not utilized in conventional fluoroscopy-based imaging modalities. As such, with certain embodiments of the Compton scattered X-ray visualizer, imager, or information provider 100, the applied X-ray beams 120 do not have to be applied exclusively, but can represent a percentage (even a minority) of the electromagnetic radiation being applied to the at least the portion of the individual 82.

Certain embodiments of the Compton scattered X-ray visualizer, imager, or information provider 100 can utilize Compton scattered X-rays that do not have to backscatter or backwardly reflect from within the at least the portion of the individual 82. Instead, certain embodiments of the Compton scattered X-ray visualizer, imager, or information provider 100 can pass at least partially through the at least the portion of the individual 82 and be somewhat deflected or forward scattered, such that as described within the at least the portion of the individual 82. The X-ray based electromagnetic radiation that is detected as "Compton scattered" information may thereby at least partially backscatter, forward scatter, reflect from, or be at least partially deflected by, the at least the portion of the individual 82. Certain embodiments of the applied X-ray from the Compton scattered X-ray visualizer, imager, or information provider 100 can be applied can be applied at various angles (ranging from perpendicular to substantially parallel to the contacting surface 168 of the at least the portion of the individual 82) relative to the surface of the matter of the at least the portion of the individual 82.

The visualization, imaging, or information can be presented to the user such as a surgeon, veterinarian, dentist, researcher, etc. by a variety of display portion means that can include, but are not limited to: an external monitor, a head-mounted display, stereoscopic projection, a scope device (i.e., endoscope, etc.). Certain portions of different embodiments of the Compton scattered X-ray visualizer, imager, or information provider 100 can be used in combination, such as a scope-based emitter portion 150 which can be used in combination with an at least partially external-based or internal-based detector portion 152 from another embodiment of the Compton scattered X-ray visualizer, imager, or information provider.

Certain embodiments of the Compton scattered X-ray visualizer, imager, or information provider 100 can be usable or are adjustable to visualize, image, and/or provide information to various controllable and/or adjustable depths. For example, certain embodiments of the Compton scattered X-ray visualizer, imager, or information provider 100 could be configured to visualize, image, and/or provide information to a depth of a few millimeters. Other embodiments could be configured to visualize, image, and/or provide information to a depth through the at least the portion of the individual 82, if provided with X-ray electromagnetic radiation having sufficient energy or of a suitable X-ray photon frequency or energy level. The depth of Compton scattered X-ray visualization, imaging, or information providing of certain embodiments of the Compton scattered X-ray visualizer, imager, or information provider 100 can be a function of frequency, energy level, or other characteristic of the X-ray photons used to generate the Compton scattered visualization, image, type of matter of the individual, as well as power applied to generate the Compton scattered X-ray visualization, image, or provided information.

For example, a user or operator can utilize certain embodiments of the Compton scattered X-ray visualizer, imager, or information provider 100 to visualize, image, and/or provide information at a variety of depths. It is envisioned that a variety of depth visualizing, imaging, or information providing modalities can be utilized for the different embodiments of the debt-controllable Compton scattered X-ray visualizer, imager, or information provider 100. With certain embodiments of the Compton scattered X-ray visualizer, imager, or information provider 100, as described in this disclosure, the Compton scattered X-ray visualization, imaging, or information providing can visualize, image, and/or provide information from the surface 168 down to and including the controlled depth of the at least the portion of the individual 82.

Certain embodiments of a robotic or automated system can utilize certain embodiments of the Compton scattered X-ray visualizer, imager, or information provider 100, such as to allow a wide variety of automated or robotic devices to operate at least partially in response to visualization, imaging, or provided information. For instance, certain embodiments of the Compton scattered X-ray visualizer, imager, or information provider could scan the at least the portion of the individual for suspicious areas such as melanomas automatically, and indicate any suspicious region to a doctor or operator to be more closely considered. Certain embodiments of the Compton scattered X-ray visualizer, imager, or information provider 100 can be configured to control a robotic device at least partially in response to the X-ray Compton scattered X-ray information. It may be envisioned that certain automated devices or robotic devices could be configured to allow surgery, internal procedures (e.g., scope-based or other), and/or other internal operations based at least in part on visualization, imaging, or information providing information obtained at least in part from the Compton scattered X-ray visualizer, imager, or information provider 100. Such automated or robotic procedures hold out the promise of considerable precision, as well as a variety of automated or remotely-controlled operation.

A variety of embodiments of the Compton scattered X-ray visualizer, imager, or information provider 100 can be configured to allow control and/or adjustment of the within the at least one visualization, imaging, or information providing depth range to the at least one prescribed visualization, imaging, or information providing depth of the Compton scattered X-ray visualization, imaging, or information providing. Certain embodiments of the Compton scattered X-ray visualizer, imager, or information provider 100 can allow an operator such as a surgeon, support person, other person, machine, robot, etc. to provide input, or manually, to control and/or adjust the depth at which the at least one depth-adjustable embodiment of the Compton scattered X-ray visualizer, imager, or information provider 100. With certain depth-adjustable embodiment of the Compton scattered X-ray visualizer, imager, or information provider 100, at least one of the selected depth that is being visualized, imaged, or have information provided can be targeted (for example, by tuning the X-ray beam intensity, energy level, frequency, or other characteristics) either manually and/or automatically.

One such technique that can be used to adjust and/or control the within the at least one visualization, imaging, or information providing depth range to the at least one prescribed visualization, imaging, or information providing depth at least partially by angling the applied X-rays relative to the surface 168 of the at least the portion of the individual. Provided the Compton scattered X-ray visualizer, imager, or information provider 100 is configured to pass through a prescribe depth of matter, the greater the angle at which the applied X-rays contact the surface 168, the lesser the travel distance of the at least one substantially scattered depth range to the at least one prescribed substantially scattered depth into the matter.

Another such technique that can be used to adjust and/or control the at least one substantially scattered depth range to the at least one prescribed substantially scattered depth by certain embodiments of the Compton scattered X-ray visualizer, imager, or information provider 100 can involve providing a depth equivalent material or device between that the applied X-rays should pass through. For example, assume that the depth equivalent material or device represents the equivalent of 2 mm. Assuming the Compton scattered X-ray visualizer, imager, or information provider 100 is configured to image at 5 mm, the image subtraction or combination effect of the depth equivalent material would result in Compton scattered X-ray visualization, imaging, or information providing down to a depth of 3 mm. A number of depth equivalent material of devices can be provided such as to allow control and/or adjustment over the desired substantially scattered depth range to the at least one prescribed substantially scattered depth.

Certain embodiments of the Compton scattered X-ray visualizer, imager, or information provider 100 may be configured to obtain the X-ray Compton scattered X-ray information in a manner capable of temporally reflecting motion (conscious or reflexive) of portion(s) of the individual 82 than are deeper than those described up to this point. For example, certain embodiments of the aberrative matter, etc. may be configured to visualize, image, and/or provide information at least one organ(s), bone(s), bone portion(s), blood vessel(s), blood capillar(ies), etc. that may be spaced relatively deeply subsurface. By altering certain operational characteristics of the X-ray based electromagnetic radiation that may be applied by the at least one emitter portion(s) 150 as described with respect to FIG. 1, as well as received by certain embodiments of the at least one detector portion(s) 152, the visualization, imaging, or information providing depth can thereby be controlled.

Considering that conventional X-rays can image by X-rays passing completely through the at least the portion of the individual, it should be understood that Compton scattered X-ray technologies can be used to visualize, image, and/or provide information a considerable depth into the at least the portion of the individual provided the X-rays are configured to travel with a suitable frequency of the X-ray photons at a suitable energy level, etc. Such Compton scattered X-ray visualization, imaging, or information providing of at least partially internal organs, bones, etc. can better be performed in some internal location that is not at least partially hidden, distorted, or obscured by bones, metal or other X-ray diffusive matter. Certain embodiments of the Compton scattered X-ray visualizer, imager, or information provider 100 may be configured such that the obtaining the X-ray Compton scattered X-ray information such as can be obtained visually.

Certain embodiments of the Compton scattered X-ray visualizer, imager, or information provider 100 can visualize, image, and/or provide information from a variety of perspectives. For instance, certain embodiments of the Compton scattered X-ray visualizer, imager, or information provider 100 can provide different types of views. Certain embodiments of the Compton scattered X-ray visualizer, imager, or information provider 100 can be configured to provide depth visualizations, images, and/or provided information and/or visualize, image, and/or provide information in substantially temporal and/or positional reflective condition, such as could be detected by the user.

Certain embodiments of the Compton scattered X-ray visualizer, imager, or information provider 100 could provide depth visualizations, images, and/or provided information and/or visualize, image, and/or provide information at absolute locations in space. For instance, a particular bone, joint, portion of an organ, etc. could be located or situated at a precise position with respect to the at least the portion of the individual 82, a device, a location in space, a building or room, etc. Such determination of a position, situation, or location could be determined using a global positioning system (GPS), another global positional program or device, or using a coordinate system or device relative to the at least the portion of the individual, or the location thereof. In addition to the location or position, there may be an indication of the condition of the particular bone, joint, portion of the organ, etc. at that location. Once such positional information is obtained, certain embodiments of the Compton scattered X-ray visualizer, imager, or information provider 100 could utilize, implant, generate at least portions of the depth visualizations, images, and/or provided information such as may be provided using an additional or alternate visualization, imaging, or information providing modality, an other application, other maps, etc.

Certain embodiments of the Compton scattered X-ray visualizer, imager, or information provider 100 that are so configured to provide good resolution should be capable of providing 100 micron, or better, resolution based on the X-ray Compton scattered X-ray technology. As described in this disclosure, streak camera, pixellated streak cameras, CCDs, avalanche detectors, and other detector-type devices can be used to provide very good resolution and accuracy. With such resolution, certain embodiments of the Compton scattered X-ray visualizer, imager, or information provider could be used to determine positional information precisely and accurately. Such combining of multiple imaging and/or visualizing modalities may limit the depth visualizing, imaging, or information providing computation necessary by certain embodiments of the Compton scattered X-ray visualizer, imager, or information provider 100 by, for example, inputting image information already derived from other sources.

Certain embodiments of the Compton scattered X-ray visualizer, imager, or information provider 100 can thereby provide for overlaying of combining of the X-ray Compton scattered X-ray visualization, imaging, or information providing with other conventional and/or imaging modalities. For example, MRI could be overlaid on certain embodiments of the Compton scattered X-ray visualizer, imager, or information provider 100. MRI provides a good example of an additional imaging modality that can be used in combination with X-rays, since MRI is generally understood to be highly accurate, provide considerable visualizations, images, and/or provided information in the medical area, and can be quite expensive. As such, certain embodiments of the Compton scattered X-ray visualizer, imager, or information provider 100 can capture or otherwise obtain temporal/positional reflective Compton scattered X-ray visualization, imaging, or information providing, and a variety of locative techniques in utilized to match recently obtained MRI or other imaging modality images (two or three dimensions) in the imaged region. For example, certain fiducials could provide position information for MRI (or other imaging modality) such as could also provide position information for certain embodiments of the Compton scattered X-ray visualizer, imager, or information provider 100.

As such, the location of the fiducials they can provide position information for MRI could be used to co-locate the MRI and/or the subsurface Compton scattered X-ray. Certain embodiments of the Compton scattered X-ray visualizer, imager, or information provider 100, once the X-ray subsurface Compton scattered X-ray depth visualizations, images, or provided information has been located with respect to the other imaging modality such as MRI, the depth visualizations, images, and/or provided information, depth visualizations, images, or provided information relating to MRI can be imported, utilized, and/or displayed by certain embodiments of the Compton scattered X-ray visualizer, imager, or information provider 100. Certain of the fiducial can be endogenous (such as blood within the blood vessel); while other fiducials can be exogenous (such as a bead which is implanted under the skin.

Certain embodiments of the Compton scattered X-ray visualizer, imager, or information provider 100 can allow providing inputting higher energy, such as may result in demarcated finer structures within the visualized, imaged, or information provided regions that are located deeper into the at least the portion of the individual. This control or adjustment of the visualization, imaging, or information providing can result since a larger percentage of the X-ray based electromagnetic radiation (e.g., photons) have the ability to be applied by the emitter portion 150 to travel within the at least the portion of the individual to the deeper regions, scatter, and travel out again to be detected. Certain embodiments of the Compton scattered X-ray visualizer, imager, or information provider 100 can provide some amount of adjustment, control, and/or shift to the X-ray based electromagnetic radiation, which with certain embodiments can be varied, adjusted, or controlled, especially when Compton scattered X-ray visualization, imaging, or information providing deeper matter, bones, or organs, etc.

Certain embodiments of the Compton scattered X-ray visualizer, imager, or information provider 100 are therefore useful in providing relatively detailed visualizations, images, and/or provided information about one or more of: matter, aberrative matter embedded in tissues, bones, organs, etc. A considerable number of conventional imaging modalities may be useful for Compton scattered X-ray visualization, imaging, or information providing at least some of the matter within the body of the individual with such resolution.

Certain embodiments of the Compton scattered X-ray visualizer, imager, or information provider 100 can provide some quantification, automated observation, and/or feedback associated with the Compton scattered X-ray in a temporal/positional reflective basis, and in certain instances at a variety of controllable depth(s). In certain instances, the Compton scattered X-ray visualization, imaging, or information providing can be performed through modifiable (in-vivo) matter with low latency. Illuminating electromagnetic characteristics selected with characteristics having intensity and wavelengths selected to limit transmission of excessive electromagnetic radiation (e.g., X-ray) into the body of the individual, and thereby limit X-ray dosages.

Certain embodiments of the Compton scattered X-ray visualizer, imager, or information provider 100 can be configured to scan across the surface 168 (or through a region) of the at least the portion of the individual 82. By comparison, certain embodiments of the Compton scattered X-ray visualizer, imager, or information provider 100 can be configured to capture at least one visualization, at least one image, and/or provide information substantially at the same time. The particular characteristics of the Compton scattered X-ray visualizer, imager, or information provider 100 imaging modality are intended to be illustrative in nature, but not limiting in scope.

At least portions of certain embodiments of the Compton scattered X-ray visualizer, imager, or information provider 100 can include scopes such as endoscopes as described with respect to FIG. 23. Within this disclosure, the term "endoscope" can, depending on context, refer to an one of a variety of scopes that can be applied at least partially internally or externally, such as to one or more of the tracts that are at least partially open that can include, but are not limited to: the gastrointestinal tract, the respiratory tract, the urinary tract, the female reproductive system, etc. Such visualization, imaging, or information providing relative to the tracts can be for a variety of purposes including, but not limited to, examination for health, research, or medical purposes, screening for cancers or tumors, injuries, illnesses, or sicknesses, reproductive conditions, etc. For example, certain embodiments of the Compton scattered X-ray visualizer, imager, or information provider can be configured as an "endotracheal tube (ET), or other tube, that can have had the appropriate components as described with respect to FIG. 1. Certain embodiments of the endoscopes can be applied into normally closed lumens, cavities, and portions of the individual such as via a small incision. Certain embodiments of the Compton scattered X-ray visualizer, imager, or information provider 100 can be used, for instance, to determine where such small incisions may be situated, for example.

Certain embodiments of the endoscope-based embodiment of the Compton scattered X-ray visualizer, imager, or information provider 100 can include, but are not limited to, a rigid or flexible tube 1102, a light delivery system 1104, and the Compton scattered X-ray visualizer, imager, or information provider component(s). For instance, certain endoscope-based embodiments of the Compton scattered X-ray visualizer, imager, or information provider 100 can be configured to include zero, 1, or more emitter portion 150; zero, one, or more Compton scattered X-ray receiving assembly 151; zero, one, or more detector portion 152; and/or zero, 1, or more display portion 154, as described with respect to FIG. 1. Other components component of the Compton scattered X-ray visualizer, imager, or information provider 100 that are not situated in the scope-based embodiment of the Compton scattered X-ray visualizer, imager, or information provider can be included in other associated embodiments of the Compton scattered X-ray visualizer, imager, or information provider.

FIGS. 34 to 37 show four embodiments of certain components of the Compton scattered X-ray visualizer, imager, or information provider 100 relative to the at least the portion of the individual 82. Certain embodiments of the Compton scattered X-ray visualizer, imager, or information provider 100 can utilize either wire-based or wireless communications to transfer data between related devices, such as the at least one detector portion 152 and the at least one display portion, as described in this disclosure. In addition, certain networking, computing, imaging, and other well known techniques may be used to facilitate certain embodiments of the Compton scattered X-ray visualizer, imager, or information provider 100, as described in this disclosure.

Figure 34:
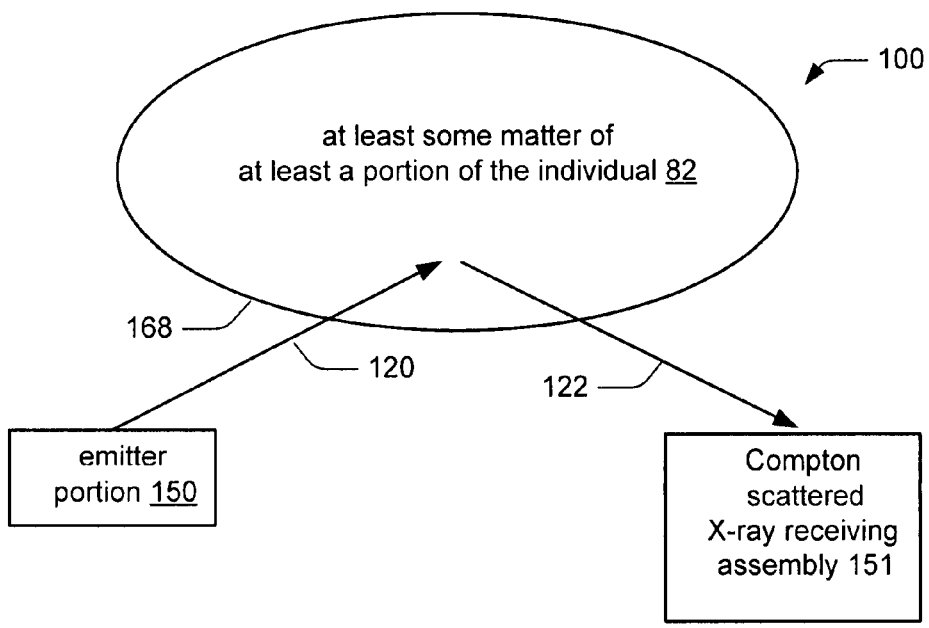
FIG. 34 shows one embodiment of the Compton scattered X-ray visualizer, imager, or information provider in which the at least one emitter portion is situated at least partially externally to the at least the portion of the individual while the at least one Compton scattered X-ray receiving assembly is situated at least partially externally to the at least the portion of the individual.

As described in this disclosure with respect to FIGS. 34 to 37, certain embodiment(s) component(s), and/or portion(s) of the Compton scattered X-ray visualizer, imager, or information provider 100 can be configured as an at least partially external device, while other embodiments can be configured as an at least partially internal device (and/or combination thereof). FIG. 34 shows one embodiment of the Compton scattered X-ray visualizer, imager, or information provider 100, in which the at least one emitter portion 150 is situated at least partially externally to the at least the portion of the individual 82; while at least a portion of the Compton scattered X-ray receiving assembly 151 is situated at least partially externally to the at least the portion of the individual.

Figure 35:
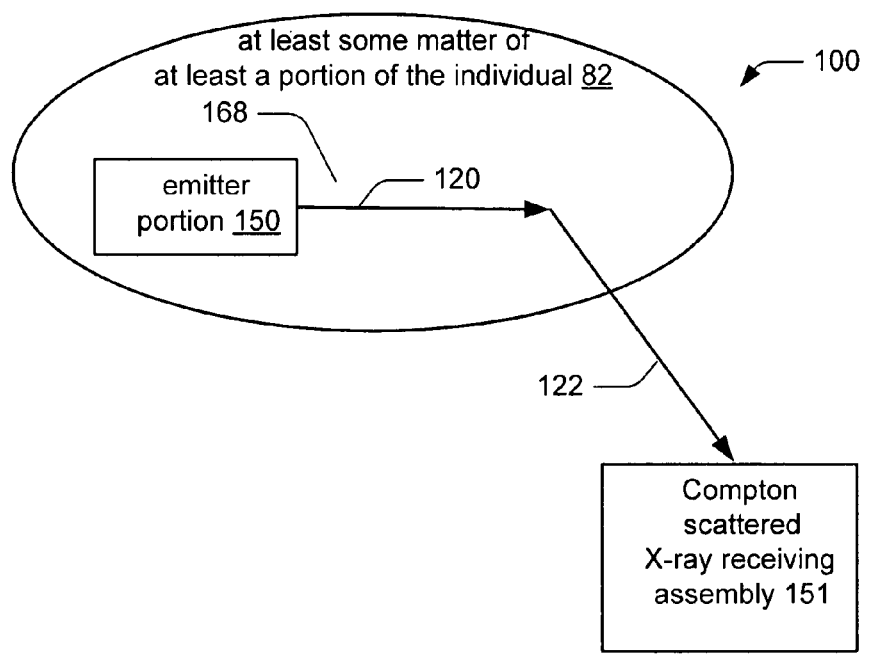
FIG. 35 shows one embodiment of the Compton scattered X-ray visualizer, imager, or information provider in which the at least one emitter portion is situated at least partially internally to the at least the portion of the individual while the at least one Compton scattered X-ray receiving assembly is situated at least partially externally to the at least the portion of the individual.

FIG. 35 shows one embodiment of the Compton scattered X-ray visualizer, imager, or information provider 100, as described with respect to FIG. 1, in which the at least one emitter portion 150 is situated at least partially internally to the at least the portion of the individual 82; while the at least a portion of the Compton scattered X-ray receiving assembly 151 is situated at least partially externally to the at least the portion of the individual.

Figure 36:
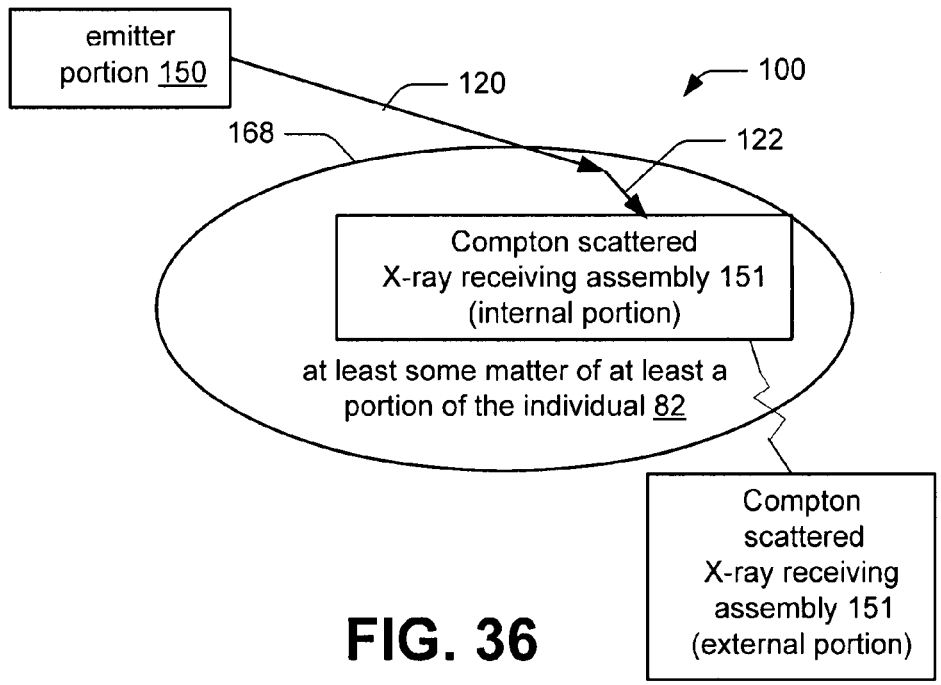
FIG. 36 shows one embodiment of the Compton scattered X-ray visualizer, imager, or information provider in which the at least one emitter portion is situated at least partially externally to the at least the portion of the individual while the at least one Compton scattered X-ray receiving assembly is situated at least partially internally to the at least the portion of the individual.

FIG. 36 shows one embodiment of the Compton scattered X-ray visualizer, imager, or information provider 100, as described with respect to FIG. 1, in which the at least one emitter portion 150 is situated at least partially externally to the at least the portion of the individual 82; while the at least a portion of the Compton scattered X-ray receiving assembly 151 is situated at least partially internally to the at least the portion of the individual. For example, as illustrated in FIG. 35, certain portions of the at least one Compton scattered X-ray receiving assembly 151 (e.g., corresponding perhaps to the detector portion 152 of FIG. 1), could be at least partially internally applied while other portions of the at least one Compton scattered X-ray receiving assembly 151 (e.g., corresponding perhaps to the display portion 154 of FIG. 1) can be at least partially externally applied. Certain embodiments of wireless, wired-based, data-transfor, image transfer, or other similar mechanism can allow for communication between the internal and external portions of the at least one Compton scattered X-ray receiving assembly 151.

Figure 37:
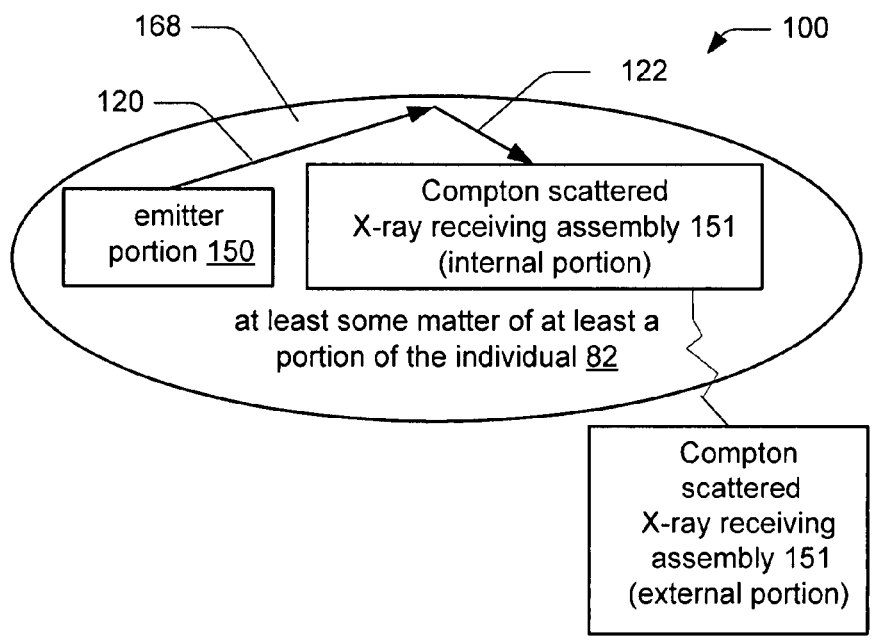
FIG. 37 shows one embodiment of the Compton scattered X-ray visualizer, imager, or information provider in which the at least one emitter portion is situated at least partially internally to the at least the portion of the individual while the Compton scattered X-ray receiving assembly is situated at least partially internally to the at least the portion of the individual.

FIG. 37 shows one embodiment of the Compton scattered X-ray visualizer, imager, or information provider 100, as described with respect to FIG. 1, in which the at least one emitter portion 150 is situated at least partially internally to the at least the portion of the individual 82; while the at least a portion of the Compton scattered X-ray receiving assembly 151 is situated at least partially internally to the at least the portion of the individual. For example, as illustrated in FIG. 37, certain portions of the at least one Compton scattered X-ray receiving assembly 151 (e.g., corresponding perhaps to the detector portion 152 of FIG. 1), could be at least partially internally applied while other portions of the at least one Compton scattered X-ray receiving assembly 151 (e.g., corresponding perhaps to the display portion 154 of FIG. 1) can be at least partially externally applied. Certain embodiments of wireless, wired-based, data-transfor, image transfer, or other similar mechanism can allow for communication between the internal and external portions of the at least one Compton scattered X-ray receiving assembly 151.

There can be a variety of embodiments of the Compton scattered X-ray visualizer, imager, or information provider 100 which may utilize a tactile feedback such as to "transfer" some type of feel or touch sensation to the user. Such tactile feedback embodiments of the Compton scattered X-ray visualizer, imager, or information provider 100 may be considered as one embodiment of the tool, as described in this disclosure such as relative to FIGS. 23, 39, and at other locations, for example. For instance, certain embodiments of the Compton scattered X-ray visualizer, imager, or information provider 100 may include, or be associated with, that can allow the operator such as a physician to "feel" at least some of the nodules such as to provide an indication as to whether they may be cancerous. The importance of the interrelationship between sight and touch is well-recognized in many health fields. For example, doctors, veterinarians, dentists, assistants, researchers, etc. often provide their analysis of combination of feeling and seeing at least a portion of the individual, in combination.

Certain embodiments of the Compton scattered X-ray visualizer, imager, or information provider 100, as described in this disclosure, thereby provide considerable sight (at least partially internally and/or at least partially externally) in the form of imaging, visualization, and/or information providing. Such "sight" as can be provider by certain embodiments of the Compton scattered X-ray visualizer, imager, or information provider 100 can be combined with "touch", which can be provider by certain embodiments of tactile feedback mechanisms. Such embodiments of the tactile feedback mechanism may include various components are mechanisms of automation, tactile feedback, remote-control, robotics, etc., as generally understood in those respective arts, and will not be described more fully in this disclosure. Certain embodiments of the tactile feedback mechanism may be particularly useful when the particular Compton scattered X-ray visualizer, imager, or information provider 100 is being applied at least partially internally to the individual, such that the user cannot always see the internal location. Such tactile feedback embodiments are especially useful for certain doctors, surgeons, veterinarians, dentists, assistants, researchers, etc. with somewhat limited senses of touch and/or sight.

In certain instances, the tactile feedback may be partially associated with the diagnosis from a medical user such as a surgeon or doctor. A number of medical diagnosis, examination, treatment, and other practices rely on a combination of sight in combination with touch. It is to be understood that during conventional breast cancer examinations, the "feel" or "touch" of the physician to detect breast cancer nodules in an important portion of examination and/or diagnosis. Proctologists, for example, are often forced to rely on touch or feel, since the ability to see potential medical situations or conditions may be limited. As such, providing certain embodiments of the Compton scattered X-ray visualizer, imager, or information provider with tactile capabilities may be particularly important in the diagnosis or treatment phases. For example, certain doctors may more directly locate or tactilely "feel" for cancers, tumors, or which may be relatively hard as compared with the surrounding matter, nodules, organs, tissue, fat, muscle, or other matter. For dental users, the tactile feedback may by utilized in conjunction with a dental drill or pick, etc., such that the Compton scattered X-ray visualizer, imager, or information provider 100 can be used to indicate the degree and/or area of dental decay, etc. during drilling, etc. It is to be understood that many types of users may similarly benefit from the tactile feedback being provided by certain tools by certain embodiments of the Compton scattered X-ray visualizer, imager, or information provider 100.

Certain embodiments of the Compton scattered X-ray visualizer, imager, or information provider 100 could be configured to provide a variety of types of tactile feedback. Tactile feedback may be based on hardness or softness of the matter, such as iron or calcium concentration, or concentration of other matter. The tactile feedback system could involve feeding a signal representing some aspect of touchability (e.g., the matter is hard, soft, resilient, etc.) from the tactile system back to the instrument, such as can be displayed, and/or provided as some tactile output to the user. Certain embodiments of the instrument may not be able to "feel" the feedback information in a similar manner as a person, and as such certain tactile output information can be returned from the at least one visualization, image, and/or provided information in image or data form. As such, the user of certain embodiments of the Compton scattered X-ray visualizer, imager, or information provider could receive feedback either visually and/or tactically.

In addition, certain types of tools can be configured to be actuated based on user input. Such tools may be configured as an endoscope, or alternately some devoted type of tool such as a cutter, gamma knife, scalpel, separator, tactile feedback provider, ablator, surgical suction, etc. Such actuation of at least portions of tool based on user input may be considered as a version of robotics, remote control, amplification, and/or automation. Certain embodiments of the Compton scattered X-ray visualizer, imager, or information provider 100 can be configured as allow controlled (e.g., robotic surgery), as well as image processing to precisely detect organs, make incisions, cut matter away, ablate matter, visualize, image, and/or provide information relating to a region in matter, etc.

Certain embodiments of the tactile feedback could be provided on a probe or other portion of the Compton scattered X-ray visualizer, imager, or information provider 100 itself, such as in an endoscope. The greater the tactile feedback can enhance certain surgical techniques for surgeons, certain dental techniques for dentists, certain veterinarian techniques for veterinarians, etc. Certain embodiments of the Compton scattered X-ray visualizer, imager, or information provider 100 can be configured as to generate a tactile response that can be detected by a person at least partially in response to the X-ray Compton scattered X-ray information. Certain embodiments of the Compton scattered X-ray visualizer, imager, or information provider 100 can be configured to be minimally invasive to locate organ, and confirm whether it is at a perceived location. Certain embodiments of the Compton scattered X-ray visualizer, imager, or information provider 100 could allow surgeons, etc. to visualize and/or operate such as to perform more complex surgeries using "keyholes", or incisions, within the patient.

Certain embodiments of the Compton scattered X-ray visualizer, imager, or information provider 100 with tactile feedback can be configured to visualize, image, and/or provide information from a location at least partially external to the at least the portion of the individual. Certain embodiments of the Compton scattered X-ray visualizer, imager, or information provider with tactile feedback can be configured to visualize, image, and/or provide information from a location at least partially internal to at least the portion of the individual (either via a normally open location such as using an endoscope or via a normally closed location such as with an incision).

Certain embodiments of the Compton scattered X-ray visualizer, imager, or information provider 100 could therefore be utilized for a variety of applications and Compton scattered X-ray visualization, imaging, or information providing techniques outside of scope of confessional X-ray. For example, certain embodiments of the Compton scattered X-ray visualizer, imager, or information provider 100 could be situated, or made viewable to the at least the portion of the individual at their bedside such as they may view. As such, certain embodiments of the Compton scattered X-ray visualizer, imager, or information provider 100 may be utilized as a relatively inexpensive alternative to MRI, for example, which doesn't necessarily enclose the body of the at least the portion of the individual as is the case with MRI, CT, etc. Certain embodiments of the Compton scattered X-ray visualizer, imager, or information provider 100 may therefore serve as a direct replacement, in certain applications, for such imaging technologies as MRI, CT, etc. In addition, certain embodiments of the Compton scattered X-ray visualizer, imager, or information provider 100 might be preferred, in certain applications, to ultrasound because of the considerable contrast of the Compton scattered X-ray visualizer, imager, or information provider.

As described in this disclosure, certain embodiments of the emitter portion 150 may be at least partially steerable. Additionally, certain embodiments of the detector portion 152 may be at least partially adjustable to control the direction which it best receives X-ray-based electromagnetic radiation. Certain embodiments of the Compton scattered X-ray visualizer, imager, or information provider 100 may therefore be configured such that the emitter portion 150 is relatively closely aligned with the detector portion 152. Similarly, certain embodiments of the Compton scattered X-ray visualizer, imager, or information provider 100 may be configured to such that the emitter portion 150 moves into an approximate alignment with the detector portion 152, in certain embodiment as to create a standing pattern such as may be utilized to visualize, image, and/or provide information relating to a region utilizing scanning, such as is generally known with certain display technologies. By utilizing such scanning embodiments of the Compton scattered X-ray visualizer, imager, or information provider 100, relatively good-quality Compton scattered X-ray visualization, imaging, or information providing can be provided. Additionally, relatively low power may be necessary (as compared to other medical imaging modalities), such as may be useful in limiting the exposure of the at least the portion of the individual to relatively high-powered X-rays, as described in this disclosure.

Certain embodiments of the Compton scattered X-ray visualizer, imager, or information provider 100 can be configured to identify a trend of pattern correlating to the change in state to a pattern corresponding to a macrostate. These patterns can be correlated to a target indicative of a particular condition. By comparing the visualized, imaged, or information provided pattern with the pattern recognized as representing a condition, illness, etc. The information, data, patterns, etc. can be, maintained in a database, the pattern of information can be used for a prognosis of the condition, illness, etc. The use of information, data, patterns, etc. as can be received by or pr processed from scattered X-ray from Compton scattered X-ray can therefore be quite useful for a variety of purposes.

Certain embodiments of the Compton scattered X-ray visualizer, imager, or information provider 100 can be configured to use selected portion of new slice info, and higher resolution info to produce composite visualize, image, and/or provide information (having enhanced resolution) as compared to original visualizations, images, or provided information. Also, producing this can be responsive to matter deformation modeling. Certain embodiments of the Compton scattered X-ray visualizer, imager, or information provider 100 can be configured to consider information that can be not only anatomically obtained, but also functionally obtained. (Instead or in addition to displaying info, correlate to a biostate, or change in state. Change in state from a plurality of locations).

Figure 39:
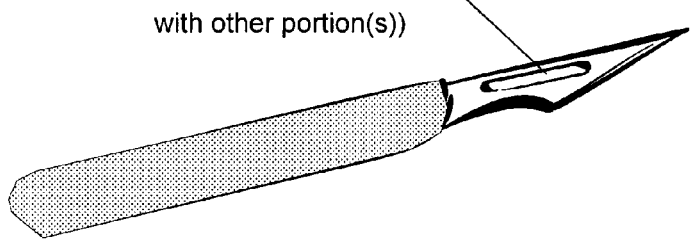
FIG. 39 shows another embodiment of the Compton scattered X-ray receiving assembly that is associated with a tool.

Certain embodiments of the Compton scattered X-ray visualizer, imager, or information provider 100 can be configured such as their at least one emitter portion 150 and their at least one detector portion 152 integral to a tool (surgical, examination, positioning, scope-type, tactile feedback provider, luminal, etc.). In certain instances, the Compton scattered X-ray visualizer, imager, or information provider 100 may provide a proximity sensor function to the tool. For example, the at least one emitter portion 150 may be sized such as to emit (in substantially $4\pi$ or $2\pi$ steradians) at a desired frequency and/or energy level based on the depth that is being examined or that the tool is being positioned, and the detector portion may be a pixellated X-ray detector portion array, an avalanche detector array, a CCD array, etc. Examples of X-ray detectors may include, but are not limited to, pixellated streak cameras, streak cameras, CCD devices, avalanche detectors, or other devices. With certain embodiments of the Compton scattered X-ray visualizer, imager, or information provider 100, the emitter portion may produce a beam, where the detector portion is not a pixellated array (e.g., including a Kulikov lens, and/or a Bragg lens). Certain embodiments of the Compton scattered X-ray visualizer, imager, or information provider 100 might include the emitter portion at the distal end of the tool, and the detector portion separated there from either in close proximity or by a considerable distance in a manner desirable to provide suitable Compton scattered X-ray visualization, imaging, or information providing. Certain embodiments of the Compton scattered X-ray visualizer, imager, or information provider 100 might be particularly useful if positioned on, integrated into, or otherwise associated with the tool (e.g., situated on the tip of a probe or cutter, on at least one tip of scissors, on forceps, on needles, etc.). FIG. 39, for example, illustrates one embodiment of the tool (surgical knife) including an embodiment of the Compton scattered X-ray visualizer, imager, or information provider 100. For the purpose of this disclosure, certain endoscopes as described with respect with FIG. 23 can be considered as tools that can include certain embodiments of the Compton scattered X-ray visualizer, imager, or information provider 100. Certain embodiments of tools may also be associated with a tactile feedback mechanism that provides at least some tactile feedback, which by themselves may be considered as another embodiment of tool within this disclosure. It may therefore be desirable to position certain embodiments of the Compton scattered X-ray visualizer, imager, or information provider 100 on, proximate to, or to provide viewability of, operative surfaces of a variety of such tools as surgical tools, tactile feedback providers, etc. Such embodiments of the Compton scattered X-ray visualizer, imager, or information provider 100 can thereby provide a visualization, imaging, or information providing from the viewpoint of the tool.

Implants, constructs, pins, screws, etc. such as may be positioned within the individual may be considered as one embodiment of the tool, which may include certain embodiments of the Compton scattered X-ray visualizer, imager, or information provider 100. Additionally, certain implants, constructs, pins, screws, etc. can be viewed as tools that in include certain embodiments of the Compton scattered X-ray visualizer, imager, or information provider 100. Certain embodiments of the Compton scattered X-ray visualizer, imager, or information provider 100 can provide an added benefit, such that when a user such as a surgeon is placing a pedicle screw, it is highly desired to stay within the pedicle because if the surgeon goes outside they may contact a nerve root. As such, the embodiment of the Compton scattered X-ray visualizer, imager, or information provider 100 can act as a pedicle guide. Certain embodiments of the Compton scattered X-ray visualizer, imager, or information provider 100 can thereby be considered to combine with a warning system that can utilize certain embodiments of the depth visualizing, imaging, or information providing controller 97. Certain embodiments of the depth visualizing, imaging, or information providing controller 97 can include, as data or information, a variety of individual information, such as patient information, injury, illness, and if the user (doctor, dentist, veterinarian, etc.) is positioning the tool at an undesired location or performing some undesired procedure (e.g., at the wrong side of the patient's body), in which instance a suitable alarm may be actuated in the event of a suitable event.

Certain embodiments of the Compton scattered X-ray visualizer, imager, or information provider 100 can thereby be configured as a surgical tool, certain of which may be configured to act as a proximity sensor, while output from others may be displayed. It is envisioned that the emitter portion 150 and/or the Compton scattered X-ray receiving assembly 151 could be integral to the surgical tool and/or tactile feedback provider. Certain embodiments of the Compton scattered X-ray visualizer, imager, or information provider 100 can be configured to image once multiple times, or can include a number of or at least one displaceable emitter portion(s) to provide scanning. In certain instances, upon the surgical tool being positioned relative to the at least the portion of the individual is configurable to emit X-ray based electromagnetic radiation suitable to image to a controllable depth into an at least one matter of at least a portion of the individual to be used to derive depth visualizations, images, or provided information at least partially in response to Compton scattered X-ray of the X-ray based electromagnetic radiation. The detector portion may also be integral to the surgical tool and/or tactile feedback provider that is operable, and as such may be alignable and/or controllable. Certain embodiments of the emitter portion may include scopes, but may also be at least partially externally situated. Certain of the at least partially internal embodiments may be inserted through insertion or via a normally open opening to be at least partially applied relative to at least a portion of the individual such as to receive at least one Compton scattered X-ray that has been Compton scattered in an at least one matter, etc. of the at least the portion of the individual.

Certain embodiments of the visualization, imaging, or information providing controlling 97 are configured particularly to generate the depth visualizations or images that can be displayed over the display portion 154 of the Compton scattered X-ray visualizer, imager, or information provider 100, as described with respect to FIG. 1, and other locations through this disclosure. By comparison, certain embodiments of the visualization, imaging, or information providing controlling 97, as described with respect to FIG. 38, can be configured to produce information that can be displayed over certain embodiments of the Compton scattered X-ray visualizer, imager, or information provider 100, which can be observed by the user and/or individual (human). Consider, for example, the embodiment of the Compton scattered X-ray visualizer, imager, or information provider 100 that can scan individuals for such aspects as cancers (e.g., breast cancer, melanomas), tumors, blood vessel locations (perhaps in diabetics to provide insulin shots), heart condition, bone fragments or portions (especially useful at certain sporting events, etc.), burn victim examination, and/or a variety of emergencies or situations which a variety of emergency, rescue, medical, as well as individuals who wish to examine themselves at locations remote from conventional imaging equipment are likely to encounter.

Certain embodiments of the Compton scattered X-ray visualizer, imager, or information provider can utilize lower power requirements and conventional imagers since they rely on Compton scattered X-ray of X-rays instead of transmission X-rays (i.e., the latter requires providing enough energy to the X-ray photons to pass the X-ray photons through the image portion of the individual, instead of scattering within the individual as with the former). Since less energies required for typical operation of the Compton scattered X-ray depth and visualizer, imager, or information provider 100; they can thereby be configured to operate with reduced input voltages. It is feasible that certain embodiments of the Compton scattered X-ray visualizer, imager, or information provider 100 can be made to use power supplies a medical clinics, homes, offices, vehicles, etc. and can thereby be made considerably more portable than conventional imaging equipment.

By allowing certain embodiments of the Compton scattered X-ray visualizer, imager, or information provider 100 to operate using relatively low power as compared to conventional imaging systems, is likely that the visualization, imaging, and/or information providing systems can be utilized in regions remote from sophisticated electrical infrastructure. As such, certain embodiments of the Compton scattered X-ray visualizer, imager, or information provider 100 can be applied to remote medical facilities, or regions, sporting events, office locations, relatively poor or remote regions, villages, islands, etc. Certain embodiments of the Compton scattered X-ray visualizer, imager, or information provider 100 can thereby be situated where the medical, dental, rescue, emergency, or other need is (e.g., where sick, injured, or other individuals to be examined may be situated), as compared to where relatively large power supplies or complex or expensive imaging equipment may be located.

As such, certain portable embodiments of the at least the portion of the Compton scattered X-ray visualizer, imager, or information provider 100 can utilize such portable energy-provided devices as fuel cells, batteries, generator, etc. By allowing a wide range of portable energy sources, such as allowed by relatively low power usage by certain embodiments of the Compton scattered X-ray visualizer, imager, or information provider 100, relatively portable embodiments of visualizing, imaging, or information providing solutions can be provided.

As such, certain user-operated embodiments of the Compton scattered X-ray visualizer, imager, or information provider 100 can be configured to be used in, and are designed to be suitable to be used in, the particular location of the user (e.g., doctor's office, operating room, emergency center, rescue vehicle, ambulance, dentist office, veterinarian, a vehicle, the individual's home or office, a remote village, etc.) to visualize, image, and/or provide information at least a portion of the individual, or receive information relating to the individual. Certain individual-operated, home-based, office based, or other remote embodiments of the Compton scattered X-ray visualizer, imager, or information provider 100 can be configured to be used in, and are designed to be suitable to be used in) the home, office, or other location of the user that can be used by the user (who may be the individual) as a home-style version to visualize, image, and/or provide information at least a portion of the individual, or receive information relating to the individual. The different user-operated or individual-operated embodiments of the Compton scattered X-ray visualizer, imager, or information provider 100 can each have varied functions and/or operations.

Considering the privacy issues, and the time required for patients to visit doctors, etc., the individual-operated embodiments of the Compton scattered X-ray visualizer, imager, or information provider 100 can be configured to allow people, and other individuals, to monitor a variety of aspects of their own condition. Consider the privacy, flexibility, independence, and other benefits that home pregnancy tests have provided for women. Certain embodiments of the Compton scattered X-ray visualizer, imager, or information provider 100 can be configured to provide depth visualization, images, and/or associated information related to a variety of other conditions, illnesses, injuries, sicknesses, and other conditional, medical, and/or routine check-up aspects. Certain embodiments of the Compton scattered X-ray visualizer, imager, or information provider 100 could even be designed based, at least partially, on X-ray radiation limiting, user input, ergonomics, quality of imaging, and other such factors; and might be updated, improved, and changed as appropriate based on usage and feedback considerations.

Certain embodiments of the individual-operated embodiments of the Compton scattered X-ray visualizer, imager, or information provider 100 can be configured to be devoted to only one, or a relatively few, devoted task (e.g., cancer or tumor scans, blood vessel locator, bone fragment detector, etc.). By being devoted to a few specific tasks, these devoted embodiments of the individual-operated embodiments of the Compton scattered X-ray visualizer, imager, or information provider 100 can be made relatively inexpensively, and relatively simple, for the individual and/or other person using it. Consider that patients, family members, friends, etc. would typically be expected to have relatively little training and/or experience with imaging systems, and a such, such embodiments should be made relative straight forward to understand with relatively little training.

By applying certain embodiments of the Compton scattered X-ray visualizer, imager, or information provider 100 to conventional imaging equipment, certain devoted tasks, logic, computer programming, electronic circuitry, and/or other processing circuitry can make relatively clear analysis, determinations, prognosis, etc. as compared certain relatively expensive and multi-use conventional imaging equipment such as MRIs and CAT scan devices. As such, a particularly exemplary embodiment of the Compton scattered X-ray visualizer, imager, or information provider 100 can be configured for a particular of a few devoted operations such as examining for such conditions, illnesses, or injuries as melanomas, cancers, tumors, bone condition, tissue condition, ligament or tendon condition, etc. Certain embodiments of the Compton scattered X-ray visualizer, imager, or information provider 100 can be designed, for example, to scan region of the individual for such aberrations as they may occur.

Thereupon, certain embodiments of the visualization, imaging, or information providing controller 97 can be configured to determine logically (using a combination of hardware, software, firmware, as described in this disclosure) whether the condition falls within limits as to require further examination, for example. Certain embodiments of the Compton scattered X-ray visualizer, imager, or information provider 100 can be configured to provide such devoted tasks with output in the form of imaging and/or visualization. Although certain embodiments of these devoted devices can more suitably, and less expensively, output one or more of a variety of information resulting at least partially from some analysis and processing in a non-image-based mode (e.g., text, graphics, analysis output, etc.) which could be of considerable use both to trained and/or untrained users.

There are a variety of techniques by which certain embodiments of the Compton scattered X-ray visualizer, imager, or information provider 100 that can visualize, image, or provide information to within a depth substantially scattered range to a prescribed substantially scattered depth in at least some matter of the at least the portion of the individual. Certain of these techniques are illustrated in FIGS. 40 and 41, for example.

Figure 40:
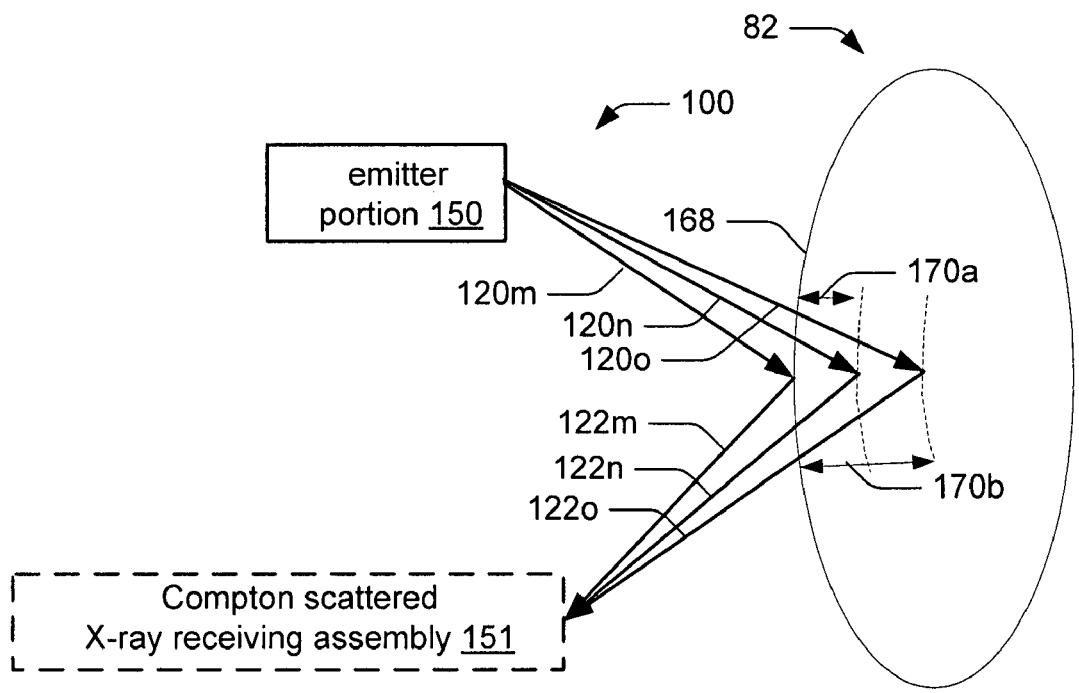
FIG. 40 shows one embodiment of the Compton scattered X-ray visualizer, imager, or information provider that is being utilized for image combination.

FIG. 40, for example, illustrates an embodiments of the Compton scattered X-ray visualizer, imager, or information provider 100 that can visualize, image, or provide information to within the depth substantially scattered range to between the prescribed substantially scattered depth 168, 170a, 170b in at least some matter of the at least the portion of the individual by applying a number of applied X-rays 120m, 120n, and 120o that respectively scatter at respective scattering events sitated at differing respective prescribed substantially scattered depth 168, 170a, 170b to provide respective scattered X-rays 122m, 122n, and 122o. Though the number of applied X-rays 120m, 120n, and 120o are illustrated as being applied at different angles (such as from multiple emitter portions are different angles, or from a single emitter portion through several collimators), it should be understood that though these applied X-rays 120m, 120n, and 120o can be applied parallel or spaced from each other, such as being provide from an array. The respective scattered X-rays 122m, 122n, and 122o can be detected by certain embodiments of the Compton scattered X-ray receiving assembly 151.

Figure 41:
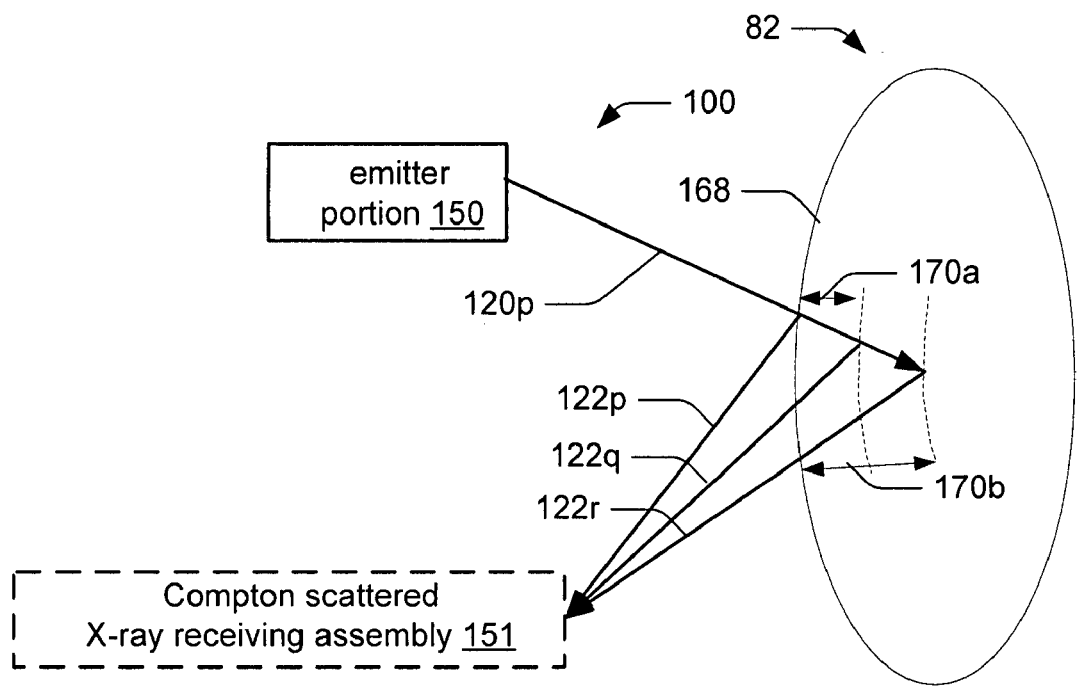
FIG. 41 shows a diagram of one embodiment of the Compton scattered X-ray visualizer, imager, or information provider that is configured to provide a time of flight measurement.

FIG. 41, for example, illustrates an embodiments of the Compton scattered X-ray visualizer, imager, or information provider 100 that can visualize, image, or provide information to within the depth substantially scattered range to between the prescribed substantially scattered depth 168, 170a, 170b in at least some matter of the at least the portion of the individual by the at least one emitter portion 150 applying a single applied X-ray 120p that scatters at respective scattering events sitated at differing respective prescribed substantially scattered depth 168, 170a, 170b to provide respective scattered X-rays 122p, 122q, and 122r. The respective scattered X-rays 122p, 122q, and 122r can be detected by certain embodiments of the Compton scattered X-ray receiving assembly 151.

Certain characteristics of electromagnetic waves, currents, flows, fields, etc. (including aspects relating to X-rays, X-ray photons, electrons, etc.) is described in *The Electrical Engineering Handbook, Second Edition*, Richard C. Dorf, CRC Press/IEEE Press, (incorporated herein by reference in its entirety). Certain types of X-rays, which may be characterized broadly as electromagnetic waves, particles, fields, currents, etc., can be controlled, adjusted, varied, weakened, intensified, directed, etc. utilizing certain shielding, shaping, and/or electromagnetic controller techniques; such as are generally understood by those skilled in electrical engineering and/or electromagnetics. Certain embodiments of the Compton scattered X-ray visualizer, imager, or information provider 100 can utilize X-rays, electromagnetic signals, particles, waves, etc. for Compton scattered X-ray visualization, imaging, or information providing.

2. Controllable and/or Adjustable Embodiments of the Compton Scattered X-Ray Visualizer, Imager, or Information Provider As described with respect to FIG. 1, certain embodiments of the Compton scattered X-ray visualizer, imager, or information provider 100 can direct the applied X-ray 120 toward matter underneath a surface of at least a portion of the individual. The applied X-ray can be scattered by the matter of the at least a portion of the individual based on Compton scattered X-ray aspects and equations, as described in this disclosure. Based upon the amount of Compton's scattering, the energy level loss of the X-ray photons during the scattering event, and other such scattering characteristics, can be considered during Compton scattered X-ray visualization, imaging, or information providing. In certain instances, the energy level of the X-ray photons being applied to the matter of the individual can be ramped up, decreased, modified, maintained, etc. as described in this disclosure with respect to FIGS. 42 to 45. Certain embodiments of the Compton scattered X-ray visualizer, imager, or information provider 100 can thereby visualize, image, or provide information relating to particular matter based at least partially on increasing, reducing, modifying, or maintaining the energy levels of the X-ray photons (and thereby conversely decreasing the frequency of the X-ray photons) included in the applied X-rays, and thereby controlling and/or adjusting the operation of the Compton scattered X-ray visualizer, imager, or information provider. As the energy level of the X-ray photons respectively increases or decreases, within the at least one visualizing, imaging, or information providing depth range to the at least one prescribed visualizing, imaging, or information providing depth of a considerable majority of the photons can thereupon generally respectively increase or decrease, though not typically in a linear fashion.

While the embodiments of the Compton scattered X-ray visualizer, imager, or information provider 100 as described with respect to FIGS. 42-45 illustrate the at least one emitter portion 150 whose output is controlled by an additional device; in actuality the distinct added device can be considered as an integral portion of the at least one emitter portion. As such, certain embodiments of the at least one emitter portion may be considered as configured to apply adjustable and/or controllable applied X-rays toward the at least some matter of the at least the portion of the individual.

As described above, there can be a variety of mechanisms that can be used to adjust and/or control certain embodiments of the Compton scattered X-ray visualizer, imager, or information provider 100, largely based on operation of the visualization, imaging, or information providing controller 97 to control and/or adjust the energy level, frequency, or other characteristics of the X-ray photons included in the applied X-ray 120. There are other mechanisms which may be utilized to control and/or adjust this depth visualizing, imaging, or information providing of certain embodiments of the Compton scattered X-ray visualizer, imager, or information provider 100.

The modification, control, adjustment, etc. in the characteristics of Compton scattered X-ray visualization, imaging, or information providing into the matter of the at least the portion of the individual may not necessarily follow a linear function relative to the increasing energy levels of the X-ray photons making up the applied X-rays. In addition, since the matter of such individuals is not homogenous, the rate of Compton scattered X-ray visualization, imaging, or information providing may vary as a function of the material within the individual being imaged. For example, certain embodiments of the Compton scattered X-ray visualizer, imager, or information provider 100 can be configured for imaging at least partially through bone would be expected to differ considerably (e.g., requiring different, likely increased, energy levels of the photons) as compared to the imaging characteristics required for less dense matter such as tissue, fluids such as blood or water, tumors, gums, various organs, etc. As such, certain embodiment of the Compton scattered X-ray visualizer, imager, or information provider 100 can be configured to adjust and/or control the at least one visualizing, imaging, or information providing depth range to the at least one prescribed visualizing, imaging, or information providing depth such as by using a variety of techniques as described in this disclosure.

Figure 42:
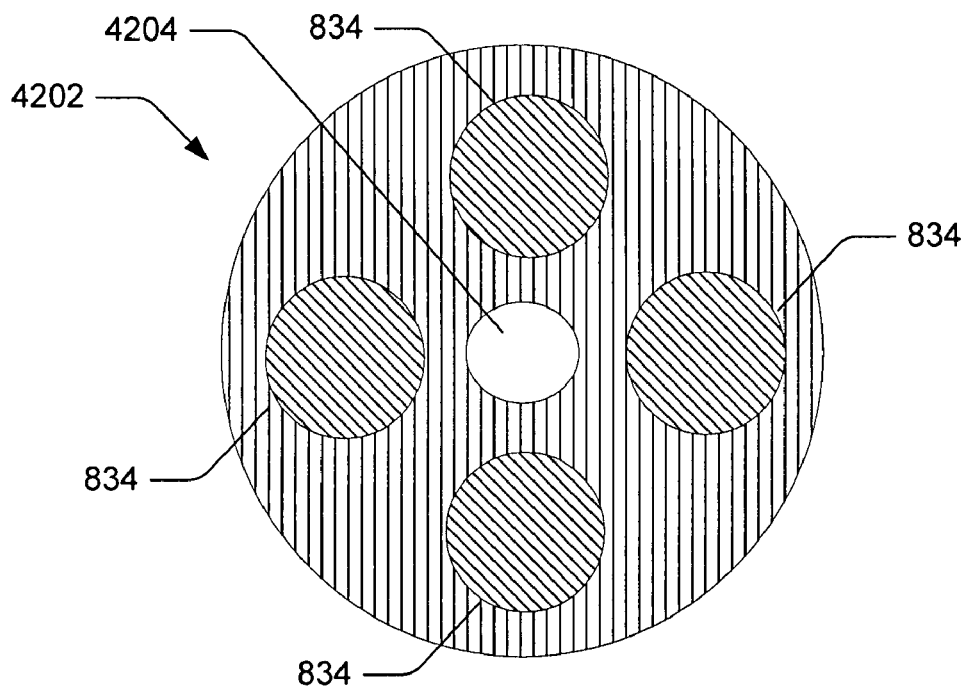
FIG. 42 shows another embodiment of the Compton scattered X-ray visualizer, imager, or information provider including an embodiment of a control or adjustment mechanism.

FIG. 42 shows another embodiment of the control or adjustment mechanism 302, in which an anode switching or modifying mechanism (e.g., to include an adjustable anode wheel, or varying photon generator, as described with respect to FIGS. 8 or 9) can allow for physically altering or changing of the anode 834. Certain embodiments of the anode 834 have been described with respect to FIGS. 8 or 9. For instance, the anode wheel has been described with respect to FIGS. 8, and is described with respect to FIG. 42. The anode wheel can be rotated (e.g., using a step or motor, etc.), such as to align a different anode such as might have different materials, configurations, and/or dimensions, etc. such as to allow a change in the anode that is in communication with the electron stream, thereby providing varied energy levels (e.g., frequencies of X-ray photons) for the applied X-ray 120. Certain embodiments of the anode wheel 4202 can be rotated or displaced about an axis 4204, such as by using a stepper motor or other suitable actuator, such as to operably position at least one anode 834 of the desired material, size, shape, configuration, etc. within the emitter portion as desired. Positioning an anode having the desired characteristics within the emitter portion as described with respect to FIG. 8 effectively generates the applied X-rays having the desired characteristics (e.g., X-ray photon energy level and corresponding frequency). Additionally, certain embodiments of the photon generator 880, as described with respect to FIG. 9, can be configured to provide X-ray photons having varied intensities and/or frequencies, such that could be used to control and/or adjust certain embodiments of the Compton scattered X-ray visualizer, imager, or information provider 100. For example, the photon generator as described with respect to FIG. 9 could include multiple distinct photons generators, each of which could be individually actuated as to provide a controllable and/or adjustable version of the applied X-ray 120 having the desired X-ray photon frequency and/or energy level characteristics.

Figure 43:
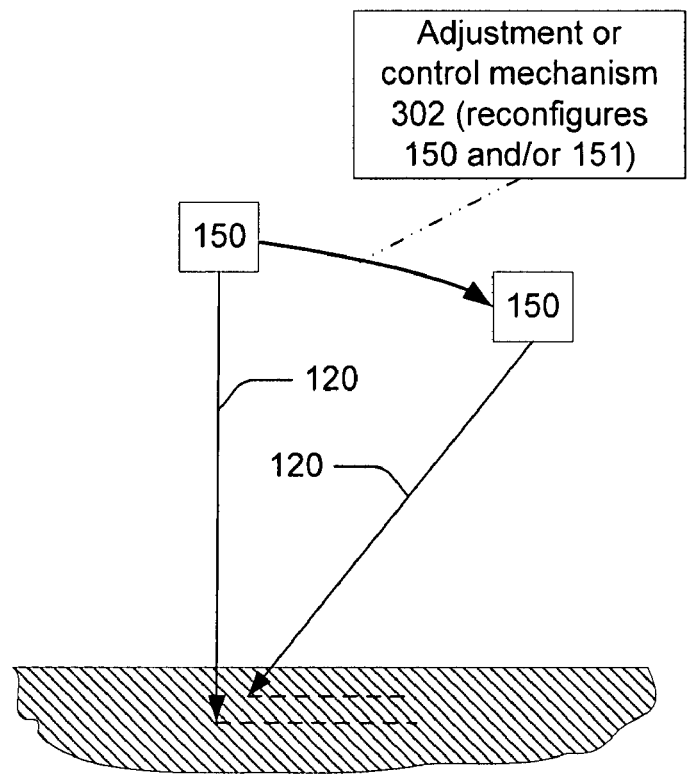
FIG. 43 shows another embodiment of the Compton scattered X-ray visualizer, imager, or information provider including another embodiment of the control or adjustment mechanism.

FIG. 43 shows another embodiment of the Compton scattered X-ray visualizer, imager, or information provider 100 including one embodiment of a control or adjustment mechanism 302 that can be utilized by certain embodiments of the Compton scattered X-ray visualizer, imager, or information provider, in which the angle of the applied X-ray 120 can be adjusted or controlled by being angled relative to the surface 168 of the at least the portion of the individual 82. As the angle of the applied X-ray 120 changes, the at least one visualizing, imaging, or information providing depth range to the at least one prescribed visualizing, imaging, or information providing depth can vary as a cosine function of the angle. As such, increasing the angle of the applied X-ray can therefore reduce the at least one visualizing, imaging, or information providing depth range to the at least one prescribed visualizing, imaging, or information providing depth in a predictable, adjustable, and/or controllable fashion.

Figure 44:
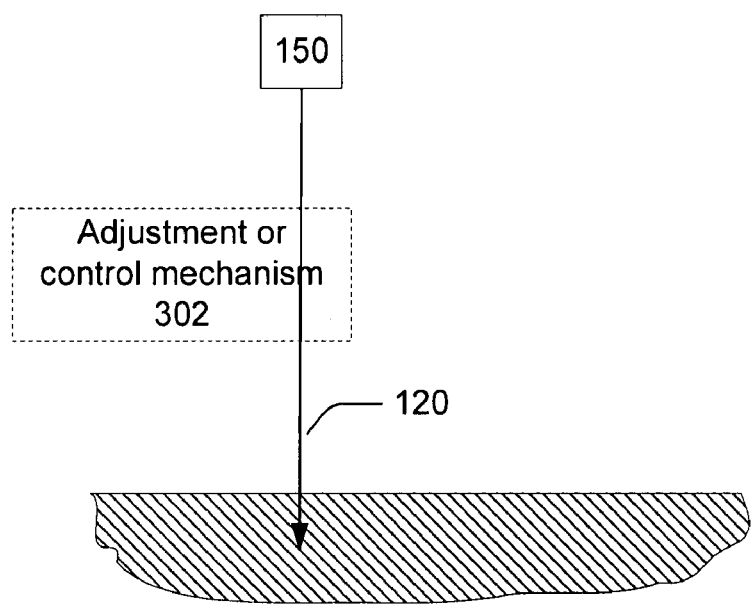
FIG. 44 shows another embodiment of the Compton scattered X-ray visualizer, imager, or information provider including yet another embodiment of the control or adjustment mechanism.

FIG. 44 shows another embodiment of the Compton scattered X-ray visualizer, imager, or information provider 100 including another embodiment of the control or adjustment mechanism 302, in which an X-ray depth-imaging depth reducing mechanism can be operationally applied between the emitter portion 150 the surface of the at least the portion of the individual (or at some other locations) as to limit the at least one depth substantially scattering range to the at least one prescribed substantially scattering depth to reduce the energy level of the X-ray photons being applied to the at least the portion of the individual. Consider that, in general, as the applied X-rays 120 travel through the matter of the at least the portion of the individual, they typically lose energy. As such, the X-ray depth-imaging depth reducing mechanism can be configured is any device or mechanism that can similarly reduce the energy level of the X-ray photons of the applied X-ray prior to being applied to the at least the portion of the individual. Certain embodiments of the adjustment or control mechanism 44 as illustrated in FIG. 44 could include an X-ray energy level or frequency modulator or modifier.

As such, the effective at least one substantial scattering within the at least one substantially scattering depth range to the at least one prescribed substantially scattering depth 120 can enter into the matter of the at least the portion of the individual can be reduced by initially passing through certain embodiments of the X-ray depth-imaging depth reducing mechanism can be reduced. Certain X-ray depth-imaging depth reducing mechanism to embodiments of the control or adjustment mechanism 302 can effectively decrease the energy level and/or frequency of the X-ray photons included in the applied X-rays 120. Various X-ray depth-imaging depth reducing mechanism to arrange for a layer of material that at least partially dissipates the energy of the X-ray photons, to at least one semiconductor device or other mechanism that can modulate X-ray frequencies and thereby reduce energies, etc.

Figure 45:
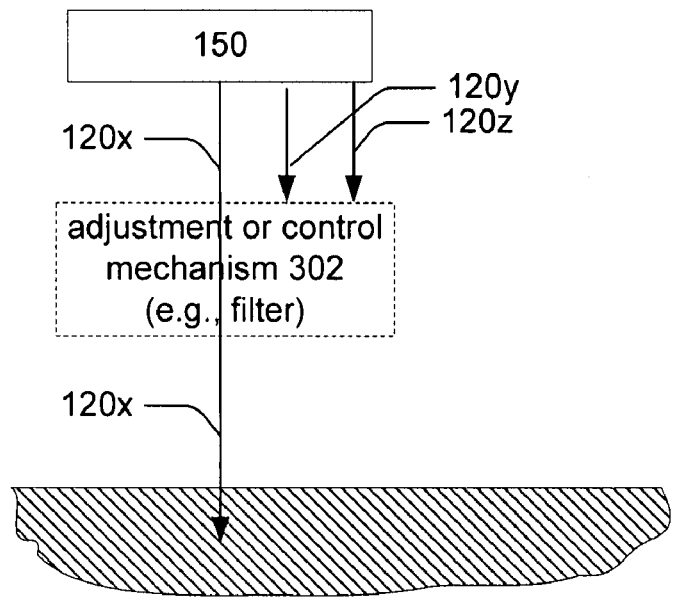
FIG. 45 shows another embodiment of the Compton scattered X-ray visualizer, imager, or information provider including another embodiment of the control or adjustment mechanism.

FIG. 45 shows another embodiment of the adjustable or controllable mechanism 302 by which a variety of filters would be applied to the applied X-ray to filter out at least certain frequency X-rays, while allowing at least other frequency X-rays to pass. Certain embodiments of the emitter portion 150 thereby can include multiple X-ray generators, multiple anodes, or multiple devices that each can generate X-rays photons having a distinct frequency. Alternately, certain embodiments of the emitter portion 150 can generate a broadband X-ray including X-rays having a range of frequencies, only certain ones of which are allowed to pass through the filter embodiment of the adjustment or control mechanism 302. For instance, FIG. 45 shows one filtering embodiment of the adjustment or control mechanism 302 that allows X-ray photons having frequency corresponding to applied X-ray $120x$ to pass, while limiting the ability of X-ray photons having frequencies corresponding to applied X-rays $120y$ and $120z$ to pass.

There are therefore a variety of configurations of various embodiments of the Compton scattered X-ray visualizer, imager, or information provider 100 that can include a variety of types of adjustment or control mechanism 302 by which the energy level of X-ray photons can be controlled or adjusted. Certain embodiments of the at least one emitter portion 150 and/or the at least one Compton scattered X-ray receiving assembly 151 can be configured in arrays, or by having slightly different operating characteristics. As such, one or more of the at least one emitter portion 150 and/or the at least one Compton scattered X-ray receiving assembly 151 can be actuated and/or deactuated, depending on characteristic, position, angle, etc. such as to allow for control and/or adjustment of the visualizing, imaging, or providing information modalities.

Additionally, certain embodiments of the Compton scattered X-ray receiving assembly 151 can be directed, positioned, angled, filtered, or otherwise operated to only receive certain scattered X-rays. While these embodiments of the Compton scattered X-ray visualizer, imager, or information provider 100 are not illustrated, it is to be understood that certain embodiments of the adjustment or control mechanism 302 can be situated relative to the at least one emitter portion 150, relative to the at least one Compton scattered X-ray receiving assembly 151, at some median location, or elsewhere. Certain embodiments of the adjustment or control mechanism 302 can be software, hardware, firmware, and/or processor intensive such as to only consider certain of the scattered X-rays as received by certain embodiments of the Compton scattered X-ray receiving assembly 151.

The various examplary embodiments of the adjustment or control mechanism 302 as described with respect to FIGS. 42 to 45 are intended to be illustrative in nature, but not limiting in scope. Any of a variety of techniques by which the frequency (and the corresponding energy level) of the X-ray photons of the applied X-rays being applied to the at least some matter of the at least a portion of the individual may be considered as another embodiment of the adjustment or control mechanism, within the scope of the present disclosure.

Additionally, certain embodiments of the adjustment or control mechanism can be applied to respectively adjust or control the X-ray photons of the scattered X-ray 122 being scattered from the scattering event within the matter of the at least the portion of the at least a portion of the individual. A variety of such adjustment or control techniques such as filtering, correlating, controlling, or selectively monitoring certain X-ray photon frequency or energy levels of the scattered X-rays.

There may be some of the X-ray photons of the applied X-ray that are being altered such as by ramping, reducing, modification, maintaining, in which the applied X-rays is applied into the matter of the individual can scatter within the at least one substantially scattered depth range to the at least one prescribed substantially scattered depth for that particular or instantaneous visualizing, imaging, or information providing period. Certain embodiments of the Compton scattered X-ray visualizer, imager, or information provider 100 can be configured to limit the effects of the X-ray photons of the Compton scattered X-rays 120 that are returning from a depth greater than the within the at least one substantially scattered depth range to the at least one prescribed substantially scattered depth. Additionally, the depth visualizing, imaging, or information providing effects of these X-ray photons of the Compton scattered X-rays 120 can be included in the Compton scattered X-ray visualization, imaging, or information providing, with any distortive effects during the ramping operation either ignored, filtered, and/or otherwise limited using signal processing techniques.

Such increase or ramping of the energy level of the applied X-ray can be performed by those embodiments of the Compton scattered X-ray visualizer, imager, or information provider 100 that can be tuned. The rate of ramping (e.g., the rate of the photon energy level) can thereby be set or controlled either manually or by setting the visualization, imaging, or information providing controller 97. Experimentation could be used to provide an indication of a suitable ramping rate for the particular matter(s) of the at least the portion of the individual.

With a ramping function, each increase in the energy of the X-ray photons of the applied X-ray such as would be expected to provide an increased in the within the at least one substantially scattered depth range to the at least one prescribed substantially scattered depth can be monitored by the Compton scattered X-ray receiving assembly. For example, certain pulse signals can initially be applied, and time of flight calculations can be utilized to determine the within the at least one substantially scattered depth range to the at least one prescribed substantially scattered depth.

3. Certain Embodiments of the Visualization, Imaging, or Information Providing Controller This disclosure describes a number of embodiments of the visualization, imaging, or information providing controller 97 as described with respect to FIG. 1, which is intended to control and/or adjust Compton scattered X-ray visualization, imaging, or information providing by the Compton scattered X-ray visualizer, imager, or information provider 100 of at least the portion of the individuals 82. As such, certain embodiments of the Compton scattered X-ray visualizer, imager, or information provider 100 can operate without, and/or with little interaction from, the visualization, imaging, or information providing controller 97. By comparison, certain embodiments of the Compton scattered X-ray visualizer, imager, or information provider 100 can utilize considerable input from, and/or entirely utilizing input from, the visualization, imaging, or information providing controller 97.

Certain embodiments of the Compton scattered X-ray visualizer, imager, or information provider 100 can thereby include the visualization, imaging, or information providing controller 97 as described with respect to FIG. 1; while other embodiments of the Compton scattered X-ray visualizer, imager, or information provider may not include utilizing the visualization, imaging, or information providing controller. For example, certain scintillator-based and/or fluoroscope-based embodiments of the Compton scattered X-ray visualizer, imager, or information provider may convert received X-ray based photons directly into viewable and/or visible photons (which may or may be amplified using a photomultiplier or CCD) to allow direct Compton scattered X-ray visualization, imaging, or information providing, which may limit the necessity of image processing that may largely rely on the visualization, imaging, or information providing controller 97. By comparison, certain embodiments of the Compton scattered X-ray visualizer, imager, or information provider 100 can utilize input from the user, such as to determine location, angle, position, resolution, X-ray frequency, energy level, time of depth visualizing, imaging, or information providing, and other such Compton scattered X-ray visualization, imaging, or information providing related factors or characteristics. Such Compton scattered X-ray visualization, imaging, or information providing characteristics may be selected, controlled, and/or altered using certain embodiments of the visualization, imaging, or information providing controller 97.

Some depth visualizing, imaging, or information providing information, data, images, signals, etc. associated with certain embodiments of the Compton scattered X-ray visualizer, imager, or information provider 100 and/or the visualization, imaging, or information providing controller 97 may be digital based, while other embodiments may be analog based. For instance, certain embodiments of the Compton scattered X-ray visualizer, imager, or information provider 100 including the visualization, imaging, or information providing controller 97, which are largely digital and/or microprocessor-based, can provide for largely automated actuation of Compton scattered X-ray visualization, imaging, or information providing and/or signals of the Compton scattered X-ray visualizer, imager, or information provider 100 and/or the Compton scattered X-ray visualizer, imager, or information provider(s) 104. A number of the components of the Compton scattered X-ray visualizer, imager, or information provider(s) 104 may rely on analog and/or digital controllers and/or computers which may be capable of generating signals with considerable power. Other lower-powered signals from the Compton scattered X-ray visualizer, imager, or information provider(s) 104 may be either analog and/or digitally controlled. Certain visualization, imaging, or information providing controller 97 that are configured to turn particular circuits on or off, for example, may be particularly efficient and/or effective if digital based. Certain embodiments of the visualization, imaging, or information providing controller 97 can be configured to, upon a normal operation, compensate for at least some distortion as can be provided by the depth visualizing, imaging, or information providing region of the at least the portion of the individual. FIG. 1 can represent a block diagram of certain respective embodiments of the Compton scattered X-ray visualizer, imager, or information provider 100 that can include the visualization, imaging, or information providing controller 97 to either control and/or adjust the Compton scattered X-ray visualization, imaging, or information providing within the Compton scattered X-ray visualizer, imager, or information provider, or some other related operations.

Certain embodiments of the Compton scattered X-ray visualizer, imager, or information provider 100 can be configured in which an energy level required to image using conventional transmissive X-ray technologies to the controllable or adjustable ones of the within the at least one visualizing, imaging, or information providing depth range to the at least one prescribed visualizing, imaging, or information providing depth. In certain instances, the energy intrusion level can be less (and in certain instances, considerably less) than the energy intrusion level required to image using conventional transmissive X-ray technology through the entirety of the at least the portion of the individual 82. By using reduced to X-ray dosages, certain embodiments of the Compton scattered X-ray visualizer, imager, or information provider 100 can image, utilize, or provide information while remaining within a safe emitted radiation level for the individual as well as though one or more users, which can result from application of smaller dosages. Certain embodiments of the visualization, imaging, or information providing controller 97 can even be configured to monitor, change, adjust, or maintain X-ray exposure levels within the at least the portion of the individual, X-ray exposure levels by the individual and/or the user(s), and/or X-ray levels in the vicinity of the individual and/or the user, etc.

Certain embodiments of the visualization, imaging, or information providing controller 97 are configured to provide control and/or adjustability of the Compton scattered X-ray visualizer, imager, or information provider 100 based, at least in part, on the Compton scattered X-ray visualization, imaging, or information providing operation and/or configuration of the Compton scattered X-ray visualizer, imager, or information provider. For example, if a user wishes to control and/or adjust an angle, a position, an X-ray photon frequency or energy level, a resolution, the within the at least one visualizing, imaging, or information providing depth range to the at least one prescribed visualizing, imaging, or information providing depth, or at least one other Compton scattered X-ray visualization, imaging, or information providing parameter; then the user could provide suitable input to the visualization, imaging, or information providing controller 97. Such input to the visualization, imaging, or information providing controller 97 can be provided via the input/output interface, which in certain embodiments may be a graphical user interface (GUI), for example.

If the user wishes to visualize, image, and/or provide information relating to a portion of the individual on a real time basis, a continuous basis, a sequential basis, or another repetitive basis, then the type of depth visualizing, imaging, or information providing can also be selected using the input/output interface 811 of the visualization, imaging, or information providing controller 97. Certain embodiments of the input/output interface 811 can additionally provide an indication to the user of some aspect of the depth visualizations, images, and/or provided information, such as if the Compton scattered X-ray visualizer, imager, or information provider is incapable of the depth imaging, visualizing, or information providing; and will likely not expose the user and/or individual to unacceptable X-ray dosages, etc.

Certain embodiments of the Compton scattered X-ray visualizer, imager, or information provider 100 can thereby include, but are not limited to, a variety of configurations of the visualization, imaging, or information providing controller 97. Certain embodiments of the visualization, imaging, or information providing controller 97 can also be at least partially computer based, controller based, mote based, cellular telephone-based, and/or electronics based. Certain embodiments of the visualization, imaging, or information providing controller can be segmented into modules, and can utilize a variety of wireless communications and/or networking technologies to allow information, data, etc. to be transferred to the various distinct portions or embodiments of the Compton scattered X-ray visualizer, imager, or information provider 100. Certain embodiments of the visualization, imaging, or information providing controller 97 can be configured as a unitary device, a networked device, a stand alone device, and/or any combination of these and other known type devices.

Certain embodiments of the visualization, imaging, or information providing controller 97 can vary as to their automation, complexity, and/or sophistication; and can be utilized to control, setup, establish, and/or maintain communications between a number of communicating devices during Compton scattered X-ray visualization, imaging, or information providing operation(s). As described within this disclosure, multiple ones of the different embodiments of the Compton scattered X-ray visualizer, imager, or information provider 100 can transfer information or data relating to the communication link to or from a remote location and/or some intermediate device as might be associated with communication, monitoring and/or other activities. Certain embodiments of the Compton scattered X-ray visualizer, imager, or information provider 100 can vary as to the particular visualization modality, imaging modality, and/or information providing modality.

Certain embodiments of the visualization, imaging, or information providing controller 97, as well as certain embodiments of the Compton scattered X-ray visualizer, imager, or information provider 100 (in general), can utilize distinct firmware, hardware, and/or software technology. For example, certain embodiments of the Compton scattered X-ray visualizer, imager, or information provider 100 can at least partially utilize one or more of: mote-based technology, microprocessor-based technology, microcomputer-based technology, display technology, imaging technology, general-purpose computer technology, specific-purpose computer technology, Application-Specific Integrated Circuits (AASICs), and/or a variety of other computer, electronics, electromagnetic, imaging, visualizing, and/or information providing technologies, such as can be utilized by certain embodiments of the visualization, imaging, or information provider controller 97.

Certain embodiments of the visualization, imaging, or information providing controller 97 can as described with respect to FIG. 1 can include depending on context a processor 803 such as a central processing unit (CPU), a memory 807, a circuit or circuit portion 809, and an input output interface (I/O) 811 that may include a bus (not shown). Certain embodiments of the visualization, imaging, or information providing controller 97 of the Compton scattered X-ray visualizer, imager, or information provider 100 can include and/or be a portion of a general-purpose computer, a specific-purpose computer, a microprocessor, a microcontroller, a personal display assistant (PDA), a cellular phone, a wireless communicating device, a hard-wired communication device, and/or any other known suitable type of communications device or phone, computer, and/or controller that can be implemented in hardware, software, electromechanical devices, and/or firmware. Certain embodiments of the processor 803, as described with respect to FIG. 1, can perform the processing and arithmetic operations for certain embodiments of the visualization, imaging, or information providing controller 97 of the Compton scattered X-ray visualizer, imager, or information provider 100. Certain embodiments of the visualization, imaging, or information providing controller 97 of the Compton scattered X-ray visualizer, imager, or information provider 100 can control the signal processing, database querying and response, computational, timing, data transfer, and other processes associated with Compton scattered X-ray visualization, imaging, or information providing such as can be adjusted by and/or controlled by certain embodiments of the visualization, imaging, or information providing controller 97 of the Compton scattered X-ray visualizer, imager, or information provider 100.

Certain embodiments of the visualization, imaging, or information providing controller 97 (depending in part of the Compton scattered X-ray visualization, imaging, or information providing process being attempted or performed by the Compton scattered X-ray visualizer, imager, or information provider 100), will undergo considerable image processing by the processor 803. Particularly, those embodiments of the Compton scattered X-ray visualizer, imager, or information provider 100 that can visualize, image, and/or provide information relating to a relatively large area, image to relatively high resolution, image continuously, sequentially, and/or repetitively will provide a large amount of images or image information. As such, certain embodiments of the components of the visualization, imaging, or information providing controller 97 should be designed and configured to handle the type of visualization, image, and/or provided information processing that the subsurface Compton scattered X-ray image processing will be exposed. Certain types of image compression (e.g., lossy and/or lossless data compression techniques) may be utilized in the visualization, imaging, or information providing controller 97 to limit production or storage of excessive volumes of redundant data.

Certain embodiments of the memory 807 of the visualization, imaging, or information providing controller 97 can include a random access memory (RAM) and/or read only memory (ROM) that together can store the computer programs, operands, and other parameters that control the operation of certain embodiments of the visualization, imaging, or information providing controller 97 of the Compton scattered X-ray visualizer, imager, or information provider 100. The memory 807 can be configurable to contain data, information, images, visualizations, image information, etc. that can be obtained, retained, or captured by that particular visualization, imaging, or information providing controller 97, as described in this disclosure.

Certain embodiments of the bus can be configurable to provide for digital information transmissions between the processor 803, circuits 809, memory 807, I/O 811, the visualization, image, and/or provided information memory or storage device (which may be integrated or removable), other portions within the Compton scattered X-ray visualizer, imager, or information provider(s) 104, and/or other portions outside of the Compton scattered X-ray visualizer, imager, or information provider(s) 104. In this disclosure, the memory 807 can be configurable as RAM, flash memory, semiconductor-based memory, of any other type of memory that can be configurable to store data pertaining to depth visualizations, images, and/or provided information. Certain embodiments of the bus can also connects I/O 811 to the portions of certain embodiments of the visualization, imaging, or information providing controller 97 of either the Compton scattered X-ray visualizer, imager, or information provider 100 that can either receive digital information from, or transmit digital information to other portions of the Compton scattered X-ray visualizer, imager, or information provider 100, or other systems and/or networking components associated therewith.

Certain embodiments of the visualization, imaging, or information providing controller 97 of the Compton scattered X-ray visualizer, imager, or information provider 100, as described with respect to FIG. 1, can include a separate, distinct, combined, and/or associated transmitter portion (not shown) that can be either included as a portion of certain embodiments of the visualization, imaging, or information providing controller 97 of the Compton scattered X-ray visualizer, imager, or information provider 100. Certain embodiments of the visualization, imaging, or information providing controller 97 can alternately be provided as a separate and/or combined unit (e.g., certain embodiments might be processor-based and/or communication technology-based).

Certain embodiments of the visualization, imaging, or information providing controller 97 of the Compton scattered X-ray visualizer, imager, or information provider 100 as described with respect to FIG. 1 can include an operation altering or controlling portion (described with respect to FIG. 32) that can be either included as a portion of certain embodiments of the visualization, imaging, or information providing controller 97 of the Compton scattered X-ray visualizer, imager, or information provider 100, or alternately can be provided as a separate or combined unit.

Certain embodiments of the memory 807 can provide an example of a memory storage portion. In certain embodiments, the monitored value includes but is not limited to: a percentage of the memory 807, an indication of data that is or can be stored in the memory 807, or for data storage or recording interval. Such memory can include information about the individual, the treatment, the user, the treating or examining facility, etc.; and also may include one or more visualization, image, or provided information as provided by certain embodiments of the Compton scattered X-ray visualizer, imager, or information provider 100, or alternately as can be provided by another visualization, image, or information source such as tomography visualizations, images, or provided information, MRI, CT scan, PET scan, etc. such as can be used to provide a combined image, visualization, or information. To provide for overflow ability for the memory 807 of certain embodiments of the visualization, imaging, or information providing controller 97 of the Compton scattered X-ray visualizer, imager, or information provider 100, a secondary storage device can be operably coupled to the memory 807 to allow a controllable transmitting of memory data from certain embodiments of the visualization, imaging, or information providing controller 97 of the Compton scattered X-ray visualizer, imager, or information provider 100 when the monitored value of data or other information within the memory 807 exceeds a prescribed value. The prescribed value can include, e.g., some percentage amount or some actual amount of the value.

In certain embodiments, a secondary communication link can be established between the certain embodiments of the visualization, imaging, or information providing controller 97 of the Compton scattered X-ray visualizer, imager, or information provider 100. The secondary communication link can be structured similar to as a communication link, or alternatively can utilize network-based computer connections, Internet connections, etc. to provide information and/or data transfer between certain embodiments of the visualization, imaging, or information providing controller 97 of the Compton scattered X-ray visualizer, imager, or information provider 100.

In certain embodiments of the visualization, imaging, or information providing controller 97 of the Compton scattered X-ray visualizer, imager, or information provider 100, the particular elements of certain embodiments of the visualization, imaging, or information providing controller 97 of the Compton scattered X-ray visualizer, imager, or information provider 100 (e.g., the processor 803, the memory 807, the circuits 809, and/or the I/O 811) can provide a monitoring function to convert raw data as displayed by an indicator. A monitoring function as provided by certain embodiments of the visualization, imaging, or information providing controller 97 of the Compton scattered X-ray visualizer, imager, or information provider 100 can be compared to a prescribed limit, such as whether the number of depth visualizations, images, and/or provided information contained in the memory 807, the amount of data contained within the memory 807, or some other measure relating to the memory is approaching some value. The limits to the value can, in different embodiments, be controlled by the user or the manufacturer of certain embodiments of the visualization, imaging, or information providing controller 97 of the Compton scattered X-ray visualizer, imager, or information provider 100. In certain embodiments, the memory 807 can store such information as data, information, displayable information, readable text, motion depth visualizations, images, and/or provided information, video depth visualizations, images, and/or provided information, and/or audio depth visualizations, images, and/or provided information, etc.

In certain embodiments, the I/O 811 provides an interface to control the transmissions of digital information between each of the components in certain embodiments of the visualization, imaging, or information providing controller 97 of the Compton scattered X-ray visualizer, imager, or information provider 100. The I/O 811 also provides an interface between the components of certain embodiments of the visualization, imaging, or information providing controller 97 of the Compton scattered X-ray visualizer, imager, or information provider 100. The circuits 809 can include such other user interface devices as a display and/or a keyboard. In other embodiments, the visualization, imaging, or information providing controller 97 of the Compton scattered X-ray visualizer, imager, or information provider 100 can be constructed as a specific-purpose computer such as an application-specific integrated circuit (ASIC), a microprocessor, a microcomputer, or other similar devices.

4. Certain Embodiments of the Compton Scattered X-Ray Visualizer, Imager, or Information Provider with Relevant Flowcharts Within the disclosure, flow charts of the type described in this disclosure apply to method steps as performed by a computer or controller as could be contained within certain embodiments of the Compton Scattered X-Ray Visualizer, imager, or information provider 100, as described in this disclosure. Additionally, the flow charts as described in this disclosure apply operations or procedures that can be performed entirely and/or largely utilizing mechanical devices, electromechanical devices, or the like, such as certain embodiments of the Compton Scattered X-Ray Visualizer, imager, or information provider 100 as described in this disclosure. The flow charts can also apply to apparatus devices, such as an antenna or a node associated therewith that can include, e.g., a general-purpose computer or specialized-purpose computer whose structure along with the software, firmware, electromechanical devices, and/or hardware, can perform the process or technique described in the flow chart.

An embodiment of the Compton Scattered X-Ray Visualizer, imager, or information provider 100 that can act to compensate for a distortion by the depth visualizer has been described with respect to FIG. 1, and elsewhere in this disclosure. There can be a variety of embodiments of the Compton Scattered X-Ray Visualizer, imager, or information provider 100 that can be used to visualize, image, or provide information etc. as described in this disclosure. There can be variety of embodiments of the Compton Scattered X-Ray Visualizer, imager, or information provider 100.

FIG. 46 shows certain embodiments of a Compton depth scattering visualizing, imaging, of information providing technique 4600 such as described with respect to, but not limited to, the Compton Scattered X-Ray Visualizer, imager, or information provider 100 of FIG. 1, and elsewhere in this disclosure. Certain embodiments of a high-level flowchart of the Compton depth scattering visualizing, imaging, of information providing technique 4600 is described with respect to FIG. 46 and can include, but is not limited to, operation 4602. Certain embodiments of operation 4602 can include, but is not limited to, determining a location of an at least one scattering event occurring within an at least some matter of at least a portion of an individual, wherein the determining the location of the at least one scattering event is based at least in part on a combination of: a relative position and/or angle at which an at least one applied X-ray being applied to the at least some matter of the at least the portion of the individual, an applied energy level of the at least one applied X-ray being applied to the at least some matter of the at least the portion of the individual, a detected location of an at least one scattered X-ray resulting from scattering of the at least one applied X-ray scattering during the at least one scattering event, and a scattered energy level of the at least one scattered X-ray. For example, certain embodiments of the Compton Scattered X-Ray Visualizer, imager, or information provider 100 as described through this disclosure can be configured to visualize, image, or provide information in tomographic-type slices based at least partially on Compton depth scattering.

FIG. 47 shows certain embodiments of a Compton depth scattering visualizing, imaging, of information providing technique 4700 such as described with respect to, but not limited to, the Compton Scattered X-Ray Visualizer, imager, or information provider 100 of FIG. 1, and elsewhere in this disclosure. Certain embodiments of a high-level flowchart of the Compton depth scattering visualizing, imaging, of information providing technique 4700 is described with respect to FIG. 47 and can include, but is not limited to, operations 4702 and/or 4704. Certain embodiments of operation 4702 can include, but is not limited to, applying at least one applied X-ray substantially toward an at least some matter of an at least a portion of an individual. For example, certain embodiments of the emitter portion 150, as described through this disclosure can be configured to apply at least some applied X-rays 120 toward the at least some matter of the at least the portion of the individual.

Certain embodiments of operation 4704 can include, but is not limited to, visualizing, imaging, or providing information of the at least some matter of the at least the portion of the individual at least partially in response to the applying the at least one applied X-ray substantially toward the at least some matter of the at least the portion of the individual, the visualizing, imaging, or providing information of the at least some matter of the at least the portion of the individual at least partially based on a combination of a relative position and an angle of the at least one applied X-ray; an applied energy level of the at least one applied X-ray; a detected location of at least one scattered X-ray which resulted from the at least one applied X-ray scattering during the at least one scattering event within the at least some matter of the at least the portion of the individual; and a scattered energy level of the at least one scattered X-ray. For example, certain embodiments of the Compton scattered X-ray visualizer, imager, or information provider can be configured to visualize, image, or provide information, as described through this disclosure at least partially based on the at least some applied X-rays 120 that are scattered within the at least some matter of the at least the portion of the individual.

In one or more various aspects, related systems include but are not limited to circuitry and/or programming for effecting the herein-referenced method aspects; the circuitry and/or programming can be virtually any combination of hardware, software, electromechanical system, and/or firmware configurable to effect the herein-referenced method aspects depending upon the design choices of the system designer.

5. Conclusion

This disclosure provides a number of embodiments of the Compton Scattered X-Ray Visualizer, imager, or information provider 100. The embodiments of the Compton Scattered X-Ray Visualizer, imager, or information provider as described with respect to this disclosure are intended to be illustrative in nature, and are not limiting its scope.

Those having skill in the art will recognize that the state of the art in computer, controller, communications, networking, and other similar technologies has progressed to the point where there is little distinction left between hardware, firmware, and/or software implementations of aspects of systems, such as may be utilized in the Compton Scattered X-Ray Visualizer, imager, or information provider. The use of hardware, firmware, and/or software can therefore generally represent (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle can vary with the context in which the processes and/or systems and/or other technologies are deployed. For example, if an implementer determines that speed and accuracy are paramount, the implementer and/or designer of the Compton Scattered X-Ray Visualizer, imager, or information provider may opt for mainly a hardware and/or firmware vehicle. In alternate embodiments, if flexibility is paramount, the implementer and/or designer may opt for mainly a software implementation. In yet other embodiments, the implementer and/or designer may opt for some combination of hardware, software, and/or firmware. Hence, there are several possible techniques by which the processes and/or devices and/or other technologies described herein may be effected, none of which is inherently superior to the other in that any vehicle to be utilized is a choice dependent upon the context in which the vehicle can be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, target individual 82 and/or collectively, by a wide range of hardware, software, firmware, or virtually any combination thereof. In Certain embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

It is to be understood by those skilled in the art that, in general, that the terms used in the disclosure, including the drawings and the appended claims (and especially as used in the bodies of the appended claims), are generally intended as "open" terms. For example, the term "including" should be interpreted as "including but not limited to"; the term "having" should be interpreted as "having at least"; and the term "includes" should be interpreted as "includes, but is not limited to"; etc. In this disclosure and the appended claims, the terms "a", "the", and "at least one" positioned prior to one or more goods, items, and/or services are intended to apply inclusively to either one or a plurality of those goods, items, and/or services.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that could have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that could have A alone, B alone, C alone, A and B together, A and C together, B and C together, and/or A, B, and C together, etc.).

Those skilled in the art will appreciate that the herein-described specific exemplary processes and/or devices and/or technologies are representative of more general processes and/or devices and/or technologies taught elsewhere herein, such as in the claims filed herewith and/or elsewhere in the present application.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method, comprising:
    determining a location of an at least one scattering event occurring within an at least some matter of at least a portion of an individual, wherein the determining the location of the at least one scattering event is based at least in part on a combination of: a relative position and/or angle at which an at least one applied X-ray being applied to the at least some matter of the at least the portion of the individual, an applied energy level of the at least one applied X-ray being applied to the at least some matter of the at least the portion of the individual, a detected location of an at least one scattered X-ray resulting from scattering of the at least one applied X-ray scattering during the at least one scattering event, and a scattered energy level of the at least one applied X-ray,
    wherein the determining the location of the at least one scattering event occurring within the at least some matter of the at least the portion of the individual, the determining the location is based at least in part on the relative position and the angle at which the at least one applied X-ray is being applied to the at least some matter of the at least the portion of the individual comprises:
    merging a first one of the at least one applied X-ray with a second one of the at least one applied X-ray.

2. A method, comprising:
    determining a location of an at least one scattering event occurring within an at least some matter of at least a portion of an individual, wherein the determining the location of the at least one scattering event is based at least in part on a combination of: a relative position and/or angle at which an at least one applied X-ray being applied to the at least some matter of the at least the portion of the individual, an applied energy level of the at least one applied X-ray being applied to the at least some matter of the at least the portion of the individual, a detected location of an at least one scattered X-ray resulting from scattering of the at least one applied X-ray scattering during the at least one scattering event, and a scattered energy level of the at least one applied X-ray,
    wherein the determining the location of the at least one scattering event occurring within the at least some matter of the at least the portion of the individual, the determining the location is based at least in part on the relative position and the angle at which the at least one applied X-ray is being applied to the at least some matter of the at least the portion of the individual comprises:
    controlling the at least one applied X-ray.

3. A method, comprising:
    determining a location of an at least one scattering event occurring within an at least some matter of at least a portion of an individual, wherein the determining the location of the at least one scattering event is based at least in part on a combination of: a relative position and/or angle at which an at least one applied X-ray being applied to the at least some matter of the at least the portion of the individual, an applied energy level of the at least one applied X-ray being applied to the at least some matter of the at least the portion of the individual, a detected location of an at least one scattered X-ray resulting from scattering of the at least one applied X-ray scattering during the at least one scattering event, and a scattered energy level of the at least one applied X-ray,
    wherein the determining the location of the at least one scattering event occurring within the at least some matter of the at least the portion of the individual, the determining the location is based at least in part on the relative position and the angle at which the at least one applied X-ray is being applied to the at least some matter of the at least the portion of the individual comprises:
    adjusting the at least one applied X-ray.

4. A method, comprising:
    determining a location of an at least one scattering event occurring within an at least some matter of at least a portion of an individual, wherein the determining the location of the at least one scattering event is based at least in part on a combination of: a relative position and/or angle at which an at least one applied X-ray being applied to the at least some matter of the at least the portion of the individual, an applied energy level of the at least one applied X-ray being applied to the at least some matter of the at least the portion of the individual, a detected location of an at least one scattered X-ray resulting from scattering of the at least one applied X-ray scattering during the at least one scattering event, and a scattered energy level of the at least one applied X-ray,
    wherein the determining the location of the at least one scattering event occurring within the at least some matter of the at least the portion of the individual, the determining the location is based at least in part on the relative position and the angle at which the at least one applied X-ray is being applied to the at least some matter of the at least the portion of the individual comprises:
    directing the at least one applied X-ray towards the at least some matter of the at least the portion of the individual.

5. The method of claim 4, wherein the determining the location of the at least one scattering event occurring within the at least some matter of the at least the portion of the individual, the determining the location is based at least in part on the relative position and the angle at which the at least one applied X-ray is being applied to the at least some matter of the at least the portion of the individual further comprises:

correlating the at least some matter at which the at least one applied X-ray is being directed with the at least some matter which is undergoing visualizing, imaging, or providing information.

6. A method, comprising:

applying at least one applied X-ray substantially toward an at least some matter of an at least a portion of an individual; and visualizing, imaging, or providing information of the at least some matter of the at least the portion of the individual at least partially in response to the applying the at least one applied X-ray substantially toward the at least some matter of the at least the portion of the individual, the visualizing, imaging, or providing information of the at least some matter of the at least the portion of the individual at least partially based on a combination of a relative position and an angle of the at least one applied X-ray; an applied energy level of the at least one applied X-ray; a detected location of at least one scattered X-ray which resulted from the at least one applied X-ray scattering during the at least one scattering event within the at least some matter of the at least the portion of the individual; and a scattered energy level of the at least one scattered X-ray.

7. The method of claim 6, wherein the applying at least one applied X-ray substantially toward the at least some matter of the at least the portion of the individual is applied within at least one substantially scattered depth range to an at least one prescribed substantially scattered depth.

8. The method of claim 6, wherein the visualizing, imaging, or providing information of the at least some matter of the at least the portion of the individual is applied at least partially within a visualizing, imaging, or information providing depth range to an at least one prescribed visualization, imaging, or information providing depth.

9. The method of claim 6, wherein the visualizing, imaging, or providing information of the at least some matter of the at least the portion of the individual is performed at a rate sufficient to substantially capture a physical motion that is consistent with an individual-based physiological process.

10. The method of claim 6, wherein the visualizing, imaging, or providing information of the at least some matter of the at least the portion of the individual is performed at a rate sufficient to substantially capture a physical motion that is consistent with a user-observable physiological process.

11. The method of claim 6, wherein the individual includes at least one from a group, the group includes a human, an animal, an organism, or a plant.

12. An apparatus, comprising:

a scattering event locating means configured for determining a location of an at least one scattering event based on a combination of: a relative position and/or angle of an at least one applied X-ray being applied to an at least some matter of at least a portion of an individual; an applied energy level of the at least one applied X-ray; a detected location of at least one scattered X-ray which resulted from the at least one applied X-ray scattering within the at least some matter of the at least the portion of the individual at the at least one scattering event; and a scattered energy level of the at least one scattered X-ray, wherein the at least one scattering event occurs within the at least some matter of the at least the portion of the individual.

13. The apparatus of claim 12, wherein scattering event locating means configured for determining the location of the at least one scattering event is used within an at least one substantially scattered X-ray depth range to an at least one prescribed substantially scattered depth.

14. The apparatus of claim 12, wherein the scattering event locating means configured for determining the location of the at least one scattering event is used within at least one visualizing, imaging, or information providing depth range to an at least one prescribed visualization, imaging, or information providing depth.

15. The apparatus of claim 12, wherein the scattering event locating means is configured for visualizing, imaging, or providing information of the at least some matter of the at least the portion of the individual at least partially in response to the determining the location of the at least one scattering event.

16. The apparatus of claim 12, wherein the scattering event locating means further comprises an at least a portion of an at least one Compton scattered X-ray receiving assembly that is configured to determine the location of the at least one scattering event.

17. The apparatus of claim 12, wherein the scattering event locating means further comprises an at least a portion of an at least one Compton scattered X-ray receiving assembly that is configured to determine the location of the at least one scattering event at least partially by crossing a first one of the at least one applied X-ray with a second one of the at least one applied X-ray.

18. The apparatus of claim 12, wherein the scattering event locating means further comprises an at least a portion of an at least one Compton scattered X-ray receiving assembly that is configured to determine the location of the at least one scattering event at least partially based on controlling or adjusting the at least one applied X-ray.

19. The apparatus of claim 12, wherein the scattering event locating means further comprises an at least a portion of an at least one Compton scattered X-ray receiving assembly that is configured to determine the location of the at least one scattering event at least partially based on directing the at least one applied X-ray towards the at least some matter of the at least the portion of the individual.

20. The apparatus of claim 12, wherein the scattering event locating means further comprises an at least a portion of an at least one Compton scattered X-ray receiving assembly that is configured to determine the location of the at least one scattering event at least partially based on:

the scattering event locating means configured to direct the at least one applied X-ray towards the at least some matter of the at least the portion of the individual; and the scattering event locating means configured to correlate the at least some matter of the at least the portion of the individual at which the at least one applied X-ray is being directed with the at least some matter of the at least the portion of the individual which is undergoing visualizing, imaging, or providing information.

21. The apparatus of claim 12, further comprising:

an at least a portion of an at least one Compton scattered X-ray receiving assembly configured to visualize, image, or provide information of the at least some matter of the at least the portion of the individual at least partially in response to the determining the location of the at least one scattering event, wherein the scattering event locating means is configured to visualize, image, or provide information across a slice of the at least some matter of the at least the portion of the individual.

22. The apparatus of claim 12, further comprising:

an at least a portion of an at least one Compton scattered X-ray receiving assembly configured to visualize, image, or provide information of the at least some matter of the at least the portion of the individual at least partially in response to the determining the location of the at least one scattering event, wherein the at least the portion of the at least one Compton scattered X-ray receiving assembly is configured to deconvolute information relating to the at least one scattered X-ray.

23. The apparatus of claim 12, further comprising:

an at least a portion of an at least one Compton scattered X-ray receiving assembly configured to visualize, image, or provide information of the at least some matter of the at least the portion of the individual at least partially in response to the determining the location of the at least one scattering event, wherein the at least the portion of the at least one Compton scattered X-ray receiving assembly is configured to transform information relating to the at least one scattered X-ray.

24. The apparatus of claim 12, further comprising:

an at least a portion of an at least one Compton scattered X-ray receiving assembly configured to visualize, image, or provide information of the at least some matter of the at least the portion of the individual at least-partially in response to the determining the location of the at least one scattering event, wherein the at least the portion of the at least one Compton scattered X-ray receiving assembly is configured to filter information relating to at least a portion of the at least one scattered X-ray.

25. The apparatus of claim 12, further comprising:

an at least a portion of an at least one Compton scattered X-ray receiving assembly configured to visualize, image, or provide information of the at least some matter of the at least the portion of the individual at least partially in response to the determining the location of the at least one scattering event, wherein the at least the portion of the at least one Compton scattered X-ray receiving assembly is configured to collimate the at least one scattered X-ray being scattered from one or more of the at least one applied X-ray.

26. The apparatus of claim 12, wherein an at least a portion of an at least one Compton scattered X-ray receiving assembly is configured to at least partially apply the at least one applied X-ray through at least a portion of an at least partially external surface of the individual.

27. The apparatus of claim 12, wherein an at least a portion of an at least one Compton scattered X-ray receiving assembly is configured to at least partially apply the at least one applied X-ray through at least a portion of an at least partially internal surface of the individual.

28. The apparatus of claim 12, wherein the at least some matter of the at least the portion of the individual includes an at least one from a matter group, the matter group including at least one from at least one tissue, an at least one bone, an at least one bone portion, an at least one bone fragment, an at least one tooth, an at least one bodily fluid or component thereof, an at least one blood or component thereof, an at least one insert or implant, an at least one metal, or an at least one vessel carrying or maintaining a fluid.

29. The apparatus of claim 12, wherein the individual includes at least one from a group, the group includes a human, an animal, an organism, or a plant.

30. An apparatus, comprising:

an at least one emitter portion configured for applying at least one applied X-ray substantially toward an at least some matter of at least a portion of an individual; and a visualizer, imager, or information provider configured for visualizing, imaging, or providing information of the at least some matter of the at least the portion of the individual at least partially in response to the determining a location of an at least one scattering event at which the at least one applied X-ray scatters within the at least some matter of the at least the portion of the individual at least partially based on a combination of: a relative position and/or angle of an at least one applied X-ray; an applied energy level of the at least one applied X-ray; a detected location of at least one scattered X-ray which resulted from the at least one applied X-ray scattering during the at least one scattering event within the at least some matter of the at least the portion of the individual; and a scattered energy level of the at least one scattered X-ray.

31. The apparatus of claim 30, wherein the at least one emitter portion configured for applying at least one applied X-ray is applied within at least one substantially scattered depth range to an at least one prescribed substantially scattered depth.

32. The apparatus of claim 30, wherein the visualizer, imager, or information provider configured for visualizing, imaging, or providing information is used within at least one visualizing, imaging, or information providing depth range to an at least one prescribed visualization, imaging, or information providing depth.

33. The apparatus of claim 30, wherein the at least some matter of the at least the portion of the individual includes an at least one from a matter group, the matter group including at least one from at least one tissue, an at least one bone, an at least one bone portion, an at least one bone fragment, an at least one tooth, an at least one bodily fluid or component thereof, an at least one blood or component thereof, an at least one insert or implant, an at least one metal, or an at least one vessel carrying or maintaining a fluid.

34. The apparatus of claim 30, wherein the individual includes at least one from a group, the group includes a human, an animal, an organism, or a plant.

35. A system, comprising:

an at least one emitter portion configured to apply at least one applied X-ray substantially toward an at least some matter of at least a portion of an individual; and an at least a portion of at least one Compton scattered X-ray receiving assembly configured to visualize, image, or provide information of the at least some matter of the at least the portion of the individual at least partially in response to the at least one emitter portion configured to determine a location of an at least one scattering event within the at least some matter of the at least the portion of the individual at least partially based on a combination of: a relative position or angle of the at least one applied X-ray relative to the at least a portion of at least one Compton scattered X-ray receiving assembly; an applied energy level of the at least one applied X-ray; a detected location of at least one scattered X-ray which resulted from the at least one applied X-ray scattering within the at least some matter of the at least the portion of the individual during the at least one scattering event within the at least some matter of the at least the portion of the individual; and a scattered energy level of the at least one scattered X-ray.

36. The system of claim 35, wherein the at least one emitter portion is configured to apply the at least one applied X-ray within at least one substantially scattered X-ray depth range to an at least one prescribed substantially scattered depth.

37. The system of claim 35, wherein the at least a portion of at least one Compton scattered X-ray receiving assembly configured to visualize, image, or provide information is operable within an at least one visualizing, imaging, or information providing depth range to an at least one prescribed visualization, imaging, or information providing depth.

38. The system of claim 35, further comprising:
a correlator configured to correlate the location at which at least one or the at least one emitter portion applies the at least one applied X-ray substantially toward the at least some matter of the at least the portion of the individual with the detected location at which the at least a portion of at least one Compton scattered X-ray receiving assembly is configured to receive the at least one scattered X-ray which resulted from the at least one applied X-ray scattering during the at least one scattering event.

39. The system of claim 35, wherein the individual includes at least one from a group, the group includes a human, an animal, an organism, or a plant.

* * * * *